US012484502B2

(12) United States Patent
Ulmasov et al.

(10) Patent No.: US 12,484,502 B2
(45) Date of Patent: Dec. 2, 2025

(54) LOW GLUCOSINOLATE PENNYCRESS MEAL AND METHODS OF MAKING

(71) Applicants: COVERCRESS INC., St. Louis, MO (US); BOARD OF TRUSTEES OF ILLINOIS STATE UNIVERSITY, Normal, IL (US); REGENTS OF THE UNIVERSITY OF MINNESOTA, Minneapolis, MN (US)

(72) Inventors: Tim Ulmasov, St. Louis, MO (US); John C. Sedbrook, Bloomington, IL (US); Michael David Marks, Roseville, MN (US); Ratan Chopra, St. Louis, MO (US)

(73) Assignees: COVERCRESS INC., St. Louis, MO (US); BOARD OF TRUSTEES OF ILLINOIS STATE UNIVERSITY, Normal, IL (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/185,179

(22) Filed: Mar. 16, 2023

(65) Prior Publication Data

US 2023/0265450 A1 Aug. 24, 2023

Related U.S. Application Data

(62) Division of application No. 17/249,431, filed on Mar. 2, 2021, now Pat. No. 11,685,927, which is a division of application No. 16/251,247, filed on Jan. 18, 2019, now Pat. No. 10,988,772.

(60) Provisional application No. 62/619,360, filed on Jan. 19, 2018.

(51) Int. Cl.
*A01H 5/10* (2018.01)
*A01H 1/02* (2006.01)
*A01H 6/20* (2018.01)

(52) U.S. Cl.
CPC ................ *A01H 6/20* (2018.05); *A01H 1/02* (2013.01); *A01H 5/10* (2013.01)

(58) Field of Classification Search
CPC ............... A01H 1/02; A01H 5/10; A01H 6/20
See application file for complete search history.

(56) References Cited

U.S. PATENT DOCUMENTS

| | | | | |
|---|---|---|---|---|
| 7,250,559 | B2 | 7/2007 | Quiros et al. | |
| 10,988,772 | B2 | 4/2021 | Ulmasov et al. | |
| 2005/0055744 | A1 | 3/2005 | Quiros et al. | |
| 2009/0306060 | A1 | 12/2009 | Watrin | |
| 2014/0027011 | A1 * | 1/2014 | Bahr ....................... | B01F 25/00 209/552 |
| 2014/0137294 | A1 | 5/2014 | Denolf et al. | |
| 2015/0005172 | A1 | 1/2015 | Robinson | |

FOREIGN PATENT DOCUMENTS

| | | | |
|---|---|---|---|
| CN | 1110310 | A | 10/1995 |
| IN | 363DEL2012 | | 4/2015 |
| WO | 2017091891 | A1 | 6/2017 |
| WO | 2018140782 | A1 | 8/2018 |

OTHER PUBLICATIONS

Zhang et al., UniProt Database, Acc. No. A0A8FOD5A0, Direct Submission, Dec. 2020.*
Lachler et al., Plant Mol. Biol., 88:119-131, 2015.*
Schweizer et al., "Arabidopsis Basic Helix-Loop-Helix Transcription Factors MYC2,MYC3, andMYC4 Regulate Glucosinolate Biosynthesis, Insect Performance, and Feeding Behavior", The Plant Cell, vol. 25:3117-3132, 36 pages Aug. 2013.
TAIR, "Protein: AT5G46760.1", TAIR Accession AASequence: 1009133781, 2 pages Jul. 26, 2017.
TAIR, "Locus AT5G46760", TAIR Accession Locus:2178555, 13 pages Feb. 27, 2022.
Extended European Search Report in EP19741528, 13 pages, mailed May 30, 2022.
Nour-Eldin et al., "Reduction of antinutritional glucosinolates in *Brassica* oilseeds by mutation of genes encoding transporters," Nature Biotechnology, vol. 35, No. 4, pp. 377-382 Apr. 2017.
Østerberg et al., "Accelerating the Domestication of New Crops: Feasibility and Approaches," Trends in Plant Science, vol. 22, No. 5, pp. 373-384 May 2017.
Yang et al., "BHLH domain-containing protein," Database Eutrema salsugineum [online], UniProtKB, Jan. 2014, Accession No. V4L837. Retrieved from the Internet: <URL:https://www.uniprot.org/uniprot/V4L837>, 2 pages, retrieved Jun. 2022.
"Opinion of the Scientific Panel on Contaminants in the Food Chain on a Request from the European Commission on Glucosinolales as Undesirable Substances in Animal Feed", The EFSA Journal, vol. 590, pp. 1-76, 2008.
Chopra et al., "The Adaptable use of *Brassica* NIRS Calibration Equations to Identify Pennycress Variants to Facilitate the Rapid Domestication of a New Winter Oilseed Crop", Industrial Crops and Products, vol. 128, pp. 55-61, 2019.
Dehaan et al., "A Pipeline Strategy for Grain Crop Domestication", Crop Science, vol. 56, pp. 917-930, 2016.
Dorn et al., "A Draft Genome of Field Pennycress (*Thlaspi arvense*) Provides Tools for the Domestication of a New Winter Biofuel Crop", DNA Research, vol. 22, No. 2, pp. 121-131, 2015.
Dorn et al., "De Novo Assembly of the Pennycress (*Thlaspi arvense*) Transcriplome Provides Tools for the Development of a Winter Cover Crop and Biodiesel Feedstock", The Plant Journal, vol. 75, pp. 1028-1038, 2013.

(Continued)

*Primary Examiner* — Phuong T Bui
(74) *Attorney, Agent, or Firm* — McKee, Voorhees & Sease, PLC

(57) ABSTRACT

Pennycress (*Thlaspi arvense*) seed, seed lots, seed meal, and compositions with reduced glucosinolate content as well as plants that yield such seed, seed lots, seed meal, and compositions are provided. Methods of making and using the pennycress plants and/or seed that provide such seed, seed lots, seed meal, and compositions are also provided.

10 Claims, 8 Drawing Sheets

Specification includes a Sequence Listing.

(56) References Cited

OTHER PUBLICATIONS

Harper et al., "Associative Transcriptomics of Traits in the Polyploid Crop Species *Brassica napus*" Nature Biotechnology, vol. 30, No. 8, pp. 798-804, Aug. 2012.
International Search Report and Written Opinion for PCT/US2019/014178 May 17, 2019.
Jordan et al., "Sustainable Commercialization of New Crops for the Agricultural Bioeconomy", Elementa: Science of the Anthropocene, vol. 4, No. 81, Jan. 8, 2016.
Kantar et al., "Perennial Grain and Oilseed Crops", Plant Biology, vol. 67, pp. 703-729, 2016.
Kliebenstein et al., "Gene Duplication in the Diversification of Secondary Metabolism: Tandem 2-Oxoglutarate-Dependent Dioxygenases Control Glucosinolate Biosynthesis in *Arabidopsis*", The Plant Cell, vol. 13, pp. 681-693, 2001.
Sedbrook et al., "New Approaches to Facilitate Rapid Domestication of a Wild Plant to an Oilseed Crop: Example Pennycress (*Thlaspi arvense* L.)", Plant Science, vol. 227, pp. 122-132, 2014.
Tripathi et al., "Glucosinolates in Animal Nutrition: A Review", Animal Feed Science and Technology, vol. 132, No. 1-2, pp. 1-27, 2007.
United States Department of Agriculture, "Advancing Field Pennycress as a New Oilseed Biodiesel Feedstock that does not Require New Land Commitments Annual Progress Report", Accession No. 1004021, 7 pages, submitted to NIFA Jan. 9, 2018.
United States Department of Agriculture, "Advancing Field Pennycress as a New Oilseed Biodiesel Feedstock that does not Require New Land Commitments Annual Progress Report", Accession No. 1004021, 7 pages, submitted to NIFA Dec. 6, 2016.
United States Department of Agriculture, "Advancing Field Pennycress as a New Oilseed Biodiesel Feedstock that does not Require New Land Commitments Annual Progress Report", Accession No. 1004021, 7 pages, submitted to NIFA Nov. 30, 2015.
University of Minnesota, "Advancing Field Pennycress as a New Oilseed Biodiesel Feedstock That Does Not Require New Land Commitments", National Institute of Food and Agriculture, 10 pages, retrieved Nov. 26, 2018.
Zhang et al., "Three Genes Encoding AOP2, a Protein Involved in Aliphatic Glucosinolate Biosynthesis, are Differentially Expressed in *Brassica rapa*", Journal of Experimental Botany, vol. 66, No. 20, pp. 6205-6218, Jul. 17, 2015.
Office Action in AR20190100118, mailed Aug. 5, 2024, 5 pages.
Dorn et al. "Predicted Gene Model Expression—Supplementary Dataset." Datasheet [Excel] (2014): 1-2332.
Hemm et al. "The *Arabidopsis* ref2 mutant is defective in the gene encoding CYP83A1 and shows both phenylpropanoid and glucosinolate phenotypes." The Plant Cell 15.1 (2003): 179-194.
Knill et al. "*Arabidopsis* branched-chain aminotransferase 3 functions in both amino acid and glucosinolate biosynthesis." Plant Physiology 146.3 (2008): 1028-1039.
Schuster et al. "Branched-chain aminotransferase4 is part of the chain elongation pathway in the biosynthesis of methionine-derived glucosinolates in *Arabidopsis*." The Plant Cell 18.10 (2006): 2664-2679.
Chopra et al. "Translational genomics using *Arabidopsis* as a model enables the characterization of pennycress genes through forward and reverse genetics." The Plant Journal (2018) 96, 1093-1105.
Mcginn et al. "Molecular tools enabling pennycress (*Thlaspi arvense*) as a model plant and oilseed cash cover crop." Plant Biotechnology Journal (2019) 17, pp. 776-788.
Fauser et al. "Both CRISPR/Cas-based nucleases and nickases can be used efficiently for genome engineering in *Arabidopsis thaliana*." The Plant Journal (2014) 79, 348-359.
Steinert et al. "Highly efficient heritable plant genome engineering using Cas9 orthologues from *Streptococcus thermophilus* and *Staphylococcus aureus*." The Plant Journal (2015) 84, 1295-1305.

* cited by examiner

A.
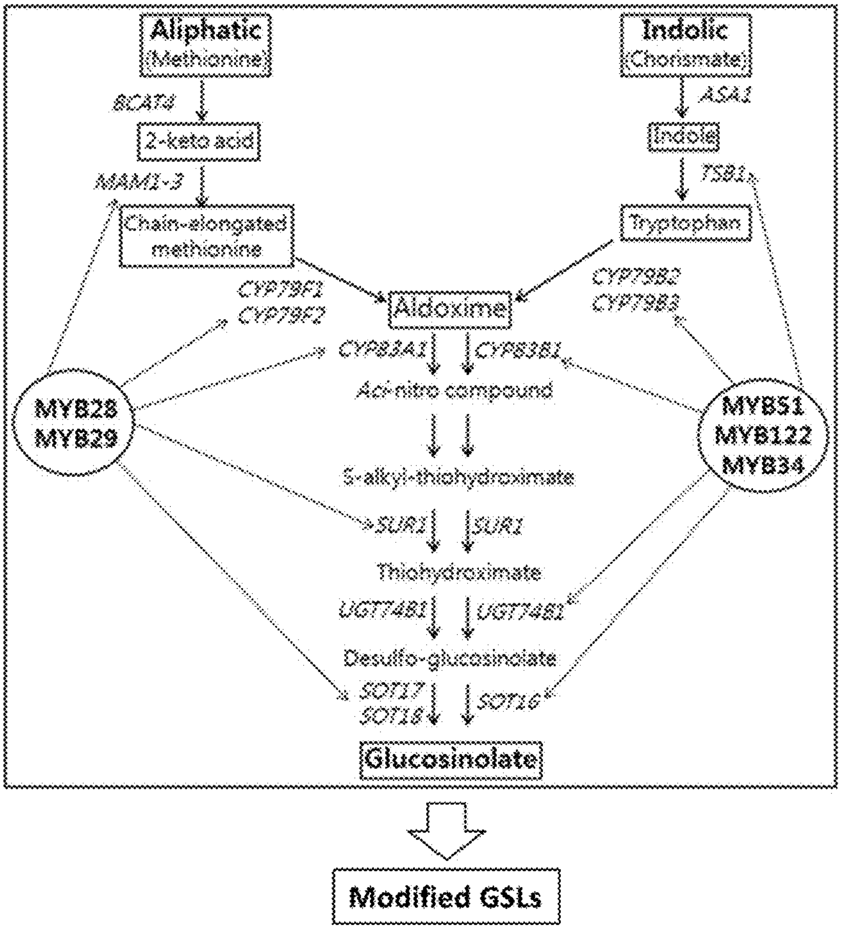
B.
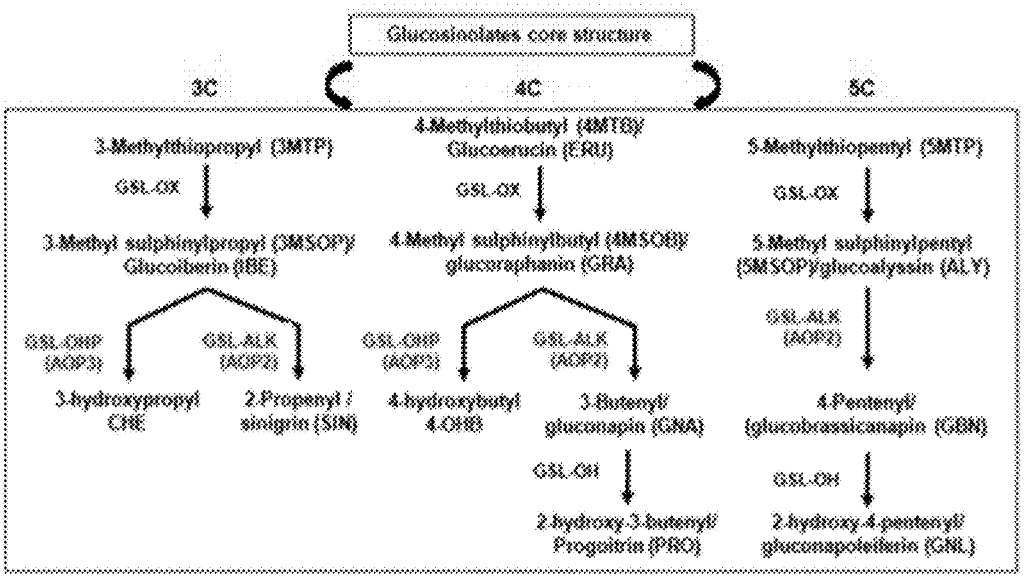
FIGURE 1A, B

A.
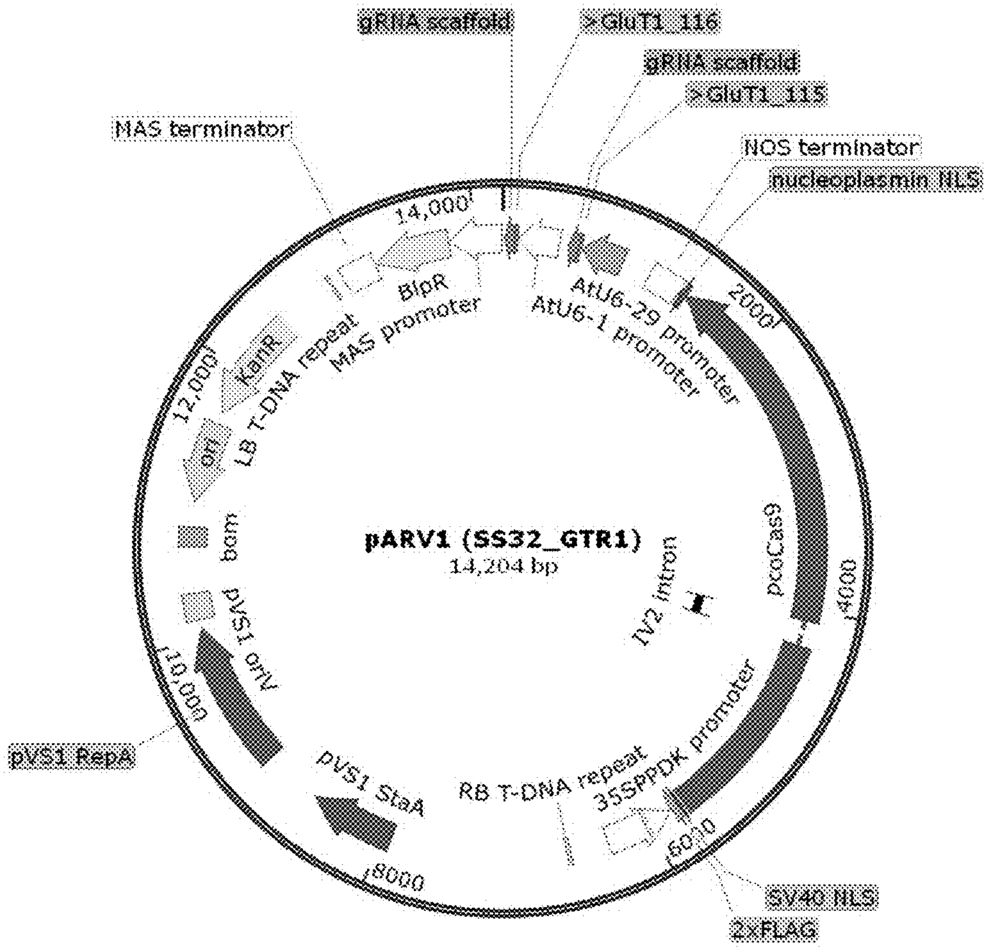
B.
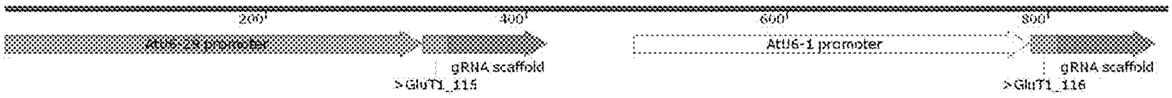
C.
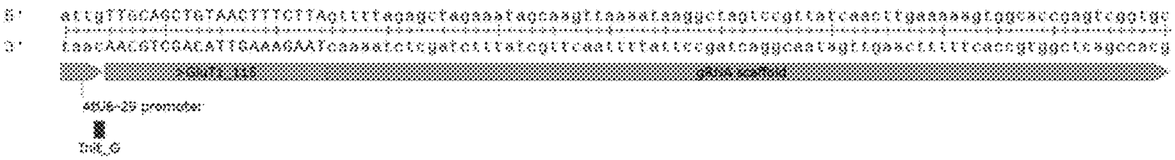
FIGURE 2A, B, C

A.
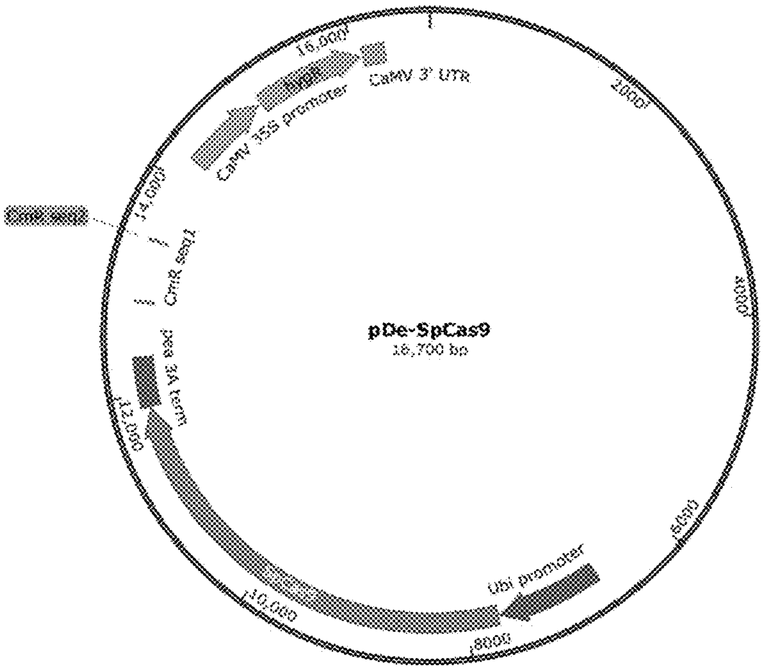
B.
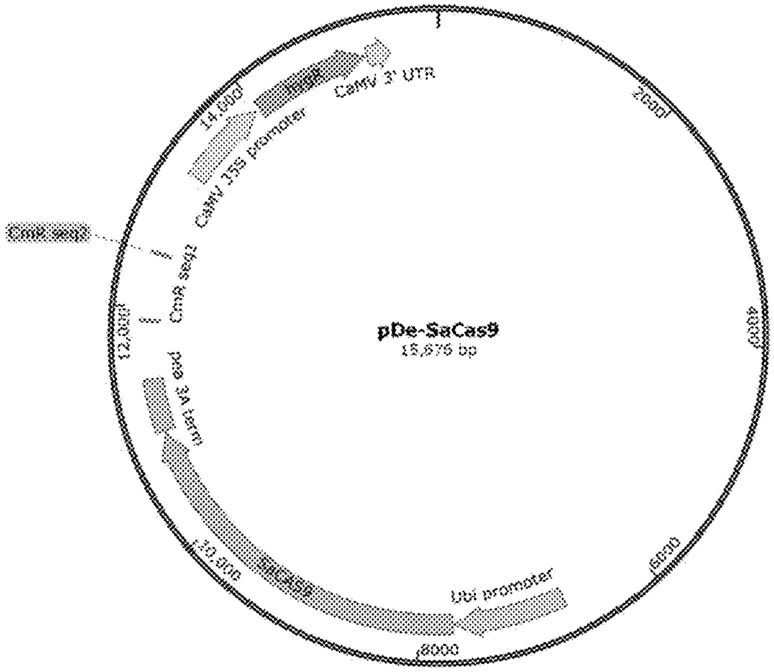
FIGURE 3A,B

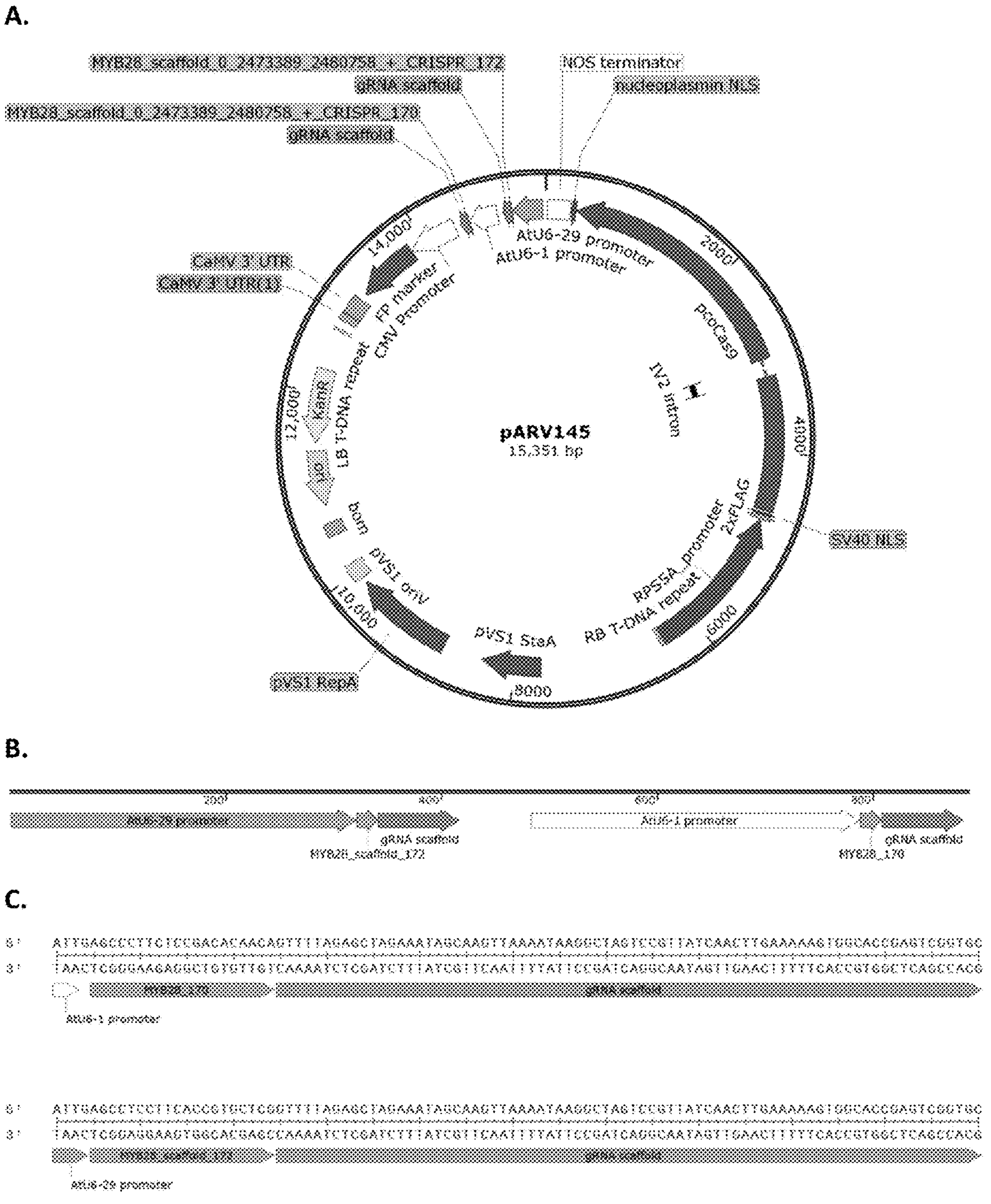
FIGURE 4A, B, C

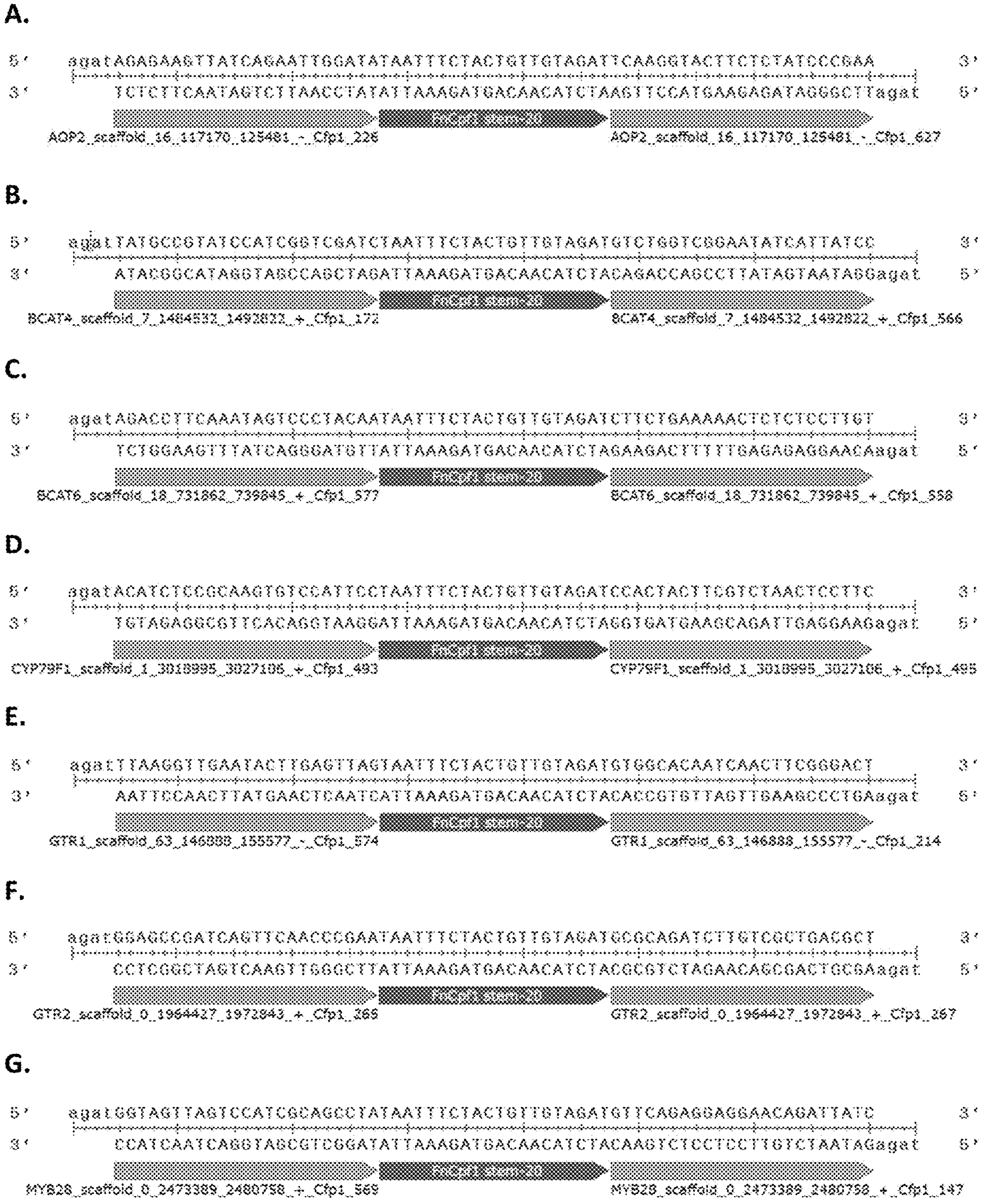
FIGURE 7A, B, C, D, E, F, G

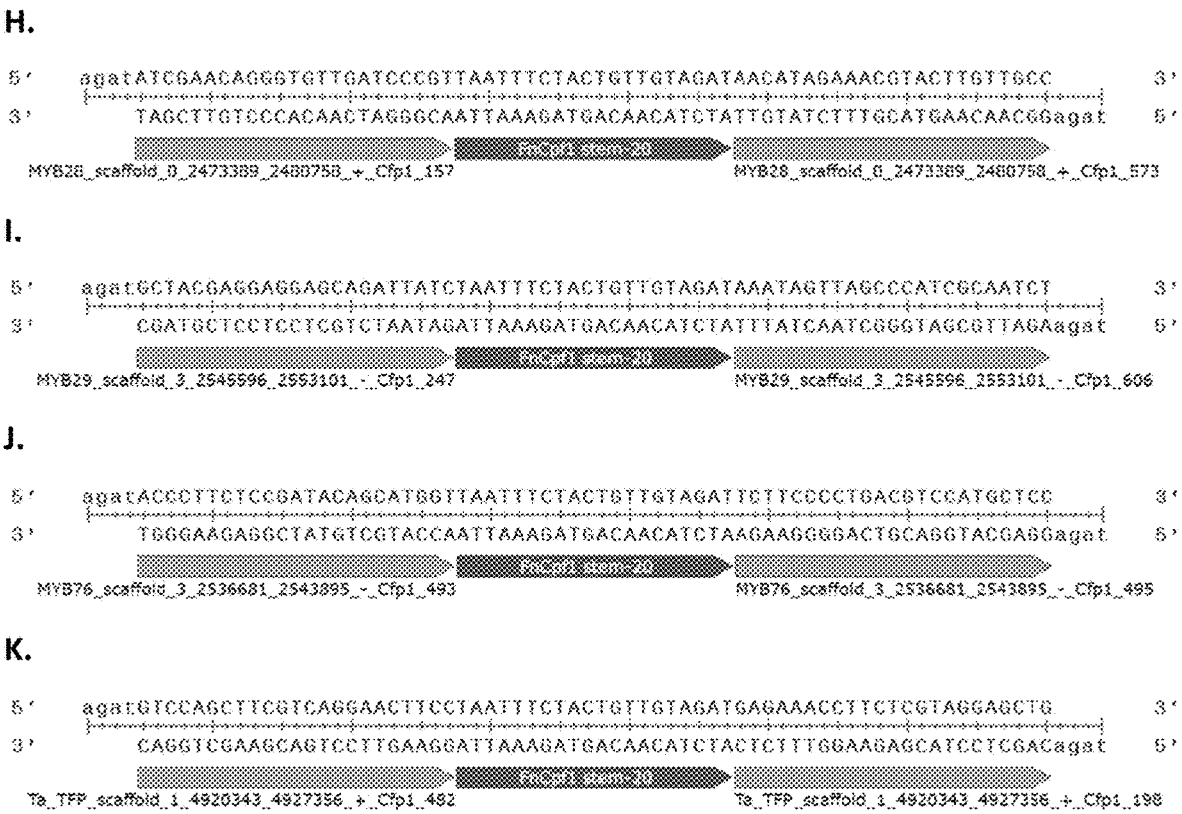
FIGURE 7H, I, J, K

LOW GLUCOSINOLATE PENNYCRESS MEAL AND METHODS OF MAKING

CROSS REFERENCE TO RELATED APPLICATIONS

This is a divisional patent application which claims priority under 35 U.S.C. § 120 to U.S. Ser. No. 17/249,431, now U.S. Pat. No. 11,685,927, filed Mar. 2, 2021, which is a divisional patent application of U.S. Ser. No. 16/251,247, now U.S. Pat. No. 10,988,772, filed Jan. 18, 2019, which claims the benefit of U.S. Provisional Patent Application No. 62/619,360, filed Jan. 19, 2018, all of which are incorporated herein by reference in their entireties.

STATEMENT REGARDING FEDERAL FUNDING

This invention was made with government support under Grant Number 2014-67009-22305 awarded by the National Institute of Food and Agriculture, USDA. The government has certain rights in the invention.

REFERENCE TO SEQUENCE LISTING SUBMITTED ELECTRONICALLY

The instant application contains a Sequence Listing which has been submitted electronically in XML format and is herein incorporated by reference in its entirety. Said XML copy, created on Mar. 13, 2023, is named "P13413US04_SequenceListing.xml" and is 406,727 bytes in size.

BACKGROUND

Different plants have seed contents that make them desirable for feed compositions. Examples are soybean, canola, rapeseed and sunflower. After crushing the seeds and recovering the oil, the resulting meal has a protein content making the meal useful as a feed ingredient for ruminants and other animals. Nevertheless, there remains a desire for improved plant seeds that can provide additional sources of nutrition to animals.

Field Pennycress *Thlaspi arvense* L. (common names: fanweed, stinkweed, field pennycress), hereafter referred to as Pennycress or pennycress, is a winter cover crop that helps to protect soil from erosion, prevent the loss of farm-field nitrogen into water systems, and retain nutrients and residues to improve soil productivity. While it is well established that cover crops provide agronomic and ecological benefits to agriculture and environment, only 5% of U.S. farmers today are using them. One reason is economics—it requires on average ~$30-50/acre to grow a cover crop on the land that is otherwise idle between two seasons of cash crops such as corn and soy. In the last 5 years, it has been recognized that pennycress could be used as a novel cover crop, because in addition to providing cover crop benefits, it produces harvestable seeds rich in oil and protein having value for feed, food, fuel, and industrial applications. Extensive testing indicates that pennycress can be interseeded over standing corn in early fall and harvested in spring prior to soybean planting (in appropriate climates). As such, its growth and development require minimal incremental inputs (e.g., no/minimum tillage, no/low nitrogen, insecticides or herbicides). Pennycress also does not directly compete with existing crops when intercropped e.g., for energy production, and the recovered oil and meal can provide an additional source of income for farmers.

Pennycress is a winter annual belonging to the Brassicaceae (mustard) family. It's related to cultivated crops, rapeseed and canola, which are also members of the Brassicaceae family. Pennycress seeds are smaller than those of canola, but they are also high in oil and protein content. They typically contain 36% oil, which is roughly twice the level found in soybean, and the oil has a very low saturated fat content (~4%). Pennycress represents a clear opportunity for sustainable optimization of agricultural systems. For example, in the U.S. Midwest, ~35M acres that remain idle could be planted with pennycress near the time of corn crop harvest, with pennycress seeds and/or plants harvested before the next soybean crop is planted. Pennycress can serve as an important winter cover crop working within the no/low-till corn and soybean rotation to guard against soil erosion and improve overall field soil nitrogen and pest management.

Pennycress seeds contain oil that is highly desirable as a feedstock for biofuels and/or chemicals and potentially as a food oil. Once the oil is obtained from pennycress seeds, either from mechanical expeller pressing or hexane extraction, the resulting meal has a high protein level with a favorable amino acid profile that could provide nutritional benefits to animals. However, studies of pennycress processing have consistently demonstrated that the meal produced has a high level of the anti-nutrient compound sinigrin (allyl-glucosinolate or 2-propenyl-glucosinolate), and as a result, without additional treatments, may not be competitive with high-value products like soybean and canola meals, ingredients commonly used in animal feed. Glucosinolates (GSLs) are secondary plant metabolites that are found in all *Brassica* plants such as rapeseed, canola, camelina, carinata and pennycress. Content and composition of GSLs vary due to plant species, agronomic practices and environmental conditions (Tripathi and Mishra, 2007). Glucosinolates and their breakdown products that are a result of hydrolysis during the processing of the seeds into animal feed can result in negative effects on animal nutrition. The toxicity of glucosinolates for animals has been primarily associated with the metabolites thiocyanates, oxazolidinethiones and nitriles. These compounds interfere with iodine uptake (thiocyanates) and the synthesis of the thyroid hormones T3 and T4 (oxazolidinethiones), leading eventually to hypothyroidism and enlargement of the thyroid gland (EFSA, 2008). The major clinical signs of toxicity described in farm animals include growth retardation, reduction in performance (milk and egg production), impaired reproductive activity, and impairment of liver and kidney functions (EFSA, 2008). A comprehensive review of the effects of glucosinolates in animal nutrition has been published by Tripathi and Mishra (2007) and EFSA (2008).

SUMMARY

Compositions comprising non-defatted pennycress seed meal that comprises less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Non-defatted pennycress seed meal that comprise less than 30, 28, 25, 16, or 15 micromoles sinigrin per gram by dry weight are provided herein.

Defatted pennycress seed meal comprising less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Compositions comprising defatted pennycress seed meal that comprise less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Pennycress seed comprising less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

Pennycress seed lots comprising pennycress seed with less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight are provided herein.

In one embodiment, this disclosure provides methods for producing low glucosinolate pennycress seeds and meal. In certain embodiments, the methods comprise genetically modifying pennycress seed (e.g., using gene editing, mutagenesis, or a transgenic approach) to suppress expression of one or more genes involved in sinigrin biosynthesis, transport, and/or hydrolysis. Genetically altered seed lots with lower sinigrin content in comparison to control seed lots that lack the genetic alteration can be obtained by these methods.

BRIEF DESCRIPTION OF THE DRAWINGS

The accompanying drawings, which are incorporated in and form a part of the specification, illustrate the embodiments of the present disclosure and together with the description, serve to explain the principles of the disclosure. In the drawings:

FIG. 1A, B illustrate glucosinolate (GSL) biosynthetic pathways for many *Brassica* plants. Panel A: A schematic diagram of aliphatic GSL pathway which begins with amino acid methionine as the precursor and is relevant for GSL modification in pennycress seed. Panel B: Various GSL forms found in *Brassica* are shown.

FIG. 2A, B, C, illustrates pARV1 (SS32 GTR1), *Agrobacterium* CRISPR-Cas9 vector and its gene editing sgRNA cassette, for targeting pennycress homolog of Glucosinolate transporter 1 (GTR1 or Glut1) gene. Panel A: Plasmid map of pARV1 (SS32 GTR1). Panel B: sgRNA cluster in pARV1, targeting nucleotides 2503-2522 and 2538-2557 of SEQ ID NO: 14. Panel C: Sequence example of one of gRNA cassettes targeting pennycress homolog of Glucosinolate transporter 1 (GTR1 or Glut1) gene.

FIG. 3A, B illustrates pDe-SpCas9 and pDe-SaCas9, *Agrobacterium* CRISPR-Cas9 base vectors for editing plant genome. gRNA cassette stuffers are inserted at the multiple cloning site between the Cas9 and HygR cassettes, replacing a small fragment of the vector with synthetic gRNA cassette.

FIG. 4A, B, C, illustrates pARV145, *Agrobacterium* CRISPR-Cas9 vector and its gene editing sgRNA cassettes, for targeting pennycress homolog ofMYB28 (HAG1) gene. Panel A: Plasmid map of pARV145. Panel B: sgRNA cluster in pARV145, targeting nucleotides 719-738 and 793-812 of SEQ ID NO: 20. Panel C: Sequence examples of gRNA cassettes targeting pennycress homolog ofMYB28 (HAG1) gene.

FIG. 7A, B, C, D, E, F, G, H, I, J, K, gRNA cassettes targeting pennycress homologs of multiple genes in glucosinolate biosynthetic/metabolic pathway. FIG. 5A illustrates a gRNA cassette stuffer, designed for insertion into the AarI-digested plant genome editing vector (such as pARV187 or pARV190) for targeting pennycress AOP2 gene, nucleotides 2367-2389 and 2419-2441 of SEQ ID NO: 2; FIG. 5B: gRNA cassette stuffer for targeting pennycress BCAT4 gene, nucleotides 2984-3006 and 3048-3070 of SEQ ID NO: 5; FIG. 5C: gRNA cassette stuffer for targeting pennycress BCAT6 gene, nucleotides 1932-1954 and 2387-2409 of SEQ ID NO: 8; FIG. 5D: gRNA cassette stuffer for targeting pennycress CYP79 gene, nucleotides 2914-2936 and 2968-2990 of SEQ ID NO: 11; FIG. 5E: gRNA cassette stuffer for targeting pennycress GTR1 gene, nucleotides 2483-2505 and 2541-2563 of SEQ ID NO: 14; FIG. 5F: gRNA cassette stuffer for targeting pennycress GTR2 gene, nucleotides 2317-2339 and 2404-2426 of SEQ ID NO: 18; FIGS. 5G and 5H: gRNA cassette stuffers for targeting pennycress MYB28 gene, nucleotides 948-970, 1001-1023, 1045-1067 and 1315-1337 of SEQ ID NO: 20; FIG. SL gRNA cassette stuffer for targeting pennycress MYB29 gene, nucleotides 2573-2595 and 2625-2647 of SEQ ID NO: 23; FIG. 5J: gRNA cassette stuffer for targeting pennycress MYB76 gene, nucleotides 1539-1561 and 1570-1592 of SEQ ID NO: 26; FIG. 5K: gRNA cassette stuffer for targeting pennycress TFP gene, nucleotides 2170-2192 and 2559-2581 of SEQ ID NO: 29.

DETAILED DESCRIPTION

Figure 5:
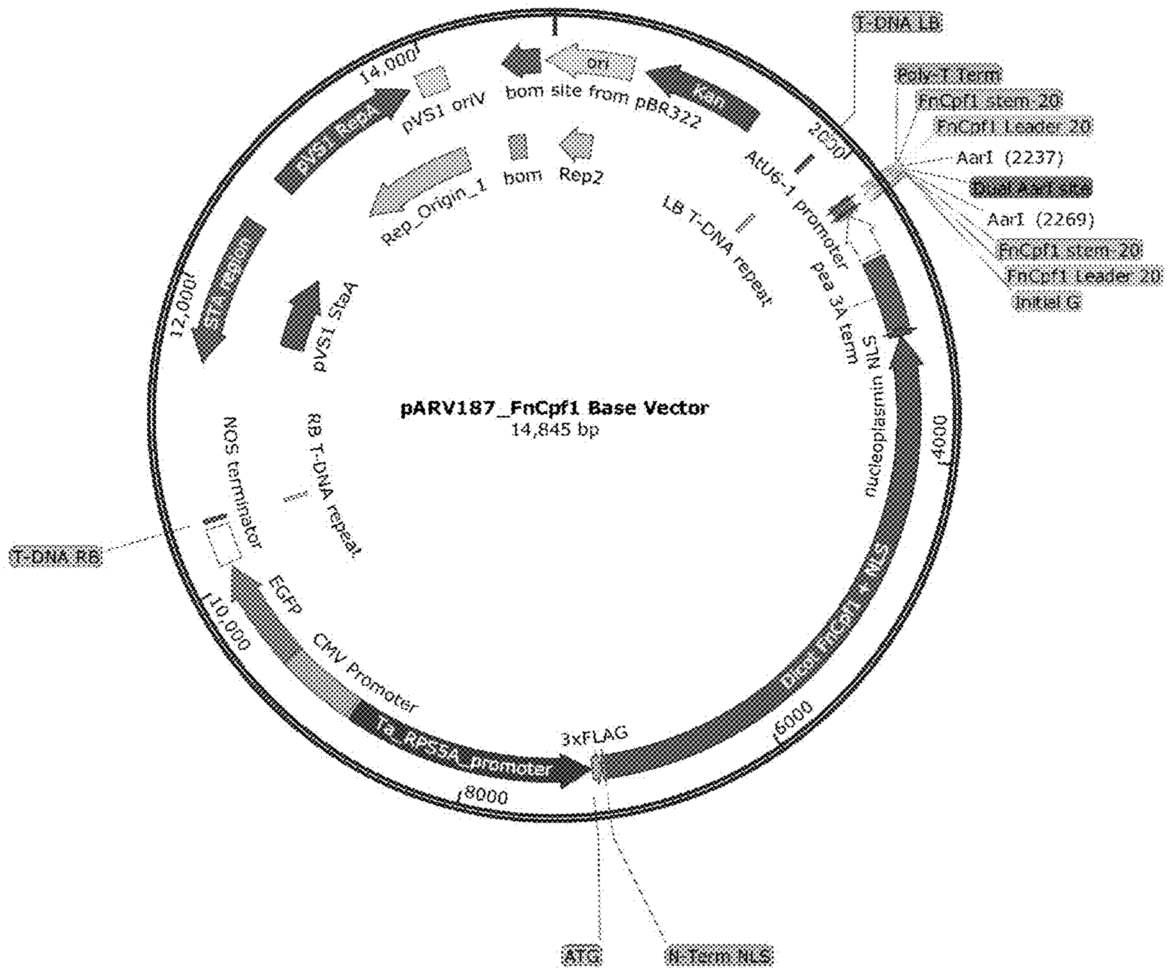
FIG. 5 illustrates pARV187, *Agrobacterium* CRISPR-FnCpf1 base vector for editing plant genome. gRNA cassette stuffers are inserted at the dual AarI site, replacing a small fragment of the vector with synthetic gRNA cassette.

The term "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "include," "includes," and "including" are to be construed as at least having the features to which they refer while not excluding any additional unspecified features.

Where a term is provided in the singular, other embodiments described by the plural of that term are also provided.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Reductions in sinigrin content of various pennycress plants, seeds, seed lots, seed meals, and compositions obtained therefrom as well as associated methods of obtaining and using such plants, seeds, seed lots, seed meals, and compositions is provided herein by suppression of certain endogenous pennycress genes. The endogenous pennycress genes that can be suppressed to provide such reductions in sinigrin content include, but are not limited to, endogenous pennycress genes set forth in the following Table 1 and allelic variants of those genes.

Suppression of certain endogenous pennycress gene expression to provide for reductions in sinigrin content can be affected by a variety of techniques including, but not limited to, loss-of-function (LOF) mutations in endogenous genes, with transgenes, or by using gene-editing- or mutagenesis-mediated genome rearrangements. In certain embodiments, the pennycress plants, seeds, seed lots, seed meals (which can be defatted or non-defatted), and related compositions can comprise one or more LOF mutations that suppress or otherwise alter expression and/or function of one or more genes, coding sequences, and/or proteins, thus resulting in reduced sinigrin content in comparison to control or wild-type pennycress seed, seed lots, and plant lots. Such LOF mutations include, but are not limited to, INDELS (insertions, deletions, and/or substitutions or any combination thereof), translocations, inversions, duplications, or any combination thereof in a promoter, and/or other regulatory elements including enhancers, a 5' untranslated region, coding region, an intron of a gene, and/or a 3' UTR of a gene. Such INDELS can introduce one or more mutations including, but not limited to, frameshift mutations, missense mutations, pre-mature translation termination codons, splice donor and/or acceptor mutations, regulatory mutations, and the like that result in a LOF mutation. In certain embodiments, the LOF mutation will result in: (a) a reduction in the enzymatic, transport, or other biochemical activity associated with the encoded polypeptide in the plant comprising the LOF mutation in comparison to a wild-type control plant; or (b) both a reduction in the enzymatic, transport or other biochemical activity (e.g., transcription factor) and a reduction in the amount of a transcript (e.g., mRNA) or polypeptide in the plant comprising the LOF mutation in comparison to a wild-type control plant. Such reductions in activity or activity and transcript levels can, in certain embodiments, comprise a reduction of at least 20%, 30%, 40%, 50%, 60%, 70%, 75%, 80%, 85%, 90%, 95%, 98%, 99%, or 100% of activity or activity and transcript levels in the LOF mutant in comparison to the activity or transcript levels in a wild-type control plant. In certain embodiments, the pennycress plants, seeds, seed lots, seed meals (which can be defatted or non-defatted), and related compositions will comprise one or more transgenes or genetic modifications that suppress or otherwise alter expression of one or more genes, coding sequences, and/or proteins, thus resulting in reduced sinigrin content in comparison to control or wild-type pennycress seed lots. Transgenes or genetic modifications that can provide for such suppression or alteration include, but are not limited to, transgenes or genome rearrangements introduced via gene editing or other mutagenesis techniques that produce small interfering RNAs (siRNAs), miRNA, or artificial miRNAs targeting a given gene or gene transcript for suppression. Such genome rearrangements include, but are not limited to, deletions, duplications, insertions, inversions, translocations, and combinations thereof. Useful genome rearrangements include, but are not limited to, rearrangements that place an endogenous promoter and/or transcriptional enhancer in proximity to 3' end of a target gene or coding sequence (e.g., a gene or coding sequence of Table 1) or within the target gene or coding sequence such that the endogenous promoter and/or enhancer drive expression of an siRNA or miRNA that suppresses or otherwise alters expression of the target gene. In certain embodiments, the transgenes or genetic modifications that suppress expression will result in: (a) a reduction in the enzymatic, transport, or other biochemical activity associated with the encoded polypeptide in the plant comprising the transgene or genome rearrangement in comparison to a wild-type control plant; or (b) both a reduction in the enzymatic or other biochemical activity and a reduction in the amount of a transcript (e.g., mRNA) or polypeptide in the plant comprising the transgene or genome rearrangement in comparison to a wild-type control plant. Such reductions in activity and transcript levels can in certain embodiments comprise a reduction of at least 20%, 30%, 40%, 50%, 60%, 70%, 75%, 80%, 85%, 90%, 95%, 98%, 99%, or 100% of activity and/or transcript levels in the transgenic plant in comparison to the activity or transcript levels in a wild-type control plant. In certain embodiments, certain genes, coding sequences, and/or proteins that can be targeted for introduction of LOF mutations or that are targeted for transgene- or genome rearrangement-mediated suppression are provided in the following Table 1 and accompanying Sequence Listing. In certain embodiments, allelic variants of the wild-type genes, coding sequences, and/or proteins provided in Table 1 and the sequence listing are targeted for introduction of LOF mutations or are targeted for transgene- or genome rearrangement-mediated suppression. Allelic variants found in distinct pennycress isolates or varieties that exhibit wild-type seed sinigrin content can be targeted for introduction of LOF mutations or are targeted for transgene- or genome rearrangement-mediated suppression to obtain seed lots having reduced sinigrin content in comparison to sinigrin content of the control seed lots of wild-type pennycress. Such allelic variants can comprise polynucleotide sequences that have at least 80%, 85%, 90%, 95%, 96%, 97%, 98%, or 99% sequence identity across the entire length of the polynucleotide sequences of the wild-type coding regions or wild-type genes of Table 1 and the sequence listing. Such allelic variants can comprise polypeptide sequences that have at least 80%, 85%, 90%, 95%, 96%, 97%, 98%, or 99% sequence identity across the entire length of the polypeptide sequences of the wild-type proteins of Table 1 and the sequence listing. Pennycress seed lots having reduced sinigrin content as described herein can comprise one or more LOF mutations in one or more genes that encode polypeptides involved in GSL biosynthesis, in GSL transport, in GSL hydrolysis, regulating expression of genes encoding GSL biosynthetic and/or transport genes (e.g., transcription factors) or can comprise transgenes or genome rearrangements that suppress expression of those biosynthetic, transporter, hydrolysis, or expression regulator (e.g., transcription factor) encoding genes. Polypeptides affecting these traits include, without limitation, AOP2, BCAT4, BCAT6, CYP79F1, CYP83A1, GTR1, GTR2, MYB28 (HAG1), MYB29, MYB76, TFP, BHLH05, IMD1, CYP79B3, MAM1, FMO-GS-Ox1, and UGT74B-1 polypeptides disclosed in Table 1 and allelic variants thereof. In certain embodiments, pennycress seed lots, plants, seeds, as well as the seed meals and compositions obtained therefrom, all having reduced sinigrin content, can comprise one or more LOF mutations found in the pennycress mutant E3 196, E5 444P1, E5 356P5, I87113, E5 543, or I87207 germplasm. Compositions comprising defatted or non-defatted seed meal obtained from any of the aforementioned seed lots, and seed cakes obtained from any of the aforementioned seed lots are also provided herein. Methods of making any of the aforementioned seed lots, compositions, seed meals, or seed cakes are also provided herein. As used herein, the phrase "seed cake" refers to the material obtained after the seeds are crushed, ground, heated, and expeller pressed or extruded prior to solvent extraction.

In certain embodiments, reductions in sinigrin content of seed lots, seed meal compositions, seed meal, or seed cake are in comparison to sinigrin content of control or wild-type seed lots, seed meal compositions, seed meal, or seed cake. Such controls include, but are not limited to, seed lots, seed meal compositions, seed meal, or seed cake obtained from control plants that lack the LOF mutations or transgene- or genome rearrangement-mediated gene suppression. In certain embodiments, control plants that lack the LOF mutations or transgene or genome rearrangement mediated gene suppression will be otherwise isogenic to the plants that contain the LOF mutations or transgene- or genome rearrangement-mediated gene suppression. In certain embodiments, the controls will comprise seed lots, seed meal compositions, seed meal, or seed cake obtained from plants that lack the LOF mutations or transgene or genome rearrangement mediated gene suppression and that were grown in parallel with the plants having the LOF mutations or transgene or genome rearrangement-mediated gene suppression. In certain embodiments, the pennycress seed lots, plants, seeds, as well as the defatted or non-defatted seed meals and compositions obtained therefrom, can comprise a less than 30, 28, 25, 16, or 15 micromoles sinigrin per gram by dry weight or about 1, 2.5, 5, or 10 to about 15, 16, 18, 20, 25, 28, or 30 micromoles sinigrin per gram by dry weight.

In certain embodiments, pennycress seed lots, plants, seeds, as well as the seed meals and compositions obtained therefrom, all having reduced sinigrin content, can include at least one loss-of-function mutation in a GSL biosynthetic coding sequence or gene (e.g., SEQ ID NO: 1, 2, 4, 5, 7, 8, 10, 11, 92, 93, 162, 163, 165, 166, 168, 169, 171, 172, 174, 175, or allelic variant thereof) and/or at least one loss-of-function mutation in a GSL transport (SEQ ID NO: 13, 14, 16, 18, or allelic variant thereof), in a GSL hydrolysis (SEQ ID NO: 28, 29, or allelic variant thereof), and/or in an expression regulator (e.g., transcription factor; SEQ ID NO: 19, 20, 22, 23, 25, 26, 159, 160, allelic variant thereof) coding sequence or gene. In certain embodiments, pennycress seed lots, plants, seeds, as well as the seed meals and compositions obtained therefrom, all having reduced sinigrin content, can include at least one loss-of-function mutation in a GSL transport coding sequence or gene (e.g., SEQ ID NO: 13, 14, 16, 18, or allelic variant thereof) and at least one loss-of-function mutation in a GSL hydrolysis (SEQ ID NO: 28, 29, or allelic variant thereof), and/or in a expression regulator (e.g., transcription factor; SEQ ID NO: 19, 20, 22, 23, 25, 26, allelic variant thereof) coding sequence or gene. In certain embodiments, pennycress seed lots, plants, seeds, as well as the seed meals and compositions obtained therefrom, all having reduced sinigrin content, can include at least one loss-of-function mutation in a GSL hydrolysis (SEQ ID NO: 28, 29, or allelic variant thereof) coding sequence or gene and/or at least one loss-of-function mutation in an expression regulator (e.g., transcription factor; SEQ ID NO: 19, 20, 22, 23, 25, 26, allelic variant thereof) coding sequence or gene. In certain embodiments, pennycress seed lots, plants, seeds, as well as the seed meals and compositions obtained therefrom, all having reduced sinigrin content, can be obtained from pennycress plants comprising the mutant E3 196, E5 444P1, E5 356P5, I87113, E5 543, or I87207 germplasm.

TABLE 1

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 1 | AOP2-CDS | WT Coding region | Plays a role in the secondary modification of aliphatic (methionine-derived) GSLs, namely the conversion of methylsulfinylalkyl GSLs to form alkenyl GSLs, and also influences aliphatic GSL accumulation | ALKENYL HYDROXALKYL PRODUCING 2 - CAPE VERDE ISLANDS, AOP2-CVI, GSL ALK enzyme, AOP (2-oxoglutarate- dependent dioxygenase) |
| 2 | AOP2-Genomic locus | WT Gene | | |
| 3 | AOP2-PRT | WT Protein | | |
| 4 | BCAT4-CDS | WT Coding region | Involved in the methionine chain elongation pathway that biosynthesis of methionine-derived glucosinolates leads to the ultimate | BCAT4 (BRANCHED-CHAIN AMINOTRANSFERASE 4) |
| 5 | BCAT4-Genomic locus | WT Gene | | |
| 6 | BCAT4-PRT | WT Protein | | |
| 7 | BCAT6-CDS | WT Coding region | Encodes a cytosolic branched-chain aminotransferase that acts on Leu, Ile, Val and also on Met. Together with BCAT4 and BCAT3, it is involved in methionine salvage and glucosinolate biosynthesis | BCAT6 (BRANCHED-CHAIN AMINOTRANSFERASE 6) |
| 8 | BCAT6-Genomic locus | WT Gene | | |
| 9 | BCAT6-PRT | WT Protein | | |
| 10 | CYP79F1-CDS | WT Coding region | Catalyzes the first committed step in | CYP79F1 (CYTOCHROME P45079F1), |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 11 | CYP79F1-Genomic locus | WT Gene | biosynthesis of the core structure of GSLs, Modulates the level of short chain methionine derived aliphatic GSLs | BUS1, BUSHY 1, SPS1, SUPERSHOOT 1 |
| 12 | CYP79F1-PRT | WT Protein | | |
| 13 | GTR1-CDS | WT Coding region | GTR1 encodes high-affinity, proton-dependent GSL-specific transporter essential for the accumulation of GSLs in seeds | GTR1 (Glucosinolate Transporter 1), NPF2.10, NRT1/PTR FAMILY 2.10 |
| 14 | GTR1-Genomic locus | WT Gene | | |
| 15 | GTR1-PRT | WT Protein | | |
| 16 | GTR2-CDS | WT Coding region | GTR2 encodes high-affinity, proton-dependent GSL-specific transporter essential for the accumulation of GSLs in seeds | GTR2 (Glucosinolate Transporter 2), NPF2.11, NRT1/PTR FAMILY 2.11 |
| 17 | GTR2-PRT | WT Protein | | |
| 18 | GTR2-Genomic locus | WT Gene | | |
| 19 | MYB28-CDS | WT Coding region | Principal regulator of aliphatic glucosinolate biosynthesis and affects the production of both short- and long-chain aliphatic glucosinolates | HAG1 (High Aliphatic Glucosinolate 1), MYB DOMAIN PROTEIN 28, PMG1 (Production of Methionine-derived Glucosinolate 1) |
| 20 | MYB28-Genomic locus | WT Gene | | |
| 21 | MYB28-PRT | WT Protein | | |
| 22 | MYB29-CDS | WT Coding region | MYB DOMAIN PROTEIN 29, a Myb transcription factor affects biosynthesis of short-chain aliphatic glucosinolates | HAG3 (High Aliphatic Glucosinolate 3), PMG2 (Production of Methionine-derived Glucosinolate 2), RAO7, (Regulator of Alternative Oxidase 1A 7) |
| 23 | MYB29-Genomic locus | WT Gene | | |
| 24 | MYB29-PRT | WT Protein | | |
| 25 | MYB76-CDS | WT Coding region | MYB DOMAIN PROTEIN 76, a Myb transcription factor affects biosynthesis of short-chain aliphatic glucosinolates. | HAG2 (High Aliphatic Glucosinolate 2), PMG2, (Production of Methionine-derived Glucosinolate 2), RAO7 (Regulator of Alternative Oxidase 1A 7) |
| 26 | MYB76-Genomic locus | WT Gene | | |
| 27 | MYB76-PRT | WT Protein | | |
| 28 | TFP-CDS | WT Coding region | Promotes the formation of allylthiocyanate as well as the epithionitrile upon myrosinase-catalyzed hydrolysis of allylglucosinolate, the major glucosinolate | Thiocyanate-forming protein (TFP) |
| 29 | TFP-Genomic locus | WT Gene | | |
| 30 | TFP-PRT | WT Protein | | |
| 31 | AOP2_scaffold_16_117170_125481_-_CRISPR_64 | Oligonucleotide | AOP2 CDS targeted for cleavage by Cpf1 enzyme; part of gRNA cassette | |
| 32 | AOP2_scaffold_16_117170_125481_-_Cfp1_226 | Oligonucleotide | AOP2 CDS targeted for cleavage by Cpf1 enzyme; part of gRNA cassette | |
| 33 | AOP2_scaffold_16_117170_125481_-_Cfp1_627 | Oligonucleotide | AOP2 CDS targeted for cleavage by Cpf1 enzyme; part of gRNA cassette | |
| 34 | AOP2_scaffold_16_117170_ | Oligonucleotide | AOP2 CDS targeted for cleavage by Cpf1 enzyme; | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | 125481_-_ CRISPR_66 | | part of gRNA cassette | |
| 35 | BCAT4_scaffold_ 7_1484532_ 1492822_+_ Cfp1_566 | Oligonucleotide | BCAT4 CDS targeted for cleavage by Cpf1 enzyme; part of gRNA cassette | |
| 36 | BCAT4_scaffold_ 7_1484532_ 1492822_+_ CRISPR_184 | Oligonucleotide | BCAT4 CDS targeted for cleavage by Cpf1 enzyme; part of gRNA cassette | |
| 37 | BCAT4_scaffold_ 7_1484532_ 1492822_+_ CRISPR_185 | Oligonucleotide | BCAT4 CDS targeted for cleavage by Cpf1 enzyme; part of gRNA cassette | |
| 38 | BCAT4_scaffold_ 7_1484532_ 1492822_+_ Cfp1_172 | Oligonucleotide | BCAT4 CDS targeted for cleavage by Cpf1 enzyme; part of gRNA cassette | |
| 39 | BCAT6_scaffold_ 18_731862_ 739845_+_ CRISPR_63 | Oligonucleotide | BCAT6 CDS targeted for cleavage by Cpf1 enzyme; part of gRNA cassette | |
| 40 | BCAT6_scaffold_ 18_731862_ 739845_+_ CRISPR_64 | Oligonucleotide | BCAT6 CDS targeted for cleavage by Cpf1 enzyme; part of gRNA cassette | |
| 41 | BCAT6_scaffold_ 18_731862_ 739845_+_ Cfp1_558 | Oligonucleotide | BCAT6 CDS targeted for cleavage by Cpf1 enzyme; part of gRNA cassette | |
| 42 | BCAT6_scaffold_ 18_731862_ 739845_+_ Cfp1_577 | Oligonucleotide | BCAT6 CDS targeted for cleavage by Cpf1 enzyme; part of gRNA cassette | |
| 43 | CYP79F1_ scaffold_1_ 3018995_ 3027106_+_ CRISPR_86 | Oligonucleotide | CYP79F1 CDS targeted for cleavage by Cpf1 enzyme; part of gRNA cassette | |
| 44 | CYP79F1_ scaffold_1_ 3018995_ 3027106_+_ Cfp1_493 | Oligonucleotide | CYP79F1 CDS targeted for cleavage by Cpf1 enzyme; part of gRNA cassette | |
| 45 | CYP79F1_ scaffold_1_ 3018995_ 3027106_+_ CRISPR_87 | Oligonucleotide | CYP79F1 CDS targeted for cleavage by Cpf1 enzyme; part of gRNA cassette | |
| 46 | CYP79F1_ scaffold_1_ 3018995_ 3027106_+_ Cfp1_495 | Oligonucleotide | CYP79F1 CDS targeted for cleavage by Cpf1 enzyme; part of gRNA cassette | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 47 | GTR1_scaffold_63_146888_155577_-_Cfp1_88 | Oligonucleotide | GTR1 CDS targeted for cleavage by Cpf1 enzyme; part of gRNA cassette | |
| 48 | GTR1_scaffold_63_146888_155577_-_Cfp1_92 | Oligonucleotide | GTR1 CDS targeted for cleavage by Cpf1 enzyme; part of gRNA cassette | |
| 49 | GTR1_scaffold_63_146888_155577_-_Cfp1_506 | Oligonucleotide | GTR1 CDS targeted for cleavage by Cpf1 enzyme; part of gRNA cassette | |
| 50 | GTR1_scaffold_63_146888_155577_-_Cfp1_525 | Oligonucleotide | GTR1 CDS targeted for cleavage by Cpf1 enzyme; part of gRNA cassette | |
| 51 | GTR1_scaffold_63_146888_155577_-_Cfp1_574 | Oligonucleotide | GTR1 CDS targeted for cleavage by Cpf1 enzyme; part of gRNA cassette | |
| 52 | GTR1_scaffold_63_146888_155577_-_Cfp1_214 | Oligonucleotide | GTR1 CDS targeted for cleavage by Cpf1 enzyme; part of gRNA cassette | |
| 53 | GTR2_scaffold_0_1964427_1972843_+_Cfp1_513 | Oligonucleotide | GTR2 CDS targeted for cleavage by Cpf1 enzyme; part of gRNA cassette | |
| 54 | GTR2_scaffold_0_1964427_1972843_+_Cfp1_537 | Oligonucleotide | GTR2 CDS targeted for cleavage by Cpf1 enzyme; part of gRNA cassette | |
| 55 | GTR2_scaffold_0_1964427_1972843_+_Cfp1_174 | Oligonucleotide | GTR2 CDS targeted for cleavage by Cpf1 enzyme; part of gRNA cassette | |
| 56 | GTR2_scaffold_0_1964427_1972843_+_Cfp1_265 | Oligonucleotide | GTR2 CDS targeted for cleavage by Cpf1 enzyme; part of gRNA cassette | |
| 57 | GTR2_scaffold_0_1964427_1972843_+_Cfp1_267 | Oligonucleotide | GTR2 CDS targeted for cleavage by Cpf1 enzyme; part of gRNA cassette | |
| 58 | MYB28_scaffold_0_2473389_2480758_+_CRISPR_170 | Oligonucleotide | MYB28 CDS targeted for cleavage by Cpf1 enzyme; part of gRNA cassette | |
| 59 | MYB28_scaffold_0_2473389_2480758_+_CRISPR_172 | Oligonucleotide | MYB28 CDS targeted for cleavage by Cpf1 enzyme; part of gRNA cassette | |
| 60 | MYB28_scaffold_0_2473389_ | Oligonucleotide | MYB28 CDS targeted for cleavage by Cpf1 enzyme; | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | 2480758_+_ Cfp1_569 | | part of gRNA cassette | |
| 61 | MYB28_scaffold_ 0_2473389_ 2480758_+_ Cfp1_147 | Oligonucleotide | MYB28 CDS targeted for cleavage by Cpf1 enzyme; part of gRNA cassette | |
| 62 | MYB28_scaffold_ 0_2473389_ 2480758_+_ Cfp1_573 | Oligonucleotide | MYB28 CDS targeted for cleavage by Cpf1 enzyme; part of gRNA cassette | |
| 63 | MYB28_scaffold_ 0_2473389_ 2480758_+_ Cfp1_157 | Oligonucleotide | MYB28 CDS targeted for cleavage by Cpf1 enzyme; part of gRNA cassette | |
| 64 | MYB29_scaffold_ 3_2545596_ 2553101_-_ CRISPR_156 | Oligonucleotide | MYB29 CDS targeted for cleavage by Cpf1 enzyme; part of gRNA cassette | |
| 65 | MYB29_scaffold_ 3_2545596_ 2553101_-_ Cfp1_606 | Oligonucleotide | MYB29 CDS targeted for cleavage by Cpf1 enzyme; part of gRNA cassette | |
| 66 | MYB29_scaffold_ 3_2545596_ 2553101_-_ CRISPR_161 | Oligonucleotide | MYB29 CDS targeted for cleavage by Cpf1 enzyme; part of gRNA cassette | |
| 67 | MYB29_scaffold_ 3_2545596_ 2553101_-_ Cfp1_247 | Oligonucleotide | MYB29 CDS targeted for cleavage by Cpf1 enzyme; part of gRNA cassette | |
| 68 | MYB76_scaffold_ 3_2536681_ 2543895_-_ CRISPR_55 | Oligonucleotide | MYB76 CDS targeted for cleavage by Cpf1 enzyme; part of gRNA cassette | |
| 69 | MYB76_scaffold_ 3_2536681_ 2543895_-_ Cfp1_493 | Oligonucleotide | MYB76 CDS targeted for cleavage by Cpf1 enzyme; part of gRNA cassette | |
| 70 | MYB76_scaffold_ 3_2536681_ 2543895_-_ CRISPR_56 | Oligonucleotide | MYB76 CDS targeted for cleavage by Cpf1 enzyme; part of gRNA cassette | |
| 71 | MYB76_scaffold_ 3_2536681_ 2543895_-_ Cfp1_495 | Oligonucleotide | MYB76 CDS targeted for cleavage by Cpf1 enzyme; part of gRNA cassette | |
| 72 | Ta_TFP_ scaffold_1_ 4920343_ 4927356_+_ CRISPR_164 | Oligonucleotide | TFP CDS targeted for cleavage by Cpf1 enzyme; part of gRNA cassette | |
| 73 | Ta_TFP_ scaffold_1_ 4920343_ | Oligonucleotide | TFP CDS targeted for cleavage by Cpf1 enzyme; part of gRNA cassette | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | 4927356_+_ Cfp1_482 | | | |
| 74 | Ta_TFP_ scaffold_1_ 4920343_ 4927356_+_ CRISPR_167 | Oligonucleotide | TFP CDS targeted for cleavage by Cpf1 enzyme; part of gRNA cassette | |
| 75 | Ta_TFP_ scaffold_1_ 4920343_ 4927356_+_ Cfp1_198 | Oligonucleotide | TFP CDS targeted for cleavage by Cpf1 enzyme; part of gRNA cassette | |
| 76 | GTR1_115 | Oligonucleotide | GTR1 CDS targeted for cleavage by SpCAS9 enzyme; part of gRNA cassette | |
| 77 | GTR1_116 | Oligonucleotide | GTR1 CDS targeted for cleavage by SpCAS9 enzyme; part of gRNA cassette | |
| 78 | GTR2_scaffold_ 0_1966458_ 1970958_+_ CRISPR_43 | Oligonucleotide | GTR2 CDS targeted for cleavage by SpCAS9 enzyme; part of gRNA cassette | |
| 79 | GTR2_scaffold_ 0_1966458_ 1970958_+_ CRISPR_46 | Oligonucleotide | GTR2 CDS targeted for cleavage by SpCAS9 enzyme; part of gRNA cassette | |
| 80 | MYB28-m1-CDS | Mutant Coding region | Mutant hag1-1 allele (−G deletion) | hag1-1 |
| 81 | MYB28-m1-PRT | Mutant Protein | Mutant hag1-1 protein (−G deletion) | |
| 82 | MYB28-m2-CDS | Mutant Coding region | Mutant hag1-2 allele (+A insertion) | hag1-2, 2172A |
| 83 | MYB28-m2-PRT | Mutant Protein | Mutant hag1-2 protein (+A insertion) | |
| 84 | MYB28-m3-CDS | Mutant Coding region | Mutant hag1 allele (+G insertion) | |
| 85 | MYB28-m3-PRT | Mutant Protein | Mutant hag1 protein (+G insertion) | |
| 86 | MYB28-m4-CDS | Mutant Coding region | Mutant hag1 allele (A -> G mutation) | |
| 87 | MYB28-m4-PRT | Mutant Protein | Mutant hag1 allele (A -> G mutation) | |
| 88 | MYB28-m5-CDS | Mutant Coding region | Mutant hag1 allele (+A insertion) | |
| 89 | MYB28-m5-PRT | Mutant Protein | Mutant hag1 protein (+A insertion) | |
| 90 | MYB28-m6-CDS | Mutant Coding region | Mutant hag1 allele (−AG deletion) | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 91 | MYB28-m6-PRT | Mutant Protein | Mutant hag 1 protein (-AG deletion) | |
| 92 | CYP83A1-CDS | WT Coding region | Biosynthetic enzyme and a member of cytochrome | REF2 |
| 93 | CYP83A1-Genomic locus | WT Gene | P450 family. Catalyzes conversion of aliphatic aldoximes to nitrile oxides | |
| 94 | CYP83A1-PRT | WT Protein | or aci-nitro compounds | |
| 95 | CYP83A1-m1-CDS | Mutant Coding region | Mutant cyp83a1 allele (G insertion) | |
| 96 | CYP83A1-m1-PRT | Mutant Protein | Mutant cyp83a1 allele (G insertion) | |
| 97 | CYP83A1-m2-CDS | Mutant Coding region | Mutant cyp83a1 allele (T -> G mutation) | |
| 98 | CYP83A1-m2-PRT | Mutant Protein | Mutant cyp83a1 allele (T -> G mutation) | |
| 99 | AOP2_sp_PS3 | Oligonucleotide | AOP2 CDS targeted for cleavage by SpCas9 enzyme; part of gRNA cassette | |
| 100 | AOP2_sp_PS1 | Oligonucleotide | AOP2 CDS targeted for cleavage by SpCas9 enzyme; part of gRNA cassette | |
| 101 | AOP2_sp_PS4 | Oligonucleotide | AOP2 CDS targeted for cleavage by SpCas9 enzyme; part of gRNA cassette | |
| 102 | AOP2_sp_PS2 | Oligonucleotide | AOP2 CDS targeted for cleavage by SpCas9 enzyme; part of gRNA cassette | |
| 103 | AOP2_sp_PS6 | Oligonucleotide | AOP2 CDS targeted for cleavage by SpCas9 enzyme; part of gRNA cassette | |
| 104 | AOP2_sa_PS1 | Oligonucleotide | AOP2 CDS targeted for cleavage by SaCas9 enzyme; part of gRNA cassette | |
| 105 | AOP2_sa_PS2 | Oligonucleotide | AOP2 CDS targeted for cleavage by SaCas9 enzyme; part of gRNA cassette | |
| 106 | HAG1_513 | Oligonucleotide | HAG1 CDS targeted for cleavage by SpCas9 enzyme; part of gRNA cassette | |
| 107 | HAG1_sp_PS1_F | Oligonucleotide | HAG1 CDS targeted for cleavage by SpCas9 enzyme; part of gRNA cassette | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 108 | HAG1/3_sp_R | Oligonucleotide | HAG1/HAG3 CDS targeted for cleavage by SpCas9 enzyme; part of gRNA cassette | |
| 109 | HAG1/2_sa_PS1_F | Oligonucleotide | HAG1/HAG2 CDS targeted for cleavage by SaCas9 enzyme; part of gRNA cassette | |
| 110 | HAG2_sp_PS1_F | Oligonucleotide | HAG2 CDS targeted for cleavage by SpCas9 enzyme; part of gRNA cassette | |
| 111 | HAG2_sp_PS2_F | Oligonucleotide | HAG2 CDS targeted for cleavage by SpCas9 enzyme; part of gRNA cassette | |
| 112 | HAG2_sp_PS3_F | Oligonucleotide | HAG2 CDS targeted for cleavage by SpCas9 enzyme; part of gRNA cassette | |
| 113 | HAG3_sp_PS2_F | Oligonucleotide | HAG3 CDS targeted for cleavage by SpCas9 enzyme; part of gRNA cassette | |
| 114 | HAG3_431 | Oligonucleotide | HAG3 CDS targeted for cleavage by SaCas9 enzyme; part of gRNA cassette | |
| 115 | HAG3_sp_knockout_1 | Oligonucleotide | HAG3 CDS targeted for cleavage by SpCas9 enzyme; part of gRNA cassette | |
| 116 | HAG3_sp_knockout_2 | Oligonucleotide | HAG3 CDS targeted for cleavage by SpCas9 enzyme; part of gRNA cassette | |
| 117 | CYP83A1_sp_PS3_F | Oligonucleotide | CYP83A1 CDS targeted for cleavage by SpCas9 enzyme; part of gRNA cassette | |
| 118 | GTR1_sp_PS1 | Oligonucleotide | GTR1 CDS targeted for cleavage by SpCas9 enzyme; part of gRNA cassette | |
| 119 | GTR1/2_sp_PS1 | Oligonucleotide | GTR1/GTR2 CDS targeted for cleavage by SpCas9 enzyme; part of gRNA cassette | |
| 120 | GTR1/2_sp_PS2 | Oligonucleotide | GTR1/GTR2 CDS targeted for cleavage by SpCas9 enzyme; part of gRNA cassette | |
| 121 | GTR1/2_sa_PS1 | Oligonucleotide | GTR1/GTR2 CDS targeted for cleavage by SaCas9 | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | | enzyme; part of gRNA cassette | |
| 122 | GTR1/2_sa_PS2 | Oligonucleotide | GTR1/GTR2 CDS targeted for cleavage by SaCas9 enzyme; part of gRNA cassette | |
| 123 | GTR1_sp_PS2_F | Oligonucleotide | GTR1 CDS targeted for cleavage by SpCas9 enzyme; part of gRNA cassette | |
| 124 | GTR1_sp_PS3_F | Oligonucleotide | GTR1 CDS targeted for cleavage by SpCas9 enzyme; part of gRNA cassette | |
| 125 | GTR1_sp_knockout_1 | Oligonucleotide | GTR1 CDS targeted for cleavage by SpCas9 enzyme; part of gRNA cassette | |
| 126 | GTR1_sp_knockout_2 | Oligonucleotide | GTR1 CDS targeted for cleavage by SpCas9 enzyme; part of gRNA cassette | |
| 127 | MYB76-m1ARV-CDS | Mutant Coding Region | TAAAGAAAGGAGCAT GGACGT (nt 35-55 of SEQ ID NO: 25) → TAAAGAAAGG-GCATGGACGT (nt 35-54 of SEQ ID NO: 127) | A427A |
| 128 | MYB76-m1ARV-PRT | Mutant Protein | Frameshift caused by 1bp deletion | |
| 129 | MYB76-m2ARV-CDS | Mutant Coding Region | CTGTATCGGAGAAGG GTTAAAGAAAGGAGC AT (nt 18-50 of SEQ ID NO: 25) -> CT---------------------------AT (nt 18-21 of SEQ ID NO: 129) | A430B |
| 130 | MYB76-m2ARV-PRT | Mutant Protein | Presumed loss of function caused by 27bp deletion | |
| 131 | MYB29-m1ARV-CDS | Mutant Coding Region | (nt 86-690 of SEQ ID NO: 22) TCCATGAA---598bp deletion---AAGGAACC (nt 72-82 of SEQ ID NO: 131) | A264A, A296A, A316B, A329B |
| 132 | MYB29-m1ARV-PRT | Mutant Protein | Truncated protein caused by large deletion | |
| 133 | MYB29-m2ARV-CDS | Mutant Coding Region | (nt 72-709 of SEQ ID NO: 22) ACTCATCT---603bp deletion---ACCGCACTG (nt 72-87 of SEQ ID NO: 133) | A361B |
| 134 | MYB29-m2ARV-PRT | Mutant Protein | Truncated protein caused by large deletion | |
| 135 | MYB29-m3ARV-CDS | Mutant Coding Region | ATCCATGAACATGGC GAAG (nt 85-103 of SEQ | A262A, A275A |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | | ID NO: 22) → ATCCATGAA(A)CATG GCGAAG (nt 85-104 of SEQ ID NO: 135), and TCAGCGTCCATGGAA GGAACCTT (nt 670-692 of SEQ ID NO: 22) → TCAGCGTCCATGGAA (A)GGAACCTT (nt 670-693 of SEQ ID NO: 135) | |
| 136 | MYB29-m3ARV-PRT | Mutant Protein | Frameshift caused by 1bp insertion (second edit also 1bp insertion) | |
| 137 | MYB29-m4ARV-CDS | Mutant Coding Region | TCAGCGTCCATGGAA GGAACCTT (nt 670-692 of SEQ ID NO: 22) → TCAGCGTCCA--- AAGGAACCTT (nt 670-689 of SEQ ID NO: 137) | A261C |
| 138 | MYB29-m4ARV-PRT | Mutant Protein | Missing M227, E228->K | |
| 139 | MYB29-m5ARV-CDS | Mutant Coding Region | TCAGCGTCCATGGAA GGAACCTT (nt 670-692 of SEQ ID NO: 22) → TCAGCGTCC---- AAGGAACCTT (nt 670-689 of SEQ ID NO: 139) | A268A |
| 140 | MYB29-m5ARV-PRT | Mutant Protein | Frameshift caused by 4bp deletion | |
| 141 | MYB29-m6ARV-CDS | Mutant Coding Region | TCAGCGTCCATGGAA GGAACCTT (nt 670-692 of SEQ ID NO: 22) → TCAGCGTCCATGGA- GGAACCTT (nt 670-691 of SEQ ID NO: 141) | A263A, A347D |
| 142 | MYB29-m6ARV-PRT | Mutant Protein | Frameshift caused by 1bp deletion | |
| 143 | GTR1-m1ARV-CDS | Mutant Coding Region | CCTCTGCGACACTTAC TTTG (nt 321-340 of SEQ ID NO: 13) → CCT-------- -----TTTG (nt 321-327 of SEQ ID NO: 143) | A382A |
| 144 | GTR1-m1ARV-PRT | Mutant Protein | Frameshift caused by 13bp deletion | |
| 145 | GTR2-m1ARV-CDS | Mutant Coding Region | AGTGCATTGTGAGAG TGCT (nt 1037-1055 of SEQ ID NO: 16) → AGTGCATT(T)GTGAG AGTGCT (nt 1037-1056 of SEQ ID NO: 145) | A412A |
| 146 | GTR2-m1ARV-PRT | Mutant Protein | Frameshift caused by 1bp insertion | |
| 147 | AOP2-m1ARV-CDS | Mutant Coding Region | TTTCCGAGAGTATGG GGATC (nt 275-294 of SEQ ID NO: 1) → TTTCCGAGAG(A)TAT | A368A |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | | GGGGATC (nt 275-295 of SEQ ID NO: 147) | |
| 148 | AOP2-m1ARV-PRT | Mutant Protein | Frameshift caused by 1bp insertion | |
| 149 | AOP2-m2ARV-CDS | Mutant Coding Region | TTTCCGAGAGTATGG GGATC (nt 275-294 of SEQ ID NO: 1) → TTTCCGAGA-- ATGGGGATC (nt 275-292 of SEQ ID NO: 149) | A377A |
| 150 | AOP2-m2ARV-PRT | Mutant Protein | Frameshift caused by 2bp deletion | |
| 151 | AOP2-m3ARV-CDS | Mutant Coding Region | TTTCCGAGAGTATGG GGATC (nt 275-294 of SEQ ID NO: 1) → TTTCCGAGAGT-- GGGGATC (nt 275-292 of SEQ ID NO: 151) | A390A |
| 152 | AOP2-m3ARV-PRT | Mutant Protein | Frameshift caused by 2bp deletion | |
| 153 | AOP2-m4ARV-CDS | Mutant Coding Region | TTTCCGAGAGTATGG GGATC (nt 275-294 of SEQ ID NO: 1) → TTTCCGAGAGT---- GGATC (nt 275-290 of SEQ ID NO: 153) | A402A |
| 154 | AOP2-m4ARV-PRT | Mutant Protein | Frameshift caused by 4bp deletion | |
| 155 | AOP2-m5ARV-CDS | Mutant Coding Region | TTTCCGAGAGTATGG GGATC (nt 275-294 of SEQ ID NO: 1) → TTTCCGAGAGT(T)ATG GGGATC (nt 275-295 of SEQ ID NO: 155) | A378A, A379A, A385A, A394A, A403B |
| 156 | AOP2-m5ARV-PRT | Mutant Protein | Frameshift caused by 1bp insertion | |
| 157 | AOP2-m6ARV-CDS | Mutant Coding Region | TTTCCGAGAGTATGG GGATC (nt 275-294 of SEQ ID NO: 1) → TTTC-- ------TGGGGATC (nt 275-286 of SEQ ID NO: 157) | A375A |
| 158 | AOP2-m6ARV-PRT | Mutant Protein | Frameshift caused by 8bp deletion | |
| 159 | BHLH05-WT-CDS | WT Coding region | basic helix-loop-helix transcription factor05 | BHLH05, MYC3, bHLH05 |
| 160 | BHLH05-WT-Genomic Locus | WT Gene | (bHLH05) transcription factor affects the biosynthesis of | |
| 161 | BHLH05-WT-PRT | WT Protein | glucosinolates | |
| 162 | IMD1-WT-CDS | WT Coding region | ISOPROPYLMALATE DEHYDROGENASE 1 | IMD1, ISOPROPYLMALATE |
| 163 | IMD1-WT-Genomic | WT Gene | (IMD1) is involved in leucine biosynthesis and | DEHYDROGENASE 1 |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | Locus | | | |
| 164 | IMD1-WT-PRT | WT Protein | methionine chain elongation required for glucosinolate biosynthesis | |
| 165 | CYP79B3-WT-CDS | WT Coding region | Encodes cytochrome P450 family 79 and is involved in biosynthesis of glucosinolates | CYP79B3, CYTOCHROME P450, FAMILY 79, SUBFAMILY B, POLYPEPTIDE 3 |
| 166 | CYP79B3-WT-Genomic Locus | WT Gene | | |
| 167 | CYP79B3-WT-PRT | WT Protein | | |
| 168 | MAM1-WT-CDS | WT Coding region | Encodes METHYLTHIOALKYL MALATE SYNTHASE 1 is involved in biosynthesis of glucosinolates | MAM1, METHYLTHIOALKYL MALATE SYNTHASE 1, gsm1 |
| 169 | MAM1-WT-Genomic Locus | WT Gene | | |
| 170 | MAM1-WT-PRT | WT Protein | | |
| 171 | Ta_FMO-GS-Ox1-WT-CDS | WT Coding region | FLAVIN-MONOOXYGENASE GLUCOSINOLATE S-OXYGENASE 1 catalyzes the conversion of methylthioalkyl glucosinolates to methylsulfinylalkyl glucosinolates | FMO GS-Ox1, FLAVIN-MONOOXYGENASE GLUCOSINOLATE S-OXYGENASE 1, |
| 172 | Ta_FMO-GS-Ox1-WT-Gemonic Locus | WT Gene | | |
| 173 | Ta_FMO-GS-Ox1-WT-PRT | WT Protein | | |
| 174 | Ta_UGT74B1-WT-CDS | WT Coding region | UDP-glucose:thiohydroximate S-glucosyltransferase involved in glucosinolate biosynthesis | UGT74B1, UDP-GLUCOSYL TRANSFERASE 74B1 |
| 175 | Ta_UGT74B1-WT-Gemonic Locus | WT Gene | | |
| 176 | Ta_UGT74B1-WT-PRT | WT Protein | | |
| 177 | Ta_FMO-GS-Ox1-1-CDS | Mutant Coding Region | TTGAGCCTCGTCTAGC TGAA (nt 653-672 of SEQ ID NO: 171)→ TTGAGCCTC<A>TC TAGCTGAA (nt 653-672 of SEQ ID NO: 177) | |
| 178 | Ta_FMO-GS-Ox1-1-PRT | Mutant Protein | Amino acid change | |
| 179 | Ta_MAM1-1-CDS | Mutant Coding Region | GCAAACATAGAGACA TTGAG (nt 464-483 of SEQ ID NO: 168)→ GCAAACATA<A>AG ACATTGAG (nt 464-483 of SEQ ID NO: 179) | E5 543 |
| 180 | Ta_MAM1-1-PRT | Mutant Protein | Amino acid change | |
| 181 | Ta_MAM1-2-CDS | Mutant Coding Region | TGTGTGTGCTGGAGC AAGAC (nt 891-910 of SEQ ID NO: 168)→ TGTGTGTGCTGGA<A> CAAGAC (nt 891-910 of SEQ ID NO: 181) | D0956 |
| 182 | Ta_MAM1-2-PRT | Mutant Protein | Amino acid change | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| 183 | Ta_AOP2-like-1MAR-CDS | Mutant Coding Region | CCGAGAGTATGGGGA TCCAG (nt 278-297 of SEQ ID NO: 1)→ CCGAGAGTATG<A> GGATCCAG (nt 278-297 of SEQ ID NO: 183) | E3196, Nutty, aop2-1 |
| 184 | Ta_AOP2-like_-_1MAR_-PRT | Mutant Protein | Amino acid change | |
| 185 | Ta_bhlh05-1-CDS | Mutant Coding Region | AGAAGGCTGGACCTA CGCGA (nt 189-208 of SEQ ID NO: 159) → AGAAGGCTG<A>CCT ACGCGA (nt 189-208 of SEQ ID NO: 185) | D3 N13P3 |
| 186 | Ta_bhlh05-1-PRT | Mutant Protein | Truncated protein caused by premature stop codon | |
| 187 | Ta_bhlh05-2-CDS | Mutant Coding Region | CGGAGACAACACAGT GATTCT (nt 246-266 of SEQ ID NO: 159) → CGGAGACAAC-CAGTGATTCT (nt 246-265 of SEQ ID NO: 187) | E5 202P2 |
| 188 | Ta_bhlh05-2-PRT | Mutant Protein | Frameshift caused by 1bp deletion | |
| 189 | Ta_bhlh05-3-CDS | Mutant Coding Region | GGCGGAACCGGAGTT TCCGA (nt 394-413 of SEQ ID NO: 159) → GGCGGAACCG<A>AG TTTCCGA (nt 394-413 of SEQ ID NO: 189) | E5 133P2, fad2-2 |
| 190 | Ta_bhlh05-3-PRT | Mutant Protein | Amino acid change | |
| 191 | Ta_myb28-5SED-CDS | Mutant Coding Region | CATCCACGAGCACGG TGAA (nt 84-103 of SEQ ID NO: 22) → CATCCACG-GCACGGTGAA (nt 84-102 of SEQ ID NO: 191) | |
| 192 | Ta_myb28-5SED-PRT | Mutant Protein | Frameshift due to 1bp deletion | |
| 193 | myb76-1SED-CDS | Mutant Coding Region | TAAAACGGTGTGGAA AGAG (nt 137-157 of SEQ ID NO: 25) → TAAAACGGT(T)GTGG AAAGAG (nt 137-156 of SEQ ID NO: 193) | |
| 194 | myb76-1SED-PRT | Mutant Protein | Frameshift due to 1bp insertion | |
| 195 | myb29-1SED-CDS | Mutant Coding Region | GCCACTTGCCCCTAG CCCTAGTCCGGCCAC GCTA (nt 381-413 of SEQ ID NO: 22) → GCCACTTG------------- TCCGGCCACGCT (nt | 2172A |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | | 381-400 of SEQ ID NO: 195) | |
| 196 | myb29-1SED-PRT | Mutant Protein | Frameshift due to 13bp deletion | |
| 197 | myb29-2SED-CDS | Mutant Coding Region | TAGCCCTAGTCCGGC CACGCTC (nt 393-414 of SEQ ID NO: 22) → TAGCCCTA------ CCACGCTC (nt 393-408 of SEQ ID NO: 197) | 2180A |
| 198 | myb29-2SED-PRT | Mutant Protein | Presumed loss of function due to 6bp deletion | |
| 199 | Ta_imd1-1-CDS | Mutant Coding Region | AGAGCCCAGAGGCAT TAAGA (nt 663-682 of SEQ ID NO: 162) → AGAGCCCA<A>AGGC ATTAAGA (nt 663-682 of SEQ ID NO: 199) | A795, tt4-1 |
| 200 | Ta_imd1-1-PRT | Mutant Protein | Amino acid change | |
| 201 | Ta_imd1-2-CDS | Mutant Coding Region | TCGGTGTATCGGGAC CTGGA (nt 1040-1059 of SEQ ID NO: 162) → TCGGTGTAT<T>GGGA CCTGGA (nt 1040-1059 of SEQ ID NO: 201) | D322 |
| 202 | Ta_imd1-2-PRT | Mutant Protein | Amino acid change | |
| 203 | Ta_cyp79b3-1-CDS | Mutant Coding Region | CTTTCCAACGGCTAC AAAAC (nt 412-431 of SEQ ID NO: 165) → CTTTCCAAC<A>GCTA CAAAAC (nt 412-431 of SEQ ID NO: 203) | I87207 |
| 204 | Ta_cyp79b3-1-PRT | Mutant Protein | Amino acid change | |
| 205 | Ta_cyp79b3-2-CDS | Mutant Coding Region | GGTCTGATCCACTTA GCTTT (nt 1328-1347 of SEQ ID NO: 165) → GGTCTGAT<T>CACTT AGCTTT (nt 1328-1347 of SEQ ID NO: 205) | E5519 |
| 206 | Ta_cyp79b3-2-PRT | Mutant Protein | Amino acid change | |
| 207 | Ta_cyp83a1-1-CDS | Mutant Coding Region | TTCAGGCCCGAGAGG TTTC (nt 1240-1258 of SEQ ID NO: 97) → TTCAGGCCC<A>AGA GGTTTC (nt 1240-1258 of SEQ ID NO: 207) | A766 |
| 208 | Ta_cyp83a1-1-PRT | Mutant Protein | Amino acid change | |
| 209 | Ta_cyp83a1-2-CDS | Mutant Coding Region | TTATCATACAAGATA GGAAA (nt 196-215 of | |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | | SEQ ID NO: 97) → TTATCATACAA(A)G ATAGGAAA (nt 196-216 of SEQ ID NO: 209) | |
| 210 | Ta_cyp83a1-2-PRT | Mutant Protein | Frameshift caused by 1bp insertion | |
| 211 | Ta cyp83a1-3-CDS | Mutant Coding Region | TTATCATACAAGATA GGAAA (nt 196-215 of SEQ ID NO: 97) → TTATCATACAA(T)G ATAGGAAA (nt 196-216 of SEQ ID NO: 211) | |
| 212 | Ta_cyp83a1-3-PRT | Mutant Protein | Frameshift caused by 1bp insertion | |
| 213 | Ta_AOP2-like aop2-2SED-CDS | Mutant Coding Region | (nt 270-318 of SEQ ID NO: 1) → CGGTCTTT-- 35bp deletion -- TGGACAAA (nt 270-285 of SEQ ID NO: 213) | |
| 214 | Ta_AOP2-like aop2-2SED-PRT | Mutant Protein | Presumed loss of function due to 33bp deletion | |
| 215 | Ta_AOP2-like aop2-3SED-CDS | Mutant Coding Region | TCCTCATGTTTTGGAC AAAGTTTA (nt 300-323 of SEQ ID NO: 1) → TCCTCAT-- TTTGGACAAAGTTA (nt 300-319 of SEQ ID NO: 215) | |
| 216 | Ta_AOP2-like aop2-3SED-PRT | Mutant Protein | Frameshift caused by 2bp deletion | |
| 217 | Ta_AOP2-like aop2-4SED-CDS | Mutant Coding Region | TCCTCATGTTTTGGAC AAAGTTTA (nt 300-323 of SEQ ID NO: 1) → TCCTCATGTTT-GACAAAGTTTA (nt 300-322 of SEQ ID NO: 217) | |
| 218 | Ta_AOP2-like aop2-4SED-PRT | Mutant Protein | Frameshift caused by 1bp deletion | |
| 219 | Ta_AOP2-like aop2-5SED-CDS | Mutant Coding Region | TCCTCATGTTTTGGAC AAAGTTTA (nt 300-323 of SEQ ID NO: 1) → TCCTCATGTTTT(T)G GACAAAGTTTA (nt 300-324 of SEQ ID NO: 219) | |
| 220 | Ta_AOP2-like aop2-5SED-PRT | Mutant Protein | Frameshift caused by 1bp insertion | |
| 221 | Ta_gtr1-1-CDS | Mutant Coding Region | CCGCAGCTCTTGCTTG CAGG (nt 1561-1580 of SEQ ID NO: 13) → CCGCAGCTCTTGTT<T> | I87113, gtr1-1 |

TABLE 1-continued

Wild-type (WT) coding regions, encoded proteins, and genes that can be targeted for introduction of LOF mutations or transgene- or genome rearrangement-mediated suppression, their mutant variants and representative genetic elements for achieving suppression of gene expression.

| SEQ ID NO: | Sequence Name | Type | Function/Nature of the mutation | Names Used and/or Representative Pennycress LOF Mutants Disclosed Herein |
|---|---|---|---|---|
| | | | GCAGG (nt 1561-1580 of SEQ ID NO: 221) | |
| 222 | Ta_gtr1-1-PRT | Mutant Protein | Amino acid change | |
| 223 | Ta_gtr1-2-CDS | Mutant Coding Region | TGAAATGCATTGTGA GAGT (nt 1145-1163 of SEQ ID NO: 13) → TGAAATGCATGTGTG AGAGT (nt 1145-1164 of SEQ ID NO: 223) | 3A5K, gtr1-2 |
| 224 | Ta_gtr1-2-PRT | Mutant Protein | Frameshift caused by 1bp insertion | |
| 225 | Ta_gtr2-1-CDS | Mutant Coding Region | AAAGAAAGTGATGAT GATCA (nt 1762-1781 of SEQ ID NO: 16) → AAAGAAAGT<A>ATG ATGATCA (nt 1762-1781 of SEQ ID NO: 225) | AX17D |
| 226 | Ta_gtr2-1-PRT | Mutant Protein | Amino acid change | |
| 227 | Ta_gtr2-2-CDS | Mutant Coding Region | AGTGCATTGTGAGAG TGCT (nt 1037-1055 of SEQ ID NO: 16) → AGTGCAT(A)TGTGAG AGTGCT (nt 1037-1056 of SEQ ID NO: 227) | 3A5C, 3A5K, gtr2-2, A427A |
| 228 | Ta_gtr2-2-PRT | Mutant Protein | Frameshift caused by 1bp insertion | A427A |
| 229 | Ta_gtr2-3-CDS | Mutant Coding Region | AGTGCATTGTGAGAG TGCT (nt 1037-1055 of SEQ ID NO: 16) → AGTGCAT(G)TGTGAG AGTGCT (nt 1037-1056 of SEQ ID NO: 229) | 3A5K, gtr2-3 |
| 230 | Ta_gtr2-3-PRT | Mutant Protein | Frameshift caused by 1bp insertion | 3A5K |
| 231 | MYB28-2180A-CDS | Mutant Coding region | Mutant hag1 allele (–GT deletion) | 2180A |
| 232 | MYB28-2180A-PRT | Mutant Protein | Mutant hag1 protein (–GT deletion) | 2180A |
| 233 | MYB28-2172A-CDS | Mutant Coding region | Mutant hag1 allele (–TG deletion) | 2172A |
| 234 | MYB28-2172A-PRT | Mutant Protein | Mutant hag1 protein (–TG deletion) | 2172A |
| 235 | Ta_gtr1-3-CDS | Mutant Coding Region | TGAAATGCATTGTGA GAGT (nt 1145-1163 of SEQ ID NO: 13) → TGAAATGCAT-GTGAGAGT (nt 1145-1164 of SEQ ID NO: 235) | 3A5C, gtr1-3 |
| 236 | Ta_gtr1-3-PRT | Mutant Protein | Frameshift caused by 1bp deletion | 3A5C |

In certain embodiments, pennycress plant seeds, seed lots, seed meal, and compositions having reduced sinigrin content as described herein can be obtained from the E3 196, E5 444P1, E5 356P5, I87113, E5 543, or I87207 pennycress mutant lines provided herein, from progeny derived from those mutant lines, from hybrids derived from those mutant lines, or from germplasm from the mutants that provide seed or seed meal comprising less than 30, 28, 25, 16, or 15 micromoles sinigrin per gram by dry weight. In certain embodiments, germplasm from the mutants that provides seed or seed meal comprising less than 30, 28, 25, 16, or 15 micromoles sinigrin per gram by dry weight can be obtained by outcrossing the E3 196, E5 444P1, E5 356P5, I87113, E5 543, or I87207 pennycress mutant lines to other pennycress lines with wild-type sinigrin levels, selfing progeny of the cross, and selecting for progeny of the self that provide seed or seed meal having less than 30, 28, 25, 16, or 15 micromoles sinigrin per gram by dry weight. In certain embodiments, germplasm from the mutants that provides seed meal comprising less than 30, 28, 25, 16, or 15 micromoles sinigrin per gram can be introgressed into the genetic background of a second pennycress line with wild-type sinigrin levels by using the second pennycress line as a recurrent parent in a series of backcrosses followed by selfs, where progeny of the selfs that seed or seed meal comprising less than 30, 28, 25, 16, or 15 micromoles sinigrin per gram by dry weight are selected and carried forward into additional crosses to the recurrent parent. In certain embodiments, the pennycress mutant E3 196, E5 444P1, E5 356P5, I87113, E5 543, and/or I87207 germplasm that provides seed meal comprising less than 30, 28, 25, 16, or 15 micromoles sinigrin per gram by dry weight can be combined in a pennycress plant to provide pennycress plant seeds, seed lots, seed meal, and compositions having reduced sinigrin content as described herein. In certain embodiments, the pennycress mutant E3 196, E5 444P1, E5 356P5, I87113, E5 543, and/or I87207 germplasm can provide pennycress plant seeds, seed lots, seed meal, and compositions comprising 1, 2.5, 5, or 10 to about 15, 16, 18, 20, 25, 28, or 30 μmol sinigrin/gm dw (gram dry weight). Germplasm combinations comprising any of: (i) E3 196 and E5 444P1 germplasm; (ii) E3 196 and I87113 or E5 444P1 germplasm; (iii) E3 196 and I87207 or E5 444P1 germplasm; (iv) I87113 and I87207 or E5 444P germplasm; (iv) E3 196, I87113, E5 444P1, and I87207 germplasm; (v) E5 356P5 and E5 543 germplasm; or (vi) any combination of E3 196, E5 444P1, E5 356P5, I87113, E5 543, and/or I87207 germplasm that provide seed or seed meal comprising less than 30, 28, 25, 16, or 15 micromoles sinigrin per gram by dry weight are provided herein. Also provided herein is the combination of any of the germplasms of the E3 196, E5 444P1, E5 356P5, I87113, E5 543, and/or I87207 pennycress mutant lines that provides for reduced sinigrin content or any of the aforementioned germplasm combinations of (i), (ii), (iii), (iv), or (v) with germplasm comprising loss-of function mutations in a GSL biosynthetic coding sequence or gene (e.g., SEQ ID NO: 1, 2, 4, 5, 7, 8, 10, 11, 92, 93, 162, 163, 165, 166, 168, 169, 171, 172, 174, 175, or allelic variant thereof), at least one loss-of-function mutation in a GSL transport coding sequence or gene (SEQ ID NO: 13, 14, 16, 18, or allelic variant thereof), in a GSL hydrolysis coding sequence or gene (SEQ ID NO: 28, 29, or allelic variant thereof), and/or in an expression regulator (e.g., transcription factor; SEQ ID NO: 19, 20, 22, 23, 25, 26, 159, 160, allelic variant thereof) coding sequence or gene.

A representative wild-type (WT) pennycress MYB28 (HAG1) coding sequence is as shown in sequence listing (SEQ ID NO: 19). The terms "MYB28" and "HAG1" are used interchangeably herein. In certain embodiments, a WT pennycress MYB28 coding sequence can have a sequence that deviates from the coding sequence set forth above (e.g., SEQ ID NO: 19), and is referred to as an allelic variant sequence. In certain embodiments, a MYB28 coding sequence allelic variant can have at least 80, at least 85, at least 90, at least 95, at least 98, or at least 99 percent sequence identity to SEQ ID NO: 19. A representative wild-type pennycress MYB28 polypeptide is shown in sequence listing (SEQ ID NO: 21). In certain embodiments, a WT pennycress MYB28 polypeptide can have a sequence that deviates from the polypeptide sequence set forth above (SEQ ID NO: 21), and is referred to as an allelic variant sequence. In certain embodiments, a WT pennycress MYB28 polypeptide can have a sequence that deviates from the polypeptide sequence set forth above (SEQ ID NO: 21), referred to herein as an allelic variant sequence, provided the polypeptide maintains its wild-type function. For example, a MYB28 polypeptide can have at least 80, at least 85, at least 90, at least 95, at least 98, or at least 99) percent sequence identity to SEQ ID NO: 21. A MYB28 polypeptide of an allelic variant can have one or more (e.g., 2, 3, 4, 5, 6, 7, 8, 9, or 10) amino acid modifications (e.g., substitutions) relative to SEQ ID NO: 21.

In certain embodiments, pennycress seed lots, plants, seeds, as well as the seed meals and compositions obtained therefrom, all having reduced sinigrin content, can include at least one loss-of-function modification in a MYB28 gene (e.g., in a MYB28 coding sequence, in a MYB28 regulatory sequence including the promoter, 5' UTR, intron, 3' UTR, or in any combination thereof) or a transgene or genome rearrangement that suppresses expression of the MYB28 gene. As used herein, a loss-of-function mutation in a MYB28 gene can be any modification that is effective to suppress MYB28 polypeptide expression or MYB28 polypeptide function. In certain embodiments, suppressed MYB28 polypeptide expression and/or MYB28 polypeptide function can comprise elimination or a reduction in such expression or function in comparison to a wild-type plant (i.e., can be complete or partial). Examples of genetic modifications that can provide for a loss-of-function mutation include, without limitation, deletions, insertions, substitutions, translocations, inversions, duplications, or any combination thereof. In certain embodiments, any of the aforementioned loss-of-function (LOF) modifications in the MYB28 gene can be combined with a loss-of-function modification in a MYB29 gene or allelic variant thereof, and/or a loss-of-function modification in a MYB76 gene or allelic variant thereof to obtain pennycress plant seeds, seed lots, seed meal, and compositions having reduced sinigrin content described herein. Plants, germplasm, seed, seed lots, seed meal, and compositions comprising: (i) MYB28 and MYB29 LOF modifications; (ii) MYB28 and MYB76 LOF modifications; (iii) MYB29 and MYB76 LOF modifications; and (iii) MYB28, MYB29 and MYB76 LOF modifications are also provided herein.

In certain embodiments, pennycress seed lots, plants, seeds, as well as the seed meals and compositions obtained therefrom, all having reduced sinigrin content, can include a deletion (e.g., a single base-pair deletion) relative to the WT pennycress MYB28 coding sequence. In certain embodiments, a modified MYB28 coding sequence can include a single base-pair deletion of the guanine (G) at nucleotide residue 20 in a WT pennycress MYB28 coding sequence (e.g., SEQ ID NO: 19 or an allelic variant thereof). For example, a single base-pair deletion of the guanine (G) at nucleotide residue at nucleotide residue 20 in a WT pennycress MYB28 coding sequence thereby producing a premature stop codon. A representative modified pennycress MYB28 coding sequence having a loss-of-function single base pair deletion is presented in SEQ ID NO: 80.

A modified or mutated pennycress MYB28 coding sequence having a loss-of-function single base pair deletion mutation (e.g., SEQ ID NO: 80) can encode a modified MYB28 polypeptide (e.g., a modified MYB28 polypeptide having suppressed MYB28 polypeptide expression and/or reduced MYB28 polypeptide function). For example, a modified pennycress MYB28 coding sequence having a single base-pair deletion (e.g., SEQ ID NO:80) can encode a modified MYB28 polypeptide. In certain embodiments, a modified MYB28 polypeptide can include a truncation resulting from the introduction of a stop codon at codon position 20 within the MYB28 open reading frame (e.g., SEQ ID NO:19). A representative truncated pennycress MYB28 polypeptide is presented in SEQ ID NO:81. The aforementioned loss-of-function modifications in a MYB28 encoding gene or a transgene or genome rearrangement that suppresses expression of the MYB28 gene thus include loss-of-function modifications in a gene encoding an MYB28 allelic variant gene, or a transgene or genome rearrangement that suppresses expression of a MYB28 allelic variant gene.

A representative WT pennycress CYP83A1 coding region is presented in SEQ ID NO:92. Two protospacer locations and adjacent protospacer-adjacent motif (PAM) sites that can be targeted by, for example, CRISPR-SpCAS9, correspond to nucleotides 190-209 (protospacer) and 210-212 (PAM site).

In certain embodiments, a WT pennycress CYP83A1 coding sequence can have a sequence that deviates from the coding sequence set forth above (e.g., SEQ ID NO:92), and is referred to as an allelic variant sequence. In certain embodiments, a CYP83A1 coding sequence allelic variant can have at least 80, at least 85, at least 90, at least 95, at least 98, or at least 99 percent sequence identity to SEQ ID NO:92. A representative WT pennycress CYP83A1 polypeptide is presented in SEQ ID NO:94.

In certain embodiments, a WT pennycress CYP83A1 polypeptide can have a sequence that deviates from the polypeptide sequence set forth above (SEQ ID NO:94), and is referred to as an allelic variant sequence, provided the polypeptide maintains its wild-type function. For example, a CYP83A1 polypeptide can have at least 80, at least 85, at least 90, at least 95, at least 98, or at least 99 percent sequence identity to SEQ ID NO:94. A CYP83A1 polypeptide can have one or more (e.g., 2, 3, 4, 5, 6, 7, 8, 9, or 10) amino acid modifications (e.g., substitutions) relative to SEQ ID NO:94.

In certain embodiments, pennycress seed lots, plants, seeds, as well as the seed meals and compositions obtained therefrom, all having reduced sinigrin content, can include a loss-of-function modification in a CYP83A1 gene (e.g., in a CYP83A1 coding sequence) or a transgene or genome rearrangement that suppresses expression of the CYP83A1 gene. As used herein, a loss-of-function mutation in a CYP83A1 gene can be any modification that is effective to suppress CYP83A1 polypeptide expression or CYP83A1 polypeptide function. In certain embodiments, suppressed CYP83A1 polypeptide expression and/or CYP83A1 polypeptide function can comprise elimination or a reduction in such expression (i.e., can be complete or partial). Examples of genetic modifications include, without limitation, deletions, insertions, substitutions, translocations, inversions, duplications, and any combination thereof. The aforementioned loss-of-function modifications in a CYP83A1 encoding gene or a transgene or genome rearrangement that suppresses expression of the CYP83A1 gene thus include loss-of-function modifications in a gene encoding an CYP83A1 allelic variant gene, or a transgene or genome rearrangement that suppresses expression of an CYP83A1 allelic variant gene.

In certain embodiments, a WT pennycress AOP2 coding sequence can have a sequence that deviates from the coding sequence set forth above (e.g., SEQ ID NO:1 or 2), and is referred to as an allelic variant sequence. In certain embodiments, a AOP2 coding sequence allelic variant can have at least 80, at least 85, at least 90, at least 95, at least 98, or at least 99 percent sequence identity to SEQ ID NO:1 or 2. In certain embodiments, a WT pennycress AOP2 polypeptide can have a sequence that deviates from the polypeptide sequence set forth above (SEQ ID NO:3), and is referred to as an allelic variant sequence provided the polypeptide maintains its wild-type function. For example, a AOP2 polypeptide allelic variant can have at least 80, at least 85, at least 90, at least 95, at least 98, or at least 99 percent sequence identity to SEQ ID NO:3. An AOP2 polypeptide allelic variant can have one or more (e.g., 2, 3, 4, 5, 6, 7, 8, 9, or 10) amino acid modifications (e.g., substitutions) relative to SEQ ID NO:3.

In certain embodiments, pennycress seed lots, plants, seeds, as well as the seed meals and compositions obtained therefrom, all having reduced sinigrin content, can include a loss-of-function modification in a AOP2 encoding gene or a transgene or genome rearrangement that suppresses expression of the AOP2 gene. As used herein, a loss-of-function mutation in a AOP2 gene can be any modification that is effective to reduce AOP2 polypeptide expression or AOP2 polypeptide function. In certain embodiments, suppressed AOP2 polypeptide expression and/or AOP2 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in an AOP2 encoding gene or a transgene or genome rearrangement that suppresses expression of the AOP2 gene thus include loss-of-function modifications in a gene encoding an AOP2 allelic variant gene, or a transgene or genome rearrangement that suppresses expression of an AOP2 allelic variant gene.

In certain embodiments, a WT pennycress BCAT4 coding sequence can have a sequence that deviates from the coding sequence set forth above (e.g., SEQ ID NO:4), and is referred to as an allelic variant sequence. In certain embodiments, a BCAT4 coding sequence allelic variant can have at least 80, at least 85, at least 90, at least 95, at least 98, or at least 99 percent sequence identity to SEQ ID NO:4. In certain embodiments, a WT pennycress BCAT4 polypeptide can have a sequence that deviates from the polypeptide sequence set forth above (SEQ ID NO:6), and is referred to as an allelic variant sequence provided the polypeptide maintains its wild-type function. For example, a BCAT4 polypeptide allelic variant can have at least 80, at least 85, at least 90, at least 95, at least 98, or at least 99 percent sequence identity to SEQ ID NO:6. A BCAT4 polypeptide allelic variant can have one or more (e.g., 2, 3, 4, 5, 6, 7, 8, 9, or 10) amino acid modifications (e.g., substitutions) relative to SEQ ID NO:76.

In certain embodiments, pennycress seed lots, plants, seeds, as well as the seed meals and compositions obtained therefrom, all having reduced sinigrin content, can include a loss-of-function modification in a BCAT4 encoding gene or a transgene or genome rearrangement that suppresses expression of the BCAT4 gene. As used herein, a loss-of-function mutation in a BCAT4 gene can be any modification that is effective to reduce BCAT4 polypeptide expression or BCAT4 polypeptide function. In certain embodiments, suppressed BCAT4 polypeptide expression and/or BCAT4 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in a BCAT4 encoding gene or a transgene or genome rearrangement that suppresses expression of the BCAT4 gene thus include loss-of-function modifications in a gene encoding a BCAT4 allelic variant gene, or a transgene or genome rearrangement that suppresses expression of a BCAT4 allelic variant gene.

In certain embodiments, a WT pennycress BCAT6 coding sequence can have a sequence that deviates from the coding sequence set forth above (e.g., SEQ ID NO:7), and is referred to as an allelic variant sequence. In certain embodiments, a BCAT6 coding sequence allelic variant can have at least 80, at least 85, at least 90, at least 95, at least 98, or at least 99 percent sequence identity to SEQ ID NO:7. In certain embodiments, a WT pennycress BCAT6 polypeptide can have a sequence that deviates from the polypeptide sequence set forth above (SEQ ID NO:9), and is referred to as an allelic variant sequence provided the polypeptide maintains its wild-type function. For example, a BCAT6 polypeptide allelic variant can have at least 80, at least 85, at least 90, at least 95, at least 98, or at least 99 percent sequence identity to SEQ ID NO:9. A BCAT6 polypeptide allelic variant can have one or more (e.g., 2, 3, 4, 5, 6, 7, 8, 9, or 10) amino acid modifications (e.g., substitutions) relative to SEQ ID NO:9.

In certain embodiments, pennycress seed lots, plants, seeds, as well as the seed meals and compositions obtained therefrom, all having reduced sinigrin content, can include a loss-of-function modification in a BCAT6 encoding gene or a transgene or genome rearrangement that suppresses expression of the BCAT6 gene. As used herein, a loss-of-function mutation in a BCAT6 gene can be any modification that is effective to reduce BCAT6 polypeptide expression or BCAT6 polypeptide function. In certain embodiments, suppressed BCAT6 polypeptide expression and/or BCAT6 polypeptide function can comprise elimination or a reduction in such expression or function (i.e., can be complete or partial). Examples of genetic modifications include, without limitation, deletions, insertions, substitutions, translocations, inversions, duplications, and any combination thereof. The aforementioned loss-of-function modifications in a BCAT6 encoding gene or a transgene or genome rearrangement that suppresses expression of the BCAT6 gene thus include loss-of-function modifications in a gene encoding a BCAT6 allelic variant gene, or a transgene or genome rearrangement that suppresses expression of a BCAT6 allelic variant gene.

In certain embodiments, pennycress seed lots, plants, seeds, as well as the seed meals and compositions obtained therefrom, all having reduced sinigrin content, can include a loss-of-function modification in a CYP79F1 encoding gene or a transgene or genome rearrangement that suppresses expression of the CYP79F1 gene. As used herein, a loss-of-function mutation in a CYP79F1 gene can be any modification that is effective to reduce CYP79F1 polypeptide expression or CYP79F1 polypeptide function. In certain embodiments, suppressed CYP79F1 polypeptide expression and/or CYP79F1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress CYP79F1 coding sequence can have a sequence that deviates from the coding sequence set forth above (e.g., SEQ ID NO:10), and is referred to as an allelic variant sequence. In certain embodiments, a CYP79F1 coding sequence allelic variant can have at least 80, at least 85, at least 90, at least 95, at least 98, or at least 99 percent sequence identity to SEQ ID NO:10. In certain embodiments, a WT pennycress CYP79F1 polypeptide can have a sequence that deviates from the polypeptide sequence set forth above (SEQ ID NO:46), and is referred to as an allelic variant sequence provided the polypeptide maintains its wild-type function. In certain embodiments, a CYP79F1 polypeptide allelic variant can have at least 80, at least 85, at least 90, at least 95, at least 98, or at least 99 percent sequence identity to SEQ ID NO:12. A CYP79F1 polypeptide allelic variant can have one or more (e.g., 2, 3, 4, 5, 6, 7, 8, 9, or 10) amino acid modifications (e.g., substitutions) relative to SEQ ID NO:12. Loss-of-function modifications in a CYP79F1 encoding gene or a transgene or genome rearrangement that suppresses expression of the CYP79F1 gene thus include loss-of-function modifications in a gene encoding a CYP79F1 allelic variant gene, or a transgene or genome rearrangement that suppresses expression of a CYP79F1 allelic variant gene.

In certain embodiments, pennycress seed lots, plants, seeds, as well as the seed meals and compositions obtained therefrom, all having reduced sinigrin content, can include a loss-of-function modification in a GTR1 encoding gene or a transgene or genome rearrangement that suppresses expression of the GTR1 gene. As used herein, a loss-of-function mutation in a GTR1 gene can be any modification that is effective to reduce GTR1 polypeptide expression or GTR1 polypeptide function. In certain embodiments, suppressed GTR1 polypeptide expression and/or GTR1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress GTR1 coding sequence can have a sequence that deviates from the coding sequence set forth above (e.g., SEQ ID NO:13), and is referred to as an allelic variant sequence. In certain embodiments, a GTR1 coding sequence allelic variant can have at least 80, at least 85, at least 90, at least 95, at least 98, or at least 99 percent sequence identity to SEQ ID NO:13. In certain embodiments, a WT pennycress GTR1 polypeptide can have a sequence that deviates from the polypeptide sequence set forth above (SEQ ID NO:15), and is referred to as an allelic variant sequence provided the polypeptide maintains its wild-type function. In certain embodiments, a GTR1 polypeptide allelic variant can have at least 80, at least 85, at least 90, at least 95, at least 98, or at least 99 percent sequence identity to SEQ ID NO:15. A GTR1 polypeptide allelic variant can have one or more (e.g., 2, 3, 4, 5, 6, 7, 8, 9, or 10) amino acid modifications (e.g., substitutions) relative to SEQ ID NO:15. The aforementioned loss-of-function modifications in a GTR1 encoding gene or a transgene or genome rearrangement that suppresses expression of the GTR1 gene thus include loss-of-function modifications in a gene encoding a GTR1 allelic variant gene, or a transgene or genome rearrangement that suppresses expression of a GTR1 allelic variant gene.

In certain embodiments, pennycress seed lots, pennycress seed lots, plants, seeds, as well as the seed meals and compositions obtained therefrom, all having reduced sinigrin content can include a complete or partial loss-of-function modification in a GTR2 encoding gene or a transgene or genome rearrangement that suppresses expression of the GTR2 gene. As used herein, a loss-of-function mutation in a GTR2 gene can be any modification that is effective to reduce GTR2 polypeptide expression or GTR2 polypeptide function. In certain embodiments, suppressed GTR2 polypeptide expression and/or GTR2 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress GTR2 coding sequence can have a sequence that deviates from the coding sequence set forth above (e.g., SEQ ID NO:16), and is referred to as an allelic variant sequence. In certain embodiments, a GTR2 coding sequence allelic variant can have at least 80, at least 85, at least 90, at least 95, at least 98, or at least 99 percent sequence identity to SEQ ID NO:16. In certain embodiments, a WT pennycress GTR2 polypeptide can have a sequence that deviates from the polypeptide sequence set forth above (SEQ ID NO:17), and is referred to as an allelic variant sequence provided the polypeptide maintains its wild-type function. In certain embodiments, a GTR2 polypeptide allelic variant can have at least 80, at least 85, at least 90, at least 95, at least 98, or at least 99 percent sequence identity to SEQ ID NO:17. A GTR2 polypeptide allelic variant can have one or more (e.g., 2, 3, 4, 5, 6, 7, 8, 9, or 10) amino acid modifications (e.g., substitutions) relative to SEQ ID NO:17. The aforementioned loss-of-function modifications in a GTR2 encoding gene or a transgene or genome rearrangement that suppresses expression of the GTR2 gene thus include loss-of-function modifications in a gene encoding a GTR2 allelic variant gene, or a transgene or genome rearrangement that suppresses expression of a GTR2 allelic variant gene.

In certain embodiments, pennycress seed lots, plants, seeds, as well as the seed meals and compositions obtained therefrom, all having reduced sinigrin content can include a complete or partial loss-of-function modification in a TFP encoding gene or a transgene or genome rearrangement that suppresses expression of the TFP gene. As used herein, a loss-of-function mutation in a TFP gene can be any modification that is effective to reduce TFP polypeptide expression or TFP polypeptide function. In certain embodiments, suppressed TFP polypeptide expression and/or TFP polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress TFP coding sequence can have a sequence that deviates from the coding sequence set forth above (e.g., SEQ ID NO:28), and is referred to as an allelic variant sequence. In certain embodiments, a TFP coding sequence allelic variant can have at least 80, at least 85, at least 90, at least 95, at least 98, or at least 99 percent sequence identity to SEQ ID NO:28. In certain embodiments, a WT pennycress TFP polypeptide can have a sequence that deviates from the polypeptide sequence set forth above (SEQ ID NO:30), and is referred to as an allelic variant sequence provided the polypeptide maintains its wild-type function. In certain embodiments, a TFP polypeptide allelic variant can have at least 80, at least 85, at least 90, at least 95, at least 98, or at least 99 percent sequence identity to SEQ ID NO:30. A TFP polypeptide allelic variant can have one or more (e.g., 2, 3, 4, 5, 6, 7, 8, 9, or 10) amino acid modifications (e.g., substitutions) relative to SEQ ID NO:30. The aforementioned loss-of-function modifications in a TFP encoding gene or a transgene or genome rearrangement that suppresses expression of the TFP gene thus include loss-of-function modifications in a gene encoding a TFP allelic variant gene, or a transgene or genome rearrangement that suppresses expression of a TFP allelic variant gene.

In certain embodiments, pennycress seed lots, plants, seeds, as well as the seed meals and compositions obtained therefrom, all having reduced sinigrin content, can include a loss-of-function modification in a BHLH05 encoding gene or a transgene or genome rearrangement that suppresses expression of the BHLH05 gene. As used herein, a loss-of-function mutation in a BHLH05 gene can be any modification that is effective to reduce BHLH05 polypeptide expression or BHLH05 polypeptide function. In certain embodiments, suppressed BHLH05 polypeptide expression and/or BHLH05 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress BHLH05 coding sequence can have a sequence that deviates from the coding sequence set forth above (e.g., SEQ ID NO:159 or 160), and is referred to as an allelic variant sequence. In certain embodiments, a BHLH05 coding sequence allelic variant can have at least 80, at least 85, at least 90, at least 95, at least 98, or at least 99 percent sequence identity to SEQ ID NO:159 or 160. In certain embodiments, a WT pennycress BHLH05 polypeptide can have a sequence that deviates from the polypeptide sequence set forth above (SEQ ID NO:161), and is referred to as an allelic variant sequence provided the polypeptide maintains its wild-type function. For example, a BHLH05 polypeptide allelic variant can have at least 80, at least 85, at least 90, at least 95, at least 98, or at least 99 percent sequence identity to SEQ ID NO: 161. An BHLH05 polypeptide allelic variant can have one or more (e.g., 2, 3, 4, 5, 6, 7, 8, 9, or 10) amino acid modifications (e.g., substitutions) relative to SEQ ID NO:161. The aforementioned loss-of-function modifications in a BHLH05 encoding gene or a transgene or genome rearrangement that suppresses expression of the BHLH05 gene thus include loss-of-function modifications in a gene encoding a BHLH05 allelic variant gene, or a transgene or genome rearrangement that suppresses expression of a BHLH05 allelic variant gene.

In certain embodiments, pennycress seed lots, plants, seeds, as well as the seed meals and compositions obtained therefrom, all having reduced sinigrin content, can include a loss-of-function modification in a IMD1 encoding gene or a transgene or genome rearrangement that suppresses expression of the IMD1 gene. As used herein, a loss-of-function mutation in a IMD1 gene can be any modification that is effective to reduce IMD1 polypeptide expression or IMD1 polypeptide function. In certain embodiments, suppressed IMD1 polypeptide expression and/or IMD1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress IMD1 coding sequence can have a sequence that deviates from the coding sequence set forth above (e.g., SEQ ID NO: 162 or 163), and is referred to as an allelic variant sequence. In certain embodiments, a IMD1 coding sequence allelic variant can have at least 80, at least 85, at least 90, at least 95, at least 98, or at least 99 percent sequence identity to SEQ ID NO: 162 or 163. In certain embodiments, a WT pennycress IMD1 polypeptide can have a sequence that deviates from the polypeptide sequence set forth above (SEQ ID NO:164), and is referred to as an allelic variant sequence provided the polypeptide maintains its wild-type function. For example, a IMD1 polypeptide allelic variant can have at least 80, at least 85, at least 90, at least 95, at least 98, or at least 99 percent sequence identity to SEQ ID NO: 164. An IMD1 polypeptide allelic variant can have one or more (e.g., 2, 3, 4, 5, 6, 7, 8, 9, or 10) amino acid modifications (e.g., substitutions) relative to SEQ ID NO:164. The aforementioned loss-of-function modifications in a IMD1 encoding gene or a transgene or genome rearrangement that suppresses expression of the IMD1 gene thus include loss-of-function modifications in a gene encoding a IMD1 allelic variant gene, or a transgene or genome rearrangement that suppresses expression of a IMD1 allelic variant gene.

In certain embodiments, pennycress seed lots, plants, seeds, as well as the seed meals and compositions obtained therefrom, all having reduced sinigrin content, can include a loss-of-function modification in a CYP79B3 encoding gene or a transgene or genome rearrangement that suppresses expression of the CYP79B3 gene. As used herein, a loss-of-function mutation in a CYP79B3 gene can be any modification that is effective to reduce CYP79B3 polypeptide expression or CYP79B3 polypeptide function. In certain embodiments, suppressed CYP79B3 polypeptide expression and/or CYP79B3 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress CYP79B3 coding sequence can have a sequence that deviates from the coding sequence set forth above (e.g., SEQ ID NO: 165 or 166), and is referred to as an allelic variant sequence. In certain embodiments, a CYP79B3 coding sequence allelic variant can have at least 80, at least 85, at least 90, at least 95, at least 98, or at least 99 percent sequence identity to SEQ ID NO: 165 or 166. In certain embodiments, a WT pennycress CYP79B3 polypeptide can have a sequence that deviates from the polypeptide sequence set forth above (SEQ ID NO:167), and is referred to as an allelic variant sequence provided the polypeptide maintains its wild-type function. For example, a CYP79B3 polypeptide allelic variant can have at least 80, at least 85, at least 90, at least 95, at least 98, or at least 99 percent sequence identity to SEQ ID NO: 167. A CYP79B3 polypeptide allelic variant can have one or more (e.g., 2, 3, 4, 5, 6, 7, 8, 9, or 10) amino acid modifications (e.g., substitutions) relative to SEQ ID NO:167. The aforementioned loss-of-function modifications in a CYP79B3 encoding gene or a transgene or genome rearrangement that suppresses expression of the CYP79B3 gene thus include loss-of-function modifications in a gene encoding a CYP79B3 allelic variant gene, or a transgene or genome rearrangement that suppresses expression of a CYP79B3 allelic variant gene.

In certain embodiments, pennycress seed lots, plants, seeds, as well as the seed meals and compositions obtained therefrom, all having reduced sinigrin content, can include a loss-of-function modification in a MAM1 encoding gene or a transgene or genome rearrangement that suppresses expression of the MAM1 gene. As used herein, a loss-of-function mutation in a MAM1 gene can be any modification that is effective to reduce MAM1 polypeptide expression or MAM1 polypeptide function. In certain embodiments, suppressed MAM1 polypeptide expression and/or MAM1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress MAM1 coding sequence can have a sequence that deviates from the coding sequence set forth above (e.g., SEQ ID NO:168 or 169), and is referred to as an allelic variant sequence. In certain embodiments, a MAM1 coding sequence allelic variant can have at least 80, at least 85, at least 90, at least 95, at least 98, or at least 99 percent sequence identity to SEQ ID NO: 168 or 169. In certain embodiments, a WT pennycress MAM1 polypeptide can have a sequence that deviates from the polypeptide sequence set forth above (SEQ ID NO:170), and is referred to as an allelic variant sequence provided the polypeptide maintains its wild-type function. For example, a MAM1 polypeptide allelic variant can have at least 80, at least 85, at least 90, at least 95, at least 98, or at least 99 percent sequence identity to SEQ ID NO: 170. A MAM1 polypeptide allelic variant can have one or more (e.g., 2, 3, 4, 5, 6, 7, 8, 9, or 10) amino acid modifications (e.g., substitutions) relative to SEQ ID NO:170. The aforementioned loss-of-function modifications in a MAM1 encoding gene or a transgene or genome rearrangement that suppresses expression of the MAM1 gene thus include loss-of-function modifications in a gene encoding a MAM1 allelic variant gene, or a transgene or genome rearrangement that suppresses expression of a MAM1 allelic variant gene.

In certain embodiments, pennycress seed lots, plants, seeds, as well as the seed meals and compositions obtained therefrom, all having reduced sinigrin content, can include a loss-of-function modification in an FMO-GS-Ox1 encoding gene or a transgene or genome rearrangement that suppresses expression of the FMO-GS-Ox1 gene. As used herein, a loss-of-function mutation in an FMO-GS-Ox1 gene can be any modification that is effective to reduce FMO-GS-Ox1 polypeptide expression or FMO-GS-Ox1 polypeptide function. In certain embodiments, suppressed FMO-GS-Ox1 polypeptide expression and/or FMO-GS-Ox1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress FMO-GS-Ox1 coding sequence can have a sequence that deviates from the coding sequence set forth above (e.g., SEQ ID NO: 171 or 172), and is referred to as an allelic variant sequence. In certain embodiments, an FMO-GS-Ox1 coding sequence allelic variant can have at least 80, at least 85, at least 90, at least 95, at least 98, or at least 99 percent sequence identity to SEQ ID NO: 171 or 172. In certain embodiments, a WT pennycress FMO-GS-Ox1 polypeptide can have a sequence that deviates from the polypeptide sequence set forth above (SEQ ID NO:173), and is referred to as an allelic variant sequence provided the polypeptide maintains its wild-type function. For example, an FMO-GS-Ox1 polypeptide allelic variant can have at least 80, at least 85, at least 90, at least 95, at least 98, or at least 99 percent sequence identity to SEQ ID NO: 173. An FMO-GS-Ox1 polypeptide allelic variant can have one or more (e.g., 2, 3, 4, 5, 6, 7, 8, 9, or 10) amino acid modifications (e.g., substitutions) relative to SEQ ID NO:173. The aforementioned loss-of-function modifications in an FMO-GS-Ox1 encoding gene or a transgene or genome rearrangement that suppresses expression of the FMO-GS-Ox1 gene thus include loss-of-function modifications in a gene encoding an FMO-GS-Ox1 allelic variant gene, or a transgene or genome rearrangement that suppresses expression of a FMO-GS-Ox1 allelic variant gene.

In certain embodiments, pennycress seed lots, plants, seeds, as well as the seed meals and compositions obtained therefrom, all having reduced sinigrin content, can include a loss-of-function modification in a UGT74B1 encoding gene or a transgene or genome rearrangement that suppresses expression of the UGT74B1 gene. As used herein, a loss-of-function mutation in a UGT74B1 gene can be any modification that is effective to reduce UGT74B1 polypeptide expression or UGT74B1 polypeptide function. In certain embodiments, suppressed UGT74B1 polypeptide expression and/or UGT74B1 polypeptide function can comprise elimination or a reduction in such expression or function (i.e., can be complete or partial). Examples of genetic modifications include, without limitation, deletions, insertions, substitutions, translocations, inversions, duplications, and any combination thereof.

In certain embodiments, a WT pennycress UGT74B1 coding sequence can have a sequence that deviates from the coding sequence set forth above (e.g., SEQ ID NO: 174 or 175), and is referred to as an allelic variant sequence. In certain embodiments, a UGT74B1 coding sequence allelic variant can have at least 80, at least 85, at least 90, at least 95, at least 98, or at least 99 percent sequence identity to SEQ ID NO: 174 or 175. In certain embodiments, a WT pennycress UGT74B1 polypeptide can have a sequence that deviates from the polypeptide sequence set forth above (SEQ ID NO:176), and is referred to as an allelic variant sequence provided the polypeptide maintains its wild-type function. For example, a UGT74B1 polypeptide allelic variant can have at least 80, at least 85, at least 90, at least 95, at least 98, or at least 99 percent sequence identity to SEQ ID NO: 176. An UGT74B1 polypeptide allelic variant can have one or more (e.g., 2, 3, 4, 5, 6, 7, 8, 9, or 10) amino acid modifications (e.g., substitutions) relative to SEQ ID NO:176. The aforementioned loss-of-function modifications in a UGT74B1 encoding gene or a transgene or genome rearrangement that suppresses expression of the UGT74B1 gene thus include loss-of-function modifications in a gene encoding a UGT74B1 allelic variant gene, or a transgene or genome rearrangement that suppresses expression of a UGT74B1 allelic variant gene.

In certain embodiments, the pennycress seeds, seed lots, seed meals (defatted and non-defatted), compositions comprising those seed meals, and pennycress plants provided herein can comprise loss-of-function mutation(s), transgene (s), and/or genomic rearrangement(s) that suppress expression and/or activity of at least two of any of the aforementioned endogenous pennycress genes or allelic variants thereof (e.g., MYB28, MYB29, MYB76, CYP83A1, AOP2, BCAT4, BCAT6, CYP79F1, GTR1, GTR2, TFP, BHLH05 IMD1, CYP79B3, MAM1, FMO-GS-Ox1, and/or UGT74B1) or encoded polypeptides). In one embodiment, the loss-of-function mutation(s), genomic rearrangement(s), and/or transgene(s) can suppress expression of both a GTR1 gene (e.g., of SEQ ID NO:15 or an allelic variant thereof) and a GTR2 gene (e.g., of SEQ ID NO:17 or an allelic variant thereof). In one embodiment, the loss-of-function mutation(s), genomic rearrangement(s), and/or transgene(s) can suppress expression and/or activity of both a MYB28 gene (e.g., of SEQ ID NO:21 or an allelic variant thereof) and a MYB29 gene (e.g., of SEQ ID NO:24 or an allelic variant thereof). In one embodiment, the loss-of-function mutation(s), transgene(s), and/or genomic rearrangement(s) can suppress expression and/or activity of both a GTR1 gene (e.g., of SEQ ID NO:15 or an allelic variant thereof) and a MYB29 gene (e.g., of SEQ ID NO:24 or an allelic variant thereof). In certain embodiments, suppression of gene expression and/or activity provided by the loss-of-function mutation(s), transgene(s), and/or genomic rearrangement(s) is partial. In certain embodiments, such partial suppression in the any of the aforementioned embodiments can comprise a reduction of at least 20%, 30%, 40%, 50%, 60%, 70%, 75%, 80%, 85%, 90%, or 95% of activity and/or transcript levels of the endogenous pennycress gene (e.g., MYB28, MYB29, MYB76, CYP83A1, AOP2, BCAT4, BCAT6, CYP79F1, GTR1, GTR2, TFP, BHLH05 IMD1, CYP79B3, MAM1, FMO-GS-Ox1, and/or UGT74B1) in the plant or a part of the plant (e.g., seed) comprising the loss-of-function mutation(s), transgene(s), and/or genomic rearrangement(s) in comparison to the activity and/or transcript levels in a wild-type control plant lacking the loss-of-function mutation (s), transgene(s), and/or genomic rearrangement(s).

In certain embodiments, a genome editing system such as a CRISPR-Cas9 system can be used to introduce one or more loss-of-function mutations into genes such as the glucosinolate biosynthesis, transporters and related regulatory genes (i.e., transcription factors) provided herewith in Table 1 and the sequence listing to obtain pennycress plants, seeds, seed lots, and compositions with reduced seed sinigrin content. For example, a CRISPR-Cas9 vector can include at least one guide sequence specific to a pennycress GTR2 sequence (see, e.g., SEQ ID NO:16) and/or at least one guide sequence specific to a pennycress GTR2 sequence (see, e.g., SEQ ID NO:17). A Cas9 enzyme will bind to and cleave within the gene when the target site is followed by a PAM sequence. For example, the canonical SpCAS9 PAM site is the sequence 5'-NGG-3', where N is any nucleotide followed by two guanine (G) nucleotides. The Cas9 component of a CRISPR-Cas9 system designed to introduce one or more loss-of-function modifications described herein can be any appropriate Cas9. In certain embodiments, the Cas9 of a CRISPR-Cas9 system described herein can be a *Streptococcus pyogenes* Cas9 (SpCas9). One example of a SpCas9 is described in Fauser et al., 2014.

The LOF mutations in any of the genes of coding sequences of Table 1 can be introduced by a variety of methods. Methods for introduction of the LOF mutations include, but are not limited to, traditional mutagenesis (e.g., Ethyl Methane Sulfonate (EMS), fast neutrons (FN), or gamma rays), TILLING, meganucleases, zinc finger nucleases, transcription activator-like effector nucleases, clustered regularly interspaced short palindromic repeat (CRISPR)-associated nuclease (e.g., Cas9, Cpf1, Cms1, *S. aureus* Cas9 variants, eSpCas9), targetrons, and the like. Various tools that can be used to introduce mutations into genes have been disclosed in Guha et al., 2017. Methods for modifying genomes by use of Cpf1 or Csm1 nucleases are disclosed in US Patent Application Publication 20180148735, which is incorporated herein by reference in its entirety, can be adapted for introduction of the LOF mutations disclosed herein. Methods for modifying genomes by use of CRISPR-CAS systems are disclosed in US Patent Application Publication 20180179547, which is incorporated herein by reference in its entirety, can be adapted for introduction of the LOF mutations disclosed herein. The genome editing reagents described herein can be introduced into a pennycress plant by any appropriate method. In certain embodiments, nucleic acids encoding the genome editing reagents can be introduced into a plant cell using *Agrobacterium*- or Ensifer mediated transformation, particle bombardment, liposome delivery, nanoparticle delivery, electroporation, polyethylene glycol (PEG) transformation, or any other method suitable for introducing a nucleic acid into a plant cell. In certain embodiments, the Site-Specific Nuclease (SSN) or other expressed gene editing reagents can be delivered as RNAs or as proteins to a plant cell and the RT, if one is used, can be delivered as DNA.

Also provided herein are defatted pennycress seed meal with reduced sinigrin content in comparison to defatted pennycress seed meal obtained from wild-type pennycress seed lots. Defatted-pennycress seed meal is a product obtained from high-pressure crushing of seed, or from a pre-press solvent extraction process, which removes oil from the whole seed. Solvents used in such extractions include, but are not limited to, hexane or mixed hexanes. The meal is the material that remains after most of the oil has been removed. The typical range of sinigrin in meal made from wild-type pennycress seed is greater than 190 micromoles sinigrin per gram meal by dry weight (μmol/gm dw). To be useful as a high protein animal feed, and competitive with other protein feedstuffs, the level of sinigrin level in meal should be less than 30 micromoles sinigrin per gram by dry weight of the meal. In certain embodiments, defatted pennycress seed meal having a sinigrin content of less than 30, 28, 25, or 15 μmol sinigrin/gm dw are provided. In certain embodiments, defatted pennycress seed meal having a sinigrin content of about 1, 2.5, 5, or 10 to about 15, 16, 18, 20, 25, 28, or 30 μmol sinigrin/gm dw is provided herein. Compositions comprising such defatted pennycress seed meal are also provided herein. Such seed meal or compositions can comprise polynucleotides encoding any of the aforementioned LOF mutations. Such seed meal or compositions can also comprise any marker that is characteristic of the pennycress mutant E3 196, E5 444P1, E5 356P5, I87113, E5 543, or I87207 germplasm. In certain embodiments, such biomarkers include a polynucleotide comprising at least one loss-of-function mutation in pennycress mutant E3 196, E5 444P1 E5 356P5, I87113, E5 543, or I87207. Mutations in the pennycress mutant E3 196, E5 444P1, E5 356P5, I87113, E5 543, or I87207 can be identified by sequencing the genomic DNA or pertinent genes (e.g., genes of Table 1) and comparing those sequences to the corresponding sequences of the parent pennycress lines from which they were obtained.

Non-defatted pennycress seed meal having less sinigrin than non-defatted control pennycress seed meal obtained from wild-type pennycress seed is provided herein. In certain embodiments, the sinigrin content of non-defatted pennycress seed meal and compositions comprising the same that are provided herein is reduced from about 1.25-, 1.5-, 2-, or 3-fold to about 4-, 5-, 6-, 7-, 10-, 20-, 40-, 50-, 60-, 70-, 80-, 100-, 120-, 140-, -160-, 180-, or 200-fold in comparison to control non-defatted pennycress seed meal and compositions comprising the same obtained from control wild-type pennycress seeds. In certain embodiments, the non-defatted pennycress seed meal is obtained from pennycress seeds that have been crushed, ground, macerated, expelled, extruded, or any combination thereof. Typically, the level of sinigrin in wild-type pennycress seed and non-defatted seed meal obtained therefrom varies from about 70 to about 150 μmol sinigrin/gm dw. To be useful as a high protein animal feed, and competitive with other protein feedstuffs, the sinigrin level in non-defatted meal should be less than 30 μmol sinigrin/gm dw of the meal. In certain embodiments, non-defatted pennycress seed meal having a sinigrin content of less than 30, 28, 25, 16, or 15 μmol sinigrin/gm dw are provided herein. In certain embodiments, non-defatted pennycress seed meal having a sinigrin content of about less than 15, 14, or 12 μmol sinigrin/gm dw is provided herein. In certain embodiments, non-defatted pennycress seed meal having a sinigrin content of 1, 2.5, 5, or 10 to about 15, 16, 18, 20, 25, 28, or 30 μmol sinigrin/gm dw are provided herein. Compositions comprising such non-defatted pennycress seed meal are also provided herein. Such seed meal or compositions can comprise polynucleotides encoding any of the aforementioned LOF mutations.

The disclosure will be further described in the following examples, which do not limit the scope of the disclosure described in the claims.

EXAMPLES

Example 1: Generation of Transgenic Pennycress Lines Harboring the CRISPR-Cas9 or CRISPR-Cpf1 or CRISPR-Cms1 Constructs

Materials and Methods

Construction of the *Thlaspi arvense* (Pennycress) AOP2, BCAT4, BCAT6, CYP79F1, CYP83A1, GTR1, GTR2, MYB28 (HAG1), HAG3 (MYB29), MYB76 and TFP Gene-Specific CRISPR Genome-Editing Vectors.

The constructs and cloning procedures for generation of the *Thlaspi arvense* (pennycress) AOP2, BCAT4, BCAT6, CYP79F1, CYP83A1, GTR1, GTR2, MYB28 (HAG1), HAG3 (MYB29), MYB76 and TFP-specific CRISPR-SpCas9 and CRISPR-SaCas9 constructs were adapted in part from the following two publications that describe general procedures for use of SaCas9 in plants: Steinert J, et. al. (2015) and Fauser F, et. al. (2014).

The plant selectable markers (formerly NPT) in the original pDe-SpCas9 and pDe-SaCas9 binary vectors were swapped for hygromycin resistance (Hygromycin phosphotransferase, or HPT) or fluorescent protein marker (FP) gene.

Vector Transformation into *Agrobacterium*

Figure 6:
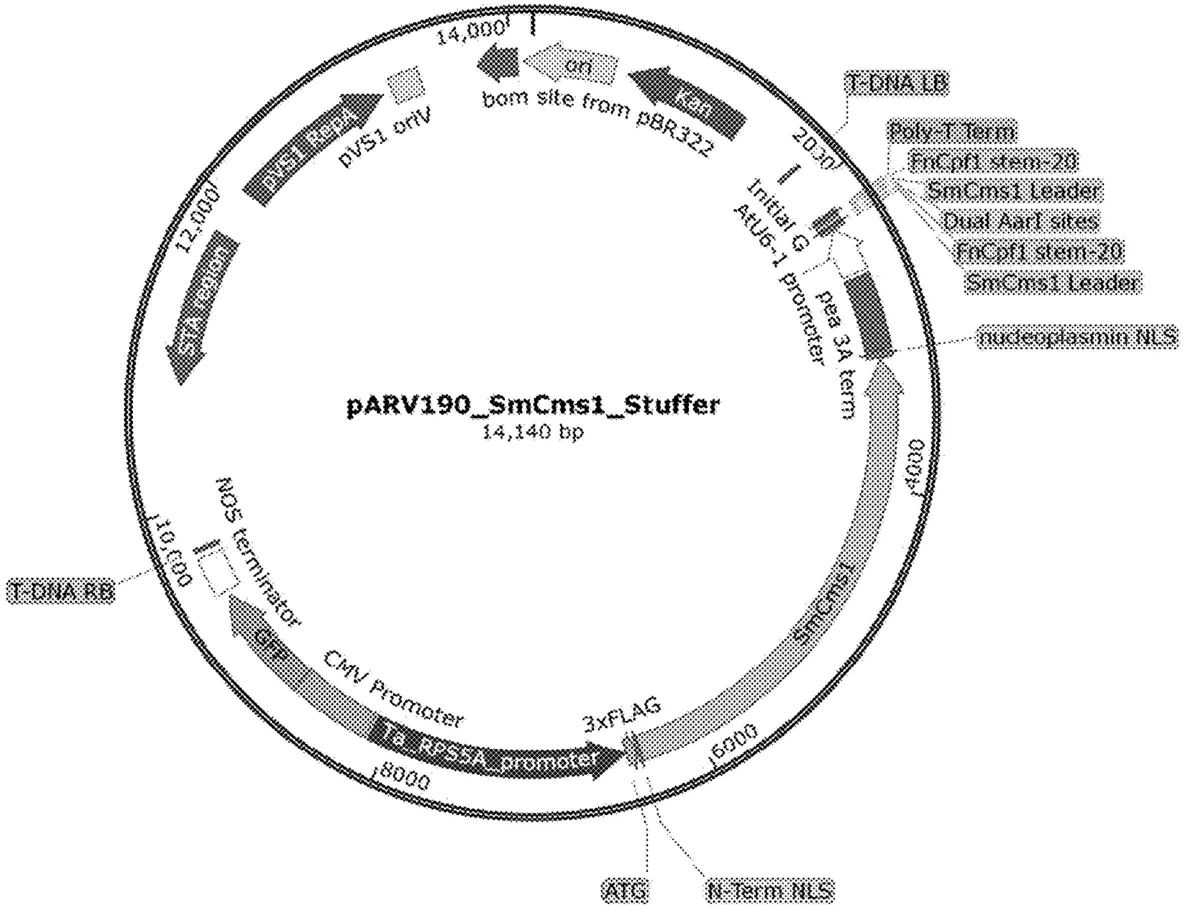
FIG. 6 illustrates pARV190, *Agrobacterium* CRISPR-SmCms1 base vector for editing plant genome. gRNA cassette stuffers are inserted at the dual AarI site, replacing a small fragment of the vector with synthetic gRNA cassette.

The pDe-SpCas9_Hyg, pDe-SaCas9_Hyg, pARV145, containing the *Streptococcus pyogenes* Cas9 (SpCas9) and the *Staphylococcus aureus* Cas9 (SaCas9) cassettes, or related vectors represented in FIGS. 1-7, with the corresponding sequence-specific protospacers were transformed into *Agrobacterium tumefaciens* strain GV3101 using the freeze/thaw method (Holsters et al, 1978).

The transformation product was plated on 1% agar Luria Broth (LB) plates with gentamycin (50 μg/ml) rifampicin (50 μg/ml) and spectinomycin (75 μg/ml). Single colonies were selected after two days of growth at 28° C.

Plant Transformation—Pennycress Floral Dip

Day One:

5 mL of LB+5 uL with appropriate antibiotics (Rifampin (50), Spectinomycin (75), and/or Gentamycin (50)) were inoculated with *Agrobacterium*. The cultures were allowed to grow, with shaking, overnight at 28° C.

Day Two (Early Morning):

25 mL of Luria Broth+25 uL appropriate antibiotics (Rifampin (50), Spectinomycin (75), and/or Gentamycin (50)) were inoculated with the initial culture from day one. The cultures were allowed to grow, with shaking, overnight at 28° C.

Day Two (Late Afternoon):

250 mL of Luria Broth+250 uL appropriate antibiotic (Rifampin (50), Spectinomycin (75), and/or Gentamycin (50)) were inoculated with 25 mL culture. The cultures were allowed to grow, with shaking, overnight at 28° C.

Day Three:

When the culture had grown to an $OD_{600}$ of ~1 (or looks thick and silky), the culture was decanted into large centrifuge tubes (all evenly weighted with analytical balance), and spun at 3,500 RPM at room temperature for 10 minutes to pellet cells. The supernatant was decanted off. The pelleted cells were resuspended in a solution of 5% sucrose and 0.02% Silwet L-77. The suspension was poured into clean beakers and placed in a vacuum chamber.

Newly flowering inflorescences of pennycress were fully submerged into the beakers, and subjected to a vacuum pressure of ~30 inches mercury (~14.7 psi) for 5 to 10 minutes.

After racemes of pennycress plants (W0011 variety; these plants were 5 generations removed from seeds) were dipped, they were covered loosely with Saran wrap to maintain humidity and kept in the dark overnight before being uncovered and placed back in the environmental growth chamber.

Screening Transgenic Plants and Growth Condition

Pennycress seeds were surface sterilized by first rinsing in 70% ethanol then incubating 10 minutes in a 30% bleach, 0.05% SDS solution before being rinsed two times with sterile water and plated on selective plates (0.8% agar/one half-strength Murashige and Skoog salts with hygromycin B selection (40 U/ml) or glufosinate (18 μg/ml). Plates were wrapped in parafilm and kept in an environmental growth chamber at 21° C., 16:8 day/night for 8 days until antibiotic or herbicide selection was apparent.

Surviving hygromycin or glufosinate-resistant $T_1$-generation seedlings were transplanted into autoclaved Redi-Earth soil mix and grown in an environmental growth chamber set to 16-hour days/8-hour nights at 21° C. and 50% humidity. T2-generation seeds were planted, and ~1.5 mg of leaf tissue from each T2-generation plant was harvested with a 3-mm hole punch, then processed using the Thermo Scientific™ Phire™ Plant Direct PCR Kit (Catalog #F130WH) as per manufacturer's instructions. PCR (20 μl volume) was performed.

Example 2: Generation and Characterization of EMS-Mutagenized Low Sinigrin Mutant Lines E3 196, E5 444P1, I87113 and I87207

Mutants carrying domestication enabling low glucosinolate trait were isolated from two mutant populations independently created using chemical mutagenesis (ethyl methanesulfonate, EMS) protocol essentially as described in the Materials and Methods section below.

In other embodiments, pennycress plants exhibiting domestication enabling traits such as reduced seed glucosinolate content and loss-of-function mutations in domestication genes can be identified in mutant populations created using fast neutrons (FN), gamma rays (y rays) or other methods of introducing genetic diversity into genomic DNA.

Materials and Methods

Solutions:

| | | |
|---|---|---|
| A) | 0.2M sodium phosphate monobasic ($NaH_2PO_4*H_2O$) | 6.9 g/250 mL |
| B) | 0.2M sodium phosphate dibasic ($NaH_2PO_4$ anhydrous) | 7.1 g/250 mL |

For 50 mL of 0.1 M sodium phosphate buffer at pH 7:

| | |
|---|---|
| 9.75 mL | A |
| 15.25 mL | B |
| 25.0 mL | $dH_2O$ |

0.2% EMS in buffer:

20 mL 0.1M Sodium Phosphate Buffer, pH 7

40 μL EMS liquid (Sigma #M0880-5G)

0.1 M sodium thiosulfate at pH 7.3:

12.4 g sodium thiosulfate in 500 mL

Primary Seed Surface Sterilization

In the Set #1 experiments, wild-type pennycress (*Thlaspi arvense*) seeds (W0011 ecotype) were surface sterilized for 10 minutes in a 30% bleach, 0.05% SDS solution before being rinsed 3× with sterile water. Sterilized seeds were immediately subjected to EMS treatment.

Ethyl Methane Sulfonate (EMS) Treatment of Pennycress Seeds

In the Set #1 experiments, sterilized pennycress seeds (41 g) were agitated in distilled water overnight. Four 250 mL Erlenmeyer flasks with 10 g seed each, and 1 g in a separate small flask as a control, were agitated. The water was decanted.

25 mLs of 0.2% EMS in 0.1M sodium phosphate buffer (pH 7) was added. The control received only phosphate buffer with no EMS. The flasks were shaken in fume hood for 18 hours. The EMS solution was decanted off into an EMS waste bottle.

To rinse the seeds, 25 ml of $dH_2O$ was added to each flask, and the flasks were shaken for 20 minutes. The rinse water was decanted into the EMS waste bottle.

To deactivate the EMS, seeds were washed for 20 minutes in 0.1M sodium thiosulfate (pH 7.3). The sodium thiosulfate solution was decanted into the EMS waste bottle.

The seeds were rinsed 4 times with dH2O for 15 minutes.

The seeds were suspended in 0.1% agarose, and germinated directly in autoclaved Redi-Earth soil mix at a density of approximately 10 seeds per 4-inch pot.

In the Set #2 experiments, 42 grams of seeds derived from pennycress accession MN106 were collected as described elsewhere (Dorn et al., 2013), and were treated with 180 ml 0.2% ethyl methanesulfonate (EMS) in a chemical flow hood. The solution and seeds were kept mixed on a rotating platform for 14 hours at room temperature. The seeds were thereafter extensively rinsed with distilled water to remove all traces of the EMS. The seeds were then dried for 24 hours on filter paper in a chemical flow hood. These seeds were considered to be the progenitors of the M1-generation of plants.

Plant Growth Conditions

In the Set #1 experiments, EMS-treated pennycress seeds were germinated and grown in an environmental growth chamber at 21° C., 16:8 6400K fluorescent light/dark, 50% humidity. Approximately 14 days after planting, plants were thinned and transplanted to a density of 4 plants per 4-inch pot. These M1-generation plants showed telltale chlorotic leaf sectors that are indicative of a successful mutagenesis.

After dry-down, these M1-generation W0011 plants were catalogued and harvested. The M2- and M3-generation seeds were surface sterilized, planted and grown according to the protocols previously described.

In the Set #2 experiments, the MN106 mutagenized seeds were sowed into two small field plots. These plots were allowed to grow over the winter. The following spring abundant albino sectors were noted on the flowering plants as an indication of a successful mutagenesis.

Identification and Characterization of Low Seed Sinigrin Mutant Lines

In the Set #1 experiments, seeds (M3-generation) from putative M2-generation mutants were planted and grown in potting soil-containing 4-inch pots in a growth chamber, harvested and the sinigrin content in the seed was assessed upon its desiccation to a moisture level of 7-9%. EMS mutagenesis typically introduces single-nucleotide transition mutations (e.g., G to A, or C to T) into plant genomes.

In the Set #2 experiments, seeds were collected from mature M1-generation MN106 plants. M2-generation seeds from batches of 10 M1-generation plants were pooled together. In all, 500 pools representing 5000 mutagenized M1-generation plants were collected. In August, each pool was sowed in a field into an individual row. Robust growth was noted in October. During the following June, M3-generation seeds were collected from approximately 8,000 mature M2-generation individual plants and stored in individual packets.

In both Sets #1 and #2 experiments, NIR spectral analysis was used to make preliminary identification of lines with reduced glucosinolate in M3-generation seeds from each packet. These seeds were scanned using a Metrohm NIRS XDS Multi Vial Analyzer or a Perten DA7250 NIR Spectroscopy Analyzer to assess the amount of sinigrin as described elsewhere (Sidhu et. al., 2014; Golebiowski et. al, 2005; Riu et. al., 2006; Xin et. al., 2014). These analyses captured information related to the approximate levels of total glucosinolate and were used to identify low sinigrin candidates. Seeds showing a significant predicted reduction were used in a wet lab analysis to confirm or determine the sinigrin amount with better accuracy.

Near infrared (NIR) spectroscopic analysis was used to determine the sinigrin content of selected seed lines E3 196, E5 444P1, I87113 and I87207 and to compare the obtained values to the range of sinigrin in corresponding wild type seeds. These mutant lines showed sinigrin content significantly below population average and along with some other representative lines and controls were further analyzed using a method adapted from (Kliebenstein et. al., 2001). Results presented in Table 2 indicate that sinigrin levels in the seeds of these mutant lines are significantly lower and are outside of the corresponding ranges found in control parental seeds.

TABLE 2

Sinigrin content in seeds from selected pennycress lines with low glucosinolates content was measured using high throughput ion-exchange chromatography-based method. A minimum of three biological replicates each consisting of 20 mg (~20 seeds) per replicate was used. Each biological replicate was split into two technical replicates that were loaded on the mini-column and treated independently after seed extraction process. Last column represents standard error of the mean for glucosinolates (primarily sinigrin) content in each line.

| | Line ID | Origin | Biological Reps | Technical Reps | Sinigrin, Mean μmoles/g seed | Std Error, Mean μmoles/g |
|---|---|---|---|---|---|---|
| 1 | E3 196 | MN106-derived | 6 | 2 | 15 | 1.6 |
| 2 | E5 444P1 | MN106-derived | 6 | 2 | 23 | 3.5 |
| 3 | I87207 | W0011-derived | 3 | 2 | 25 | 4.1 |
| 4 | I87113 | W0011-derived | 6 | 2 | 30 | 4.5 |
| 5 | I87102 | W0011-derived | 3 | 2 | 94 | 8.0 |
| 6 | I87383 | W0011-derived | 3 | 2 | 96 | 10.7 |
| 7 | E5 051 P1 | MN106-derived | 3 | 2 | 99 | 8.9 |
| 8 | I87256 | W0011 wild type | 3 | 2 | 110 | 9.2 |
| 9 | E5 101 P1 | MN106-derived | 3 | 2 | 102 | 10.1 |
| 10 | E5 484P6 | MN106-derived | 3 | 2 | 106 | 10.4 |
| 11 | 1120/1062 1-13 | ARV breeding | 3 | 2 | 101 | 12.1 |
| 12 | 1082/1008 3-12-1 | ARV breeding | 3 | 2 | 106 | 12.2 |
| 13 | 1053/1023 2-5-1 | ARV breeding | 3 | 2 | 112 | 5.9 |
| 14 | Y1067 | ARV low fiber | 3 | 2 | 129 | 9.4 |
| 15 | Y1126 | ARV low fiber | 3 | 2 | 128 | 10.2 |
| 16 | Beecher (WT parent) | USDA | 120 | 2 | 103 | 2.5 |
| 17 | W0011 (WT parent) | WIU/ISU | 6 | 2 | 102 | 6.4 |
| 18 | MN106 (WT parent) | UMN | 6 | 2 | 116 | 8.5 |

Example 3. Identification of Underlying Gene Mutations in EMS-Generated Low Seed Sinigrin Mutant Lines Genomic DNA was extracted from each mutant, and each sample was subjected to whole-genome sequencing (adapted from Zhang, X., et al., 2018) and extensive bioinformatic analysis to identify induced mutations resulting in amino acid substitutions. For every gene target described in Table 1, a sequence from the mutant line was compared to a WT sequence from the parental line. If the EMS-induced change resulted in a non-silent mutation (amino acid change or a stop codon), the mutation was considered to be a candidate for the low sinigrin phenotype. Once the mutation was identified, a co-segregation analysis in the F2 single seeds or F3 families derived from each of these mutants was performed. This whole-genome sequencing (WGS) revealed that E3 196 (Nutty) line contains a mutation in a predicted pennycress ALKNYL HYDROXALKYL PRODUCING (AOP) polypeptide involved in the last step of sinigrin biosynthesis, while the I87113 line carries a homozygous mutation in the GTR1 gene which encodes a glucosinolate transporter.

Mutation in the AOP2-Like Gene Co-Segregates with Low Glucosinolate Phenotype in Seeds and Vegetative Tissues of Mutant E3 196 (Nutty) Pennycress Line.

In order to demonstrate that the mutation in the AOP2 gene discovered in the E3 196 (Nutty) mutant is responsible for the low sinigrin phenotype, a segregating F2 population from the cross of homozygous Nutty mutant with WT MN106 parental line was performed. The results are presented in Table 3.

TABLE 3

Glucosinolates content in seeds and vegetative tissues from the segregating population created using mutant pennycress line E3 196 (Nutty). Each line was genotyped for the presence of G97R mutation found in AOP2 gene variant in E3 196 (Nutty) using standard sequencing. Moisture and sinigrin content in seeds were measured using NIRS, whereas total glucosinolates content in fresh tissue was determined using a wet-lab method described in Chopra et al. (2019).

| | NIR sample # | Genotype, G97R | Moisture, % | Sinigrin, µmoles/g seed | Glucosinolates µmoles/g tissue |
|---|---|---|---|---|---|
| 1 | 15 | wt | 7.3 | 115.4 | 26.1 |
| 2 | 23 | wt | 7.6 | 98.3 | 23.9 |
| 3 | 29 | wt | 7.1 | 101.1 | 20.7 |
| 4 | 34 | wt | 7.1 | 108.1 | 9.7 |
| 5 | 35 | wt | 7.3 | 111.3 | 24.6 |
| 6 | 37 | wt | 7.4 | 115.1 | 13.8 |
| 7 | 38 | wt | 7.3 | 106.0 | 7.8 |
| 8 | 8 | homo | 7.5 | 4.9 | 0.7 |
| 9 | 12 | homo | 7.5 | 9.2 | 0.5 |
| 10 | 17 | homo | 7.0 | 6.9 | 1.4 |
| 11 | 24 | homo | 7.7 | 13.7 | 0.4 |
| 12 | 28 | homo | 7.4 | 7.4 | 0.3 |
| 13 | 41 | homo | 6.9 | 2.1 | 2.1 |
| 14 | 1 | het | 6.9 | 107.7 | 19.0 |
| 15 | 6 | het | 7.1 | 106.3 | 21.5 |
| 16 | 7 | het | 7.1 | 102.0 | 23.9 |
| 17 | 10 | het | 7.7 | 110.0 | 25.6 |
| 18 | 13 | het | 7.3 | 95.4 | 28.6 |
| 19 | 14 | het | 7.5 | 100.4 | 17.2 |
| 20 | 19 | het | 7.4 | 89.8 | 17.7 |
| 21 | 22 | het | 7.4 | 108.1 | 24.4 |
| 22 | 26 | het | 7.4 | 103.5 | 23.3 |
| 23 | 27 | het | 7.6 | 99.6 | 23.7 |
| 24 | 32 | het | 7.0 | 114.3 | n/a |
| 25 | 33 | het | 7.2 | 103.6 | 23.6 |
| | Average | WT | | 107.9 | 18.1 |
| | Average | HET | | 103.4 | 22.6 |
| | Average | HOMO | | 7.4 | 0.9 |

The results presented in Table 3 strongly indicate that the G97R mutation present in the AOP2 gene variant in mutant line E3 196 (Nutty) mutant line results in ~20-fold reduction of total glucosinolates content in dry seeds and vegetative tissues of the mutant plant.

Mutation in the Homolog of GTR1 Gene Results in Low Glucosinolate Phenotype in Seeds and Vegetative Tissues of Mutant I87113 Pennycress Line.

Using a WGS approach, the I87113 line was found to carry a homozygous mutation believed to confer a L491F amino acid change in GTR1, a glucosinolate transporter and a member of a major facilitator superfamily. In 98 Embryophyta sequences this position is in a conserved transmembrane helical region and is populated exclusively with small hydrophobic AAs, suggesting that the L491F-causing mutation results in at least a partial loss of function. Indeed, in a separate set of NIRS and wet-lab experiments, the progeny of the I87113 mutant has consistently demonstrated a significant reduction in glucosinolates levels in dry seeds (~30% of the WT level).

TABLE 4

Sinigrin content in seeds of gtr1-1 mutant I87113 as determined using a wet-lab method described in Chopra et. al. (2019).

| Line ID | Generation/ Type | Sinigrin, Mean µmoles/g seed | Std Error, Mean µmoles/g |
|---|---|---|---|
| I87113 | M3 | 25 | 4 |
| I87113 | M3 | 30 | 4 |
| I87113 | M4 | 33 | 2 |
| W0011 | Control | 98 | 4 |
| Beecher | Control | 101.4 | 7 |

Example 4: Discovery and Characterization of Other Mutant Lines with Low Sinigrin Content in Seeds In the process of whole genome sequencing (WGS) of multiple EMS-mutagenized lines segregating for useful traits (flowering, pod-shattering, oil, protein and fiber content, etc.) mutations in other genes described as potential targets for suppression in Table 1 were identified. In these cases, mutations were present almost exclusively in a heterozygous form, consistent with the fact that they were not selected based on a low glucosinolate phenotype which typically requires a homozygous LOF mutation. Instead, they were identified using this opportunistic approach because the original seed stock was very heavily mutagenized (with an estimated 1,000-2,000 mutations per haploid genome), which makes the presence of more than one potentially useful mutation in the same line relatively likely. Because these lines were selected exclusively based on presence of non-silent mutations, most are expected to be in non-conserved regions and have little or no impact on corresponding gene functions. Nevertheless, these lines were subjected to NIRS and wet-lab assays in order to determine the effects of the identified mutations on glucosinolate content in seeds. The results are summarized in Table 5.

TABLE 5

Sinigrin content in seeds of the segregating populations created using mutant pennycress lines identified via WGS. The genotypes of each mother line were determined using standard sequencing. Moisture and sinigrin content in seeds were measured using NIRS whereas, total glucosinolates content in dry seeds was determined using a wet-lab procedure described in (Chopra et. al., 2019).

| | Line Name | Gene Affected | Moisture % | NIRS Sinigrin, µmoles/g seed | Wet-Lab Glucosinolate µmoles/g seed | Genotype of the mother line |
|---|---|---|---|---|---|---|
| 1 | A7 11 | FMO_GS-OX1 | 7.6 | 103.3 | 113.5 | HET |
| 2 | A7 66 - CYP83A1 Mut | CYP83A1 | 7.3 | 101.0 | 123.5 | HOM |
| 3 | A7 66 - CYP83A1 WT | CYP83A1 | 8.1 | 85.3 | 119.2 | WT |
| 4 | A7 95 | IMD1 | 4.9 | 115.5 | 115.1 | HOM |
| 5 | D3 22 | IMD1 | 8.3 | 96.6 | 120.0 | HET |
| 6 | D3 N13P3 - F2 (Mut) - 16 | bHLH05 (MYC3) | 17.1 | 81.1 | 66.0 | HOM |
| 7 | D3 N13P3 - F2 (Mut) - 22 | bHLH05 (MYC3) | 12.3 | 80.2 | 91.4 | HOM |
| 8 | D3 N13P3 - F2 (Wt) -11 | bHLH05 (MYC3) | 13.7 | 119.1 | 125.1 | WT |
| 9 | D3 N13P3 - F2 (Wt) -12 | bHLH05 (MYC3) | 16.8 | 122.8 | 118.8 | WT |
| 10 | E5 133P2-1 | bHLH05 (MYC3) | 7.5 | 63.6 | 86.0 | unknown |
| 11 | E5 133P2-2 | bHLH05 (MYC3) | 8.1 | 90.3 | 107.9 | unknown |
| 12 | E5 133P2-3 | bHLH05 (MYC3) | 7.9 | 57.9 | 94.9 | unknown |
| 13 | E5 356P5 | FMO_GS-OX1 | 7.5 | 92.5 | 96.7 | HET |
| 14 | E5 519 - CYP79B3 Mut 309 | CYP79B3 | 7.9 | 91.8 | 110.2 | HOM |
| 15 | E5 519 - CYP79B3 Mut 311 | CYP79B3 | 8.1 | 80.9 | 108.4 | HOM |
| 16 | E5 543 | MAM1 | 6.3 | 57.9 | 89.7 | HET |
| 17 | MN106 #33 | Wt | 8.2 | 91.2 | 106.6 | WT |
| 18 | A7 137 | Wt | 7.7 | 99.8 | 104.0 | WT |
| 19 | E5 301P1 | Wt | 8.3 | 94.5 | 99.0 | WT |

This analysis suggested that some of the mutations (such as in FMO-GS-Ox1 and MAM1 genes) may have at least a partial impact on corresponding protein function. To test this hypothesis, the seeds from the progeny of the original heterozygous lines (segregating in a typical 1:2:1 Mendelian ratio) were subjected to a single-seed wet-lab assay and PCR-based genotyping. The results summarized in Table 6 suggest that mutations in FMO-GS-Ox1 and MAM1 may result in reduction of glucosinolates in dry seeds of homozygous mutant lines (40-60% of WT level).

TABLE 6

Glucosinolates content in seeds of the segregating populations created using mutant pennycress lines. Total glucosinolates content (µmoles/g) in single seeds was determined using a wet-lab method described in Chopra et al. (2019).

| | Gene | WT | Mutant |
|---|---|---|---|
| 1 | CYP83A1 | 138 (±12.22) | 113 (±19.72) |
| 2 | FMO-GS-Ox1 | 106 (±10.4) | 64 (±3.98) |
| 3 | MAM1 | 127 (±8.82) | 51 (±4.67) |

Example 5. Identification and Characterization of CRISPR-Induced Mutations in Target Genes Related to Glucosinolate Pathway and Seed Accumulation Gene editing using Cas9, Cpf1 and Cms1 nucleases typically introduces a double-stranded break into a targeted genome area in close proximity to the nuclease's PAM site. During non-homologous end-joining process (NHEJ) double-stranded breaks are repaired, at times resulting in the introduction of INDELS-type mutations at the repair location in targeted genomes. To identify plants with small INDELS in targeted genes of interest, standard Sanger sequencing and/or T7 endonuclease assays (Guschin et. al., 2010) were employed. Standard PCR protocols followed by Sanger sequencing were used to identify and characterize larger (several hundred base pairs) deletions. Sequence analyses revealed that multiple guide RNAs/CRISPR nuclease combinations were effective in generating loss-of-function (LOF) mutations in gene targets described in Table 1. Plants carrying LOF mutations were grown to the next generation and the phenotypes in seeds or vegetative tissues were confirmed using analytical methods.

Multiple mutations in the MYB28 (HAG1) gene were identified, including frameshift mutations likely conferring complete loss of gene function, but no reduction in sinigrin was observed in any of the corresponding homozygous mutant lines (Table 7). On the other hand, mutations in another MYB family member, MYB29 (HAGS), did result in sinigrin reduction, on average, by 35-50% (Tables 7-9). However, in vegetative tissues of myb28/myb29 (hag1/hag3) mutations stack, a dramatic reductions in glucosinolate content relative to WT controls were observed, suggesting a redundancy in the MYB28 and MYB29 gene functions.

TABLE 7

Sinigrin levels as determined using a wet-lab method described in Chopra et al. (2019), in homozygous lines generated using CRISPR-induced mutagenesis in selected gene targets described in Table 1.

| | Gene Name(s) | Line Name Genotype | Gene ratio n | Sinigrin, µmoles/g seed | Glucosinolates µmoles/g fresh tissue | % Control |
|---|---|---|---|---|---|---|
| 1 | WT Control (Beecher) | WT-Beecher | | 105 | 46.1 | n/a |
| 2 | WT Control (W0011) | WT-W0011 | | 94.3 | 40.1 ± 5.7 | n/a |
| 3 | MYB28 (HAG1) | hag1-1 (homozygous − G deletion) | T2 | 98.1 | | 98% |
| 4 | MYB28 (HAG1) | hag1-2 (homozygous + A insertion) | T3 | 100.7 | | 101% |
| 5 | MYB28 (HAG1) MYB29 (HAG3) Stack | 2180A (hag1 het − 2bp; hag3-2 homo − 6 bp) | T1 | | 26.0 ± 3.1 | 65% |
| 6 | MYB28 (HAG1)/ MYB29 (HAG3) stack | 2172A (hag1 biallelic − 2bp, +A; hag3-1 homo − 13 bp) | T1 | | 1.1 ± 0.3 | 3% |
| 7 | GTR1/GTR2 stack | 3A5K (gtr1-2 homo + G, gtr 2-3 chimeric + G, +A, WT) | T2 | 20.6 | | 21% |
| 8 | GTR1/GTR2 stack | 3A5C (gtr1-3 het − T, gtr2-2 homo + A) | T2 | 48.9 | | 49% |

TABLE 8

Sinigrin levels in single T2-generation seeds obtained from selected biallelic/homozygous MYB29 (HAG3)-edited lines (wet-lab method, normalized to µmoles/g seed).

| Seed # | WT Control | Line A263A | Line A264A | Line A269A |
|---|---|---|---|---|
| 1 | 117.9 | 70.8 | 121.5 | 77.4 |
| 2 | 106.7 | 58.8 | 103.5 | 84.1 |
| 3 | 119.6 | 46.5 | 94.5 | 60.6 |
| 4 | 124.6 | 42.1 | 70.5 | 56.3 |
| 5 | 130.3 | 64.5 | 84.7 | 56.2 |
| 6 | 123.9 | 51.3 | 86.1 | 54.6 |
| 7 | 111.7 | 56.4 | 94.1 | 62.1 |
| 8 | 126.5 | 45.4 | 89.6 | 41.9 |
| 9 | 127.5 | 52.1 | 114.0 | 57.1 |
| 10 | 125.1 | 45.9 | 83.5 | 51.5 |
| 11 | 124.5 | 44.0 | 71.3 | 63.3 |
| 12 | 116.1 | 49.8 | 68.7 | 57.2 |
| 13 | 126.1 | 75.7 | 113.4 | 85.7 |
| 14 | 128.1 | 53.0 | 73.2 | 61.5 |

TABLE 8-continued

Sinigrin levels in single T2-generation seeds obtained from selected biallelic/homozygous MYB29 (HAG3)-edited lines (wet-lab method, normalized to µmoles/g seed).

| Seed # | WT Control | Line A263A | Line A264A | Line A269A |
|---|---|---|---|---|
| 15 | 115.9 | 46.7 | 84.9 | 87.3 |
| 16 | 114.4 | 46.2 | 74.6 | 69.2 |
| 17 | 103.2 | 55.3 | 101.6 | 86.8 |
| 18 | 114.5 | 54.3 | 99.6 | 81.5 |
| 19 | 101.4 | 47.6 | 116.8 | 56.2 |
| 20 | 150.0 | 98.4 | 62.6 | 41.5 |
| 21 | 127.1 | 48.1 | 71.1 | 63.7 |
| 22 | 135.0 | 58.6 | 101.3 | 60.8 |
| 23 | 133.7 | 70.3 | 78.3 | 48.1 |
| 24 | 126.9 | 51.5 | 83.3 | 65.7 |
| AVE, µmoles/g | 122.1 | 55.5 | 89.3 | 63.8 |
| STDEV | 10.8 | 12.8 | 16.8 | 13.6 |
| % Control | 100% | 45% | 73% | 52% |

TABLE 9

Sinigrin levels in vegetative tissues from selected 4-weeks old T2-generation plants grown from biallelically modified MYB29 (HAG3) CRISPR-mutated line A269A (wet-lab method, normalized to µmoles/g fresh tissue punch).

| | WT | A269A, line # | | | | | | | |
|---|---|---|---|---|---|---|---|---|---|
| BioRep # | Control | 13 | 16 | 21 | 22 | 11 | 14 | 19 | 24 |
| 1 | 19.8 | 4.0 | 7.5 | 3.0 | 3.4 | 3.9 | 8.3 | 7.9 | 8.2 |
| 2 | 19.9 | 4.1 | 5.6 | 3.1 | 5.7 | 2.7 | 6.9 | 5.6 | 8.4 |
| 3 | 16.4 | 3.4 | 5.0 | 3.6 | 5.8 | 2.8 | 7.0 | 6.4 | 7.8 |
| AVERAGE | 18.7 | 3.8 | 6.0 | 3.2 | 5.0 | 3.1 | 7.4 | 6.6 | 8.1 |
| STDEV | 2.0 | 0.4 | 1.3 | 0.3 | 1.4 | 0.7 | 0.8 | 1.2 | 0.3 |
| % Control | 100% | 20% | 32% | 17% | 27% | 17% | 40% | 35% | 43% |

TABLE 10

Sinigrin levels in vegetative tissues from selected T1-generation seedlings grown from biallelically modified AOP2 lines (wet-lab method, normalized to μmoles/4.3 mg fresh tissue punch). Tissue samples were harvested from cauline leaves when plants were setting pods (wet-lab method, normalized to μmoles/g fresh tissue punch). T1 plants are generally chimeric for the edits, resulting in overestimated sinigrin numbers and increased variability.

| BioRep # | 2032 WT control | A370A | A379A | A381A | A380A |
|---|---|---|---|---|---|
| 1 | 7.9 | 0.2 | 1.4 | −0.3 | 0.3 |
| 2 | 4.6 | 2.1 | 0.6 | 0.1 | 0.3 |
| 3 | 4.1 | 0.4 | 0.1 | 6.9 | 0.4 |
| 4 | 4.0 | −0.4 | 2.9 | 7.2 | −0.6 |
| 5 | 4.2 | 3.5 | 0.5 | 0.1 | −0.4 |
| 6 | 1.6 | 4.1 | 0.9 | 0.1 | −0.4 |
| AVERAGE | 4.4 | 1.7 | 1.1 | 2.3 | −0.1 |
| STDEV | 2.0 | 1.9 | 1.0 | 3.6 | 0.4 |
| % Control | 100% | 38% | 24% | 53% | −1% |

REFERENCES

Tripathi, M. K., & Mishra, A. S. (2007). Glucosinolates in animal nutrition: A review. *Animal Feed Science and Technology,* 132 (1-2), 1-27.

EFSA Panel on Contaminants in the Food Chain. (2008). Glucosinolates as undesirable substances in animal feed—scientific opinion of the panel on contaminants in the food chain. *EFSA Journal,* 590, 1-76.

Fauser F., Schiml S., & Puchta H. (2014). Both CRISPR/Cas-based nucleases and nickases can be used efficiently for genome engineering in *Arabidopsis thaliana. Plant J*79: 348-359.

Guha T. K., Wai A, & Hausner G. (2017). Programmable Genome Editing Tools and their Regulation for Efficient Genome Engineering, *Computational and Structural Biotechnology Journal,* 15, 146-160.

Guschin D Y, Waite A J, Katibah G E, Miller J C, Holmes M C, & Rebar E J. (2010) A rapid and general assay for monitoring endogenous gene modification. In: *Engineered zinc finger proteins:* 247-256. Humana Press, Totowa, N.J.

Holsters, M., De Waele, D., Depicker, A., Messens, E., Van Montagu, M., & Schell, J. (1978). Transfection and transformation of *Agrobacterium tumefaciens. Molecular and General Genetics* 163(2), 181-187.

Steinert J., Schiml S., Fauser F., & Puchta H. (2015). Highly efficient heritable plant genome engineering using Cas9 orthologues from *Streptococcus thermophilus* and *Staphylococcus aureus. The Plant Journal* 84:1295-305.

Kliebenstein, D. J., Lambrix, V. M., Reichelt, M., Gershenzon, J., & Mitchell-Olds, T. (2001). Gene duplication in the diversification of secondary metabolism: tandem 2-oxoglutarate-dependent dioxygenases control glucosinolate biosynthesis in *Arabidopsis. The Plant Cell,* 13(3), 681-693.

Chopra, R., Folstad, N., Lyons, J., Ulmasov, T., Gallaher, C., Sullivan, L., McGovern, A., Mitacek, R., Frels, K., Altendorf, K. Killam, A. Ismail, B., Anderson, J. A., Wyse, D. L. & Marks, M. D. (2019). The adaptable use of *Brassica* NIRS calibration equations to identify pennycress variants to facilitate the rapid domestication of a new winter oilseed crop. *Industrial Crops and Products,* 128, 55-61.

Sidhu, H. K., Haagenson, D. M., Rahman, M., & Wiesenborn, D. P. (2014). Diode Array Near Infrared Spectrometer Calibrations for Composition Analysis of Single Plant Canola (*Brassica napus*) Seed. *Applied Engineering in Agriculture,* 30(1), 69-76.

Golebiowski, T., Leong, A. S., & Panozzo, J. F. (2005). Near infrared reflectance spectroscopy of oil in intact canola seed (*Brassica napus* L.). II. Association between principal components and oil content. *Journal of Near Infrared Spectroscopy,* 13(5), 255-264.

Riu, Y. K., Huang, K. L., Wang, W. M., Guo, J., Jin, Y. H., & Luo, Y. B. (2006). Detection of erucic acid and glucosinolate in intact rapeseed by near-infrared diffuse reflectance spectroscopy. *Guang pu xue yu guang pu fen xi=Guang pu,* 26(12), 2190-2192.

Xin, H., Khan, N. A., Falk, K. C., & Yu, P. (2014). Mid-infrared spectral characteristics of lipid molecular structures in *Brassica carinata* seeds: relationship to oil content, fatty acid and glucosinolate profiles, polyphenols, and condensed tannins. *Journal of Agricultural and Food Chemistry,* 62(32), 7977-7988.

Dorn, K. M., Fankhauser, J. D., Wyse, D. L., & Marks, M. D. (2013). De novo assembly of the pennycress (*Thlaspi arvense*) transcriptome provides tools for the development of a winter cover crop and biodiesel feedstock. *The Plant Journal,* 75(6), 1028-1038.

Zhang, X., Li, R., Chen, L., Niu, S., Chen, L., Gao, J., Wen, J., Yi, B., Ma, C., Tu, J. and Fu, T., (2018). Fine-mapping and candidate gene analysis of the *Brassica juncea* white-flowered mutant Bjpc2 using the whole-genome resequencing. *Molecular Genetics and Genomics,* 293(2), pp. 359-370.

OTHER EMBODIMENTS

It is to be understood that while certain embodiments have been described in conjunction with the detailed description thereof and examples, the foregoing description is intended to illustrate and not limit the scope of the disclosure. Other aspects, advantages, and modifications are within the scope of the following embodiments and claims.

Embodiment 1. A composition comprising non-defatted pennycress seed meal that comprises less than 30, 28, 25, 16, or 15 micromoles sinigrin per gram by dry weight.

Embodiment 2. The composition of embodiment 1, wherein said seed meal comprises about 1, 2.5, 5, or 10 to about 15, 16, 18, 20, or 25 micromoles sinigrin per gram by dry weight.

Embodiment 3. The composition of any one of embodiments 1 or 2, wherein said composition has an oil content of about 30% or 35% to about 40% or 50% by dry weight.

Embodiment 4. The composition of any one of embodiments 1 to 3, wherein said composition further comprises a preservative, a dust preventing agent, a bulking agent, a flowing agent, or any combination thereof.

Embodiment 5. The composition of any one of embodiments 1 to 4, wherein said pennycress seed meal is obtained from pennycress seeds that have been crushed, ground, macerated, expelled, extruded, or any combination thereof.

Embodiment 6. The composition of any one of embodiments 1 to 5, wherein said composition comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof (ii) a detectable amount of a polynucleotide comprising at least one loss-of-function mutation in pennycress mutant E3 196, E5 444P1, E5 356P5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 7. A non-defatted pennycress seed meal that comprises less than 30, 28, 25, 16, or 15 micromoles sinigrin per gram by dry weight.

Embodiment 8. The seed meal of embodiment 7, wherein said seed meal comprises about 1, 2.5, 5, or 10 to about 15, 16, 18, 20, or 25 micromoles sinigrin per gram by dry weight.

Embodiment 9. The seed meal of embodiment 7 or 8, wherein said composition has an oil content of 30% or 35% to 40% or 50% by dry weight.

Embodiment 10. The seed meal of any one of embodiments 7 to 9, wherein said seed meal comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 356P5, I87113, or E5 543; or (ii) crushed, ground, and/or macerated seed of pennycress mutant lines E3 196, E5 356P5, I87113, E5 543, or germplasm therefrom.

Embodiment 11. A pennycress seed comprising less than 30, 28, 25, 16, or 15 micromoles sinigrin per gram by dry weight.

Embodiment 12. The pennycress seed of embodiment 11, wherein the seed comprises about 1, 2.5, 5, or 10 to about 15, 16, 18, 20, or 25 micromoles sinigrin per gram by dry weight.

Embodiment 13. The pennycress seed of embodiment 11 or 12, wherein the seed comprises: (i) at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; (ii) at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (iii) seed of pennycress mutant lines E3 196, E5 444P1, E5 356P5, I87113, E5 543, I87207, or germplasm therefrom.

Embodiment 14. The pennycress seed of any one of embodiments 11 to 13, wherein the seed comprises at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 15. The pennycress seed of any one of embodiments 11 to 14, wherein the seed comprises at least one loss-of-function mutation in at least one endogenous pennycress gene encoding a sinigrin biosynthetic enzyme and/or at least one loss-of-function mutation in at least one endogenous pennycress gene encoding a sinigrin transporter.

Embodiment 16. The pennycress seed of embodiment 15, wherein: (i) the sinigrin biosynthetic enzyme comprises a polypeptide selected from the group consisting of SEQ ID NO: 3, 6, 9, 12, 21, 24, 27, 94 162, 163, 165, 166, 168, 169, 171, 172, 174, 175, and allelic variants thereof; or (ii) the pennycress seed comprises a loss-of-function mutation in an endogenous pennycress gene encoding the polypeptide of SEQ ID NO: 21 or an allelic variant thereof and a loss-of-function mutation in an endogenous pennycress gene encoding the polypeptide of a SEQ ID NO: 24 or an allelic variant thereof.

Embodiment 17. The pennycress seed of embodiment 15 or 16, wherein: (i) the sinigrin transporter comprises a polypeptide selected from the group consisting of SEQ ID NO: 15, 17 and allelic variants thereof; (ii) the pennycress seed comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 17 or an allelic variant thereof; or (iii) the pennycress seed comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 24 or an allelic variant thereof.

Embodiment 18. A seed lot comprising a population of pennycress seeds comprising less than 30, 28, 25, 16, or 15 micromoles sinigrin per gram by dry weight.

Embodiment 19. The seed lot of embodiment 18, wherein the pennycress seeds comprise 1, 2.5, 5, or 10 to 15, 16, 18, 20, or 25 micromoles sinigrin per gram by dry weight.

Embodiment 20. The seed lot of embodiment 18 or 19, wherein the seed comprises: (i) at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (ii) at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof; or (ii) seed of pennycress mutant lines E3 196, E5 356P5, I87113, E5 543, or germplasm therefrom.

Embodiment 21. The seed lot of any one of embodiments 18 to 20, wherein the seed comprises at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 22. The seed lot of any one of embodiments 18 to 20, wherein the seed comprises at least one loss-of-function mutation in at least one endogenous pennycress gene encoding a sinigrin biosynthetic enzyme and/or at least one loss-of-function mutation in at least one endogenous pennycress gene encoding a sinigrin transporter.

Embodiment 23. The seed lot of embodiment 22, wherein: (i) the sinigrin biosynthetic enzyme comprises a polypeptide selected from the group consisting of SEQ ID NO: 3, 6, 9, 12, 21, 24, 27, 94, 164, 167, 170, 173, 176, and allelic variants thereof; or (ii) the pennycress seed lot comprises a loss-of-function mutation in an endogenous pennycress gene encoding the polypeptide of SEQ ID NO: 21 or an allelic variant thereof and a loss-of-function mutation in an endogenous pennycress gene encoding the polypeptide of a SEQ ID NO: 24 or an allelic variant thereof.

Embodiment 24. The seed lot of embodiment 22 or 23, wherein: (i) the sinigrin transporter comprises a polypeptide selected from the group consisting of SEQ ID NO: 15, 17 and allelic variants thereof; (ii) the pennycress seed lot comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 17 or an allelic variant thereof; or (iii) the pennycress seed lot comprises a loss-of-function mutation in an endogenous pennycress gene encoding the polypeptide of SEQ ID NO: 15 or an allelic variant thereof and a loss-of-function mutation in an endogenous pennycress gene encoding the polypeptide of a SEQ ID NO: 24 or an allelic variant thereof.

Embodiment 25. The seed lot of any one of embodiments 18 to 24, wherein said population of pennycress seeds comprise seeds having at least one loss-of-function mutation in an endogenous pennycress gene that encodes SEQ ID NO:2 or an allelic variant thereof.

Embodiment 26. The seed lot of any one of embodiments 18 to 25, wherein the loss-of-function mutation in the gene encoding SEQ ID NO:2 or the allelic variant thereof comprises an insertion, deletion, or substitution of one or more nucleotides.

Embodiment 27. The seed lot of embodiment 26, wherein the loss-of-function mutation in the gene encoding SEQ ID NO:2 or the allelic variant thereof comprises a mutation that introduces a pre-mature stop codon or frameshift mutation at codon positions 1-108 of SEQ ID NO:1 or an allelic variant thereof.

Embodiment 28. The seed lot of embodiment 26, wherein the loss-of-function mutation is in a polynucleotide encoding MYB28, MYB29, MYB76, or any combination thereof.

Embodiment 29. The seed lot of any one of embodiments 18 to 28, wherein the population comprises at least 10 seeds comprising less than 25 micromoles sinigrin per gram by dry weight or 1, 2.5, 5, or 10 to 15, 16, 18, 20, or 25 micromoles sinigrin per gram by dry weight.

Embodiment 30. The seed lot of any one of embodiments 18 to 29, wherein at least 95% of the pennycress seeds in the seed lot are seeds comprising less than 30, 28, 25, 16, or 15 micromoles sinigrin per gram by dry weight or 1, 2.5, 5, or 10 to 15, 16, 18, 20, or 25 micromoles sinigrin per gram by dry weight.

Embodiment 31. The seed lot of any one of embodiments 18 to 30, wherein less than 5% of the seeds in said seed lot have greater than 25 or 30 micromoles sinigrin per gram by dry weight.

Embodiment 32. The seed lot of any one of embodiments 18 to 31, wherein said seeds further comprise an agriculturally acceptable excipient or adjuvant.

Embodiment 33. The seed lot of any one of embodiments 18 to 32, wherein said seeds further comprise a fungicide, a safener, or any combination thereof.

Embodiment 34. A method of making non-defatted pennycress seed meal comprising less than 30, 28, 25, 16, or 15 micromoles sinigrin per gram by dry weight or 1, 2.5, 5, or 10 to 15, 16, 18, 20, or 25 micromoles sinigrin per gram by dry weight, comprising the step of grinding, macerating, extruding, and/or crushing the seed lot of any one of embodiments 18 to 32 thereby obtaining the non-defatted seed meal.

Embodiment 35. A method of making defatted pennycress seed meal comprising less than 30 micromoles sinigrin per gram by dry weight or about 1, 2.5, 5, or 10 to about 15, 16, 18, 20, 25, 28, or 30 micromoles sinigrin per gram by dry weight, comprising the steps of solvent extracting the seed lot of any one of embodiments 18 to 32, and separating the extracted seed meal from the solvent, thereby obtaining the defatted seed meal.

Embodiment 36. Pennycress seed meal comprising less than 30, 28, or micromoles sinigrin per gram by dry weight or about 1, 2.5, 5, or 10 to about 15, 16, 18, 20, 25, 28, or 30 micromoles sinigrin per gram by dry weight, wherein the seed meal is defatted.

Embodiment 37. The seed meal of embodiment 36, wherein said seed meal has an oil content of about 0% or 0.5% to about 12% or 15% by dry weight.

Embodiment 38. The pennycress seed meal of embodiments 36 or 37, wherein said meal comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 444P1, E5 356P5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 39. The pennycress seed meal of any one of embodiments 36 to 38, wherein said meal comprises ground and/or macerated seed of a population of pennycress seeds comprising seeds having at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof.

Embodiment 40. The pennycress seed meal of any one of embodiments 36 to 39, wherein said meal comprises ground and/or macerated seed of a population of pennycress seeds comprising seeds having at least one loss-of-function mutation in at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof.

Embodiment 41. The pennycress seed meal of any one of embodiments 36 to 40, wherein said meal comprises ground and/or macerated seed of a population of pennycress seeds comprising seeds having at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof.

Embodiment 42. A composition comprising defatted pennycress seed meal that comprises less than 30, 28, 25, 16, or 15 micromoles sinigrin per gram by dry weight.

Embodiment 43. The composition of embodiment 42, wherein said seed meal comprises about 1, 2.5, 5, or 10 to about 15, 16, 18, 20, 25, 28, or 30 micromoles sinigrin per gram by dry weight.

Embodiment 44. The composition of embodiments 42 or 43, wherein said composition has an oil content of about 0% or 0.5% to about 12% or 15% by dry weight.

Embodiment 45. The composition of any one of embodiments 42 to 44, wherein said composition further comprises a preservative, a dust preventing agent, a bulking agent, a flowing agent, or any combination thereof.

Embodiment 46. The composition of any one of embodiments 42 to 45, wherein said composition comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof (ii) a detectable amount of a polynucleotide comprising at least one loss-of-function mutation in pennycress mutant E3 196, E5 444P1, E5 356P5, I87113, E5 543, or I87207; or (iii) crushed, ground, and/or macerated seed of pennycress mutant lines E3 196, E5 444P1, E5 356P5, I87113, I87207, E5 543, or germplasm therefrom.

Embodiment 47. Pennycress seed cake comprising 30 micromoles sinigrin per gram by dry weight or about 1, 2.5, 5, or 10 to about 15, 16, 18, 20, 25, 28, or 30 micromoles sinigrin per gram by dry weight.

Embodiment 48. The seed cake of embodiment 47, wherein said seed cake has an oil content of about 0% or 0.5% to about 12% or 15% by dry weight.

Embodiment 49. The pennycress seed cake of embodiment 47, wherein the cake comprises crushed or expelled seed of the seed lot of any one of embodiments 18 to 33.

Embodiment 50. The pennycress seed cake of any one of embodiments 47 to 49, wherein the cake comprises: (i) a detectable amount of a polynucleotide comprising at least one loss-of-function mutation in at least one endogenous pennycress coding sequence or gene comprising a polynucleotide sequence selected from the group consisting of SEQ ID NO: 1, 2, 4, 5, 7, 8, 10, 11, 13, 14, 16, 18, 19, 20, 22, 23, 25, 26, 28, 29, 92, 93, 159, 160, 162, 163, 165, 166, 168, 169, 171, 172, 174, 175, and allelic variants thereof; (ii) a detectable amount of a polynucleotide comprising at least one loss-of-function mutation in pennycress mutant E3 196, E5 444P1, E5 356P5, I87113, E5 543, or I87207; or (iii) seed cake obtained from seed of pennycress mutant lines E3 196, E5 444P1, E5 356P5, I87113, I87207, E5 543, or germplasm therefrom.

Embodiment 51. A method of making a pennycress seed lot comprising the steps of:

(a) introducing at least one loss-of-function mutation in at least one endogenous pennycress gene encoding a polypeptide selected from the group consisting of SEQ ID NO: 3, 6, 9, 12, 15, 17, 21, 24, 27, 30, 92, 93, 159, 160, 162, 163, 165, 166, 168, 169, 171, 172, 174, 175, and allelic variants thereof;
(b) selecting germplasm that is homozygous for said loss-of-function mutation; and,
(c) harvesting seed from the homozygous germplasm, thereby obtaining a seed lot, wherein said seed lot comprises a population of pennycress seed having less than 30, 28, 25, 16, or 15 micromoles sinigrin per gram by dry weight.

Embodiment 52. The method of embodiment 51, wherein the harvested seed of the seed lot comprise 1, 2.5, 5, or 10 to 15, 16, 18, 20, or 25 micromoles sinigrin per gram by dry weight.

Embodiment 53. The method of embodiment 51 or 52, wherein said harvested seed of the seed lot comprises the seed lot of any one of embodiments 18 to 33.

Embodiment 54. A method of making a pennycress seed lot comprising the steps of:

(a) introducing at least one transgene or genome rearrangement that suppresses expression of at least one endogenous pennycress gene encoding a polypeptide selected from the group consisting of SEQ ID NO: 3, 6, 9, 12, 15, 17, 21, 24, 27, 30, 94, 161, 164, 167, 170, 173, 176, and allelic variants thereof into a pennycress plant genome;
(b) selecting a transgenic plant line that comprises said transgene or genome rearrangement; and,
(c) harvesting seed from the transgenic plant line, thereby obtaining a seed lot, wherein said seed lot comprises a population of pennycress seed having less than 30, 28, 25, 16, or 15 micromoles sinigrin per gram by dry weight.

Embodiment 55. The method of embodiment 54, wherein the harvested seed of the seed lot comprise 1, 2.5, 5, or 10 to 15, 16, 18, 20, or 25 micromoles sinigrin per gram by dry weight.

Embodiment 56. The method of embodiment 54 or 55, wherein said harvested seed comprise a seed lot of any one of embodiments 18 to 33.

What is claimed is:

1. A pennycress seed comprising a loss-of-function mutation in at least one endogenous pennycress gene encoding the polypeptide of SEQ ID NO: 6 or an allelic variant thereof, wherein said loss-of-function mutation reduces expression of said polypeptide and/or reduces enzymatic activity of the polypeptide of SEQ ID NO: 6 or said allelic variant thereof, wherein said allelic variant of SEQ ID NO: 6 has at least 99% sequence identity to SEQ ID NO: 6, and wherein said seed exhibits a reduction in sinigrin content in comparison to the sinigrin content of a control seed which lacks said loss-of-function mutation.

2. The pennycress seed of claim 1, wherein the seed comprises the loss-of-function mutation in the endogenous pennycress gene encoding the polypeptide of SEQ ID NO: 6.

3. The pennycress seed of claim 1, wherein the seed comprises the loss-of-function mutation in the endogenous pennycress gene comprising the polynucleotide sequence of SEQ ID NO: 4 which encodes the polypeptide of SEQ ID NO: 6 or an allelic variant thereof having at least 99% sequence identity to SEQ ID NO: 4 which encodes the allelic variant of the polypeptide of SEQ ID NO: 6, respectively.

4. The pennycress seed of claim 3, wherein the seed comprises the loss-of-function mutation in the endogenous pennycress gene comprising the polynucleotide sequence of SEQ ID NO: 4.

5. A pennycress seed lot comprising a population of the pennycress seed of claim 1.

6. The pennycress seed lot of claim 5, wherein said seed lot further comprises an agriculturally acceptable excipient or adjuvant.

7. The pennycress seed lot of claim 5, wherein said seed lot further comprises a fungicide, a safener, or any combination thereof.

8. Pennycress plants comprising a loss-of-function mutation in least one endogenous pennycress gene encoding the polypeptide of SEQ ID NO: 6 or an allelic variant thereof, wherein said loss-of-function mutation reduces expression of said polypeptide and/or reduces enzymatic activity of the polypeptide of SEQ ID NO: 6 or said allelic variant thereof, wherein said allelic variant of SEQ ID NO: 6 has at least 99% sequence identity to SEQ ID NO: 6, and wherein a seed lot obtained from the plants exhibits a reduction in sinigrin content in comparison to the sinigrin content of a control seed lot which lacks said loss-of-function mutation.

9. A method for obtaining a progeny plant from a pennycress plant, wherein said pennycress plant comprises a loss-of-function mutation in at least one endogenous pennycress gene encoding the polypeptide of SEQ ID NO: 6 or an allelic variant thereof, wherein said loss-of-function mutation reduces expression of said polypeptide and/or reduces enzymatic activity of the polypeptide of SEQ ID NO: 6 or said allelic variant thereof, wherein said allelic variant of SEQ ID NO: 6 has at least 99% sequence identity to SEQ ID NO: 6, and wherein a seed lot obtained from said pennycress plant exhibits a reduction in sinigrin content in comparison to the sinigrin content of a control seed lot which lacks said loss-of-function mutation, said method comprising crossing said pennycress plant of to a pennycress plant with wild-type sinigrin levels, selfing a progeny plant of the cross, and selecting a progeny plant of the selfing that provides a seed lot that exhibits a reduction in sinigrin content in comparison to the sinigrin content of a control seed lot which lacks said loss-of-function mutation.

10. A method for making a pennycress seed lot comprising harvesting seeds from the pennycress plants of claim 8.

* * * * *

SEQUENCE LISTING

```
Sequence total quantity: 261
SEQ ID NO: 1            moltype = DNA  length = 1365
FEATURE                 Location/Qualifiers
source                  1..1365
                        mol_type = genomic DNA
                        organism = Thlaspi arvense
SEQUENCE: 1
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagtatggg gatccaggat  300
cctcatgttt tggacaaagt ttacgagttt actcaacttc tacgtcctga tcattgtgac  360
ggtaacaaga gcatcagcga aacgatccag acgttttcag agaagttatc agaattggat  420
ataatggtga gaagaatggt aatggaaagc ttcgggatag agaagtacct tgacaaacac  480
ctgaactcaa cgaattaccg tctgcggctg atgaagtata tagcaccgcc tgatgctgat  540
gctactaatg ttgcggctga tgccaaagat gctgatgata atgctaagac gattacaaat  600
gataaagttg atgcggctgg tgctaatgat gtagatgctg gtgatatcgc taatggtatt  660
gctaatcttc atattggtga tgatgctaac gctggtgcta atggtgctgg tgttgatgct  720
aatgatggtg gtgaggatgc taagactggt gaggatgcta agactggtga atgtgctagt  780
gttaagtcta atgccgaaga tggtactgat gttaatgcca gtgctgatgc tggtgttact  840
gttggctcta atgctgatgc taatgctaat gctaatgcta atactagtac tgatgctggt  900
gttggcgata gtgttaaagc taatggtggt gctgatgatg ttgagaagaa attgggtcta  960
ccttctcaca ctgataagaa ccttataacg gtgctttatc aatacgagat tgaaggcttg  1020
```

```
gaggttctaa ccaaagatga caagtggatc agactcaaac catctcataa ttctttcgtt  1080
gttatggctg gagattctct atacgcactt atgaatggta gactaactcg tccctttcat  1140
cgagtaagag taacggagaa aaagaagaca agatattcaa tagcattgtt ctcggctcca  1200
accgcagatt acatcataga cacaccaaaa gaacttgtgg acgagaagca tccacgtatc  1260
ttcgaaccat ttaactataa cgacttgatg agtttctatc atagtgaagc tggtcgtaaa  1320
gctcgatcta ctcttgatgc tttctgtgcc gtctctcgag cataa                 1365

SEQ ID NO: 2            moltype = DNA  length = 5220
FEATURE                 Location/Qualifiers
source                  1..5220
                        mol_type = genomic DNA
                        organism = Thlaspi arvense
SEQUENCE: 2
gaacactcgt gaagtaaaac ggctcacggg ccgcatcgcc gcccttaaca gattcatttt  60
tcgatcaacc gacaagtgtc tccccttcta ccaacttctc tgtggtaaaa agcacttcaa  120
gtgggacaaa aaggctttcg gccaactcaa ggagtatcta tcaacgccac cagtcctagc  180
gaagcccgag ctcggcaaaa tgctttacct ctacgtcgcc gtatctcact cggccgtcag  240
cggcgtactc gtcaaagaaa accggggcga gcagaagccg atcttttatg tgagcaagtc  300
attggacgga cctgagagta gatattctac gatggaaaag ctcgcactcg cagtagtaat  360
ctcagcccgg aagttgcgtc cctatttcca atcacactca atcacggttc tcacaaatca  420
accgctgcga acagtcctgc acagcccaag tcaatcgggg caaatgacga tgtgggccgt  480
tgagttaagc gaatacgaca tcaactacaa gaacaggacg tgcgccaagt ctcaggtctt  540
tgccgatttc ctcatagagc taccactcga ctctactccc gtggactctc ccaccgtcgt  600
gcaatggtcg ctatatgtcg acggctcgtc atctcgaaat ggatcgggta tcggagtcag  660
attaatatcg ccaattggaa aaatcctcga gcagtcattt tgccttgagt ttgcggcgtc  720
caacaacgaa gcagaatacg aagctcttat cgccggcctg tgcctggcaa aagcaatagg  780
attaaggcaa atccaagcat tctgtgattc ccagctagta gctagtcaat tcaatggtga  840
ctacgaagca aaaaatgaac gaatggatgc ctacttaaaa gtaatccaaa acctttcaaa  900
ggacttcgac gatctcaccc tcaccaaaat cctgcacagt gataattctc cagtcgatgc  960
gctggccgcc ctcgcgtcaa tctccgaccc aaacctttac cgtatgatac ctgtaaagag  1020
catcaaaact ccgaatggga gacttggtaa aaagtaaaga taaccacgaa aaaagaaagg  1080
ataattatga ataataatat tcataattca tttaggaaaa tgttcattaa tattacatta  1140
aaaatataat atttatctaa actaaaaatt aattatttct cgaaagaaaa ataaaatatc  1200
gagagataga aaatagattt aaaccatctt agttagaatt aaatttccca aacaggctta  1260
gtttgtaaaa atcgagtcgt tataataata atcaaaatct aatacaccaa aaaacaaagg  1320
aagaaaacaa ctgactcgtc atagcctata gccaatttga ttttggcatt ttgcgaccca  1380
acaaatccaa aggtaagtgg gtttacctct atatataaat ttgcatgaaa gtaattactg  1440
aaaatagtta ttatataatt ggtgccgaca acgtcaacaa acacaattat tcattacatt  1500
attgtacacg ttcatgctca tgcacatgta ctttattgat tttcacacaa tacataaact  1560
taattacttc ttctcccctc cgaagttatt aatattacaa tatcaaatac ttatcacaca  1620
aattaaacag aagtcaacta atccaaaacc ctttatttga tactacatag ttttgcaaat  1680
tagttgactc ttttgaaaac caccaaaact cgtaacgtaa cgcacacgta tgggttcact  1740
ttcaaacact cctcagcttc cagtcatcta cctctcggac caaaccctaa aaccaggaag  1800
ctcaaagtgg gttgaagtca ggagtgatgt ccgtaaagct cttgaagagt acggcggttt  1860
cgaggtgtcg tacgatagag tgtcggagga gcttaagaag tcggttttgc aagccatgga  1920
agagcttttc gcgttaccag ttgaggctaa acagagaaac gtctctccta aacccttcag  1980
cggttattcc actcataacg gtctttccga gagtatgggg atccaggatc ctcatgtttt  2040
ggacaaagtt tacgagttta ctcaacttct acgtcctgat cattgtgacg gtaacaagag  2100
catcaggtaa tttgtgaaaa atactcaata ttgcttcata atataaaaat actcaatatt  2160
gcttcctaat ctttttggca gtttatttca ctacataaaa taaacccgct tttacatttt  2220
tattgtttgt ggtataagaa tattagttca ctcaaacagc atgaaactaa taattgaaat  2280
tttgtatttg tgtgaaaaac tttagttcac ttaaataaca tttttgttgt ttgtgttgta  2340
aacagcgaaa cgatccagac gttttcagag aagttatcag aattggatat aatggtgaga  2400
agaatggtaa tggaaagctt cgggatagag aagtaccttg acaaacacct gaactcaacg  2460
aattaccgtc tgcggctgat gaagtatata gcaccgcctg atgctgatgc tactaatgtt  2520
gcggctgatg ccaaagatgc tgatgataat gctaagacga ttacaaatga taaagttgat  2580
gcggctggtg ctaatgatgt agatgctggt gatatcgcta atggtattgc taatcttcat  2640
attggtgatg atgctaacgc tggtgctaat ggtgctggtg ttgatgctaa tgatggtggt  2700
gaggatgcta agactggtga ggatgctaag actggtgaat gtgctagtgt taagtctaat  2760
gccgaagatg gtactgatgt taatgccagt gctgatgctg gtgttactgt tggctctaat  2820
gctgatgcta atgctaatgc taatgctaat actagtactg atgctggtgt tggcgatagt  2880
gttaaagcta atggtggtgc tgatgatgtt gagaagaaat tgggtctacc ttctcacact  2940
gataagaacc ttataacggt gctttatcaa tacgagattg aaggcttgga ggttctaacc  3000
aaagatgaca agtggatcag actcaaacca tctcataatt ctttcgttgt tatggctgga  3060
gattctctat acgtaagttt ccaacttctt cttcttcttc tttttctttt tttaagttga  3120
cactcacacg tactgacgta cacgttggtg gatttaaaag taaccctagt ggagaagaag  3180
atgaattttc atttacatta tatcataaac ctacttttta aattagaata agaataatta  3240
aaactaaacc catttttttat tggctcacta tggcctaaag aatataatta aaatattata  3300
taggctcaat aagtcataat attctttagc ctatagaata tttttaaagt attcaataat  3360
taaaattatt ttatagcata tagaatattt tatgggctca ataattacaa gtattctaca  3420
ggatcaccat ggcctaaaga ataatcaaaa gtaaaccgaa ttttaaaatt acaggtatag  3480
agaaagaaaa aagaaagcta aaattaaaac caagaataag ttaaaaatgt atgagaagta  3540
acaaacttag tggcgaaaaa gagaaaaaga ttattattca gtcacgttca cgctcactat  3600
ggaccaactt atcctataga aactattaat attttcttga ttttattcgc tcttatcact  3660
ttcacaagtg catgtttgac taaaagcgtt ataacatgat gttttgtttt cttctgatca  3720
tgatctcttg ctgttactta caaacaaaac aaatggtgat tttgtttttg ttttttttttg  3780
caggcactta tgaatggtag actaactcgt ccctttcatc gagtaagagt aacggagaaa  3840
aagaagacaa gatattcaat agcattgttc tcggctccaa ccgcagatta catcatagac  3900
acaccaaaag aacttgtgga cgagaagcat ccacgtatct tcgaaccatt taactataac  3960
```

```
gacttgatga gtttctatca tagtgaagct ggtcgtaaag ctcgatctac tcttgatgct  4020
ttctgtgccg tctctcgagc ataagttctt atttcctttg ctgtgcaaat ccgaaacacg  4080
tttacaaaat ttacatcagt tctttagtta ttataccaac gacaaaaaaa aaagaaaaca  4140
ttcaaaaatc ataaggagag taccgatgga gtttctcgtg atccaaagac accaacttgg  4200
tttttgcttc cgtacgtgct gactgctgag aaagtaagtg ttggagtgtc ccatttatac  4260
aaaaatttca taatactttc aacacatgtt gcttttcagt tcttttggct ttttctgtag  4320
agaaacacat ataatgaata tacaaaggga ggaaagttgg tgaatttatc acacacaaaa  4380
taaaaacatt aagttggtga atcgtttcct tccttttatt gagtctcaat acattgtatt  4440
attaccttta gagtataaga tgaacaccaa cttaacgact aacctaacct tcctttttt  4500
ttttttgaa aaacaaactt aggctatgaa tatcaatagt ttttaatatg agtttaatag  4560
tttttggtta aaaattttaa agttgaaaaa gaagttttga ggaagaaacc taatatgagt  4620
tttatagttt ttgtttttgt ttttaaagaa ctctatatag agaagttttc gaagatcgta  4680
gtggccaata aaatagtttt ctcaaaaact aaaacaaaaa gtacattata aactacaaaa  4740
tattctcagt cttatcctta attagctaac taactaaaca ctataaccct agttacattc  4800
taaccattgt ataaccattg tataagatat acatttagaa ttctcagcta gtgaaatgat  4860
ttttgtaaag taaagcaata atgaagagaa aaaggagaac agcacatctt taaagtaatc  4920
tctttttgat tgatctcggt tggatccaac tgtgcatttg agtactatgg agcaaaaagc  4980
tgacgtttta actgcatcca cacatcacct cgggaatgtt tctggaaaac cttctcgaga  5040
taagattgaa agtagaagat gatcattgat gaataatctt caacattgtt acaaaatata  5100
agtaaagtat ttacgaggtg aaattttgag tgataactag ttctagtttc tctttaacta  5160
gagctttatc tcatgcataa taccaaataa cttctttttt ttttataaga tccgtatgcc  5220
```

```
SEQ ID NO: 3            moltype = AA  length = 454
FEATURE                 Location/Qualifiers
source                  1..454
                        mol_type = protein
                        organism = Thlaspi arvense
SEQUENCE: 3
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSESMGIQD PHVLDKVYEF TQLLRPDHCD  120
GNKSISETIQ TFSEKLSELD IMVRRMVMES FGIEKYLDKH LNSTNYRLRL MKYIAPPDAD  180
ATNVAADAKD ADDNAKTITN DKVDAAGAND VDAGDIANGI ANLHIGDDAN AGANGAGVDA  240
NDGGEDAKTG EDAKTGECAS VKSNAEDGTD VNASADAGVT VGSNADANAN ANANTSTDAG  300
VGDSVKANGG ADDVEKKLGL PSHTDKNLIT VLYQYEIEGL EVLTKDDKWI RLKPSHNSFV  360
VMAGDSLYAL MNGRLTRPFH RVRVTEKKKT RYSIALFSAP TADYIIDTPK ELVDEKHPRI  420
FEPFNYNDLM SFYHSEAGRK ARSTLDAFCA VSRA                              454
```

```
SEQ ID NO: 4            moltype = DNA  length = 1071
FEATURE                 Location/Qualifiers
source                  1..1071
                        mol_type = genomic DNA
                        organism = Thlaspi arvense
SEQUENCE: 4
atggctcctt ctgcgcaacc agttcctaca agtgtttcgg atgagaaata cgcaaatgtg  60
aagtgggaag agttagggtt cgggtttgtt cgtacggaca atatgtatgt tgccaagtgc  120
aaacatggag agagtttcca agagggaact gttgttcctt atgctgattt ccaaatcagc  180
ccttgctctg cagttcttaa ttatggccag ggtttatatg aagggctgaa ggcttacagg  240
acagaagatg gccggataat gatattccga ccagaccaaa acggtctccg ccttcaagcc  300
ggagccaaga gactttgtat gccgtatcca tcggtcgatc aatttgtctc cgccgtcaaa  360
caagttgttc ttgccaacaa gaaatggatt cctcctccgg ggaaaggaac attgtatatc  420
agacctattt tgttcggaag tggtcctata cttggctcac ttccggtccc tgagtacacc  480
ttctcagtat ttgcttgtcc cgttggacgt tttcacaagg ataactctgg cttgaacctg  540
aaaattgaag ataagtttcg ccgcgctttt cctagtggaa ccggtggtgt gaagagtatc  600
acaaactatt ctcctgtttg gataacattg gcagaggcga aagctcaggg tttctctgat  660
gttttgtttt tggatgctgc aactggcaaa aacgtcgaag agcttttcgc ttccaacatt  720
ttcatagtca agggaaatgt tgtgtcgact ccagaaattt caggaactat tttgcccgga  780
gtcacacgaa aaagtatcat tgaattaact cgtgatttcg gctacaaggt tgaggaacgt  840
gttgttcccc ttgaggatct tctcgactcg gaagaagttt tctgcactgg cactgctgcg  900
attgtgacaa ctattgcgtc cgtaaccttc aaagacaaaa agaccggatt caaaacagga  960
gaaaaaacat tggccgcgaa gctctttgcg acgttaatgg atatccagat gggtcgggtc  1020
gaggataaga agggatggac ggtggaggtt gaccggtgcc accagggttg a           1071
```

```
SEQ ID NO: 5            moltype = DNA  length = 6184
FEATURE                 Location/Qualifiers
source                  1..6184
                        mol_type = genomic DNA
                        organism = Thlaspi arvense
SEQUENCE: 5
ggaagttgca acgaaagctt cagaagctca acgggaatgt taagtgacag agacaacaac  60
agcaacaaca ataaccgaga gttcgaggcg gaagttgcaa cattaagcaa tgtaaaacac  120
ataaacgttg tgaagttgtt gtgtagcata acgagtgaag acagcaagtt gcttgtgtat  180
gagtttatgc ctaatggaag cttgtgggaa cagttgcacg agcgtcgtgg tgagcaagag  240
attggatggc gtgtgagaca aacgatagct ttaggagctg ctaaagggct ggagtatctg  300
caccatgggt tagatcggcc tgtgattcat cgtgacgtca agtccagcaa tatcttgctt  360
gatgaggagt ggagaccaag gattgctgat tttggattgg ctaaaatcat tcagtctgat  420
tcggttcaac gagatttctc tgctcctctc gttgaaggaa ctctcggtta cattgcccct  480
ggtacgtcgt cttttctttg gtttaatgaa actatataaa ccctaaacca gaacatgaac  540
tatccgaatt ttacaacctt ataaaattat ctccaagttt cttgcttctc aagcttcaaa  600
ttccttgcgt ttctatatac agtttcttaa cttctctcag ttgcaaataa tttctatgac  660
```

-continued

```
gtacacagaa tacgcctaca ctacgagcgt gaacgagaag agcgacgtat acagctttgg  720
ggtggttcta atggagttgg tgacggggaa gaagccggtg gaggcagagt tcggagagga  780
cagagacatc gtcatgtggg tttggaacag gagcaaggag atgaacagag agaagatgat  840
ggagatcatc gatccgatta tacaaaatga atacaaagag gatgctctta aagtgttgac  900
aattgctttg ttatgtactg ccaagtctcc tcaggttaga ccgtttatga aatcagtggt  960
ttgtatgctg gagaaaacag agccttcttg caacaacaaa agtggagaag caagttacgt  1020
tgtgagtgat gatgaggaga ttactgatgt ttaatagctc atagattgaa caaactcaca  1080
gaagggttac ttgtcaatct agctcatgtc taaggaccaa gaatataatt tttttccaa  1140
atagttataa aattatacag aacttttagg aattgttcta agattataca agagtttttt  1200
tttttttttt tttgccagcg gaaagtttca atatttccaa gttcttagaa atataatcca  1260
gttatccaaa taattagtat ctatataaaa caaatttgag ttgttcacaa agatagtttg  1320
gccgagtggt ctaaggcgcc agatttaggc tctggtccga aagggcgtgg gttcaaatcc  1380
cacagctgtc agaattttat ttcatttgac ttataaattt ttcgggtgct cttccttcaa  1440
cttttcaatg ttcacgtagt tcgtcatttt cctcatcggc ggtatggatg ctggacggtg  1500
gagattcgtc ttcctcctat aattagttgc ctgtatttgg aaactaattg aaagaaataa  1560
catgaagaag aaaaaaagaa agaaagagtg gtggatatac atgtacatga gaaagaaata  1620
gaaagtcaat gaaaaatcga ggaccgaagg ggaataatat aattcgaaaa aagtatatgt  1680
attatgtata gacatgtaag gtgtaacgta ctaacatgtt ggtgcatgaa taaaatttta  1740
tttagtaaaa atggatacaa cttaaaaaaa acagaaattt gggggaaaaa gttatcacaa  1800
ttatgaagaa caagttacta gtatatatat attaatgttt ttcttttaga aaacaaaagt  1860
attcttattt ttaagacttt taatttagaa aaatgattac cttaatacaa ctggatgaat  1920
tcgtattatt tattcaaatg gaaaactaca caagaacaaa tactatagtt ttgaggaaga  1980
ataaaagaaa actgaaaagg catgaatgtt tatttatatt attattacca acaacttttt  2040
aaaattatta catcacaagg gcatgacata atatgataaa cacagagatc cagagacatc  2100
ttcagatgtt ttcttagcta tactatagta tgaaaacaca gagatccaga gacatcttca  2160
gatgttttct tagctatagt atttatataa ttgtcaagtt atacggcttc aagttatggc  2220
tccttctgcg caaccagttc ctacaaggta aaatatatca ttgcaaatat tataatagtc  2280
tcgcatttgc atgtttaaat ctgttactat gatctatgat ttgctgatga tagtttcttt  2340
tacagtgttt cggatgagaa atacgcaaat gtgaagtggg aagagttagg gttcgggttt  2400
gttcgtacgg acaatatgta tgttgccaag tgcaaacatg gagagagttt ccaagaggga  2460
actgttgttc cttatgctga tttccaaatc agcccttgct ctgcagttct taattatggc  2520
caggtttgtt attaatcaat agagatcaaa cttattaaga aaaatttata tcatcagaaa  2580
gaagatataa ccatcaccat atatagaact aatatcgttt tagcattgca tgcatatttg  2640
agctattaga catttaaaat tttgaaaaga taatagaata taaatcaaac gaaatgattt  2700
aaaagtgtta atatgatgat attcttatca agtaaattgt ttcatcaaat aattactata  2760
atatgtttca attcaaagaa aatctagata tgtataacaa cataagtagt ctaactgccc  2820
ccattaaaat gaactaatga gctttcttaa aatatttatg aagaattaaa ttattagatg  2880
ctagattgag tgatgcggaa gcaaagtagt ctgaaatatt tgtaatttgg aaataaatag  2940
ggtttatatg aagggctgaa ggcttacagg acagaagatg gccggataat gatattccga  3000
ccagaccaaa acggtctccg ccttcaagcc ggagccaaga gactttgtat gccgtatcca  3060
tcggtcgatc aatttgtctc cgccgtcaaa caagttgttc ttgccaacaa gaaatgggta  3120
tgtacaggct cggttccaaa agaaaaaaat ctggaccgct caaaaaaacc aaactgtgtt  3180
ctacataaat tctaaatttt gaaattatgg tcgtgttagg cataattgta aaagaaaaaa  3240
aaatgcttta gaatgcttca aaaggcaaat aaatgtaatt tctatgcatt tttcaagata  3300
ttaaatctta acaaatgtat atattttaaa aattatatta atgttcttct ttgaatttta  3360
tatatataca gattcctcct ccggggaaag gaacattgta tatcagacct attttgttcg  3420
gaagtggtcc tatacttggc tcacttccgg tccctgagta caccttctca gtatttgctt  3480
gtcccgttgg acgttttcac aaggtgagtg ttcttgtcaa tatatattat ttttatttta  3540
gtttaaacag taatagacta gagcaatttt ttggaatgat tttgattata atatgttttc  3600
tggtatagga taactctggc ttgaacctga aaattgaaga taagtttcgc cgcgcttttc  3660
ctagtggaac cggtggtgtg aagagtatca caaactattc tcctgtaagt ttgaaaacgt  3720
acatcaaatt tgatattaac atgattagct gtgttttaga tttttgtatg aacgattaat  3780
agttaattaa tataacggat aatttttct taatgaaggt ttggataaca ttggcagagg  3840
cgaaagctca gggtttctct gatgttttgt ttttggatgc tgcaactggc aaaaacgtcg  3900
aagagctttt cgcttccaac attttcatag tcaaggtaat tatatatata aatatatata  3960
tatataatac gttttgaaag agttttaaag aatattaaga tcgatgtgat atggtctgta  4020
tagggaaatg ttgtgtcgac tccagaaatt tcaggaacta ttttgcccgg agtcacacga  4080
aaaagtatca ttgaattaac tcgtgatttc ggctacaagg tttgaatatt tcaataccat  4140
gatattataa tttttttttt ttttgaaaaa gggtttcatg atattataat tttatccatg  4200
ttgattttgt aaataatcta gtttttttttc cttggattct tattataata ggttgaggaa  4260
cgtgttgttc cccttgagga tcttctcgac tcggaagaag ttttctgcac tggcactgct  4320
gcgattgtga caactattgc gtccgtaacc ttcaaagaca aaaagtaatg ttttattcca  4380
catctaatca tttttctcaa caaaataaga agaaaaataa aacaaataca gaataactat  4440
accatgattt aaatctggat tttgctttat tctcatatat aagtttgact aaaaattggg  4500
tgtacatatt caatgcgtac aggaccggat tcaaaacagg agaaaaaaca ttggccgcga  4560
agctctttgc gacgttaatg gatatccaga tgggtcgggt cgaggataag aagggatgga  4620
cggtggaggt tgaccggtgc caccagggtt gaggatttgc ggtttgagta gagttgcttt  4680
ttgtgtaaga aactttgagt tgtctataaa gctttggact gcttctcttt atatattcgt  4740
tcacaacaat gtttattata ttaaaaatag taataattta ggcgaaaata ataaggatat  4800
tttctatcca tcttttttttg ttgttaaagc tttttttatcc attgttttaa gcaattaact  4860
tttattctat tctattatat cagttcaaag aataggcttt ttcttggcac aaaataatag  4920
gtttcaaatg tacatatata caacatatat ttgttaattg ataatcaaat gtatctcagt  4980
gatccgatta agtttatata tgcctaatgt tttttttatct atacgtttat ttaatattaa  5040
ccttatagct ctgtattttt tttttgatg tatttatata tgactaactt ttggttggtt  5100
atttcaccaa cttatttgtt tagagaaaaa taaattggga actctagtta gatcacagaa  5160
taatcatcac gtggagaaac ccatttgttt ctcgtcacgt ggagaaaacg ttaagcttta  5220
aaattttctt tttaattatt attatctcgc gggtatggct ggaagaaaga gagtgtttaa  5280
aatgtgaatg cgctcttagt taggtgaagg ttaataggta ggagggtagg tcaaatgtgt  5340
atcagtagtg atggataaaa aatttaaact gtagataatt tctaacaaaa aaacatataa  5400
```

```
taaattacat tttcactttt cagtatgcca caaacctata tatgattcaa aaagcatttt  5460
tctactcaga aagctgagag aagtaacaat tttggttatt agcaaaaaaa ttcgttcatg  5520
ttttttcttt tcttctgtca gtgtatttgt atgctcaact tctagtcttg attataccgt  5580
agtatgccac tactaattgt tgttttcttc atattgcaaa aacacttaaa attgcaaata  5640
tcggaccaat aagcaaaccc caaagtactt taaacgacca ctttctttgt tttttttatta  5700
ttagacattc aaagttgatt gtttcttact taacctaaac ttaggcagat aaaatattct  5760
tgaatataga tccatgactt gagtcactac tgcaacgaag gcgtctttag tttttgagcg  5820
aagtcgtgag agtttagctt ctcattcatc actctgaatt tctcttttat cctctttatc  5880
tgttcaaaac attaaaaaca aaagtatgtt attagcataa agctgtctca tacttggtta  5940
tacgtagacc atatttagtt tttcaatagc aaatacaaaa gtaaagcatg atcataagat  6000
tcagggtcaa ggtttggttt acccttctca gctcgatctc cgtgcttcgt ttcttttgat  6060
caagtgattg ccggagattc gtgatgtcga aaatactatc aaggtcgtct tcaaatgcgt  6120
tttccaactc ttcccggaga agagcaggta acttatcgac aataggcatc aggagaaaac  6180
agtt                                                              6184

SEQ ID NO: 6            moltype = AA  length = 356
FEATURE                 Location/Qualifiers
source                  1..356
                        mol_type = protein
                        organism = Thlaspi arvense
SEQUENCE: 6
MAPSAQPVPT SVSDEKYANV KWEELGFGFV RTDNMYVAKC KHGESFQEGT VVPYADFQIS  60
PCSAVLNYGQ GLYEGLKAYR TEDGRIMIFR PDQNGLRLQA GAKRLCMPYP SVDQFVSAVK  120
QVVLANKKWI PPPGKGTLYI RPILFGSGPI LGSLPVPEYT FSVFACPVGR FHKDNSGLNL  180
KIEDKFRRAF PSGTGGVKSI TNYSPVWITL AEAKAQGFSD VLFLDAATGK NVEELFASNI  240
FIVKGNVVST PEISGTILPG VTRKSIIELT RDFGYKVEER VVPLEDLLDS EEVFCTGTAA  300
IVTTIASVTF KDKKTGFKTG EKTLAAKLFA TLMDIQMGRV EDKKGWTVEV DRCHQG      356

SEQ ID NO: 7            moltype = DNA  length = 1080
FEATURE                 Location/Qualifiers
source                  1..1080
                        mol_type = genomic DNA
                        organism = Thlaspi arvense
SEQUENCE: 7
atggctccat ctgtgcagcc ttcttcatca cctcttcgta caagtgaagg agatgaaaaa  60
tacgcgaatg tgaaatggga agagcttgga ttcactctga ctccgacaga ttacatgtat  120
gtggcgaaat gcagacaagg agagagtttt tcagaaggaa agattgttcc ttatggggac  180
atttcaatca gcccttgttc tccgattctc aattatggcc agggactatt tgaaggtctc  240
aaagcttaca ggacagaaga cgaccggatc aggcttttca gacctgaaga aaacgctcgt  300
cgtatgcaaa caggtgcgga taggctttgt atgacaccac cttctctgga gcaattcgtc  360
gactcagtta agcaaaccgt gcttgccaac aagaaatggg ttcctcctcc gggtaaagga  420
gctttgtata taaggccttt gctaataggg agtggcgcta tacttggagt tgctccatca  480
cctgagtaca ctttcctcat ttacgcatct cccgtaggag attaccacaa ggtaagctca  540
ggcttgaacc taaaagttga tcataagtat caccgagccc attcgggtgg aacgggcggt  600
gtcaagagct gcactaacta ttctccagtt gtgaaatcga tggtcgaagc aaagtcgtcg  660
ggtttctctg atgtcttgtt cctggattcg gcaactggta gaaacatcga agaggtttct  720
gcttgtaaca tctttattgt caaggggaac attgtgtcca caccaccaac ttcaggaacc  780
attttaccag gaatcacaag gaaaagcata atcgagctag ctcgtgatct cagctaccag  840
gttcaagaac gtgatgtttc tgtggaggag ctcctagaag cagaggaagc tttctgcacg  900
ggaactgcag tggtcgtgaa agctgttgaa actgtgacct tccatgacaa gaaggtaaag  960
ttcaggacag gagaagcagc gttgtgcacg aagcttcact cgatgctgac gagtattcaa  1020
acaggtcttg ttgaagatac caaaggttgg atggtggaga tcgatccttg tcaaggttga  1080

SEQ ID NO: 8            moltype = DNA  length = 5021
FEATURE                 Location/Qualifiers
source                  1..5021
                        mol_type = genomic DNA
                        organism = Thlaspi arvense
SEQUENCE: 8
atgtccaatt tctctactcc tttcacctca aaactaagct tttcaaccaa aaccgaggga  60
ttagacccgt tcccatgatc atttacagga ggataaccaa cctcaatagt tacaaaaatg  120
gaatctccag gcctgtacac atctttatcc gtttgcacac ttagagtcgg tttgagattg  180
cttccaggaa cacccgaaga gtcattaacg tcgctagtac tgccgatccc caaaaatgaa  240
aaccttgatg ataacatagc ttcaacggct gtgttccttc acagatataa ctagcaaagc  300
agagaagctg actagactaa atccctgaga acagtttgat taggcataaa gcctgcgaaa  360
ttgacgaaag aagagtttag agaacagatg agcaaccctt tgaaggttat agaaaatgcc  420
tcaaacgtag aactgagagc aagtaaaaag agtcataagg tacaaaagaa agactcgcaa  480
tccagcgtgt ttcgaaatat cgatcataga tccagagaat gtgcagaggc ccagaaatta  540
gggtttctag ggagaagaag gtgacttaca cgtgatgacg agaatgatca cgtgagttgg  600
aggagcaaga aaaccagatt caaggttcgt caaattggca gcaagtagct taaagaatgg  660
caatcaaatc cagagagaag acgacgcgga tcgctaagat cataaaacca attccgaaca  720
gatgtcgctc acagtcagat tcacagagac tgagcttcta aaaaaaaaca gagacaccgg  780
aaaaaagtct tcaaagccga gagtccggca acagaatcct ccgccgtaag aaacggggaa  840
atgtccagaa aagcttaaag gttaagtttt ctgcagtaaa ccggaaaaga tgaattcagc  900
ttctcgagag caaaataacg aagcagctag tgaggtgatc cagctctata tttccccctct  960
cctaagcttc tctggtgctt caaaattgcc agtggtgtcc ttcttttgga ttttatcagg  1020
ttgaaattag atggatctgg ttgccgttga aggtttctct cgtcgggaaa tctggatcga  1080
agggacgatt gaaacaaaat gcttccccat ctggtttcgg caaatcttcc tcagcttctt  1140
cttcactcgg caaaaattat ggtcctctta tatgttattg ggcttctact tgggttcaat  1200
```

-continued

```
ggttctgttg ggtcctttga aaatttaatg ttcaaaaaaa aaacacaagt atatataacg  1260
tcgaaaaaaa caaatagagc catggtttag tttcaacaat gtctcataaa ttaaagaccg  1320
gtcacatctt tttttttttt ttgaaaataa gaccggtcac atcttttcaa caaagaacgg  1380
caactttagt ttatttagtc tttagccatc agccttttta tagtttgaag attctacgag  1440
tcatgtgtgt gtaaagggaa tataaacaaa atacgaaaga caaaaggaat caaagggttt  1500
gtttgttgtc gctataaaac gacgcgtgat aagccgctcc taaagcacgt gaccgctcta  1560
agcctctgct tcgcttcact tcacttctct ctctctcttt gtcttcctct ttccatggct  1620
ccatctgtgc agccttcttc atcacctctt cgtacaaggt taataaaatc atcaaccttt  1680
catgaaaatt tattggaaaa aaaagatttc ttttttttcat taaagtcgtg aatctcctga  1740
tctgggtatc tcgtgtttgt tcctgtcgtt tatttataac tattttattc atttgtgtga  1800
tttttataac ttttggtggc atgcattgaa atttaaaaca gtgaaggaga tgaaaaatac  1860
gcgaatgtga aatgggaaga gcttggattc actctgactc cgacagatta catgtatgtg  1920
gcgaaatgca gacaaggaga gagtttttca gaaggaaaga ttgttcctta tggggacatt  1980
tcaatcagcc cttgttctcc gattctcaat tatggccagg ttttgttctt acaatcactt  2040
atatggttgt gcaagcttgc tgaatctcac tggattatag gacttttggg tttcattaga  2100
gcatgattca ttaactagtg agggcgcaaa atgatccgca gattgcgtaa agctgtttta  2160
tttgagtgta tgagcgagca aaagtttaga actttagtgt ttatgtacat gcatgtgagg  2220
atttgagaga agaccttgcg atgattcatt agttagacgc tttcatcaaa aactattgag  2280
gggcgaaaaa tgaagattgt gtaaagttgt ttgctttgag tgtataaaag agcaaaagct  2340
ttgaacttta gtgtttgaga gaaaactttc ctctatgcgt ttggctttgt agggactatt  2400
tgaaggtctc aaagcttaca ggacagaaga cgaccggatc aggcttttca gacctgaaga  2460
aaacgctcgt cgtatgcaaa caggtgcgga taggctttgt atgacaccac cttctctgga  2520
gcaattcgtc gactcagtta agcaaaccgt gcttgccaac aagaaaatggg tatggactat  2580
gaactatgga ccaatgtctc tctattcaga tatgattctt gatctctaca agtttctaaa  2640
agtgtgttgt tatgtttttt tggttttttt atttggtttt aggttcctcc tccgggtaaa  2700
ggagctttgt atataaggcc tttgctaata gggagtggcg ctatacttgg agttgctcca  2760
tcacctgagt acactttcct catttacgca tctcccgtag gagattacca caaggttaga  2820
tttttgtgc tgctgttttt gaagcaaact ctgccaaaaa gactcgttaa atggttaagc  2880
cggtttttc tcaggtaagc tcaggcttga acctaaaagt tgatcataag tatcaccgag  2940
cccattcggg tggaacgggc ggtgtcaaga gctgcactaa ctattctcca gtaagtaaag  3000
agacaccaga aacatttcat ccatggcaac aggtttaggg aatatatata tgtttttctc  3060
tgatttcttc ttgtataaat tttgaaaagg ttgtgaaatc gatggtcgaa gcaaagtcgt  3120
cgggtttctc tgatgtcttg ttcctggatt cggcaactgg tagaaacatc gaagaggttt  3180
ctgcttgtaa catctttatt gtcaaggtaa ataatgagat tcaaaggctt atcacatcta  3240
atactgaaga tttttataca cttcgtagta atcattcaaa tttttagggg aacattgtgt  3300
ccacaccacc aacttcagga accattttac caggaatcac aaggaaaagc ataatcgagc  3360
tagctcgtga tctcagctac caggttgcaa caatttttaa ttcactctat atagttatac  3420
cctttcatat atatatatat atatagactc tgaggaggta gttcacaatg tgatcacagg  3480
ttcaagaacg tgatgtttct gtggaggagc tcctagaagc agaggaagct ttctgcacgg  3540
gaactgcagt ggtcgtgaaa gctgttgaaa ctgtgacctt ccatgacaag aagtaattag  3600
tttcttctat tttgcagata taaagaccct aacaatcaaa tctttcttgg gttacatagt  3660
gctgatacct cgggtcatgt ctgcctttga ccacagggta aagttcagga caggagaagc  3720
agcgttgtgc acgaagcttc actcgatgct gacgagtatt caaacaggtc ttgttgaaga  3780
taccaaaggt tggatggtgg agatcgatcc ttgtcaaggt tgaaaagctg ttgcaaaatt  3840
cgcttactcg ttctgtatcg tttcttttct cttagtgttt tcttttatga gacttgtaat  3900
gaagaactct taaaagataa ggtacaacaa ggtcgttcaa taagtgacta ggattcgtcc  3960
cggtccatat catttgcttt gttgttctcc actgtagcct agtagttaaa atgcataaaa  4020
cccatgatcc aaaaaatgat tcaatgaacc aatctaaatt tgtaagtttc atatattggt  4080
tgagtgatgt agcagaaatc tacaaagttt cattcgtaca aatacaaact taaaggacgg  4140
gagaatgaaa gatgtttggg caccgaccaa tcggttcaat tactgttttg actcgaatga  4200
aaaaagatat atttttaat ttttcacttt tttagaaatc gaaaactaaa aaaaaaaaaa  4260
tcattgacag ctgtgggatt tgaacccacg ccctttcgga ccagagccta aatctggcgc  4320
cttagaccac tcggccaaac tatcattgtt gacaagtttt tagtaatgtt taacttaact  4380
aaacatgtac tatcttcggt atttttgctt ttattattat tagggaagat tacacatata  4440
gcacaaattt attattttat tactagatta gcttttaatt ttttttttac tgactaaatt  4500
tttgtgtccg taatatccat taatcatttg ttatgaaaaa tcatatttac aagaatgcca  4560
ttattatttt tttctaactc agcaaaaaat agttaataat tacgaaaaat gccattatat  4620
tcgaaaaaat ctattgtacc agaactgcta atgtatgatg acatacttaa ttttataaac  4680
atacttattt ttagcagtac acttttgtca cagatttatt cagaataata gacttatatc  4740
aataagtctc tcatatgaag caatatactt ttttcagaga aaaggtattt ttgctgataa  4800
acttatttct tagacttgtt atgttttgac catagattta cttattttta ataaactaat  4860
tttttgtaat agacttattt cacatactta tattttgcac gatagactaa tatgtatatg  4920
agtgataact gataacagat ttaaatttta cgttctgaat gatgatagac ttatcgttag  4980
ttttgtatta gtctgctatc attaaaagac ttattttatt t                      5021
```

```
SEQ ID NO: 9            moltype = AA  length = 359
FEATURE                 Location/Qualifiers
source                  1..359
                        mol_type = protein
                        organism = Thlaspi arvense
SEQUENCE: 9
MAPSVQPSSS PLRTSEGDEK YANVKWEELG FTLTPTDYMY VAKCRQGESF SEGKIVPYGD  60
ISISPCSPIL NYGQGLFEGL KAYRTEDDRI RLFRPEENAR RMQTGADRLC MTPPSLEQFV  120
DSVKQTVLAN KKWVPPPGKG ALYIRPLLIG SGAILGVAPS PEYTFLIYAS PVGDYHKVSS  180
GLNLKVDHKY HRAHSGGTGG VKSCTNYSPV VKSMVEAKSS GFSDVLFLDS ATGRNIEEVS  240
ACNIFIVKGN IVSTPPTSGT ILPGITRKSI IELARDLSYQ VQERDVSVEE LLEAEEAFCT  300
GTAVVVKAVE TVTFHDKKVK FRTGEAALCT KLHSMLTSIQ TGLVEDTKGW MVEIDPCQG   359

SEQ ID NO: 10           moltype = DNA  length = 1551
```

```
FEATURE                Location/Qualifiers
source                 1..1551
                       mol_type = genomic DNA
                       organism = Thlaspi arvense
SEQUENCE: 10
atggcatcaa tcactttact gggccgaata ctagcaagac ccatcaaaac caaagaccgg  60
tctcgccagc ttcctcctgg tccacgagga tggcccatcc tcggcaatct acccgaactc  120
atcatgactc gtcctaggca caagtatttc gcccttgcca tgaaagagct caaatccgag  180
atcggatgtt tcaacttagc cggagtccac gccatcatca taaactccga cgagatcgct  240
agagaagcgt ttagagagcg agacgccgac ttcgcggaca ggcctgatct tttcaacatg  300
aggaccatcg gagacaatca caaatcaatg gggatttcac cttacggtga acaattcatg  360
aagatgaaaa gagtgatcac aacggagatt atgtccgtta aaacattgaa catgttgatg  420
gctgcgagaa ccatcgaagc ggataatctc attgcttacc ttctatcgat gtatcaacga  480
ggcgagacct gcgacgttag agaattctcg agggtttatg gttacacggt gaccatgaga  540
atgttgtttg gaagaagaca tgtcacgaga gaaaacattt tttccgatga aggaagacta  600
ggaaaagctg aaaaacatca tcttgaggcg attttcgaaa ccctaaactg tttgccgagc  660
ttttctcctg cggattacgt agaaaaatgg ttgcaaggat ggaacgtcga tggtcaagag  720
gagagggtga tagtgaatag taatattgtt cgtagttaca acaatccgat aatcgacgag  780
agggtcgcgt tatggaggga gaaaggtggt aaggctgctg ttgaagattg gattgatacg  840
ttcattacgc taaaagatga aaacggaaag tacttggtca cgccagacga aatcaaagct  900
caatgcgttg aattttgtat agcagcgatc gataatccgg caaataacat ggaatggaca  960
cttgcggaga tgttaaagaa cccggagatt ctgaggaaag ctgtgaagga gttagacgaa  1020
gtagtgggaa aagagaggct tgttcaagaa tcagacatac cgaatctaaa ctacttaaaa  1080
gcttgttgcc gagaaacatt caggattcac ccaagtgctc attatgtccc ttctcatgcg  1140
gctcgtcaag ataccactct cgggggatat ttcattccca aaggtagcca cattcatgta  1200
agccgtccgg gactaggccg gaaccctaaa atatggaaag atccattggt attcaaaccg  1260
gagcgccacc tcgaaggaga cggaatcaca aaagaggttt ctctggtcga gacagagttg  1320
cgtttcatct cgtttggcac cggtcgacgt ggctgcatcg gtgttaaagt cgggacgatc  1380
atgatggtta taatgttggc taggtttctt caagggttta actggaaact ccatcctgct  1440
tatggaccgt taagtctaga ggaagatgat gcattgctta tggctaagcc tctgctcttg  1500
tccattgagc cacgcttggc accaaacctt tacccaaaat tccgcccttg a           1551

SEQ ID NO: 11          moltype = DNA  length = 4847
FEATURE                Location/Qualifiers
source                 1..4847
                       mol_type = genomic DNA
                       organism = Thlaspi arvense
SEQUENCE: 11
gatattatcc ctaatataaa ttgcttcccg ctttcctgaa atatgttgat attcgattgc  60
aaacgtttgt tgtcgattat ccatatatag cgtaattgct ttatcgttgt actaatagtt  120
atttttgagt atttggtata taaaaaaaaa aattgtgtaa gaaaataata aaaatggttt  180
cttatagccg cttcggattt ccaaaaaggc aagaagggct ctttgtatgt atcatatatg  240
caaagatggt tacaacctaa atcagtgtaa gttaggtgga tattgattta ctgcatgtga  300
tgcactaatt ctatctgtta attgttcaga ataagatgtg tttttaacgt atactatata  360
gttggacttg gatcgaatct tcttttttt ttttcctttt tggatttctt gttgttcagt  420
tttggtttgt ttagaatcgt aaatttgact cagtttgact tttgattttc tcaaaccacg  480
gacacagcca caggacgaaa aacagaaaga aataaaacta catcatgaat ccaaatgatg  540
aaagtaattt ccattgaagc tgacgacact catggaaatt cgatagagaa catctaaacg  600
tggttaccta cccaagagct cccatctagt ttctattcca aaaattcctt tattctgaat  660
cactttttgc tttctctctc tctttcaagt gttgcacatt ttacatttat tcttttttt  720
tcattttctt ttaataagaa actactacta taatattaat gtagacaaat tcttaactaa  780
tatcatttat ttatcttttt ttcctttcaa aacaaacata tatcatttag tacatttatg  840
aaaacaccat tagattgatg tactttatga aaatatatta aactatcata ttaaaacata  900
tcctacttaa gagttttagg aatgattttc aatcatcagt ctcaccaaca taatttgcga  960
gtagggatcg gattaaccta tgggacctcc tcgatccacc tcatatggga atgggagagc  1020
ctccagtctc cacccaagga ctcaagtagc tagatagtaa gttagatagt gtgatacaag  1080
actgtagtac tgtacgctag gcacgtttgt tacgtgtgag tctgtgacag tgctctagtt  1140
ttgctaccca ttctacgtac ctcctacgta atggcgctaa gtggcagaac tatctgcctc  1200
agaaactagt tatcattatt tttcttctat tttgctaaac atgcttagaa attttgattt  1260
tatttagtta acaaatgtac aaattgaaat gaaacaataa agcttttcct attaaacatg  1320
attagccgct gaaaattaga tacaaaatat ataaacgtga tttccttaca gctagtacct  1380
acccataagc ccaaacccca cacgtgagca tcgcatgcgc atgaaatcga atctataaat  1440
acttgaaaca caagacaatt ccccaatatc aaattatcgc tagtgttcat tgctaacgag  1500
cacacagctc tctctacaca gacacacaaa catgatgacg atgctgagga gccttaccac  1560
atcattacca taccctttc aaatcctact agtctttatc atctccatgg catcaatcac  1620
tttactgggc cgaatactag caagacccat caaaaccaaa gaccggtctc gccagcttcc  1680
tcctggtcca cgaggatggc ccatcctcgg caatctaccc gaactcatca tgactcgtcc  1740
taggcacaag tatttcgccc ttgccatgaa agagctcaaa tccgagatcg gatgtttcaa  1800
cttagccgga gtccacgcca tcatcataaa ctccgacgag atcgctagag aagcgtttag  1860
agagcgagac gccgacttcg cggacaggcc tgatcttttc aacatgagga ccatcggaga  1920
caatcacaaa tcaatgggga tttcacctta cggtgaacaa ttcatgaaga tgaaaagagt  1980
gatcacaacg gagattatgt ccgttaaaac attgaacatg ttgatggctg cgagaaccat  2040
cgaagcggat aatctcattg cttaccttct atcgatgtat caacgaggcg agacctgcga  2100
cgttagagaa ttctcgaggg tttatggtta cacggtgacc atgagaatgt tgtttggaag  2160
aagacatgtc acgagagaaa acattttttc cgatgaagga agactaggaa aagctgaaaa  2220
acatcatctt gaggcgattt tcgaaaccct aaactgtttg ccgagctttt ctcctgcgga  2280
ttacgtagaa aaatggttgc aaggatggaa cgtcgatggt caagaggaga gggtgatagt  2340
gaatagtaat attgttcgta gttacaacaa tccgataatc gacgagaggg tcgcgttatg  2400
gagggagaaa ggtggtaagg ctgctgttga agattggatt gatacgttca ttacgctaaa  2460
```

```
agatgaaaac ggaaagtact tggtcacgcc agacgaaatc aaagctcaat gcgttgtaag  2520
taaaaaaaaa atttatttat tgttgatcat catcactaat tagatctata tttactgaat  2580
aattaataat ttaatatgac gatcatcgaa atatatatta ctgatgattc tactgaaaat  2640
ggttatgact tatgagtcat gagaacttta aaagatctgt tgcagccata tttttacaga  2700
tgattgtttg gatactactt acaaagttat aattaagtaa cttaaaaatc attttaaaag  2760
tacaaatatt tagtaataca aaaaatggat tagaaacaaa aaaaatggca tctattttga  2820
tatttttacg tgacgaatca acttttgatc attgtttggt gttttgttac aggaattttg  2880
tatagcagcg atcgataatc cggcaaataa catggaatgg acacttgcgg agatgttaaa  2940
gaacccggag attctgagga aagctgtgaa ggagttagac gaagtagtgg gaaaagagag  3000
gcttgttcaa gaatcagaca taccgaatct aaactactta aaagcttgtt gccgagaaac  3060
attcaggatt cacccaagtg ctcattatgt cccttctcat gcggctcgtc aagataccac  3120
tctcgggga tatttcattc ccaaaggtaa aacaaactgt gttttttcgt aggattttgc  3180
atttttatca ctagcaagtc aatacatgca tagtttagct taacatgtag ttgagccacc  3240
aataattcga tatgatactt atattaaaaa agtatcggtt ttggacaggt agccacattc  3300
atgtaagccg tccgggacta ggccggaacc ctaaaatatg gaaagatcca ttggtattca  3360
aaccggagcg ccacctcgaa ggagacggaa tcacaaaaga ggtttctctg gtcgagacag  3420
agttgcgttt catctcgttt ggcaccggtc gacgtggctg catcggtgtt aaagtcggga  3480
cgatcatgat ggttataatg ttggctaggt ttcttcaagg gtttaactgg aaactccatc  3540
ctgcttatgg accgttaagt ctagaggaag atgatgcatt gcttatggct aagcctctgc  3600
tcttgtccat tgagccacgc ttggcaccaa acctttaccc aaaattccgc ccttgagaaa  3660
agaacaagac tccttgttgt ttctctgttc tgttctacaa cgctttgtca ttactatgtt  3720
atgttacttt acttggcacc cagtcgtttg ttgttgtttt agactatcct tggctaaata  3780
tcgccatcgt ttcatttgtg tatttttttt ttctttttct atcactgtaa cttaataaca  3840
atcaaacatt ccgagtcatt atacttatag ccaataagtg aggatcagtt taataaagtt  3900
gagattgtta tagattataa tattaaatgg tgaatcctta cgtagacaat attaaaagtc  3960
gatggctcgt gccatggtta taaatattaa caatacttta agctattaaa tcagttagta  4020
cgtagacaaa taaaaattaa accgtttaat agagaaggtc ggtgcatggc cggatgtgat  4080
ggtgcggctc attttcttat aaatatcatt aatattattc tgttcatccc gcatttgttt  4140
tacccgtttt acaccatctt cattcgaaac ctcaactctt cagtcttcaa tatggagtat  4200
aatataacgt aaaactatct accataatta ttttcaaaaa aaaaaaaaac tatctaccat  4260
aatcatccta tattaaattt ttatatgtta acattatata ataatgcatt aaaccattaa  4320
ctctctaata tgtgtttgcc aaattaagtt cactttcgaa cagattaaat tatcttttca  4380
tttgaccctc ttatactgaa aattaattat tttggttata tttctgtaaa ttttgtaaga  4440
cgttaatgca ccgtaagtct ctcaaggaga atgaaggata tgcaatgtat attttattaa  4500
tataaagata ttgaactaat cacataatga tacatggtca aatacgtttt tttaagattt  4560
cttaaacaag aattttgtct ctcttctcct tttttattaa tttatatttt taattgttag  4620
aaattacgtt agatgcaact gatggaaata ttcttagatt ctagagatga atttgcttct  4680
gactaccgaa atggaaagat agaggcagga aagccagtaa gaaaatttca ttggaattgg  4740
tctgtcagat gagttaataa agcaatattg ttgacttttt tttttttttt tgaaagggta  4800
tagttctgag ttgtaaaatg gattgaatca aaagtttgat gatagac              4847

SEQ ID NO: 12           moltype = AA  length = 516
FEATURE                 Location/Qualifiers
source                  1..516
                        mol_type = protein
                        organism = Thlaspi arvense
SEQUENCE: 12
MASITLLGRI LARPIKTKDR SRQLPPGPRG WPILGNLPEL IMTRPRHKYF ALAMKELKSE  60
IGCFNLAGVH AIIINSDEIA REAFRERDAD FADRPDLFNM RTIGDNHKSM GISPYGEQFM  120
KMKRVITTEI MSVKTLNMLM AARTIEADNL IAYLLSMYQR GETCDVREFS RVYGYTVTMR  180
MLFGRRHVTR ENIFSDEGRL GKAEKHHLEA IFETLNCLPS FSPADYVEKW LQGWNVDGQE  240
ERVIVNSNIV RSYNNPIIDE RVALWREKGG KAAVEDWIDT FITLKDENGK YLVTPDEIKA  300
QCVEFCIAAI DNPANNMEWT LAEMLKNPEI LRKAVKELDE VVGKERLVQE SDIPNLNYLK  360
ACCRETFRIH PSAHYVPSHA ARQDTTLGGY FIPKGSHIHV SRPGLGRNPK IWKDPLVFKP  420
ERHLEGDGIT KEVSLVETEL RFISFGTGRR GCIGVKVGTI MMVIMLARFL QGFNWKLHPA  480
YGPLSLEEDD ALLMAKPLLL SIEPRLAPNL YPKFRP                             516

SEQ ID NO: 13           moltype = DNA  length = 1854
FEATURE                 Location/Qualifiers
source                  1..1854
                        mol_type = genomic DNA
                        organism = Thlaspi arvense
SEQUENCE: 13
atggagagaa agccctttga ggttgagacg acggagaatc acaaacccta ctccaccgtc  60
gatggcggtg gcgttggttc tgatttgaga tcgccggtcg attcatttga tgacgagcag  120
aaaaagctcg tttacagagg ctggaaagtc atgcctttta tcattggtaa tgagacattt  180
gagaagattg ggatcatagg gacattatca aaccttcttt tgtacctaac tcaagtattc  240
aaccttaaga aagttacagc tgcaacaatc atcaatgcct ttagtggcac aatcaacttc  300
gggactttca tcgctgcttt cctctgcgac acttactttg gtcgctacaa gactctcagt  360
gtagctgtca tcgcttgttt cctgggatcg cttgtgatat tactgacggc tgcagttcct  420
gcattgcacc cgactccatg tggaacacat agctggtgcc aagggccaag cccgggccag  480
atcgcgttct tgctgctggg tttagcgttt cttgtggtcg gtgcgggtgg gatcaggccg  540
tgtaacttgg cttttggagc tgatcagttc aaccccaaat ccgaatccgg gaagaaagga  600
atcaacagct tctttaactg gtatttcttc accttcacgt ttgcgcagat cgtctcgctc  660
acgctggtcg tgtatatcca gtcgaacgtg agctggacga tcggtttgct catccctgtg  720
gctctgatgt tcttggcctg cgtcatcttc tttgctggac ataaactgta tgtgaaagtg  780
aaagcctcgg gtagtccctt ggctagtatc ggtcacgtta tcacggcagc gatcaagaaa  840
cgagggttga agcaagttaa gcagccttgg ctcgatcttt acaaccacat tccaactaac  900
tatccaaact ccaccttgaa atacaccgac cagtttaggt ttcttgacaa agcagcgatt  960
```

```
atgacccctg aggacaagct gaattccgat ggagctgctt tcgatccatg gaccctatgt  1020
acattgcaga aagtggaaga agtgaaatgc attgtgagag tgattccgat ctggtttgct  1080
tgcgcgattt actacctcac tgtaactata cagatgactt atccggtctt ccaagcgcag  1140
cagagcgacc ggagattggg ttctggtggc ttcaagatcc ccgcagccac ctatgtggtg  1200
ttcttgatgt cgggtatgac tgttttcatc gtgttctacg accgtgtcct tgtcccgttg  1260
ctcagaagag tgaccgggtt agaaaccggt ttgaccctct tgcagagagt cggatcaggg  1320
atcttctttg ccatgttgag tttgttggtc tccgggttcg tagaggaacg gagaagaacc  1380
ttcgccctga cgaaaccgac tctcgggatg gagccacgag cgggagagat ctcctccatg  1440
tcggccatgt ggctgattcc gcagctcttg cttgcaggcg taggagaggc ttttacagcc  1500
attggacaga tggagtttta ttacaagcag ttccctgaga acatgaagag cttcgctggc  1560
tctatcttct atgtcggtgc aggtgtttcg agctatcttg ctagcttctt gatctcgact  1620
gttcatcgaa gaactgaaca ttcaccctcc gggaactggt tagctgagga tctgaacaaa  1680
gggagactcg attacttcta cttcatgctc accggaatca tggtcgttaa catggtttac  1740
ttcttgataa tgtctaaatg gtatagatac aaaggcatta acgatgaagc gaattctttg  1800
gtcgagacca atgaagaaga gaccaagcag aaacaagtca agaattctgt ctga        1854

SEQ ID NO: 14           moltype = DNA  length = 5463
FEATURE                 Location/Qualifiers
source                  1..5463
                        mol_type = genomic DNA
                        organism = Thlaspi arvense
SEQUENCE: 14
actccgggcg cgcatccgga ctctggagat tatggcggca ccacgagtaa gaccggatct  60
gctatcgtgc tagggttcgt gatctcgtgg tttccgagtc ccaagagaca gaggaggtgg  120
ctgagattgg attctctccc ataatctttc tccttagcgg ctcatttcct gtgtcccaga  180
cgcctttgcg atcctccgtg cgatggctct tcttctgatg cgcctatttg gtcaaactca  240
tggtttttgc cctttcttta ttttttacac tcgcagtttg tggtgggtgc atgctttcaa  300
acctacttgt agagaccttg ttgtacccct tgttctttca ggatttatta tataaataaa  360
caatgacttt ttcatgtttt atttttattt tttagtccta gaactttgac atgcacctta  420
atcgtacata tacgactaaa ctcgtgcttc aatcgaacag actttctaat ctggagtgag  480
caccataaat ctttgctata ccttatgaat gaactgaact tctgtgcgta tttttagtgt  540
gctgcggttt tccagaaaat gggtcaatgt atgactcgac tactgggatc cgcatgctct  600
tgttgtctgt tttatctgca ggaaacaagc gtttggcctg acacatacgt tcctgtgaca  660
gcgataatcg ttgctctgaa taacaggcac acagtatgag tgctcttgac tgggtggagc  720
tttggatgtc ttcaagggct ggctttgctt cgcttaagtc cctcgaaatg tgcatcttcg  780
ggatggcgac cttctaggga aagttgcttc tgagcctggt ggccgagccc atctccggga  840
gcgaggtttc ctctccgctc tactgctcct ttgttcttct gccatgtggc accccagaac  900
gactgttgtt gcctctgacc gccgtggatt ttaacatttt cggcgattaa ttgcttgact  960
acttcttttg tggtgttgta tatcaatatt tctcttttct tcttctaacg ataattatta  1020
agacataaat tataaaatcc gtacagaagt atgtgtttgt ctaaatgtta gaaattacgt  1080
tgttttcaag tttcatcttc tctaacttct catatctaaa caaatatata tctatatata  1140
ttctgttatg ccaaataaat atatatttag tttgtaataa aattatattt atttatatta  1200
tttattcata cggtatatat gataattatg ttaaaatatt atatcatatt ataaaaagtt  1260
ttaaaataat attaaaatta aattgactta cattatttta atattatata tgatttatta  1320
atattatctg ttaataaatt catataattt aatttatttt tttaaaaata aatttagtaa  1380
tatatttaat aaacatcatg gtagatttta gacattttat aaagtagggt ttgtctttta  1440
atagtaaaaa tcagttaaac agatcggaaa aatgagtcat tcacacatgt ctctatcctc  1500
cacagccaaa ttgaccattg tttgattttc cccttttgtc cagattcgga caattcccac  1560
tggatccatc cactatataa caagacgata gagcgaagct tgagatgaag agtagagtca  1620
tcctcagcca tagagagaga agagataaga agaataataa cattaacaac aaagacatct  1680
cctgtaattt cacacagatt gaaaccatgg agagaaagcc ctttgaggtt gagacgacgg  1740
agaatcacaa accctactcc accgtcgatg gcggtggcgt tggttctgat ttgagatcgc  1800
cggtcgattc atttgatgac gagcagaaaa agctcgttta cagaggctgg aaagtcatgc  1860
cttttatcat tggtaacgct ttttttctct cttcagacat cgtgtttttt tttttttttt  1920
tttttaatta cactctgttt tgtgtccctt tgtcggattt taaacacctc ccggagaaaa  1980
agaaatgaga aagtaaaatt caacattttg tccgtgattt gtttaatttc attctctttt  2040
tctcttctct ttgatttgac ctgactgtgt caaaaatcgt cgtgctttga gatttagaaa  2100
tgaaattgtt tctaaaaaaa cgagatttga ttgaaaccta gatcaaaacc agaggaaatt  2160
tcactagatc tagagaaaga aatattacaa ttgtttttct tttcaaatat ttttaatttt  2220
ccgccgaaag agactccgaa tcatgcaaga taagtggata agatttgaga attttgtacg  2280
gttgaagaca aagtttctgg gagttagatc agttattaga tgaattgtgt gtttccgttt  2340
caaagctgtg aattaaattt taaaagtttt attaccttat ttttggttta actaatcatt  2400
tatttttgtt tttttcttga caggtaatga gacatttgag aagattggga tcatagggac  2460
attatcaaac cttcttttgt acctaactca agtattcaac cttaagaaag ttacagctgc  2520
aacaatcatc aatgccttta gtggcacaat caacttcggg actttcatcg ctgctttcct  2580
ctgcgacact tactttggtc gctacaagac tctcagtgta gctgtcatcg cttgtttcct  2640
ggtactaaca attgatcttg aaatggaata ttataaacgt caagattcag tctttttctt  2700
tactaaaaaa ccattttttt acgtctttgt agggatcgct tgtgatatta ctgacggctg  2760
cagttcctgc attgcacccg actccatgtg gaacacatag ctggtgccaa gggccaagcc  2820
cgggccagat cgcgttcttg ctgctgggtt tagcgtttct tgtggtcggt gcgggtggga  2880
tcaggccgtg taacttggct tttggagctg atcagttcaa ccccaaatcc gaatccggga  2940
agaaaggaat caacagcttc tttaactggt atttcttcac cttcacgttt gcgcagatcg  3000
tctcgctcac gctggtcgtg tatatccagt cgaacgtgag ctggacgatc ggtttgctca  3060
tccctgtggc tctgatgttc ttggcctgcg tcatcttctt tgctggacat aaactgtatg  3120
tgaaagtgaa agcctcgggt agtcccttgg ctagtatcgg tcacgttatc acggcagcga  3180
tcaagaaacg agggttgaag caagttaagc agccttggct cgatctttac aaccacattc  3240
caactaacta tccaaactcc accttgaaat acaccgacca gtttaggtaa acccaacatt  3300
tctctctctc tctgtttcta tgttcccttt gcttttatat taatctcttg ctgagcaata  3360
ctggtttgtt atgtttgcta ggtttcttga caaagcagcg attatgaccc ctgaggacaa  3420
```

-continued

```
gctgaattcc gatggagctg ctttcgatcc atggacccta tgtacattgc agaaagtgga  3480
agaagtgaaa tgcattgtga gagtgattcc gatctggttt gcttgcgcga tttactacct  3540
cactgtaact atacagatga cttatccggt cttccaagcg cagcagagcg accggagatt  3600
gggttctggt ggcttcaaga tccccgcagc cacctatgtg gtgttcttga tgtcgggtat  3660
gactgttttc atcgtgttct acgaccgtgt ccttgtcccg ttgctcagaa gagtgaccgg  3720
gttagaaacc ggtttgaccc tcttgcagag agtcggatca gggatcttct ttgccatgtt  3780
gagtttgttg gtctccgggt tcgtagagga acggagaaga accttcgccc tgacgaaacc  3840
gactctcggg atggagccac gagcgggaga gatctcctcc atgtcggcca tgtggctgat  3900
tccgcagctc ttgcttgcag gcgtaggaga ggcttttaca gccattggac agatggagtt  3960
ttattacaag cagttccctg agaacatgaa gagcttcgct ggctctatct tctatgtcgg  4020
tgcaggtgtt tcgagctatc ttgctagctt cttgatctcg actgttcatc gaagaactga  4080
acattcaccc tccgggaact ggttagctga ggatctgaac aaagggagac tcgattactt  4140
ctacttcatg ctcaccggaa tcatggtcgt taacatggtt tacttcttga taatgtctaa  4200
atggtataga tacaaaggca ttaacgatga agcgaattct ttggtcgaga ccaatgaaga  4260
agagaccaag cagaaacaag tcaagaattc tgtctgatct gtaaaacttt tattattttt  4320
ggtcttctaa ttcagtctct actctttgtt gtttgtactc cattagagaa aatgaatgaa  4380
ggagaaatat aataatacct tagcgttttt gtcgaataag atttttctgc taaattcaaa  4440
ctgtgtatga agtttgttgt ttcgtcacga accactaaaa gaagactaca aggattgtga  4500
ttttttttat gtattaaagc caaaaagaga ggttctttta tgtatctttg tccaagaatg  4560
taaaagaaag aagaagaaaa aaaatggcca aatagttcgg aggacctctg caaaggtgtg  4620
aagaagaaga tgaggttatc cagaaatgtt ttcttcttct cttctccgtc tttataaatt  4680
acattggaaa attattcagg acgaatcgag aggtagaagc tttccttcag gcattgctat  4740
atacaaaata tttgggttat tttcgtgtgg gagattgatt tagctgagga aagctttata  4800
cttttattat cttctggtct ctaaagttgc ttagaaggtc ttagagattg gggaaatcac  4860
aattaccaat caagtgccaa gctcgaaagt agcaaggatt gtgataaagt cgttggataa  4920
tagaccgttg cttctgtatt gcctagtgga tatttcctga gttaaagatg ggtacacaat  4980
aaagggtgga caaaaagtag gcggggtctt agacttgatt tggcaaatga caatcactta  5040
tataagctaa tggcaacata accgtctctc tcaccaatac atgccgaatt tgaagcactc  5100
tgatttgagc cagtactaaa aacatggagc ttgaacctga gcttgaaact gatggaaaag  5160
agcttatagc cgatgttgga cagtttaaag ccgaggtaaa acagtttgag gccgaggtga  5220
aagagttagt agccgaggta agacagctgg aggccgagct gacgcaactt gaagccgagg  5280
tgaagcaaga tacttcggat gagcttgtag cagaggataa gcttgtagct gaggaagcag  5340
ttcgtcttgg agttaatcgt gagacaaaat agagaagaca tgatcctaaa cctccctggt  5400
ttttgatcca aagaatatca acaaatggac aagtggttca taagcactct ttttccctta  5460
ctt                                                                5463
```

```
SEQ ID NO: 15          moltype = AA  length = 617
FEATURE                Location/Qualifiers
source                 1..617
                       mol_type = protein
                       organism = Thlaspi arvense
SEQUENCE: 15
MERKPFEVET TENHKPYSTV DGGGVGSDLR SPVDSFDDEQ KKLVYRGWKV MPFIIGNETF  60
EKIGIIGTLS NLLLYLTQVF NLKKVTAATI INAFSGTINF GTFIAAFLCD TYFGRYKTLS  120
VAVIACFLGS LVILLTAAVP ALHPTPCGTH SWCQGPSPGQ IAFLLLGLAF LVVGAGGIRP  180
CNLAFGADQF NPKSESGKKG INSFFNWYFF TFTFAQIVSL TLVVYIQSNV SWTIGLLIPV  240
ALMFLACVIF FAGHKLYVKV KASGSPLASI GHVITAAIKK RGLKQVKQPW LDLYNHIPTN  300
YPNSTLKYTD QFRFLDKAAI MTPEDKLNSD GAAFDPWTLC TLQKVEEVKC IVRVIPIWFA  360
CAIYYLTVTI QMTYPVFQAQ QSDRRLGSGG FKIPAATYVV FLMSGMTVFI VFYDRVLVPL  420
LRRVTGLETG LTLLQRVGSG IFFAMLSLLV SGFVEERRRT FALTKPTLGM EPRAGEISSM  480
SAMWLIPQLL LAGVGEAFTA IGQMEFYYKQ FPENMKSFAG SIFYVGAGVS SYLASFLIST  540
VHRRTEHSPS GNWLAEDLNK GRLDYFYFML TGIMVVNMVY FLIMSKWYRY KGINDEANSL  600
VETNEEETKQ KQVKNSV                                                617
```

```
SEQ ID NO: 16          moltype = DNA  length = 1842
FEATURE                Location/Qualifiers
source                 1..1842
                       mol_type = genomic DNA
                       organism = Thlaspi arvense
SEQUENCE: 16
atggagagac agcctctcga actcgagtct acggatcacc aaaaaccttc ccccgccgtc  60
tacggtggct ctgttacgac ggttgattct gttgaggaag aagttcagga gaaaaaagtc  120
gtatatagag gctggaaagt catgcccttt atcattggaa atgagacatt cgagaagctt  180
gggatcattg gaacactatc aaaccttctg gttttttaa cagctgtctt caacatgaag  240
agtatcacag ctgcaacaat cattaacgca ttcagtggca caataaattt cggaactttc  300
gttgctgctt tcctctgcga cacttacttc ggtcgataca agacactaac cgtcgcggtc  360
atcgcctgtt ttcttggatc acttgtgata ctattgacag ctgcagtgcc acaactgcac  420
ccagctccat gtggaacagc gagctcgtgc agcggtccaa gcggtgggca aatcgcgttt  480
cttctgatgg gtctcgggtt tcttgtagtt ggagcgggcg ggatcagacc gtgcaatcta  540
gctttcggag ccgatcagtt caacccgaag agcgagtcag ggagaagagg gactgatagt  600
ttcttcaatt ggtacttctt cagcttcact ttcgcgcaga tcttgtcgct gacgctagtg  660
gtctacatcc agtctaacgt cagctggacg atcggtctaa ccataccggt ggttctaatg  720
ttcttggcct ccgtgatctt ctttgcggga gataagctgt atgtgaaagt caaggcctcg  780
ggtagtccat tggctggtat agctcaagtg atcattgttg caatcaagaa acgcggatta  840
aagcccgtga aacagccttg gcttaacctc tacaattact gccctccaaa acacgcaaac  900
tccattctca aatacaccga ccaattcaga tttcttgata aggcggcgat cttggctccc  960
gaggacaagt tggaggcgga tggtaagcct gcggatccat ggaagctgtg tacgatgcaa  1020
caggtggaag aagtgaagtg cattgtgaga gtgcttccta tatggttcgc tgcatcaatc  1080
tactacgtaa ccataaccca gcaaatgaca tatccggtct tccaagccct gcagagcgat  1140
```

```
cgtcgcttag gctcgggagg gttcgtgatc cccgcagcca cctacgtggt cttcttgatg  1200
acagggatga cggttttcat catcatctac gaccgtctcc tcgtgcctac cttgagaaga  1260
ataaccggtc tagacaccgg gatcacgctc ctgcagagaa tcggaaccgg gatcttcttc  1320
gcctttgcaa gcttagtagt ctccggtttc gtcgaggagc ggaggagaca cattgcgctg  1380
actaaaccaa ctcttggcat ggcgccaaga aaaggagaaa tctcctcaat gtcagctatg  1440
tggctcatcc cgcagctcac tctctcgggt gtagccgagg cgtttggagc catcggacag  1500
atggagtttt actacaagca gttcccagaa aacatgagga gtttcgcggg ttccatcttt  1560
tatgtaggaa taggggtttc gagttacctc ggcagcttct tgattgcaac ggttcaccgg  1620
acgacgcaga actcggcggg tggtaactgg ttggctgagg atttgaacaa aggcagattg  1680
gattacttct atttcatgat cgctggaatc ttggctgtta atttcgccta cttcttggtc  1740
gtgtcaagat ggtataggta caaagaaagt gatgatgatc aaaagacagc ttctgaaacc  1800
aatggagatg tcatcaaaca acaagacaag aacactgcct ga                     1842

SEQ ID NO: 17           moltype = AA  length = 613
FEATURE                 Location/Qualifiers
source                  1..613
                        mol_type = protein
                        organism = Thlaspi arvense
SEQUENCE: 17
MERQPLELES TDHQKPSPAV YGGSVTTVDS VEEEVQEKKV VYRGWKVMPF IIGNETFEKL  60
GIIGTLSNLL VFLTAVFNMK SITAATIINA FSGTINFGTF VAAFLCDTYF GRYKTLTVAV  120
IACFLGSLVI LLTAAVPQLH PAPCGTASSC SGPSGGQIAF LLMGLGFLVV GAGGIRPCNL  180
AFGADQFNPK SESGRRGTDS FFNWYFFSFT FAQILSLTLV VYIQSNVSWT IGLTIPVVLM  240
FLASVIFFAG DKLYVKVKAS GSPLAGIAQV IIVAIKKRGL KPVKQPWLNL YNYCPPKHAN  300
SILKYTDQFR FLDKAAILAP EDKLEADGKP ADPWKLCTMQ QVEEVKCIVR VLPIWFAASI  360
YYVTITQQMT YPVFQALQSD RRLGSGGFVI PAATYVVFLM TGMTVFIIIY DRLLVPTLRR  420
ITGLDTGITL LQRIGTGIFF AFASLVVSGF VEERRRHIAL TKPTLGMAPR KGEISSMSAM  480
WLIPQLTLSG VAEAFGAIGQ MEFYYKQFPE NMRSFAGSIF YVGIGVSSYL GSFLIATVHR  540
TTQNSAGGNW LAEDLNKGRL DYFYFMIAGI LAVNFAYFLV VSRWYRYKES DDDQKTASET  600
NGDVIKQQDK NTA                                                     613

SEQ ID NO: 18           moltype = DNA  length = 5002
FEATURE                 Location/Qualifiers
source                  1..5002
                        mol_type = genomic DNA
                        organism = Thlaspi arvense
SEQUENCE: 18
tgccatgaat ctctgaactg gagtgaacaa aacctttttg tatatcgttg atcgcatttc  60
tttgacaact acaagcaact aaatatgaaa gcatatgctt gaggatttta tttgaggatc  120
aaattggtaa aatgaaagag attaaagttg aattgaagcc caagttgaag agattgaaat  180
aatggcacac atcccttatt ggtgtcatgt ctgactaatt ttaccaacat ggcaacatct  240
cataagtaat attgaatatc aggctttgtg atttctacaa ttaattttaa cagttttaac  300
tgatatggtc caagactcgc tattgaatag aaatcaaaaa gccatatcca acatctctgt  360
taaatgtagt cttaggtcgg ttacttgtat acgttttaaa tgattcaaaa aattggcgcc  420
tcatcattta tccgattgta gagtaaaatt aaaataatat cataagaaat tataattttc  480
tctaatccac aaagattgtc ttacatctta tgtactttat attacaatat agagcaatat  540
atctgaatta gtctttggaa aaaaaatctg aatcaaataa aatcgaacgc aagtaaaatt  600
cttaaaataa cttctagtat gtaaaaaata ttcttatttt ctggttaaag tacacgtaaa  660
aattatataa attactagaa tatatattca tgacaaaaga gtataagtat agtatataac  720
ctcgaaatca taacaagaaa atttaatgaa gatggatata tatatagtat acagtcgaaa  780
aataaagaga agaagaagaa gaagaagata aataaataaa taagaaaatg gatgatggaa  840
aacaatttga agaagaagaa gataaataaa taaataagaa aatggatgat ggaaaacaat  900
ttgactgaaa gtggacggag agcttaaaga acgtgccgtt attaagaggg agtgttatga  960
tggggccaag ggcacttgaa atggaatcta cattttcatg tatttttttt ctgtttcttt  1020
tgaagagaag tttatttttt ttgtaagaaa aggagaaaag ataattaata aaaaatgtaa  1080
tattttaatc tctaacacag ctctctttca cggccaaatt cacaaattac cactttgtct  1140
agattccggc atctccacca tcctcttcct tcttaccact atatagtcta taaatagaga  1200
cggctctaag ataaagaaca gagtcatcat tagcctttga gacaaataca acagacaaaa  1260
caaggaagta caatttaaaa aaaatggaga gacagcctct cgaactcgag tctacggatc  1320
accaaaaacc ttcccccgcc gtctacggtg gctctgttac gacggttgat tctgttgagg  1380
aagaagttca ggagaaaaaa gtcgtatata gaggctggaa agtcatgccc tttatcattg  1440
gtaaatattt accgttttta acactttttt ttcttggtcc tggaaactat ttttttcagt  1500
tggattcatg tagttaggaa ttacccataa aatcataaga aaaagatcga aaacatcagt  1560
cttgctcgaa gacttgcttg gtttgaattt tttttttttt tttaaatttg aaagattctc  1620
tgtgttgttt gtcttaagct ttgacttagt caaacagtaa cttaagacaa aaagaaggac  1680
atcttgaaat tgaggagatt ttataacata actaatcaag aattaatttt aaaacacaga  1740
tttcatctaa ctgtttgatt cttggtttgg tttctgatac aatcaaatgc aaagcttgaa  1800
acttaatctt catttttgtt gttgttatca ggaaatgaga cattcgagaa gcttgggatc  1860
attggaacac tatcaaacct tctggttttt ttaacagctg tcttcaacat gaagagtatc  1920
acagctgcaa caatcattaa cgcattcagt ggcacaataa atttcggaac tttcgttgct  1980
gctttcctct gcgacactta cttcggtcga tacaagacac taaccgtcgc ggtcatcgcc  2040
tgttttcttg taaaaaccca tcctttcttg tcttgtcttt cttcctccac aagcatatat  2100
atacaagcgg aaaaaactta tcggtgaaat ggtttctttt tgtagggatc acttgtgata  2160
ctattgacag ctgcagtgcc acaactgcac ccagctccat gtggaacagc gagctcgtgc  2220
agcggtccaa gcggtgggca aatcgcgttt cttctgatgg gtctcgggtt tcttgtagtt  2280
ggagcgggcg ggatcagacc gtgcaatcta gctttcggag ccgatcagtt caaccccgaag  2340
agcgagtcag ggagaagagg gactgatagt ttcttcaatt ggtacttctt cagcttcact  2400
ttcgcgcaga tcttgtcgct gacgctagtg gtctacatcc agtctaacgt cagctggacg  2460
atcggtctaa ccataccggt ggttctaatg ttcttggcct ccgtgatctt ctttgcggga  2520
```

```
gataagctgt atgtgaaagt caaggcctcg ggtagtccat tggctggtat agctcaagtg  2580
atcattgttg caatcaagaa acgcggatta aagcccgtga aacagccttg gcttaacctc  2640
tacaattact gccctccaaa acacgcaaac tccattctca aatacaccga ccaattcagg  2700
taaccaaaaa acttaaactt gttttccttt aagagtcttt tttattgtca ggatgttctt  2760
tactcagaga aaggttcctg ttttgggcag atttcttgat aaggcggcga tcttggctcc  2820
cgaggacaag ttggaggcgg atggtaagcc tgcggatcca tggaagctgt gtacgatgca  2880
acaggtggaa gaagtgaagt gcattgtgag agtgcttcct atatggttcg ctgcatcaat  2940
ctactacgta accataaccc agcaaatgac atatccggtc ttccaagccc tgcagagcga  3000
tcgtcgctta ggctcgggag ggttcgtgat ccccgcagcc acctacgtgg tcttcttgat  3060
gacagggatg acggttttca tcatcatcta cgaccgtctc ctcgtgccta ccttgagaag  3120
aataaccggt ctagacaccg ggatcacgct cctgcagaga atcggaaccg ggatcttctt  3180
cgcctttgca agcttagtag tctccggttt cgtcgaggag cggaggagac acattgcgct  3240
gactaaacca actcttggca tggcgccaag aaaaggagaa atctcctcaa tgtcagctat  3300
gtggctcatc ccgcagctca ctctctcggg tgtagccgag gcgtttggag ccatcggaca  3360
gatggagttt tactacaagc agttcccaga aaacatgagg agtttcgcgg gttccatctt  3420
ttatgtagga ataggggttt cgagttacct cggcagcttc ttgattgcaa cggttcaccg  3480
gacgacgcag aactcggcgg gtggtaactg gttggctgag gatttgaaca aaggcagatt  3540
ggattacttc tatttcatga tcgctggaat cttggctgtt aatttcgcct acttcttggt  3600
cgtgtcaaga tggtataggt acaaagaaag tgatgatgat caaaagacag cttctgaaac  3660
caatggagat gtcatcaaac aacaagacaa gaacactgcc tgatcattat gggtttctca  3720
tcttctcgac ttagtttttg gtcagcttcg atccccttttg gattttcttg gaataagccc  3780
atagagaaac caagtaatca tcatatactt gttctcgctc ttttttttc ttttcctcgt  3840
ttatatttaa atcacttctc tttctttcta tcattgtgga caaaaaggga aattataaca  3900
tcaaatgtaa tgcaaaaata aaaaaaaatt tgtcttacac tttgaggatg ctgtttctat  3960
ttctgccatt cttcatcata caagagaaca aacttacaag aaggaaacaa accgaccaaa  4020
taatactact aaggcctttg atacttatat gcataatttg tatcgaagtt tcaaacagag  4080
atattgagac gagtcgtggg ctttctctct acgattttgt cagactgtgt aagattgttg  4140
aatggtttca atgtcgagac cttttagcct cacgacagat tcaacgtgac ccttgagtgt  4200
gtgaagctcc cgcaacctat caaagtgtaa gagagaatga gacaaatcac aaatgttccg  4260
gttcgaccaa aacaaagcaa aaacaaacgt tccggttttg tgttccttct ctgaccctca  4320
cggctcacag gaagaaacta ggcttaccta gcgatctcgg ctcttctctt tgcttcttca  4380
gccatttggg aaagctcgtt gaaatgggtt cgctctggga acattttagc atctggtgct  4440
tgcaggccat gtagcgttct ctgtgcgtgc gcccattgta gctccctttg ttctttccca  4500
aaatccttct gcctcgtgaa tgcaatctat ggaaacgagt ttacatgaaa gatcaagtac  4560
agataaagaa aatggaaaga ggtgaaatga gaagaaaata tgtttgcttt ttgatactta  4620
ccctttgctc aataacaagg tcccaggctc tgccgctaag ggcgtaccga atcaagaact  4680
tgatgatatc aagaggaata tagaacacaa tgttgtagag ccaaatgacc ccggcccatc  4740
cccacccgat cccttcgatc gcagcaaagc tccaattcgc atagacggca attagagtag  4800
ccacctgttt ggaagaaaat ggtcaagaaa acagtgattt caaaacttct tacttgagtg  4860
ctgaccacag atagtgtgta gtgtcacact aaccaattgt gcgacgataa aggctatcac  4920
aagcaacatc ccaggacgtt ccacataaga ccaactccgt gaccgggtca caaagattag  4980
cgcctgacta ataatgctga ct                                            5002
```

```
SEQ ID NO: 19          moltype = DNA  length = 1110
FEATURE                Location/Qualifiers
source                 1..1110
                       mol_type = genomic DNA
                       organism = Thlaspi arvense
SEQUENCE: 19
atgtcaagaa agccgtgttg tgtcggagaa gggctgaaga aaggggcatg gaccaccgaa  60
gaagacaaga aactcatctc ttacatccac gagcacggtg aaggaggctg gcgcgacatt  120
ccccaaaaag ctgggttgaa acggtgtgga aagagttgta ggctgcgatg gactaactac  180
ctaaaacctg agatcaaaag aggcgagttt agttcagagg aggaacagat tatcattatg  240
cttcatgctt ctcgtggcaa caagtggtcg gtcatagcga gacatttacc tagaagaaca  300
gacaacgaga tcaagaacta ctggaacacg catctcaaaa aacgtttgat cgaacagggt  360
gttgatcccg tgactcacaa gcctctagct tccaactccg gccctactgc caccacgccg  420
cctgagaatt tgcatttcct agatgaatct agctcagaca agcaatactc tcggtcgagc  480
tcaatgcctt ccctgtctcg tcttccttcc tccggattca acacggtttc cgagatagcc  540
agcaatgttg ggacaccagt tcaggtcggt tccttgagtt gcaagaaacg ttttaagaaa  600
tcgagttcga catcaaggct tctgaacaaa tttgcggcta aggccacttc catcaaagat  660
atattgtcgg cttccatgga aggtagctcg agtgctgcta ctacaatatc acatgcaagc  720
tttttaaatg gcttttctga gcagagtcgc aatgaagagg atagttctaa cgcatccctg  780
acaaatactc tagccgaatt tgatcccttc tctcagtcat cgttgtaccc ggagcatgag  840
atcaatgtta cttctgatat cggcatggac caggtttacg atttctcaca atttctcgaa  900
aagctcggga gtgaaggcca caacgaactg aatgtcgagt atggtcatga tcttcttatg  960
tccgatgttt cgcaagaagt ctcatcacct agcgttgatg atcaagacaa tatgattgga  1020
agcttcgaag gttggtcaaa ttatcttctt gaccatgctg attttatata tgacaccgac  1080
tcagattccc tcgaaaagca tttcatgtga                                    1110
```

```
SEQ ID NO: 20          moltype = DNA  length = 2745
FEATURE                Location/Qualifiers
source                 1..2745
                       mol_type = genomic DNA
                       organism = Thlaspi arvense
SEQUENCE: 20
ccacattgga tccatgttat ttattgtgtg tgcaaactca ttcaattcca tgtataatac  60
tcataaattc atttaatttg atactccaat ttttttattc tatgaaaatt gaatatttaa  120
taatttaggg ttattaattt aatataattt atctagtaag aaagcgcatt ttcctaacca  180
aaataaatat atatatatat ataccaaaat atagtaatat acaacatcgc tttgcaaaca  240
```

```
ttgttcttat aaaaaaagaa taacgaacta gctataacta attaatctat ttaaaataag  300
aataatttac atactctgtg tatatatata gaggagcata gctcgtaagc tcaccaccat  360
cacacaatcc atgcctcttg gtttttcttc ttcagcttct tgattctaat cttagtgtcg  420
taatattata agaataggac aaaaaaaaag atttggggct ctacgtgaaa aacatgaaaa  480
cgcctagcag ctctgtggga aagacccaag agcgtttctc gattagtctc atattcagat  540
gcatcagagt tctcataaac agatctattt cttacttatc tttttagaaa aattcctttc  600
aaattttact ttccttaaga atagtgttct ctacattttt tttcttgggt gttcgtgaga  660
ggttatatga attttttgtc attagtgttc atatcggaag aagatgtcaa gaaagccgtg  720
ttgtgtcgga gaagggctga agaaaggggc atggaccacc gaagaagaca agaaactcat  780
ctcttacatc cacgagcacg gtgaaggagg ctggcgcgac attccccaaa aagctggtta  840
atatctctat taaaatctat acatgttcaa ttagtatttc ttgtatgaaa tttttataat  900
caatatggtg ttaactaaat agggttgaaa cggtgtggaa agagttgtag gctgcgatgg  960
actaactacc taaaacctga gatcaaaaga ggcgagttta gttcagagga ggaacagatt  1020
atcattatgc ttcatgcttc tcgtggcaac aagtacgttt ctatgtttaa atgtgtgtgt  1080
atatatgtat cctcgaataa acaatgaaat gcatgaaaag gtttcatata tattacttta  1140
attaaagata caattattat tctaatatcg tgtcttccat attatatttt aatcgccttt  1200
gatctttgaa tctcttcttct tatcgttagg tggtcggtca tagcgagaca tttacctaga  1260
agaacagaca acgagatcaa gaactactgg aacacgcatc tcaaaaaacg tttgatcgaa  1320
cagggtgttg atcccgtgac tcacaagcct ctagcttcca actccggccc tactgccacc  1380
acgccgcctg agaatttgca tttcctagat gaatctagct cagacaagca atactctcgg  1440
tcgagctcaa tgccttccct gtctcgtctt ccttcctccg gattcaacac ggtttccgag  1500
atagccagca atgttgggac accagttcag gtcggttcct tgagttgcaa gaaacgtttt  1560
aagaaatcga gttcgacatc aaggcttctg aacaaatttg cggctaaggc cacttccatc  1620
aaagatatat tgtcggcttc catggaaggt agctcgagtg ctgctactac aatatcacat  1680
gcaagctttt taaatggctt ttctgagcag agtcgcaatg aagaggatag ttctaacgca  1740
tccctgacaa atactctagc cgaatttgat cccttctctc agtcatcgtt gtacccggag  1800
catgagatca atgttacttc tgatatcggc atggaccagg tttacgattt ctcacaattt  1860
ctcgaaaagc tcgggagtga aggccacaac gaactgaatg tcgagtatgg tcatgatctt  1920
cttatgtccg atgtttcgca agaagtctca tcacctagcg ttgatgatca agacaatatg  1980
attggaagct tcgaaggttg gtcaaattat cttcttgacc atgctgattt tatatatgac  2040
accgactcag attccctcga aaagcatttc atgtgaatcc tcgtatccaa acggaaaggt  2100
ttcaaactat ttaaaacttt cctgaaccac aatttatgta tgtctttctt atttggaact  2160
tttagtatat gtccaagtct ccaagatctc atggttattt aatcccaggt ttagggtttg  2220
tgtgatgtta agtaagggtg aatctttata tatgaattag ggtttctctg acattgagaa  2280
ccatgcattg cggatcaatt ggtaattgat tgcacgagcc acgatgtttc ttttataatg  2340
tttattacta ataaagcttg ttttgttatc gtatttcata atagcatcca ttatcatcat  2400
tttttttggg tttatactta aagtccacat tccatcataa acatcaatca tgcacttttt  2460
tggttttcat actcttcttt atgattaaat aattgtttcc aactttccat ggcatgaagg  2520
tggttgtatc tttcgttgga tctgaaccga ccacaatata ataaataagt aagtttttaa  2580
aataaatgat aaaaaaaggc tcaaacgaca gagacgttcc aagaaaaagt gtaaacgtgt  2640
ggtccataaa caattgagac gaaagctaaa gatcaagagg tgaattaagc agataactgg  2700
aattttgtga cccgacaaat attatcttaa aacgaaatct aatgt             2745
```

```
SEQ ID NO: 21          moltype = AA  length = 369
FEATURE                Location/Qualifiers
source                 1..369
                       mol_type = protein
                       organism = Thlaspi arvense
SEQUENCE: 21
MSRKPCCVGE GLKKGAWTTE EDKKLISYIH EHGEGGWRDI PQKAGLKRCG KSCRLRWTNY  60
LKPEIKRGEF SSEEEQIIIM LHASRGNKWS VIARHLPRRT DNEIKNYWNT HLKKRLIEQG  120
VDPVTHKPLA SNSGPTATTP PENLHFLDES SSDKQYSRSS SMPSLSRLPS SGFNTVSEIA  180
SNVGTPVQVG SLSCKKRFKK SSSTSRLLNK FAAKATSIKD ILSASMEGSS SAATTISHAS  240
FLNGFSEQSR NEEDSSNASL TNTLAEFDPF SQSSLYPEHE INVTSDIGMD QVYDFSQFLE  300
KLGSEGHNEL NVEYGHDLLM SDVSQEVSSP SVDDQDNMIG SFEGWSNYLL DHADFIYDTD  360
SDSLEKHFM                                                        369
```

```
SEQ ID NO: 22          moltype = DNA  length = 1080
FEATURE                Location/Qualifiers
source                 1..1080
                       mol_type = genomic DNA
                       organism = Thlaspi arvense
SEQUENCE: 22
atgtcaagaa agccatgttg tgtgggagaa gggctgaaga aaggagcatg gaccgccgaa  60
gaagacaaga aactcatctc ttacatccat gaacatggcg aaggaggctg gcgtgacatt  120
ccccaaaaag ctggactaaa acgatgtgga aaaagttgta gattgcgatg ggctaactat  180
ttgaaaccgg atatcaagag aggagaattt agctacgagg aggagcagat tatcatcatg  240
cttcacgctt cccgtggcaa caagtggtcg gtcatagcga gacatttgcc caaaaggaca  300
gacaacgaga tcaagaacta ttggaacaca caccttaaaa aacgccttat cgatcaaggt  360
attgatcccg tgacccacaa gccacttgcc cctagcccta gtccggccac gctcaagcct  420
tctgatttcc aagatgactc atcaaacctg ggaaactcgg atgagcattc acattcgggt  480
tctatgtctc caaaatctct tcctccgtct tcaagctcct gcaatctagc ggagataagc  540
agcagtgatg agacaccgaa aaatgatggt tccttgaaat ccaagaaacg ttcttttaag  600
agatcaagtt ctacatcaaa gctgttaaac aaagttgcat ctagggctgc ttccattgga  660
aatatcttat cagcgtccat ggaaggaacc ttggttagct ctaccgcact gtctccatgt  720
ctcaatgatg acttttccga agctagccaa ttccagatgg acgaatatga tccattccct  780
cagtcgtctg aacacataac tgatcatatg aaggaggaca ccggcatgat ctttgatctc  840
aacaactccg aatatgattt ctcgcagttt ctcgagcaat ttagtaacga aggcgaagaa  900
accgagaaca ttgggggata taatcaagat ctcctttcgt ctgacgtctc atcaccaagc  960
```

```
gttgatgaag acaatatgat gggaaacata accggttccg gttggtccag ttatcttgtt  1020
gaccattccg attttgttta tgacaagatc caagataacg acgacaggaa cttcatatga  1080

SEQ ID NO: 23          moltype = DNA  length = 5588
FEATURE                Location/Qualifiers
source                 1..5588
                       mol_type = genomic DNA
                       organism = Thlaspi arvense
SEQUENCE: 23
aaattcaagt ttgataatat atgttgttaa gttaattttt tactaagtaa gtgtacattc  60
attatgacga ttccaaaatc taattttctc aattaagtcc aaaacaaaac agaaattata  120
aaatttccaa ttcgtttcaa ccctcgtgac caggtccgta tgataacaat taaaaaggat  180
cagtgtcaac atatttgttt ctattcatca caagtctcct ccaaacatat ttgaaacact  240
ggcaagggac attttataat gtttgtgtcc acggtctgaa tatccctttt tattcatttg  300
aatattaccc taattaaaga agccacctcc gagaaaaagt tcaggtgaac tctgctctgg  360
tacatccata taagtgggcg attctaatgc catattaatt aacacttgtc actttttctt  420
ggtgcataga cacaaaattt accaattcag ctagttaagc tataattaac taattcagat  480
tcatactgtc atcataatca gttaaaatcc atgcaaagcg atactaatct tatacagtgc  540
atgatgatag tctatgttgt tttttgtttt ttaattaacg cttaattatc caaagatcaa  600
attaatcagg cgccctttaa atcgtctctc catggcgttc atgttttatt tgtatcagtc  660
atcacagttt attcaagttg catttatgat catgaaagtg acagcctaag caactaacat  720
accaaaaacc atgaatagtt ttgttcaaag tttcgctaaa cgatggttga actgggtcta  780
atgtcctatt ttttcccaaa ttgattatgc cttcttagcc ctttttataa acaaaaactg  840
ggtctaatgt cgggactact atttatatat tttttaaaaa ataattctaa cattttaatg  900
cattataatt tataattata tgttcagtat tgcataaagc atataaaaaa ccaaattaag  960
acataatata tttttattaa aattaataaa ttataaattt aagttgaatg aagtcgtcaa  1020
attttacact taactaatca tttttctttt gagttaactc tgcaagttcc gaagaggcat  1080
aactattaga aacaatagtg aagtccaagt gagatgtgag atgtgagatg agaagaaaca  1140
aacattgata agtaagcaaa attactattt aatattttga atacagctcc tagtgtttca  1200
gggatagcca aagtggcaaa caaataggac cgaggctgaa aacgaacacg tgatgattaa  1260
tcgcatatat atatatatat aataaaatag taataaatac gctaataatt atgaaaaatg  1320
ataatggttt ttatctgtgc aataaaaaag aatttatcaa tatgttttct ttaaacatat  1380
ttattaaaca cgttatagat ggttttatcc gtatcatttt actgctacaa catacatgtt  1440
ttttttttaa tatataaaca tatatatata tatatatttt ctaatatggt cttataattt  1500
gtctattaga aaccatagac gatgttactc tttacctaat aatctctaat gaaaatgata  1560
tgatgataac catatttgtg acctttttcg ggtcggcact gcaattatca attcaattac  1620
tatcagaaaa ctattgcaat tatgaaaacc atattttttta agtctctctc aaactattta  1680
acagttttta aaataaagaa actatttgaa cagttccacg tccaaaagaa gatgatgaac  1740
gctcactacc cttttaatga ggttttttttt ttgttatttc atctgaaatc acaatgtaaa  1800
cctttacaaa agagccatgt agctaccaaa aagagccttg atatgtctag gaaccacaca  1860
ttgatgagtt aatattgtat ttattttttt agatttattt attttatttt attttacgta  1920
ggcttttaaa agtattctga cacgagtgcg cactataagg cttataaata gatgctcata  1980
tacatacata attaactcat tacagagaag tatctcacaa tgtcttagat ctttgataca  2040
tctacaactt ttttttact agcgttttca aatgttactg aaaatgaaaa cacaaaatca  2100
ctcaacgatc taccatagtt tttcagttag tttcatattc agatgcatca gagttctcat  2160
caacagatct attggtctct tgccttaatt tagacgacat ttctgagttc ttttcccctt  2220
tgctactcat cttctttagg ttgcgagatt tttgtgtgtg ttaaacttat aggtcgtatg  2280
taaatctata gatattgtat atatatccga aggaaaaaaa ggagaaaaat gtcaagaaag  2340
ccatgttgtg tgggagaagg gctgaagaaa ggagcatgga ccgccgaaga agacaagaaa  2400
ctcatctctt acatccatga acatggcgaa ggaggctggc gtgacattcc ccaaaaagct  2460
ggtatattac acatatatag cttatagtta aaccaagcat aatctatgat ctaattgatg  2520
tttatatggc tgtggtgttt aattaggact aaaacgatgt ggaaaaagtt gtagattgcg  2580
atgggctaac tatttgaaac cggatatcaa gagaggagaa tttagctacg aggaggagca  2640
gattatcatc atgcttcacg cttcccgtgg caacaagtaa tacatatata cttaagtcaa  2700
aattcatata ttaattctca atcttaaatt aagcattaat aatttgtttt ctcttgtttt  2760
aacgttattt tcattttttt aaaaaccaat gtcctgttga attttattta taaaaataaa  2820
atattcaacc tcaagtcaaa gttgatttaa aaatagttat aagttgggat aaagatacca  2880
ggaacaactt atttttatat aaaaaatgaa ctttctaact tcatcttaat ttgtgtaaaa  2940
actgtcaaaa agtacgtatt atatattgcg aaacagggga gtgcactgaa agttttgata  3000
tattctactt ttctttgacg tccttactat aggtggtcgg tcatagcgag acatttgccc  3060
aaaaggacag acaacgagat caagaactat tggaacacac accttaaaaa acgccttatc  3120
gatcaaggta ttgatcccgt gacccacaag ccacttgccc ctagccctag tccggccacg  3180
ctcaagcctt ctgatttcca agatgactca tcaaacctgg gaaactcgga tgagcattca  3240
cattcgggtt ctatgtctcc aaaatctctt cctccgtctt caagctcctg caatctagcg  3300
gagataagca gcagtgatga gacaccgaaa aatgatggtt ccttgaaatc caagaaacgt  3360
tcttttaaga gatcaagttc tacatcaaag ctgttaaaca aagttgcatc tagggctgct  3420
tccattggaa atatcttatc agcgtccatg gaaggaacct tggttagctc taccgcactg  3480
tctccatgtc tcaatgatga cttttccgaa gctagccaat tccagatgga cgaatatgat  3540
ccattccctc agtcgtctga acacataact gatcatatga aggaggacac cggcatgatc  3600
tttgatctca acaactccga atatgatttc tcgcagtttc tcgagcaatt tagtaacgaa  3660
ggcgaagaaa ccgagaacat tgggggatat aatcaagatc tcctttcgtc tgacgtctca  3720
tcaccaagcg ttgatgaaga caatatgatg ggaaacataa ccggttccgg ttggtccagt  3780
tatcttgttg accattccga ttttgtttat gacaagatcc aagataacga cgacaggaac  3840
ttcatatgac cagttgattg ctacccggac ttgagttgag tggttaatta agggtttcac  3900
tatattaatt tttctaagat gttttcgtaa gttattaatt aagggtcact atagggttat  3960
ccaataaggg attctcttag ttagagaacc atgtgttccc ctggatcaat tagtatttga  4020
tttgcgggag acacgagtta tttttttttg ctttaagaac tgttaagagt aaatattaaa  4080
taaagcttgc attttcataa ttccattatg tataattatt ctgtatattt aaatatcaat  4140
catgctaaga gtaattattc tggatagatt tagaggaact tacgaacgta acaaggatta  4200
```

```
aaaagtgact atttttagct gacataaact tttaacatgc cttcatgacc caaaatctaa  4260
actacttttt ggagctttcg catgcgttca ctgtactaca atcatttgat ttaaagtttg  4320
agcgttagat tagaacagat gagccgtgtt accaaaaata tatggaagaa aatgtaagac  4380
attttagaat tttggggatg aaactcccat taaaaaaaaa ccccctacct acgaataaag  4440
tcattgaagt tttttagag atgaattttt ttttgggggt tgcataaaca tgatttttta  4500
cacttgtata ttagaagtat atataactgg aaacattaaa taaatgagat agttaaaatt  4560
aaatgaattg aatactaaac tagtggagca gagttaaaaa agagaataat ttgcttttct  4620
cgtaaactaa tttgcagaga gatatatact tgatatactt taacgttaca gcaaaatatc  4680
ttaagaaaaa gttaagaaaa tttagtcaaa aataaaaaat ttcagtaaat gtatttagta  4740
agacgataca ctctagattt tgttcattta aaactaataa tctggcgatc ataaacaact  4800
tctcggaaaa ccaaaagcaa tatattgata aagtttttg tgtggtaaat attcataaag  4860
tctgtagata ttgtttttt aatttagata taaagtattt cgatctttcg taatcgaacg  4920
tggggcagaa acgcaccatc ctttttcttt tcgacataac atggaaaata gcaaaaatct  4980
atattagtac gacgaatacc agtaaataaa taaaaacaaa caagaaataa aaatgctgtt  5040
cccaatctgt gtatatatat ggtccacaaa tacataatta ttttcagaag ctaaagaaca  5100
ataagtgagc aaacataatt ggattagtga cccgacatat acagtattgt gtgcaaagtt  5160
aataaacatt caatgatata aatatcatca taattcatag tatgtgtgat acaaggagct  5220
ttggttttta tgtggctaca cgtcaacgac tcaattcctg tttttatatc ttagaaactt  5280
ggtttgctac cgacaatctg tagctaccgc tgattcctaa tcgatttaga tcttgaacac  5340
acataatcaa ttcacacgca gtatcttgtc ttctaaactt gcagcccata aaccttttg  5400
cctgataaaa ctctcaatat gcagcacaca ggttacaggt attgagtgtc ttgaatcatc  5460
tccaacatct tcagactcga ctgtactttt ctttgactta ggcgatagtt acgtatattg  5520
atacgtaata gtgacttata tatctatctt tcaatctcat ttggattcaa gtgcgtataa  5580
cttaaaca                                                           5588
```

```
SEQ ID NO: 24          moltype = AA  length = 359
FEATURE                Location/Qualifiers
source                 1..359
                       mol_type = protein
                       organism = Thlaspi arvense
SEQUENCE: 24
MSRKPCCVGE GLKKGAWTAE EDKKLISYIH EHGEGGWRDI PQKAGLKRCG KSCRLRWANY  60
LKPDIKRGEF SYEEEQIIIM LHASRGNKWS VIARHLPKRT DNEIKNYWNT HLKKRLIDQG  120
IDPVTHKPLA PSPSPATLKP SDFQDDSSNL GNSDEHSHSG SMSPKSLPPS SSSCNLAEIS  180
SSDETPKNDG SLKSKKRSFK RSSSTSKLLN KVASRAASIG NILSASMEGT LVSSTALSPC  240
LNDDFSEASQ FQMDEYDPFP QSSEHITDHM KEDTGMIFDL NNSEYDFSQF LEQFSNEGEE  300
TENIGGYNQD LLSSDVSSPS VDEDNMMGNI TGSGWSSYLV DHSDFVYDKI QDNDDRNFI   359
```

```
SEQ ID NO: 25          moltype = DNA  length = 1017
FEATURE                Location/Qualifiers
source                 1..1017
                       mol_type = genomic DNA
                       organism = Thlaspi arvense
SEQUENCE: 25
atgtcgaaaa gaccatgctg tatcggagaa gggttaaaga aaggagcatg gacgtcaggg  60
gaagacaaaa aactcatctc ttatatccat gaacatggcg aaggaggttg gcgtgacatt  120
cccgaaaaag ctgggctaaa acggtgtgga aagagttgca gactgcgatg ggcgaactat  180
ttgaaccccg atatcaagag aggaggattt agctacgagg aagaacagat catcatcatg  240
cttcatgctt ctcgtggcaa caagtggtca gtcatagcaa gacatttgcc gcaaagaaca  300
gacaacgaga tcaaaaacta ttggaacaca catctcaaga aacgcctgat caataagagc  360
actgattccg tgacccacaa gcctctagct tcctctaacc ctagtcctac cgagcgtaag  420
aagctcgatt cccaagaaga atccaatccc aaggagcagt cgttacagcc gggttcgaag  480
tctccagtat ctctttccct ttcttcgagt ttcaacgaca ctgtacccga gatcatgacc  540
agtgatgaga cgcctctaga aagtggtttc ttgagttgca aaaaaagtgt cgagagatcg  600
agctcaacat caaggctttt aaacaaagtt gcagctagag cttcttccat cgggagtatc  660
ttatcaacct ccatagaagg aactttgaga tctcctgcat cgtcctcatg tctcccaaac  720
tcattgtgtc aatcatctga acacaacaag gatcaagatc tcggtacgag cattgatctt  780
agcatccccg attacgatta ctcccacttt ctcgagcact tcatcaatag cgaagacgaa  840
gccgaaaaca ttggtggctg caatcaagat ctccttatgt ccgatttccc atcaacatta  900
gtggataaag aaaatatgaa ttttgaagac ataaccggtt ggtcaagtta tcttctcgac  960
catcccagtt ttacgtatga atcggaacaa gattccgacg acaacaactt gttatga     1017
```

```
SEQ ID NO: 26          moltype = DNA  length = 3950
FEATURE                Location/Qualifiers
source                 1..3950
                       mol_type = genomic DNA
                       organism = Thlaspi arvense
SEQUENCE: 26
ggtaatccat cggaaagttt atacggatta tcgacgactt gctttcgtcg gaaatttaag  60
acgaattttc gatgacttgc aacattccgt ccatttgtaa tcgacgaatc atttttgtcg  120
aaaatttccg acggattttt gacaaaaatg gccgtcgctt ctttcttgta gtgtataata  180
aatgcgcttt aatttagata tttcggtatt gtgcatttag taggtgaagt atattaatta  240
tatatcctag aaacaaagat tagtagaatt ttgatccagt ggcttgctaa taaataggac  300
tcaagagcgg ttttgataca tcaaatctat gattcaaact tcaaaatatg tgatttcttg  360
catattatga atacaaagat actcagggat ggatacgtac gtgctctgaa ttaatcgaat  420
cttgtgccac aatttatggt gtgcaaattg gattattaat ttgtaataga catgaatatt  480
aaaaataaaa catatttaat ctgaaaaatt tcagaacatc gtagatcaga taacatctgg  540
attcgagatg gagagaaaaa aaaaaaagta gattgtggcc ttgtgggcga ttctagtggg  600
acatctgctg aattagagaa agaaatggtt aaatgttaaa atattttaga ttggatagta  660
```

```
tctgaagtag agaccacaga aaaagaaaaa aagtgaattg tgggtgagcc tagaggaaca  720
aggctgtgac atacgtggga agacagacga aagagcccaa aaacgtgcac cgtccaagat  780
tctctatacg tacctaacct ccttccaggg actcttcact tgacacttac acttacactt  840
gcacttgcac tcactcacac tcacactcac actcacactc acacttacac tcaaacttag  900
ccagctaatt ttgttttaat ttgtattggt gatttgactg atgaataata taacaacggc  960
aacatcaacg gttatagagt ggaaaaaaaa aaaaaccgcg aactacacat cttgtaaata  1020
ttagtttaga tgtcattgtc tcccatatcg agacgtagac acgtcgtaag cgatttttat  1080
tttttttgtc actcttcaaa tgatatatag aaaacttggt tttcttcaca tgtttatcaa  1140
cggtaaaatt gtagatgtaa tctaaattaa taaattaata tttacaagat gtgtcattca  1200
ttctaatcac gttcatttta tatttatgta taacactaca gtagcggata agcttagtat  1260
gtgcagaaag aatgggtaga atcgtacgtg ggtttacaag tttattgtca tgagtaatat  1320
atactagatc taagctaaaa aaaaacaaat attagaccct taaaatgaac acatacggta  1380
ttacgatctt atacacataa tctcgcggtt aatctcaacg gaccatgcat catatgtaat  1440
tatattaaat aaacatcagt ctctctatat atccttgatt tacaatatct tttctttctg  1500
cacatttttt cgaaatgcaa agaaggaatg tcgaaaagac catgctgtat cggagaaggg  1560
ttaaagaaag gagcatggac gtcaggggaa gacaaaaaac tcatctctta tatccatgaa  1620
catggcgaag gaggttggcg tgacattccc gaaaaagctg gtacatgcat ttcatttaca  1680
gattttgtaa tatttattta tcgaattgat ctttatatgc ttttcatttt ctgagtttaa  1740
ttagggctaa aacggtgtgg aaagagttgc agactgcgat gggcgaacta tttgaacccc  1800
gatatcaaga gaggaggatt tagctacgag gaagaacaga tcatcatcat gcttcatgct  1860
tctcgtggca acaagtacta caacgtttgc ctatatattt gtttttgtat atgcatgtaa  1920
tacaatcatc aacgtataca taactttacg acacgatcaa tgtaattgga ctgtactata  1980
tttttattta ggtggtcagt catagcaaga catttgccgc aaagaacaga caacgagatc  2040
aaaaactatt ggaacacaca tctcaagaaa cgcctgatca ataagagcac tgattccgtg  2100
acccacaagc ctctagcttc ctctaaccct agtcctaccg agcgtaagaa gctcgattcc  2160
caagaagaat ccaatcccaa ggagcagtcg ttacagccgg gttcgaagtc tccagtatct  2220
ctttcccttt cttcgagttt caacgacact gtacccgaga tcatgaccag tgatgagacg  2280
cctctagaaa gtggtttctt gagttgcaaa aaaagtgtcg agagatcgag ctcaacatca  2340
aggcttttaa acaaagttgc agctagagct tcttccatcg ggagtatctt atcaacctcc  2400
atagaaggaa ctttgagatc tcctgcatcg tcctcatgtc tcccaaactc attgtgtcaa  2460
tcatctgaac acaacaagga tcaagatctc ggtacgagca ttgatcttag catccccgat  2520
tacgattact cccactttct cgagcacttc atcaatagcg aagacgaagc cgaaaacatt  2580
ggtggctgca atcaagatct ccttatgtcc gatttcccat caacattagt ggataaagaa  2640
aatatgaatt ttgaagacat aaccggttgg tcaagttatc ttctcgacca tcccagtttt  2700
acgtatgaat cggaacaaga ttccgacgac aacaacttgt tatgatctat ctgtctgtgg  2760
ctcgtcacct gctcattgaa ccaggggctg accagttaat ctcatgttgg tatgtccaag  2820
ataaggggtt caatatctta gataaatttc aacttgttaa attgcgttac tagattattt  2880
agtaagaggc acttatgtaa taaaaaaaaa accatgtact cccgtgtatc gaatagtatt  2940
gatttgatct gcgtaagagt ttttcttata actattttgt aaaatatatg ttgaataaat  3000
taagctttat gcatgtgtac cttttttttaa taaaaaaaaa actaagcttt atggtccaca  3060
aacactacca aaaggtaaag agcaatgatt gagcaacaaa attggatggg tgacctggcg  3120
aatctttatt aatgttcaat gaaatgatca tacatttatg ggaagctttt gtttctatgt  3180
gcatggctgt acatgaataa tttaattttt ttattggtcg tgttacatca ttatcaaaaa  3240
cattccatca aattcattta catatatgcg aatatgcgat tatgatgaac aactccacga  3300
tacagttttc cacatgtgac acacacggat ctgtaacaga tagagacata gagttgcaca  3360
tcaaaatctt tcgataagat ttgtatctat caatatacag aaacttgtct gcatttgtta  3420
ggaatcgaac ctcaaatata tggtgtagta ggtcaagggc tttcacaatt ttactgttgt  3480
tgtgtgtaaa actgatcgtg tgaagtgaac gttcagaaaa aagaatactt cctctctatg  3540
tttttctaca cttaatttag ttttgtgcct aaaaatataa tttcaatagt aaataatact  3600
tgacgtggtt tattacagaa aaagttacat acagtataaa tgtaagaatt acatacagaa  3660
agaatcatgt tagcattcat tcaaagaaaa aatggaatta tgttagcaaa tcaagtcgat  3720
ctaagtttta ttacatgttg gcattcatta aacccttgca gtatctgaaa agaattgctc  3780
tccacaccag accaagtccg gttcgataat accatgattg ctattggaaa acgtcgtacc  3840
gagacataag aaccggtagt aagttaatta cgaaagtagc cttacagcta aacaatcggt  3900
agtctaaact ctgaagcgat cgcgattagc cccttgggag tgattgggag             3950

SEQ ID NO: 27          moltype = AA  length = 338
FEATURE                Location/Qualifiers
source                 1..338
                       mol_type = protein
                       organism = Thlaspi arvense
SEQUENCE: 27
MSKRPCCIGE GLKKGAWTSG EDKKLISYIH EHGEGGWRDI PEKAGLKRCG KSCRLRWANY  60
LNPDIKRGGF SYEEEQIIIM LHASRGNKWS VIARHLPQRT DNEIKNYWNT HLKKRLINKS  120
TDSVTHKPLA SSNPSPTERK KLDSQEESNP KEQSLQPGSK SPVSLSLSSS FNDTVPEIMT  180
SDETPLESGF LSCKKSVERS SSTSRLLNKV AARASSIGSI LSTSIEGTLR SPASSSCLPN  240
SLCQSSEHNK DQDLGTSIDL SIPDYDYSHF LEHFINSEDE AENIGGCNQD LLMSDFPSTL  300
VDKENMNFED ITGWSSYLLD HPSFTYESEQ DSDDNNLL                          338

SEQ ID NO: 28          moltype = DNA  length = 1047
FEATURE                Location/Qualifiers
source                 1..1047
                       mol_type = genomic DNA
                       organism = Thlaspi arvense
SEQUENCE: 28
atggctcgga ctttgcaagg cgagtggatg aaggtggagc agaaaggagg acaagtacca  60
gcaccgagaa gctcacacgg catagccgtg atcggagaca agctctattg tttcggcggc  120
gaggatccgc catatgagtc catcgacaac gacctttatg tctttgactt caacacccac  180
acttggtcaa tcgctccggc caacggagac gttccaaaga ccagagtctt aggcacccgc  240
```

```
atggtggccg tgggaacgaa gctctatgtg ttcggaggcc gcaataaaca gttagagttc  300
gaggactttt actcgtacga tacggtgaaa gaggagtgga agttcctgac gaagctggac  360
gaaaagggag gacccgaagc tcgtactttc cattcgatga cttcagatga aaaccacgtg  420
tacgtgttcg gtggggtgag caaaggaggg ctgaatgcaa ccccctttcg gttcaggacg  480
atcgaggcct ataacattgc tgaagggaaa tgggctcagc tccctgaccc tggagaggat  540
ttcgagaaaa gaggaatggc cggattcctt gtggtgcaag gcaagctttg ggtgttttac  600
ggattcgcga ctgcgaatga tcctaagata cccacactct acgggtccca ggactacgag  660
tctaatcgtg tgcactgcta tgatcccgct actcaaaaat ggaccgaagt ggagaccaca  720
ggtttcgaga aaccttctcg taggagctgt tttgcgcatg cggctgtggg gaaatatata  780
ataatattcg gaggtgagat tgagcgggac ccagaagcac atcaaggtcc ggggacgttg  840
tcccgtgagg gttttgcgtt ggacactgag acattggtgt gggagaggta tgaaggagga  900
ccaatcaaac cgagcaaccg cggttgggtg gcctccacga cgaccaccat caacggaaag  960
aaaggtctgc tcgtgcatgg agggaaactt atgaccaacg agcgcaccga tgagatgtac  1020
ttcttcgcag tcaattcctc cacgtaa                                      1047

SEQ ID NO: 29          moltype = DNA  length = 4094
FEATURE                Location/Qualifiers
source                 1..4094
                       mol_type = genomic DNA
                       organism = Thlaspi arvense
SEQUENCE: 29
cgaacatttt tttttttgg caaacacact tagaacgtga tcacaatcca aggaaaccca  60
gcactcgatg cctaaatatc tgaagttgat gcaaaaactg aaatataaag tttagtatag  120
atagataact ggttatattt atagaagaca accgaaaggt tctgcaaaag gggtagtttt  180
tatactagtt caatctaaca aatgatcagt tttttttgg gcaaatataa tcagtttgtt  240
tatatatata tatatatatt tttggtcaat tgtttattta tatataacac actattttat  300
atcatatcat tctaaatttc taatgggttt aaatttttta ttactatgca attaaaatac  360
acagctcata tattgaacta aatagttgta aataatttta ggtgaattac aaattgttat  420
cacctatatc tatattatta atttcgaatc aggaaagtaa cattttgttc actaaagcta  480
aaagcctaaa agtatgataa aatgttcaaa atggtgaata aagaatgata tggggtttaa  540
gtgtttaact ggtaatatta cagcgataca caaaatagga aaaaaaaaca ataatttttg  600
tatctcgtgt taaaagtcaa acaaatgtac aattatgcta agatagtttg ataacgctgc  660
tttagatatt tttgtggtgt ttgctgtttt aaaaattgtt gtatttttga aaattatatg  720
gtagaaaaaa aagaaaagaa atgttccaca acgcaataaa aatcaagttt gaagatatcg  780
atcatgtttt atagtaataa gcaaaaaaaa acaaacacat gcatcatcat catcaagcta  840
tcaagtaaca atcatgtttc atagtaataa gcaatatcat catcatgctg tcaagtatca  900
atcatgtttc atagttttaa gcaatatgaa ttaacacatg catcatcatc ttcatgcttt  960
aatttagact aacatgtggc gcagaaaccg agaagctcac acggcatata tacccgtcgc  1020
ctaacagcta tgttagcttt tgttaatctt catgactgtg gcacatctct ttgagcactg  1080
cgcaccatcc atgcatgttt tctaactgct ccaagacctt ttatcctaaa caaacacaat  1140
tattcattct cctttctga tttattttct gttttttttt tgccaactga ttttctgatt  1200
tatcgctcac tcgcgaagat atttttgtaa gggagattta ccaactaagc ttaaagaaat  1260
taatatgctt ctcacatttt ttagataata atttaacact ttcacttcct ttttgggggt  1320
acaaaatacc cacaagttca cagaaattca taagcaccac acagttggaa atatcttctt  1380
ctttttttc ttttctttt tgtttgttaa acaatcaata attggagata ccttgacacg  1440
cagaattgtt tagcctatat atagaagagc agcgaaagaa gaggagacac acaaacaaat  1500
agaaaagaaa agaaaaaaag agttgaatat tgcagctatg gctcggactt tgcaaggcga  1560
gtggatgaag gtattgccta cttagtcaag gatttttatt taagatatta attttgcacg  1620
agagaagcat aagccatagg ctatgtatta tgtatatatg tataatattg gttattagta  1680
aaaagttatg tatgacaaca cccttaattc ccatgttctc gacacgttat accccattcg  1740
tatccctcct gaaaagaggg gatgttgatg gtttacttgt aattaacctg tcatgtattc  1800
gaatgattaa ccggctcatc agtatccgtt ttaaccatca attcattttg gtcactggtt  1860
gacaggtgga gcagaaagga ggacaagtac cagcaccgag aagctcacac ggcatagccg  1920
tgatcggaga caagctctat tgtttcggcg gcgaggatcc gccatatgag tccatcgaca  1980
acgaccttta tgtctttgac ttcaacaccc acacttggtc aatcgctccg gccaacggag  2040
acgttccaaa gaccagagtc ttaggcaccc gcatggtggc cgtgggaacg aagctctatg  2100
tgttcggagg ccgcaataaa cagttagagt tcgaggactt ttactcgtac gatacggtga  2160
aagaggagtg gaagttcctg acgaagctgg acgaaaaggg aggacccgaa gctcgtactt  2220
tccattcgat gacttcagat gaaaaccacg tgtacgtgtt cggtggggtg agcaaaggag  2280
ggctgaatgc aacccccttt cggttcagga cgatcgaggc ctataacatt gctgaaggga  2340
aatgggctca gctccctgac cctggagagg atttcgagaa aagaggaatg gccggattcc  2400
ttgtggtgca aggcaagctt tgggtgtttt acggattcgc gactgcgaat gatcctaaga  2460
tacccacact ctacgggtcc caggactacg agtctaatcg tgtgcactgc tatgatcccg  2520
ctactcaaaa atggaccgaa gtggagacca caggtttcga gaaaccttct cgtaggagct  2580
gttttgcgca tgcggctgtg gggaaatata taataatatt cggaggtgag attgagcggg  2640
acccagaagc acatcaaggt ccggggacgt tgtcccgtga gggttttgcg ttggacactg  2700
agacattggt gtgggagagg tatgaaggag gaccaatcaa accgagcaac cgcggttggg  2760
tggcctccac gacgaccacc atcaacggaa agaaaggtct gctcgtgcat ggagggaaac  2820
ttatgaccaa cgagcgcacc gatgagatgt acttcttcgc agtcaattcc tccacgtaat  2880
caatgctctc tcaccctcca aggtctgttt gtgtgtgtgg ggggtcaagg ttttatatga  2940
ttcaataaag gtttgtgaga ccttcagaaa ctcaccctat cgtcgctgtt ttcctttta  3000
aatattatta tcaaataaaa taaatgtgtg tgctgtgtga ctgtgtgtgg ggtttggaaa  3060
ctattatcat tggaataata tgtgtgtttt gtgtacgtgt gagtataata aaatcataaa  3120
ttatactatg aaattatcta cttatttgtc gtatcattta acttccctca atcgccataa  3180
catttattca tgtgtatcca agtggatgac gaaactatat ctaccaattc taatttggaa  3240
gcattatgat tttttttgcg attttgaaat ttaaaagtgg gatagagtaa atatttggaa  3300
agcatgggaa tatttatttt cctaactgga ttataaaaaa aactgtattt atagttattt  3360
catgggtata aaaaaagata tgtttttagt taaataattg atattttata ttatagatta  3420
aatttaagtg tatagtatat acacctttta atattatttg atgtcgggtg ttttatcata  3480
```

```
taaatataaa tataaacaat actaataata tgtatactgt atataccttt ttaacacttt  3540
ttttttaata ctaacatata acacattgaa atagtcatac gcagcgccaa tattttagct  3600
tgaaggttaa taatttgata tgttgagctc ttgcatcatt cgagatccaa aaagcatcca  3660
caaaaataca aaacatcagt aattaattag cttttgcttg gagagtttga gggcagtcat  3720
cattcatttt cagcttaatc tggaaagcat tatagttcaa acattatttt cagattctta  3780
acttcctttt ttagctgact ttactttccc ttgcgtatag ttttggatta aagattatca  3840
gagaaatcca catgagattt cagatttgat gaaaatgaag aaaaactttt taagtttgga  3900
aaatgataaa tgtatcagct ctggtcaaag atgagatcga aataggccca ctggactatc  3960
ttggggaaca agctttaagc cttcgaaaaa aaggctgttt ccgcttgttt tattattacc  4020
aaacagatag aaagatgtct taatagtttc ttgttctata aaagtcttat tacagacact  4080
cttaaaactc tctt                                                   4094

SEQ ID NO: 30          moltype = AA  length = 348
FEATURE                Location/Qualifiers
source                 1..348
                       mol_type = protein
                       organism = Thlaspi arvense
SEQUENCE: 30
MARTLQGEWM KVEQKGGQVP APRSSHGIAV IGDKLYCFGG EDPPYESIDN DLYVFDFNTH  60
TWSIAPANGD VPKTRVLGTR MVAVGTKLYV FGGRNKQLEF EDFYSYDTVK EEWKFLTKLD  120
EKGGPEARTF HSMTSDENHV YVFGGVSKGG LNATPFRFRT IEAYNIAEGK WAQLPDPGED  180
FEKRGMAGFL VVQGKLWVFY GFATANDPKI PTLYGSQDYE SNRVHCYDPA TQKWTEVETT  240
GFEKPSRRSC FAHAAVGKYI IIFGGEIERD PEAHQGPGTL SREGFALDTE TLVWERYEGG  300
PIKPSNRGWV ASTTTTINGK KGLLVHGGKL MTNERTDEMY FFAVNSST              348

SEQ ID NO: 31          moltype = DNA  length = 19
FEATURE                Location/Qualifiers
source                 1..19
                       mol_type = genomic DNA
                       organism = Thlaspi arvense
SEQUENCE: 31
acgatcttcg aaaacttct                                              19

SEQ ID NO: 32          moltype = DNA  length = 22
FEATURE                Location/Qualifiers
source                 1..22
                       mol_type = genomic DNA
                       organism = Thlaspi arvense
SEQUENCE: 32
atcttcgaaa acttctctat at                                          22

SEQ ID NO: 33          moltype = DNA  length = 22
FEATURE                Location/Qualifiers
source                 1..22
                       mol_type = genomic DNA
                       organism = Thlaspi arvense
SEQUENCE: 33
aagaaaccta atatgagttt ta                                          22

SEQ ID NO: 34          moltype = DNA  length = 19
FEATURE                Location/Qualifiers
source                 1..19
                       mol_type = genomic DNA
                       organism = Thlaspi arvense
SEQUENCE: 34
tttttcaact ttaaaattt                                              19

SEQ ID NO: 35          moltype = DNA  length = 22
FEATURE                Location/Qualifiers
source                 1..22
                       mol_type = genomic DNA
                       organism = Thlaspi arvense
SEQUENCE: 35
aaacactgta aaagaaacta tc                                          22

SEQ ID NO: 36          moltype = DNA  length = 19
FEATURE                Location/Qualifiers
source                 1..19
                       mol_type = genomic DNA
                       organism = Thlaspi arvense
SEQUENCE: 36
acatttgcgt atttctcat                                              19

SEQ ID NO: 37          moltype = DNA  length = 19
FEATURE                Location/Qualifiers
source                 1..19
                       mol_type = genomic DNA
                       organism = Thlaspi arvense
SEQUENCE: 37
```

```
cgaaccctaa ctcttccca                                              19

SEQ ID NO: 38          moltype = DNA  length = 22
FEATURE                Location/Qualifiers
source                 1..22
                       mol_type = genomic DNA
                       organism = Thlaspi arvense
SEQUENCE: 38
tcgggtttgt tcgtacggac aa                                          22

SEQ ID NO: 39          moltype = DNA  length = 19
FEATURE                Location/Qualifiers
source                 1..19
                       mol_type = genomic DNA
                       organism = Thlaspi arvense
SEQUENCE: 39
tcgctaagat cataaaacc                                              19

SEQ ID NO: 40          moltype = DNA  length = 19
FEATURE                Location/Qualifiers
source                 1..19
                       mol_type = genomic DNA
                       organism = Thlaspi arvense
SEQUENCE: 40
agattcacag agactgagc                                              19

SEQ ID NO: 41          moltype = DNA  length = 22
FEATURE                Location/Qualifiers
source                 1..22
                       mol_type = genomic DNA
                       organism = Thlaspi arvense
SEQUENCE: 41
aagacttttt tccggtgtct ct                                          22

SEQ ID NO: 42          moltype = DNA  length = 22
FEATURE                Location/Qualifiers
source                 1..22
                       mol_type = genomic DNA
                       organism = Thlaspi arvense
SEQUENCE: 42
gtgttttttt tttgaacatt aa                                          22

SEQ ID NO: 43          moltype = DNA  length = 19
FEATURE                Location/Qualifiers
source                 1..19
                       mol_type = genomic DNA
                       organism = Thlaspi arvense
SEQUENCE: 43
agacaattcc ccaatatca                                              19

SEQ ID NO: 44          moltype = DNA  length = 22
FEATURE                Location/Qualifiers
source                 1..22
                       mol_type = genomic DNA
                       organism = Thlaspi arvense
SEQUENCE: 44
gtgataattt gatattgggg aa                                          22

SEQ ID NO: 45          moltype = DNA  length = 19
FEATURE                Location/Qualifiers
source                 1..19
                       mol_type = genomic DNA
                       organism = Thlaspi arvense
SEQUENCE: 45
agtgttcatt gctaacgag                                              19

SEQ ID NO: 46          moltype = DNA  length = 22
FEATURE                Location/Qualifiers
source                 1..22
                       mol_type = genomic DNA
                       organism = Thlaspi arvense
SEQUENCE: 46
catgtttgtg tgtctgtgta ga                                          22

SEQ ID NO: 47          moltype = DNA  length = 22
FEATURE                Location/Qualifiers
source                 1..22
                       mol_type = genomic DNA
                       organism = Thlaspi arvense
```

```
SEQUENCE: 47
gtttctccgg gactccctta tg                                            22

SEQ ID NO: 48          moltype = DNA  length = 22
FEATURE                Location/Qualifiers
source                 1..22
                       mol_type = genomic DNA
                       organism = Thlaspi arvense
SEQUENCE: 48
ggggttcctc aagcagaggt tc                                            22

SEQ ID NO: 49          moltype = DNA  length = 22
FEATURE                Location/Qualifiers
source                 1..22
                       mol_type = genomic DNA
                       organism = Thlaspi arvense
SEQUENCE: 49
gtgcaagcgc tctacaagga aa                                            22

SEQ ID NO: 50          moltype = DNA  length = 22
FEATURE                Location/Qualifiers
source                 1..22
                       mol_type = genomic DNA
                       organism = Thlaspi arvense
SEQUENCE: 50
gagtccggat gcgcgcccgg ag                                            22

SEQ ID NO: 51          moltype = DNA  length = 22
FEATURE                Location/Qualifiers
source                 1..22
                       mol_type = genomic DNA
                       organism = Thlaspi arvense
SEQUENCE: 51
gaagttagag aagatgaaac tt                                            22

SEQ ID NO: 52          moltype = DNA  length = 22
FEATURE                Location/Qualifiers
source                 1..22
                       mol_type = genomic DNA
                       organism = Thlaspi arvense
SEQUENCE: 52
ttatgccaaa taaatatata tt                                            22

SEQ ID NO: 53          moltype = DNA  length = 22
FEATURE                Location/Qualifiers
source                 1..22
                       mol_type = genomic DNA
                       organism = Thlaspi arvense
SEQUENCE: 53
aaacgtgctt ttcgagaaaa aa                                            22

SEQ ID NO: 54          moltype = DNA  length = 22
FEATURE                Location/Qualifiers
source                 1..22
                       mol_type = genomic DNA
                       organism = Thlaspi arvense
SEQUENCE: 54
atattaacaa tggaaattta ca                                            22

SEQ ID NO: 55          moltype = DNA  length = 22
FEATURE                Location/Qualifiers
source                 1..22
                       mol_type = genomic DNA
                       organism = Thlaspi arvense
SEQUENCE: 55
tttgcttctt attccctttt tc                                            22

SEQ ID NO: 56          moltype = DNA  length = 22
FEATURE                Location/Qualifiers
source                 1..22
                       mol_type = genomic DNA
                       organism = Thlaspi arvense
SEQUENCE: 56
aaaaattata taaattacta ga                                            22

SEQ ID NO: 57          moltype = DNA  length = 22
FEATURE                Location/Qualifiers
source                 1..22
                       mol_type = genomic DNA
```

```
                        organism = Thlaspi arvense
SEQUENCE: 57
aatgaagatg gatatatata ta                                              22

SEQ ID NO: 58           moltype = DNA  length = 19
FEATURE                 Location/Qualifiers
source                  1..19
                        mol_type = genomic DNA
                        organism = Thlaspi arvense
SEQUENCE: 58
accgattggt gcaagcaga                                                  19

SEQ ID NO: 59           moltype = DNA  length = 19
FEATURE                 Location/Qualifiers
source                  1..19
                        mol_type = genomic DNA
                        organism = Thlaspi arvense
SEQUENCE: 59
tcaactaact tagatggcc                                                  19

SEQ ID NO: 60           moltype = DNA  length = 22
FEATURE                 Location/Qualifiers
source                  1..22
                        mol_type = genomic DNA
                        organism = Thlaspi arvense
SEQUENCE: 60
aataagctgc acacctacag tt                                              22

SEQ ID NO: 61           moltype = DNA  length = 22
FEATURE                 Location/Qualifiers
source                  1..22
                        mol_type = genomic DNA
                        organism = Thlaspi arvense
SEQUENCE: 61
attttaattg aagagtgggg aa                                              22

SEQ ID NO: 62           moltype = DNA  length = 22
FEATURE                 Location/Qualifiers
source                  1..22
                        mol_type = genomic DNA
                        organism = Thlaspi arvense
SEQUENCE: 62
tgaaaagaaa tctcaaacca cc                                              22

SEQ ID NO: 63           moltype = DNA  length = 22
FEATURE                 Location/Qualifiers
source                  1..22
                        mol_type = genomic DNA
                        organism = Thlaspi arvense
SEQUENCE: 63
ctactcgtta actagcacaa ac                                              22

SEQ ID NO: 64           moltype = DNA  length = 19
FEATURE                 Location/Qualifiers
source                  1..19
                        mol_type = genomic DNA
                        organism = Thlaspi arvense
SEQUENCE: 64
agtttcttta ttttaaaaa                                                  19

SEQ ID NO: 65           moltype = DNA  length = 22
FEATURE                 Location/Qualifiers
source                  1..22
                        mol_type = genomic DNA
                        organism = Thlaspi arvense
SEQUENCE: 65
atacttttaa aagcctacgt aa                                              22

SEQ ID NO: 66           moltype = DNA  length = 19
FEATURE                 Location/Qualifiers
source                  1..19
                        mol_type = genomic DNA
                        organism = Thlaspi arvense
SEQUENCE: 66
agccttatag tgcgcactc                                                  19

SEQ ID NO: 67           moltype = DNA  length = 22
FEATURE                 Location/Qualifiers
source                  1..22
```

```
                        mol_type = genomic DNA
                        organism = Thlaspi arvense
SEQUENCE: 67
aaatagatgc tcatatacat ac                                              22

SEQ ID NO: 68           moltype = DNA  length = 19
FEATURE                 Location/Qualifiers
source                  1..19
                        mol_type = genomic DNA
                        organism = Thlaspi arvense
SEQUENCE: 68
aagacgaatt ttcaatgac                                                  19

SEQ ID NO: 69           moltype = DNA  length = 22
FEATURE                 Location/Qualifiers
source                  1..22
                        mol_type = genomic DNA
                        organism = Thlaspi arvense
SEQUENCE: 69
gaatgttgca agtcattgaa aa                                              22

SEQ ID NO: 70           moltype = DNA  length = 19
FEATURE                 Location/Qualifiers
source                  1..19
                        mol_type = genomic DNA
                        organism = Thlaspi arvense
SEQUENCE: 70
cattccgtcc atttgtaac                                                  19

SEQ ID NO: 71           moltype = DNA  length = 22
FEATURE                 Location/Qualifiers
source                  1..22
                        mol_type = genomic DNA
                        organism = Thlaspi arvense
SEQUENCE: 71
acaaaaatga ttcgtcggtt ac                                              22

SEQ ID NO: 72           moltype = DNA  length = 19
FEATURE                 Location/Qualifiers
source                  1..19
                        mol_type = genomic DNA
                        organism = Thlaspi arvense
SEQUENCE: 72
aaactatgaa acatgattg                                                  19

SEQ ID NO: 73           moltype = DNA  length = 22
FEATURE                 Location/Qualifiers
source                  1..22
                        mol_type = genomic DNA
                        organism = Thlaspi arvense
SEQUENCE: 73
tcatgaagat taacaaaagc ta                                              22

SEQ ID NO: 74           moltype = DNA  length = 19
FEATURE                 Location/Qualifiers
source                  1..19
                        mol_type = genomic DNA
                        organism = Thlaspi arvense
SEQUENCE: 74
gccacagtca tgaagatta                                                  19

SEQ ID NO: 75           moltype = DNA  length = 22
FEATURE                 Location/Qualifiers
source                  1..22
                        mol_type = genomic DNA
                        organism = Thlaspi arvense
SEQUENCE: 75
tggagatacc ttgacacgca ga                                              22

SEQ ID NO: 76           moltype = DNA  length = 20
FEATURE                 Location/Qualifiers
source                  1..20
                        mol_type = genomic DNA
                        organism = Thlaspi arvense
SEQUENCE: 76
ttgcagctgt aactttctta                                                 20

SEQ ID NO: 77           moltype = DNA  length = 20
FEATURE                 Location/Qualifiers
```

```
source                  1..20
                        mol_type = genomic DNA
                        organism = Thlaspi arvense
SEQUENCE: 77
gaagttgatt gtgccactaa                                              20

SEQ ID NO: 78           moltype = DNA  length = 20
FEATURE                 Location/Qualifiers
source                  1..20
                        mol_type = genomic DNA
                        organism = Thlaspi arvense
SEQUENCE: 78
gatcggtcta accataccgg                                              20

SEQ ID NO: 79           moltype = DNA  length = 20
FEATURE                 Location/Qualifiers
source                  1..20
                        mol_type = genomic DNA
                        organism = Thlaspi arvense
SEQUENCE: 79
attgttgcaa tcaagaaacg                                              20

SEQ ID NO: 80           moltype = DNA  length = 1109
FEATURE                 Location/Qualifiers
source                  1..1109
                        mol_type = genomic DNA
                        organism = Thlaspi arvense
SEQUENCE: 80
atgtcaagaa agccgtgttt gtcggagaag ggctgaagaa aggggcatgg accaccgaag  60
aagacaagaa actcatctct tacatccacg agcacggtga aggaggctgg cgcgacattc  120
cccaaaaagc tgggttgaaa cggtgtggaa agagttgtag gctgcgatgg actaactacc  180
taaaacctga gatcaaaaga ggcgagttta gttcagagga ggaacagatt atcattatgc  240
ttcatgcttc tcgtggcaac aagtggtcgg tcatagcgag acatttacct agaagaacag  300
acaacgagat caagaactac tggaacacgc atctcaaaaa acgtttgatc gaacagggtg  360
ttgatcccgt gactcacaag cctctagctt ccaactccgg ccctactgcc accacgccgc  420
ctgagaattt gcatttccta gatgaatcta gctcagacaa gcaatactct cggtcgagct  480
caatgccttc cctgtctcgt cttccttcct ccggattcaa cacggtttcc gagatagcca  540
gcaatgttgg gacaccagtt caggtcggtt ccttgagttg caagaaacgt tttaagaaat  600
cgagttcgac atcaaggctt ctgaacaaat ttgcggctaa ggccacttcc atcaaagata  660
tattgtcggc ttccatggaa ggtagctcga gtgctgctac tacaatatca catgcaagct  720
ttttaaatgg cttttctgag cagagtcgca atgaagagga tagttctaac gcatccctga  780
caaatactct agccgaattt gatcccttct ctcagtcatc gttgtacccg gagcatgaga  840
tcaatgttac ttctgatatc ggcatggacc aggtttacga tttctcacaa tttctcgaaa  900
agctcgggag tgaaggccac aacgaactga atgtcgagta tggtcatgat cttcttatgt  960
ccgatgtttc gcaagaagtc tcatcaccta gcgttgatga tcaagacaat atgattggaa  1020
gcttcgaagg ttggtcaaat tatcttcttg accatgctga ttttatatat gacaccgact  1080
cagattccct cgaaaagcat ttcatgtga                                    1109

SEQ ID NO: 81           moltype = AA  length = 11
FEATURE                 Location/Qualifiers
source                  1..11
                        mol_type = protein
                        organism = Thlaspi arvense
SEQUENCE: 81
MSRKPCLSEK G                                                       11

SEQ ID NO: 82           moltype = DNA  length = 1111
FEATURE                 Location/Qualifiers
source                  1..1111
                        mol_type = genomic DNA
                        organism = Thlaspi arvense
SEQUENCE: 82
atgtcaagaa agccgtgttg atgtcggaga agggctgaag aaaggggcat ggaccaccga  60
agaagacaag aaactcatct cttacatcca cgagcacggt gaaggaggct ggcgcgacat  120
tccccaaaaa gctgggttga aacggtgtgg aaagagttgt aggctgcgat ggactaacta  180
cctaaaacct gagatcaaaa gaggcgagtt tagttcagag gaggaacaga ttatcattat  240
gcttcatgct tctcgtggca acaagtggtc ggtcatagcg agacatttac ctagaagaac  300
agacaacgag atcaagaact actggaacac gcatctcaaa aaacgtttga tcgaacaggg  360
tgttgatccc gtgactcaca agcctctagc ttccaactcc ggccctactg ccaccacgcc  420
gcctgagaat ttgcatttcc tagatgaatc tagctcagac aagcaatact ctcggtcgag  480
ctcaatgcct tccctgtctc gtcttccttc ctccggattc aacacggttt ccgagatagc  540
cagcaatgtt gggacaccag ttcaggtcgg ttccttgagt tgcaagaaac gttttaagaa  600
atcgagttcg acatcaaggc ttctgaacaa atttgcggct aaggccactt ccatcaaaga  660
tatattgtcg gcttccatgg aaggtagctc gagtgctgct actacaatat cacatgcaag  720
ctttttaaat ggcttttctg agcagagtcg caatgaagag gatagttcta acgcatccct  780
gacaaatact ctagccgaat ttgatccctt ctctcagtca tcgttgtacc cggagcatga  840
gatcaatgtt acttctgata tcggcatgga ccaggtttac gatttctcac aatttctcga  900
aaagctcggg agtgaaggcc acaacgaact gaatgtcgag tatggtcatg atcttcttat  960
gtccgatgtt tcgcaagaag tctcatcacc tagcgttgat gatcaagaca atatgattgg  1020
```

```
aagcttcgaa ggttggtcaa attatcttct tgaccatgct gattttatat atgacaccga  1080
ctcagattcc ctcgaaaagc atttcatgtg a                                 1111

SEQ ID NO: 83          moltype = AA  length = 6
FEATURE                Location/Qualifiers
source                 1..6
                       mol_type = protein
                       organism = Thlaspi arvense
SEQUENCE: 83
MSRKPC                                                             6

SEQ ID NO: 84          moltype = DNA  length = 1111
FEATURE                Location/Qualifiers
source                 1..1111
                       mol_type = genomic DNA
                       organism = Thlaspi arvense
SEQUENCE: 84
atgtcaagaa agccgtgttg tgtcggagaa gggctgaaga aaggggcatg gaccaccgaa  60
gaagacaaga aactcatctc ttacatccac gaggcacggt gaaggaggct ggcgcgacat  120
tccccaaaaa gctgggttga aacggtgtgg aaagagttgt aggctgcgat ggactaacta  180
cctaaaacct gagatcaaaa gaggcgagtt tagttcagag gaggaacaga ttatcattat  240
gcttcatgct tctcgtggca acaagtggtc ggtcatagcg agacatttac ctagaagaac  300
agacaacgag atcaagaact actggaacac gcatctcaaa aaacgtttga tcgaacaggg  360
tgttgatccc gtgactcaca agcctctagc ttccaactcc ggccctactg ccaccacgcc  420
gcctgagaat ttgcatttcc tagatgaatc tagctcagac aagcaatact ctcggtcgag  480
ctcaatgcct tccctgtctc gtcttccttc ctccggattc aacacggttt ccgagatagc  540
cagcaatgtt gggacaccag ttcaggtcgg ttccttgagt tgcaagaaac gttttaagaa  600
atcgagttcg acatcaaggc ttctgaacaa atttgcggct aaggccactt ccatcaaaga  660
tatattgtcg gcttccatgg aaggtagctc gagtgctgct actacaatat cacatgcaag  720
ctttttaaat ggcttttctg agcagagtcg caatgaagag gatagttcta acgcatccct  780
gacaaatact ctagccgaat ttgatccctt ctctcagtca tcgttgtacc cggagcatga  840
gatcaatgtt acttctgata tcggcatgga ccaggtttac gatttctcac aatttctcga  900
aaagctcggg agtgaaggcc acaacgaact gaatgtcgag tatggtcatg atcttcttat  960
gtccgatgtt tcgcaagaag tctcatcacc tagcgttgat gatcaagaca atatgattgg  1020
aagcttcgaa ggttggtcaa attatcttct tgaccatgct gattttatat atgacaccga  1080
ctcagattcc ctcgaaaagc atttcatgtg a                                 1111

SEQ ID NO: 85          moltype = AA  length = 33
FEATURE                Location/Qualifiers
source                 1..33
                       mol_type = protein
                       organism = Thlaspi arvense
SEQUENCE: 85
MSRKPCCVGE GLKKGAWTTE EDKKLISYIH EAR                               33

SEQ ID NO: 86          moltype = DNA  length = 1110
FEATURE                Location/Qualifiers
source                 1..1110
                       mol_type = genomic DNA
                       organism = Thlaspi arvense
SEQUENCE: 86
atgtcaagaa agccgtgttg tgtcggagaa gggctgaaga aaggggcatg gaccaccgaa  60
gaagacaaga aactcatctc ttacatccac gggcacggtg aaggaggctg gcgcgacatt  120
ccccaaaaag ctgggttgaa acggtgtgga aagagttgta ggctgcgatg gactaactac  180
ctaaaacctg agatcaaaag aggcgagttt agttcagagg aggaacagat tatcattatg  240
cttcatgctt ctcgtggcaa caagtggtcg gtcatagcga gacatttacc tagaagaaca  300
gacaacgaga tcaagaacta ctggaacacg catctcaaaa aacgtttgat cgaacagggt  360
gttgatcccg tgactcacaa gcctctagct tccaactccg gccctactgc caccacgccg  420
cctgagaatt tgcatttcct agatgaatct agctcagaca agcaatactc tcggtcgagc  480
tcaatgcctt ccctgtctcg tcttccttcc tccggattca acacggtttc cgagatagcc  540
agcaatgttg ggacaccagt tcaggtcggt tccttgagtt gcaagaaacg ttttaagaaa  600
tcgagttcga catcaaggct tctgaacaaa tttgcggcta aggccacttc catcaaagat  660
atattgtcgg cttccatgga aggtagctcg agtgctgcta ctacaatatc acatgcaagc  720
tttttaaatg gcttttctga gcagagtcgc aatgaagagg atagttctaa cgcatccctg  780
acaaatactc tagccgaatt tgatcccttc tctcagtcat cgttgtaccc ggagcatgag  840
atcaatgtta cttctgatat cggcatggac caggtttacg atttctcaca atttctcgaa  900
aagctcggga gtgaaggcca caacgaactg aatgtcgagt atggtcatga tcttcttatg  960
tccgatgttt cgcaagaagt ctcatcacct agcgttgatg atcaagacaa tatgattgga  1020
agcttcgaag gttggtcaaa ttatcttctt gaccatgctg attttatata tgacaccgac  1080
tcagattccc tcgaaaagca tttcatgtga                                  1110

SEQ ID NO: 87          moltype = AA  length = 369
FEATURE                Location/Qualifiers
source                 1..369
                       mol_type = protein
                       organism = Thlaspi arvense
SEQUENCE: 87
MSRKPCCVGE GLKKGAWTTE EDKKLISYIH GHGEGGWRDI PQKAGLKRCG KSCRLRWTNY  60
LKPEIKRGEF SSEEEQIIIM LHASRGNKWS VIARHLPRRT DNEIKNYWNT HLKKRLIEQG  120
```

```
VDPVTHKPLA SNSGPTATTP PENLHFLDES SSDKQYSRSS SMPSLSRLPS SGFNTVSEIA  180
SNVGTPVQVG SLSCKKRFKK SSSTSRLLNK FAAKATSIKD ILSASMEGSS SAATTISHAS  240
FLNGFSEQSR NEEDSSNASL TNTLAEFDPF SQSSLYPEHE INVTSDIGMD QVYDFSQFLE  300
KLGSEGHNEL NVEYGHDLLM SDVSQEVSSP SVDDQDNMIG SFEGWSNYLL DHADFIYDTD  360
SDSLEKHFM                                                         369

SEQ ID NO: 88          moltype = DNA  length = 1111
FEATURE                Location/Qualifiers
source                 1..1111
                       mol_type = genomic DNA
                       organism = Thlaspi arvense
SEQUENCE: 88
atgtcaagaa agccgtgttg tgtcggagaa gggctgaaga aaggggcatg gaccaccgaa  60
gaagacaaga aactcatctc ttacatccac gaagcacggt gaaggaggct ggcgcgacat  120
tccccaaaaa gctgggttga aacggtgtgg aaagagttgt aggctgcgat ggactaacta  180
cctaaaacct gagatcaaaa gaggcgagtt tagttcagag gaggaacaga ttatcattat  240
gcttcatgct tctcgtggca acaagtggtc ggtcatagcg agacatttac ctagaagaac  300
agacaacgag atcaagaact actggaacac gcatctcaaa aaacgtttga tcgaacaggg  360
tgttgatccc gtgactcaca agcctctagc ttccaactcc ggccctactg ccaccacgcc  420
gcctgagaat ttgcatttcc tagatgaatc tagctcagac aagcaatact ctcggtcgag  480
ctcaatgcct tccctgtctc gtcttccttc ctccggattc aacacggttt ccgagatagc  540
cagcaatgtt gggacaccag ttcaggtcgg ttccttgagt tgcaagaaac gttttaagaa  600
atcgagttcg acatcaaggc ttctgaacaa atttgcggct aaggccactt ccatcaaaga  660
tatattgtcg gcttccatgg aaggtagctc gagtgctgct actacaatat cacatgcaag  720
ctttttaaat ggcttttctg agcagagtcg caatgaagag gatagttcta acgcatccct  780
gacaaatact ctagccgaat ttgatccctt ctctcagtca tcgttgtacc cggagcatga  840
gatcaatgtt acttctgata tcggcatgga ccaggtttac gatttctcac aatttctcga  900
aaagctcggg agtgaaggcc acaacgaact gaatgtcgag tatggtcatg atcttcttat  960
gtccgatgtt tcgcaagaag tctcatcacc tagcgttgat gatcaagaca atatgattgg  1020
aagcttcgaa ggttggtcaa attatcttct tgaccatgct gattttatat atgacaccga  1080
ctcagattcc ctcgaaaagc atttcatgtg a                                1111

SEQ ID NO: 89          moltype = AA  length = 33
FEATURE                Location/Qualifiers
source                 1..33
                       mol_type = protein
                       organism = Thlaspi arvense
SEQUENCE: 89
MSRKPCCVGE GLKKGAWTTE EDKKLISYIH EAR                              33

SEQ ID NO: 90          moltype = DNA  length = 1108
FEATURE                Location/Qualifiers
source                 1..1108
                       mol_type = genomic DNA
                       organism = Thlaspi arvense
SEQUENCE: 90
atgtcaagaa agccgtgttg tgtcggagaa gggctgaaga aaggggcatg gaccaccgaa  60
gaagacaaga aactcatctc ttacatccac gcacggtgaa ggaggctggc gcgacattcc  120
ccaaaaagct gggttgaaac ggtgtggaaa gagttgtagg ctgcgatgga ctaactacct  180
aaaacctgag atcaaaagag gcgagtttag ttcagaggag gaacagatta tcattatgct  240
tcatgcttct cgtggcaaca agtggtcggt catagcgaga catttaccta gaagaacaga  300
caacgagatc aagaactact ggaacacgca tctcaaaaaa cgtttgatcg aacagggtgt  360
tgatcccgtg actcacaagc ctctagcttc caactccggc cctactgcca ccacgccgcc  420
tgagaatttg catttcctag atgaatctag ctcagacaag caatactctc ggtcgagctc  480
aatgccttcc ctgtctcgtc ttccttcctc cggattcaac acggtttccg agatagccag  540
caatgttggg acaccagttc aggtcggttc cttgagttgc aagaaacgtt ttaagaaatc  600
gagttcgaca tcaaggcttc tgaacaaatt tgcggctaag gccacttcca tcaaagatat  660
attgtcggct tccatggaag gtagctcgag tgctgctact acaatatcac atgcaagctt  720
tttaaatggc ttttctgagc agagtcgcaa tgaagaggat agttctaacg catccctgac  780
aaatactcta gccgaatttg atcccttctc tcagtcatcg ttgtacccgg agcatgagat  840
caatgttact tctgatatcg gcatggacca ggtttacgat ttctcacaat ttctcgaaaa  900
gctcgggagt gaaggccaca acgaactgaa tgtcgagtat ggtcatgatc ttcttatgtc  960
cgatgtttcg caagaagtct catcacctag cgttgatgat caagacaata tgattggaag  1020
cttcgaaggt tggtcaaatt atcttcttga ccatgctgat tttatatatg acaccgactc  1080
agattccctc gaaaagcatt tcatgtga                                    1108

SEQ ID NO: 91          moltype = AA  length = 32
FEATURE                Location/Qualifiers
source                 1..32
                       mol_type = protein
                       organism = Thlaspi arvense
SEQUENCE: 91
MSRKPCCVGE GLKKGAWTTE EDKKLISYIH AR                               32

SEQ ID NO: 92          moltype = DNA  length = 1509
FEATURE                Location/Qualifiers
source                 1..1509
                       mol_type = genomic DNA
                       organism = Thlaspi arvense
```

```
SEQUENCE: 92
atggaagata tcatcatcgg cgttgtggct ctcgccgccg ttctcctctt cttcctctac  60
caaagcccaa aaaccaaacg gtataagctg cctcccggcc cacggccgct tccggtgatc  120
ggaaacctcc accagcttag ccaggttaac ccacaacggt tcttctatgg atgggccaaa  180
aaatatggac caatcttatc atacaagata ggaaacaaaa caatgatggt aatttcttcg  240
gctgagctaa ccaaagagct tctcaagacg caagatgtca acttcgccaa ccggcctcct  300
caccgtggtc acgagctcat gacctacggc cgaagtgaca tggcgatgaa ccactacaca  360
ccgttgtacc gggagatgag gaagatgggc atgaaccact tgttctcccc cactcgtgta  420
gccaccttta agcacgtacg ggaggaggag gctaggagga tgatgtttaa gatcgagaag  480
gctgcggaga gatctgaacc ggtcgatata agcgagctta tgttgacctt cacgaactcg  540
gttgtgtgta ggcaagcttt cgggaagaag tacaatgaag atggggaaga gatgaagaga  600
ttcatcagga ttctttatgg gactcagagc gtattgggga agattttttt ctctgatttt  660
ttcccgttta ctcgctacgt tcttgataat tggaccggcc tcacgaaata tatgatggac  720
tgttttgaaa gacaagacac ttacatacaa gagattatcg atgagacact tgatcccaac  780
aaggtaaagc cagaaacgga gagcatgatc gatctcttga tggaggtcta caaagaacaa  840
ccattcgcct ccaagttcac aattgggaat gtcaaaggcg ttatcttgaa tatagtggtt  900
gcgggaaccg acacggcggc tgcggcggtt gtgtggggga tgacgtatct aatgaagtac  960
cctcaagtta tgaagaaagc tcaagcagaa gtgagagagt atgcaaaaga gaaagatcta  1020
acgtttatta ctgaagacga cgtcaagaac cttccttact tcagagcttt agttaaagaa  1080
accttaagga tcgaaccagt gattcctctc cttatccctc gttgttgcat tcaagacacc  1140
aagatcgccg gttacgatgt ccccgcgggg accacggtca acgtaaacgc gtgggcggtg  1200
tcacgcgacg agaaggagtg gggcccaaac cctgatgaat tcaggcccga gaggtttctt  1260
gagaaggacg tggacttcaa aggcacggac tatgagttta taccgtttgg gtcaggccgg  1320
agaatgtgcc ctggaatgcg tcttggcgcg gcgatgatcg aggttccgta tgcgaacctt  1380
ttgctcaact ttgacttcaa acttgctgat ggactgaaac cagaagagat caacatggat  1440
gttatgacag gtcttgctat gcacaaggcg gttcatctca ggcttgttcc cgagaaagtg  1500
aggaagtga                                                           1509

SEQ ID NO: 93           moltype = DNA  length = 4468
FEATURE                 Location/Qualifiers
source                  1..4468
                        mol_type = genomic DNA
                        organism = Thlaspi arvense
SEQUENCE: 93
atggcaagac ttgatattcg agtcggtaaa atcgtcaagg ctcggaaaca tcctaacgca  60
gattcattgt atttggaaga gatcgatgtt ggaggaggtg aagttcgcac cgttgtgagt  120
ggactggtca aatacatacc tcttgaggag atgcaggttt gttaaatctc cacgaatcaa  180
acctaaccta gtcatctgct ttcatcccaa tatatctgac tgttcttttt ggacagaacc  240
gtatggtttg tgttctttgc aacttgaagc cggcgaaaat gagggatgtt atgtcacaag  300
cgatggttct tgccgcttct agtagtgatg gcagcaaggt aaaagtccac aagaatgagt  360
ctctgacctg ttcatcgtta cgctatatcc atttcgttta tagataattt gtttttttggg  420
aactttcagg ttgagttagt cgagcctcct gaatctgcta agatcggaga gagggttagg  480
tttgccgggt ttgaaggcga gccagacgat gttttaaacc ctaagaagaa aatatgggag  540
acacttgtgg tggatctgca cacaaatgag aatctagttg cttgctacaa agatttgcct  600
ttcactacag attcaggtgt atgcaaggtt tcatccatca gcaatggtac aatccggtaa  660
aaaagcttta agttggtctt tatctttctt catttctctc tctctctttt gaggggaaac  720
acatttttct gagatttcat ttgaagaatt gattctatta acaaaccttg tcttgtaaac  780
tcaaactcgt cactttttttg gttcttaatt tggttttgag aaacaatatg ttaatttttt  840
ctttagacaa acttggtagg ccttttggta tatcaatatc agcttttttat actggacccg  900
gacggaaagc aaccacacaa gttgttgagg tttcgatgat agtgtataaa taattatcgt  960
atttatcaaa aggtcaatca catcatttat ttattttcag taacaacttt gtaataaagt  1020
cttccgcaag caaacttttg tgcaaatttc ttggaaactc agtttgcgac aaactacaaa  1080
gtaaatgttg gctatgtatg acatcgttat gattagttca aagtacctta ggtaaatttg  1140
gttttacttt tgtatttata aaattgagta tgttttagaa ttctagctat atatgtcagc  1200
gtatgttaca tttttctgta taagattgga ttgtactata gtgcataggc ccggggttgg  1260
tttagaccac tcagtgaagc aagttaaata aagatctgtg taaactacaa atagatatgg  1320
acaaatatga ctgcgactgc atgaaagtat ataaccatat atgttaatta aaagcatagg  1380
acattagagg gaccttgggt aggtgaaggt gtttctcaac tctaacacgt gaggttttca  1440
taagtaggta gtaaaaaagg agtaagcgtt ttgattataa aattagattt cggtttaatt  1500
cggttatggt atttggtttg gtaaagaaga aaaggaatgc aattaataat ttctctatat  1560
attaaggagc tgtgtgctgt ttatgtacca ctcaaaagta gtaagtaaac aactaagaat  1620
ggaagatatc atcatcggcg ttgtggctct cgccgccgtt ctcctcttct tcctctacca  1680
aagcccaaaa accaaacggt ataagctgcc tcccggccca cggccgcttc cggtgatcgg  1740
aaacctccac cagcttagcc aggttaaccc acaacggttc ttctatggat gggccaaaaa  1800
atatggacca atcttatcat acaagatagg aaacaaaaca atgatggtaa tttcttcggc  1860
tgagctaacc aaagagcttc tcaagacgca agatgtcaac ttcgccaacc ggcctcctca  1920
ccgtggtcac gagctcatga cctacggccg aagtgacatg gcgatgaacc actacacacc  1980
gttgtaccgg gagatgagga agatgggcat gaaccacttg ttctccccca ctcgtgtagc  2040
cacctttaag cacgtacggg aggaggaggc taggaggatg atgtttaaga tcgagaaggc  2100
tgcggagaga tctgaaccgg tcgatataag cgagcttatg ttgaccttca cgaactcggt  2160
tgtgtgtagg caagctttcg ggaagaagta caatgaagat ggggaagaga tgaagagatt  2220
catcaggatt ctttatggga ctcagagcgt attggggaag atttttttct ctgatttttt  2280
cccgtttact cgctacgttc ttgataattg gaccggcctc acgaaatata tgatggactg  2340
ttttgaaaga caagacactt acatacaaga gattatcgat gagacacttg atcccaacaa  2400
ggtaaagcca gaaacggaga gcatgatcga tctcttgatg gaggtctaca aagaacaacc  2460
attcgcctcc aagttcacaa ttgggaatgt caaaggcgtt atcttggtac gtataaaacc  2520
acttctcaat tttcttttgt tttgaatcgt tgcttgtgct acaagcaccc actcgcttgc  2580
gtttcactct tcttttcgtt gttgtgtttc aaaagaatat agtggttgcg ggaaccgaca  2640
cggcggctgc ggcggttgtg tgggggatga cgtatctaat gaagtaccct caagttatga  2700
```

```
agaaagctca agcagaagtg agagagtatg caaaagagaa agatctaacg tttattactg  2760
aagacgacgt caagaacctt ccttacttca gagctttagt taaagaaacc ttaaggatcg  2820
aaccagtgat tcctctcctt atccctcgtt gttgcattca agacaccaag atcgccggtt  2880
acgatgtccc cgcggggacc acggtcaacg taaacgcgtg ggcggtgtca cgcgacgaga  2940
aggagtgggg cccaaaccct gatgaattca ggcccgagag gtttcttgag aaggacgtgg  3000
acttcaaagg cacggactat gagtttatac cgtttgggtc aggccggaga atgtgccctg  3060
gaatgcgtct tggcgcggcg atgatcgagg ttccgtatgc gaacctttg ctcaactttg  3120
acttcaaact tgctgatgga ctgaaaccag aagagatcaa catggatgtt atgacaggtc  3180
ttgctatgca caaggcggtt catctcaggc ttgttcccga gaaagtgagg aagtgacagt  3240
ttctagtagt aaaataaatc tctcactctt gttatataat atattgttcc ctaaagcgta  3300
ctatgcttta aggtttggtt tctgtattaa gtggcaatcg tctctcttat aatttttcct  3360
tttacatcaa acgacttacg caaaaaagct agatagccga gccaaaaggt cgtcttggta  3420
cataagaaaa aaaaaccaaa gcaaaagaga acataaatga ttaaattagg ctttttttt  3480
ttcttgtgat tcatttaagt tgattcctcg aaacatgttg accactcatg ggttcatta   3540
ataatttcca aaacaaagct tctaagtcat agtgaagtga caagagccta tcctaagcca  3600
ctaaacgcgg ctcaagtctt ctatgagcca tcacactagt gactggacaa atgttagctg  3660
ttttgatatc cagtggactc gcgggtcttt ggtcctgatg aaccacgtaa tctattagaa  3720
tatatactag ctcaaagggt acttgtgttc aatcaataga tttcctcttt agatagtctt  3780
ttataggtaa tattagatca acgtaatatt agtttaaggg aaattcttat cgaagttcat  3840
tataaaatga aaaaaatatt attagttttt ttttgtaata caaacaaata ttaattttt   3900
tttctccaaa atatcacttt cagaatatca attttcaaaa tactaatatt tattttaaaa  3960
atatttataa aacttaacaa aggtctctta acaatataat aataataatt ttaatatagt  4020
ataattgtat ggtttaattt taaggtttct taaaaaagtt aaattaaatt atctcaaagt  4080
ttgatttgag agaccctttt cattcttttc ttcccaactt ttattatttt taatattaga  4140
aactttttta aatacttcta atgaagatgt tctaataatt tatacaaaat aataaactat  4200
gcaaacctta taaaatcctt ttgcaagaaa tataatatac atatctacaa aagaattggt  4260
tctgcatctg tattttcctt ctccatgtag acattctttc tagtttttct acccacatga  4320
cttgtatttt cttattctta gcattttgta attatgtata acaatgcctt ctcatatttt  4380
tatgtgtttt ctcatcttgt tatatggacg tcgaattatc attgcccata ttattttatc  4440
catgattttt tgttttatgt tttcagaa                                      4468
```

```
SEQ ID NO: 94          moltype = AA  length = 502
FEATURE                Location/Qualifiers
source                 1..502
                       mol_type = protein
                       organism = Thlaspi arvense
SEQUENCE: 94
MEDIIIGVVA LAAVLLFFLY QSPKTKRYKL PPGPRPLPVI GNLHQLSQVN PQRFFYGWAK  60
KYGPILSYKI GNKTMMVISS AELTKELLKT QDVNFANRPP HRGHELMTYG RSDMAMNHYT  120
PLYREMRKMG MNHLFSPTRV ATFKHVREEE ARRMMFKIEK AAERSEPVDI SELMLTFTNS  180
VVCRQAFGKK YNEDGEEMKR FIRILYGTQS VLGKIFFSDF FPFTRYVLDN WTGLTKYMMD  240
CFERQDTYIQ EIIDETLDPN KVKPETESMI DLLMEVYKEQ PFASKFTIGN VKGVILNIVV  300
AGTDTAAAAV VWGMTYLMKY PQVMKKAQAE VREYAKEKDL TFITEDDVKN LPYFRALVKE  360
TLRIEPVIPL LIPRCCIQDT KIAGYDVPAG TTVNVNAWAV SRDEKEWGPN PDEFRPERFL  420
EKDVDFKGTD YEFIPFGSGR RMCPGMRLGA AMIEVPYANL LLNFDFKLAD GLKPEEINMD  480
VMTGLAMHKA VHLRLVPEKV RK                                            502
```

```
SEQ ID NO: 95          moltype = DNA  length = 1510
FEATURE                Location/Qualifiers
source                 1..1510
                       mol_type = genomic DNA
                       organism = Thlaspi arvense
SEQUENCE: 95
atggaagata tcatcatcgg cgttgtggct ctcgccgccg ttctcctctt cttcctctac  60
caaagcccaa aaaccaaacg gtataagctg cctcccggcc cacggccgct tccggtgatc  120
ggaaacctcc accagcttag ccaggttaac ccacaacggt tcttctatgg atgggccaaa  180
aaatatggac caatcttatc ataccaagat aggaaacaaa acaatgatgg taatttcttc  240
ggctgagcta accaaagagc ttctcaagac gcaagatgtc aacttcgcca accggcctcc  300
tcaccgtggt cacgagctca tgacctacgg ccgaagtgac atggcgatga accactacac  360
accgttgtac cgggagatga ggaagatggg catgaaccac ttgttctccc ccactcgtgt  420
agccaccttt aagcacgtac gggaggagga ggctaggagg atgatgttta agatcgagaa  480
ggctgcggag agatctgaac cggtcgatat aagcgagctt atgttgacct tcacgaactc  540
ggttgtgtgt aggcaagctt tcgggaagaa gtacaatgaa gatggggaag agatgaagag  600
attcatcagg attctttatg ggactcagag cgtattgggg aagatttttt tctctgattt  660
tttcccgttt actcgctacg ttcttgataa ttggaccggc ctcacgaaat atatgatgga  720
ctgttttgaa agacaagaca cttacataca agagattatc gatgagacac ttgatcccaa  780
caaggtaaag ccagaaacgg agagcatgat cgatctcttg atggaggtct acaaagaaca  840
accattcgcc tccaagttca caattgggaa tgtcaaaggc gttatcttga atatagtggt  900
tgcgggaacc gacacggcgg ctgcggcggt tgtgtggggg atgacgtatc taatgaagta  960
ccctcaagtt atgaagaaag ctcaagcaga agtgagagag tatgcaaaag agaaagatct  1020
aacgtttatt actgaagacg acgtcaagaa ccttccttac ttcagagctt tagttaaaga  1080
aaccttaagg atcgaaccag tgattcctct ccttatccct cgttgttgca ttcaagacac  1140
caagatcgcc ggttacgatg tccccgcggg gaccacggtc aacgtaaacg cgtgggcggt  1200
gtcacgcgac gagaaggagt ggggcccaaa ccctgatgaa ttcaggcccg agaggtttct  1260
tgagaaggac gtggacttca aaggcacgga ctatgagttt ataccgtttg ggtcaggccg  1320
gagaatgtgc cctggaatgc gtcttggcgc ggcgatgatc gaggttccgt atgcgaacct  1380
tttgctcaac tttgacttca aacttgctga tggactgaaa ccagaagaga tcaacatgga  1440
tgttatgaca ggtcttgcta tgcacaaggc ggttcatctc aggcttgttc ccgagaaagt  1500
gaggaagtga                                                          1510
```

```
SEQ ID NO: 96          moltype = AA  length = 81
FEATURE                Location/Qualifiers
source                 1..81
                       mol_type = protein
                       organism = Thlaspi arvense
SEQUENCE: 96
MEDIIIGVVA LAAVLLFFLY QSPKTKRYKL PPGPRPLPVI GNLHQLSQVN PQRFFYGWAK  60
KYGPILSYQD RKQNNDGNFF G                                            81

SEQ ID NO: 97          moltype = DNA  length = 1509
FEATURE                Location/Qualifiers
source                 1..1509
                       mol_type = genomic DNA
                       organism = Thlaspi arvense
SEQUENCE: 97
atggaagata tcatcatcgg cgttgtggct ctcgccgccg ttctcctctt cttcctctac  60
caaagcccaa aaaccaaacg gtataagctg cctcccggcc cacggccgct tccggtgatc  120
ggaaacctcc accagcttag ccaggttaac ccacaacggt tcttctatgg atgggccaaa  180
aaatatggac caatcttatc atccaagata ggaaacaaaa caatgatggt aatttcttcg  240
gctgagctaa ccaaagagct tctcaagacg caagatgtca acttcgccaa ccggcctcct  300
caccgtggtc acgagctcat gacctacggc cgaagtgaca tggcgatgaa ccactacaca  360
ccgttgtacc gggagatgag gaagatgggc atgaaccact tgttctcccc cactcgtgta  420
gccaccttta agcacgtacg ggaggaggag gctaggagga tgatgtttaa gatcgagaag  480
gctgcggaga gatctgaacc ggtcgatata agcgagctta tgttgacctt cacgaactcg  540
gttgtgtgta ggcaagcttt cgggaagaag tacaatgaag atggggaaga gatgaagaga  600
ttcatcagga ttctttatgg gactcagagc gtattgggga agattttttt ctctgatttt  660
ttcccgttta ctcgctacgt tcttgataat tggaccggcc tcacgaaata tatgatggac  720
tgttttgaaa gacaagacac ttacatacaa gagattatcg atgagacact tgatcccaac  780
aaggtaaagc cagaaacgga gagcatgatc gatctcttga tggaggtcta caaagaacaa  840
ccattcgcct ccaagttcac aattgggaat gtcaaaggcg ttatcttgaa tatagtggtt  900
gcgggaaccg acacggcggc tgcggcggtt gtgtggggga tgacgtatct aatgaagtac  960
cctcaagtta tgaagaaagc tcaagcagaa gtgagagagt atgcaaaaga gaaagatcta  1020
acgtttatta ctgaagacga cgtcaagaac cttccttact tcagagcttt agttaaagaa  1080
accttaagga tcgaaccagt gattcctctc cttatccctc gttgttgcat tcaagacacc  1140
aagatcgccg gttacgatgt ccccgcgggg accacggtca acgtaaacgc gtgggcggtg  1200
tcacgcgacg agaaggagtg gggcccaaac cctgatgaat tcaggcccga gaggtttctt  1260
gagaaggacg tggacttcaa aggcacggac tatgagttta taccgtttgg gtcaggccgg  1320
agaatgtgcc ctggaatgcg tcttggcgcg gcgatgatcg aggttccgta tgcgaacctt  1380
ttgctcaact ttgacttcaa acttgctgat ggactgaaac cagaagagat caacatggat  1440
gttatgacag gtcttgctat gcacaaggcg gttcatctca ggcttgttcc cgagaaagtg  1500
aggaagtga                                                          1509

SEQ ID NO: 98          moltype = AA  length = 502
FEATURE                Location/Qualifiers
source                 1..502
                       mol_type = protein
                       organism = Thlaspi arvense
SEQUENCE: 98
MEDIIIGVVA LAAVLLFFLY QSPKTKRYKL PPGPRPLPVI GNLHQLSQVN PQRFFYGWAK  60
KYGPILSSKI GNKTMMVISS AELTKELLKT QDVNFANRPP HRGHELMTYG RSDMAMNHYT  120
PLYREMRKMG MNHLFSPTRV ATFKHVREEE ARRMMFKIEK AAERSEPVDI SELMLTFTNS  180
VVCRQAFGKK YNEDGEEMKR FIRILYGTQS VLGKIFFSDF FPFTRYVLDN WTGLTKYMMD  240
CFERQDTYIQ EIIDETLDPN KVKPETESMI DLLMEVYKEQ PFASKFTIGN VKGVILNIVV  300
AGTDTAAAAV VWGMTYLMKY PQVMKKAQAE VREYAKEKDL TFITEDDVKN LPYFRALVKE  360
TLRIEPVIPL LIPRCCIQDT KIAGYDVPAG TTVNVNAWAV SRDEKEWGPN PDEFRPERFL  420
EKDVDFKGTD YEFIPFGSGR RMCPGMRLGA AMIEVPYANL LLNFDFKLAD GLKPEEINMD  480
VMTGLAMHKA VHLRLVPEKV RK                                           502

SEQ ID NO: 99          moltype = DNA  length = 20
FEATURE                Location/Qualifiers
source                 1..20
                       mol_type = genomic DNA
                       organism = Thlaspi arvense
SEQUENCE: 99
ggtgtcgtac gatagagtgt                                              20

SEQ ID NO: 100         moltype = DNA  length = 20
FEATURE                Location/Qualifiers
source                 1..20
                       mol_type = genomic DNA
                       organism = Thlaspi arvense
SEQUENCE: 100
acggtctttc cgagagtatg                                              20

SEQ ID NO: 101         moltype = DNA  length = 19
FEATURE                Location/Qualifiers
source                 1..19
                       mol_type = genomic DNA
```

```
                        organism = Thlaspi arvense
SEQUENCE: 101
atccaggatc ctcatgttt                                                19

SEQ ID NO: 102          moltype = DNA  length = 20
FEATURE                 Location/Qualifiers
source                  1..20
                        mol_type = genomic DNA
                        organism = Thlaspi arvense
SEQUENCE: 102
actcaacgaa ttaccgtctg                                               20

SEQ ID NO: 103          moltype = DNA  length = 20
FEATURE                 Location/Qualifiers
source                  1..20
                        mol_type = genomic DNA
                        organism = Thlaspi arvense
SEQUENCE: 103
gttaagtcta atgccgaaga                                               20

SEQ ID NO: 104          moltype = DNA  length = 20
FEATURE                 Location/Qualifiers
source                  1..20
                        mol_type = genomic DNA
                        organism = Thlaspi arvense
SEQUENCE: 104
ccactcataa cggtctttcc                                               20

SEQ ID NO: 105          moltype = DNA  length = 20
FEATURE                 Location/Qualifiers
source                  1..20
                        mol_type = genomic DNA
                        organism = Thlaspi arvense
SEQUENCE: 105
ccactcataa cggtctttcc                                               20

SEQ ID NO: 106          moltype = DNA  length = 20
FEATURE                 Location/Qualifiers
source                  1..20
                        mol_type = genomic DNA
                        organism = Thlaspi arvense
SEQUENCE: 106
agcctccttc accgtgctcg                                               20

SEQ ID NO: 107          moltype = DNA  length = 20
FEATURE                 Location/Qualifiers
source                  1..20
                        mol_type = genomic DNA
                        organism = Thlaspi arvense
SEQUENCE: 107
tcaagaaagc cgtgttgtgt                                               20

SEQ ID NO: 108          moltype = DNA  length = 20
FEATURE                 Location/Qualifiers
source                  1..20
                        mol_type = genomic DNA
                        organism = Thlaspi arvense
SEQUENCE: 108
aagaagacaa gaaactcatc                                               20

SEQ ID NO: 109          moltype = DNA  length = 19
FEATURE                 Location/Qualifiers
source                  1..19
                        mol_type = genomic DNA
                        organism = Thlaspi arvense
SEQUENCE: 109
agggttgaaa cggtgtgga                                                19

SEQ ID NO: 110          moltype = DNA  length = 20
FEATURE                 Location/Qualifiers
source                  1..20
                        mol_type = genomic DNA
                        organism = Thlaspi arvense
SEQUENCE: 110
gaccatgctg tatcggagaa                                               20

SEQ ID NO: 111          moltype = DNA  length = 20
FEATURE                 Location/Qualifiers
source                  1..20
```

```
                         mol_type = genomic DNA
                         organism = Thlaspi arvense
SEQUENCE: 111
aaggagcagt cgttacagcc                                                   20

SEQ ID NO: 112           moltype = DNA  length = 20
FEATURE                  Location/Qualifiers
source                   1..20
                         mol_type = genomic DNA
                         organism = Thlaspi arvense
SEQUENCE: 112
gacgaagccg aaaacattgg                                                   20

SEQ ID NO: 113           moltype = DNA  length = 20
FEATURE                  Location/Qualifiers
source                   1..20
                         mol_type = genomic DNA
                         organism = Thlaspi arvense
SEQUENCE: 113
acttgcccct agccctagtc                                                   20

SEQ ID NO: 114           moltype = DNA  length = 20
FEATURE                  Location/Qualifiers
source                   1..20
                         mol_type = genomic DNA
                         organism = Thlaspi arvense
SEQUENCE: 114
actcggatga gcattcacat                                                   20

SEQ ID NO: 115           moltype = DNA  length = 20
FEATURE                  Location/Qualifiers
source                   1..20
                         mol_type = genomic DNA
                         organism = Thlaspi arvense
SEQUENCE: 115
tgaacatggc gaaggaggct                                                   20

SEQ ID NO: 116           moltype = DNA  length = 20
FEATURE                  Location/Qualifiers
source                   1..20
                         mol_type = genomic DNA
                         organism = Thlaspi arvense
SEQUENCE: 116
tggaaggaac cttggttagc                                                   20

SEQ ID NO: 117           moltype = DNA  length = 20
FEATURE                  Location/Qualifiers
source                   1..20
                         mol_type = genomic DNA
                         organism = Thlaspi arvense
SEQUENCE: 117
ccaatcttat catacaagat                                                   20

SEQ ID NO: 118           moltype = DNA  length = 20
FEATURE                  Location/Qualifiers
source                   1..20
                         mol_type = genomic DNA
                         organism = Thlaspi arvense
SEQUENCE: 118
aaaccctact ccaccgtcga                                                   20

SEQ ID NO: 119           moltype = DNA  length = 20
FEATURE                  Location/Qualifiers
source                   1..20
                         mol_type = genomic DNA
                         organism = Thlaspi arvense
SEQUENCE: 119
gaagaagtga aatgcattgt                                                   20

SEQ ID NO: 120           moltype = DNA  length = 20
FEATURE                  Location/Qualifiers
source                   1..20
                         mol_type = genomic DNA
                         organism = Thlaspi arvense
SEQUENCE: 120
ttcctctgcg acacttactt                                                   20

SEQ ID NO: 121           moltype = DNA  length = 20
FEATURE                  Location/Qualifiers
```

```
source                  1..20
                        mol_type = genomic DNA
                        organism = Thlaspi arvense
SEQUENCE: 121
gaagaagtga aatgcattgt                                         20

SEQ ID NO: 122          moltype = DNA  length = 20
FEATURE                 Location/Qualifiers
source                  1..20
                        mol_type = genomic DNA
                        organism = Thlaspi arvense
SEQUENCE: 122
tgtatgtgaa agtcaaagcc                                         20

SEQ ID NO: 123          moltype = DNA  length = 20
FEATURE                 Location/Qualifiers
source                  1..20
                        mol_type = genomic DNA
                        organism = Thlaspi arvense
SEQUENCE: 123
tccaagcgca gcagagcgac                                         20

SEQ ID NO: 124          moltype = DNA  length = 20
FEATURE                 Location/Qualifiers
source                  1..20
                        mol_type = genomic DNA
                        organism = Thlaspi arvense
SEQUENCE: 124
tctcctccat gtcggccatg                                         20

SEQ ID NO: 125          moltype = DNA  length = 20
FEATURE                 Location/Qualifiers
source                  1..20
                        mol_type = genomic DNA
                        organism = Thlaspi arvense
SEQUENCE: 125
ccctactcca ccgtcgatgg                                         20

SEQ ID NO: 126          moltype = DNA  length = 20
FEATURE                 Location/Qualifiers
source                  1..20
                        mol_type = genomic DNA
                        organism = Thlaspi arvense
SEQUENCE: 126
actctcggga tggagccacg                                         20

SEQ ID NO: 127          moltype = DNA  length = 1016
FEATURE                 Location/Qualifiers
source                  1..1016
                        mol_type = genomic DNA
                        organism = Thlaspi arvense
SEQUENCE: 127
atgtcgaaaa gaccatgctg tatcggagaa gggttaaaga aagggcatgg acgtcagggg  60
aagacaaaaa actcatctct tatatccatg aacatggcga aggaggttgg cgtgacattc  120
ccgaaaaagc tgggctaaaa cggtgtggaa agagttgcag actgcgatgg gcgaactatt  180
tgaaccccga tatcaagaga ggaggattta gctacgagga agaacagatc atcatcatgc  240
ttcatgcttc tcgtggcaac aagtggtcag tcatagcaag acatttgccg caaagaacag  300
acaacgagat caaaaactat tggaacacac atctcaagaa acgcctgatc aataagagca  360
ctgattccgt gacccacaag cctctagctt cctctaaccc tagtcctacc gagcgtaaga  420
agctcgattc ccaagaagaa tccaatccca aggagcagtc gttacagccg ggttcgaagt  480
ctccagtatc tctttccctt tcttcgagtt tcaacgacac tgtacccgag atcatgacca  540
gtgatgagac gcctctagaa agtggtttct tgagttgcaa aaaaagtgtc gagagatcga  600
gctcaacatc aaggctttta aacaaagttg cagctagagc ttcttccatc gggagtatct  660
tatcaacctc catagaagga actttgagat ctcctgcatc gtcctcatgt ctcccaaact  720
cattgtgtca atcatctgaa cacaacaagg atcaagatct cggtacgagc attgatctta  780
gcatccccga ttacgattac tcccactttc tcgagcactt catcaatagc gaagacgaag  840
ccgaaaacat tggtggctgc aatcaagatc tccttatgtc cgatttccca tcaacattag  900
tggataaaga aaatatgaat tttgaagaca taaccggttg gtcaagttat cttctcgacc  960
atcccagttt tacgtatgaa tcggaacaag attccgacga caacaacttg ttatga      1016

SEQ ID NO: 128          moltype = AA  length = 45
FEATURE                 Location/Qualifiers
source                  1..45
                        mol_type = protein
                        organism = Thlaspi arvense
SEQUENCE: 128
MSKRPCCIGE GLKKGHGRQG KTKNSSLISM NMAKEVGVTF PKKLG             45

SEQ ID NO: 129          moltype = DNA  length = 989
```

```
FEATURE               Location/Qualifiers
source                1..989
                      mol_type = genomic DNA
                      organism = Thlaspi arvense
SEQUENCE: 129
atgtcgaaaa gaccatgcta tggacgtcag gggaagacaa aaaactcatc tcttatatcc  60
atgaacatgg cgaaggaggt tggcgtgaca ttcccgaaaa agctgggcta aaacggtgtg  120
gaaagagttg cagactgcga tgggcgaact atttgaaccc cgatatcaag agaggaggat  180
ttagctacga ggaagaacag atcatcatca tgcttcatgc ttctcgtggc aacaagtggt  240
cagtcatagc aagacatttg ccgcaaagaa cagacaacga gatcaaaaac tattggaaca  300
cacatctcaa gaaacgcctg atcaataaga gcactgattc cgtgacccac aagcctctag  360
cttcctctaa ccctagtcct accgagcgta agaagctcga ttcccaagaa gaatccaatc  420
ccaaggagca gtcgttacag ccgggttcga agtctccagt atctctttcc ctttcttcga  480
gtttcaacga cactgtaccc gagatcatga ccagtgatga gacgcctcta gaaagtggtt  540
tcttgagttg caaaaaaagt gtcgagagat cgagctcaac atcaaggctt ttaaacaaag  600
ttgcagctag agcttcttcc atcgggagta tcttatcaac ctccatagaa ggaactttga  660
gatctcctgc atcgtcctca tgtctcccaa actcattgtg tcaatcatct gaacacaaca  720
aggatcaaga tctcggtacg agcattgatc ttagcatccc cgattacgat tactcccact  780
ttctcgagca cttcatcaat agcgaagacg aagccgaaaa cattggtggc tgcaatcaag  840
atctccttat gtccgatttc ccatcaacat tagtggataa agaaaatatg aattttgaag  900
acataaccgg ttggtcaagt tatcttctcg accatcccag ttttacgtat gaatcggaac  960
aagattccga cgacaacaac ttgttatga                                    989

SEQ ID NO: 130        moltype = AA  length = 36
FEATURE               Location/Qualifiers
source                1..36
                      mol_type = protein
                      organism = Thlaspi arvense
SEQUENCE: 130
MSKRPCYGRQ GKTKNSSLIS MNMAKEVGVT FPKKLG                             36

SEQ ID NO: 131        moltype = DNA  length = 491
FEATURE               Location/Qualifiers
source                1..491
                      mol_type = genomic DNA
                      organism = Thlaspi arvense
SEQUENCE: 131
atgtcaagaa agccatgttg tgtgggagaa gggctgaaga aaggagcatg gaccgccgaa  60
gaagacaaga aactcatctc ttacatccat gaaaaggaac cttggttagc tctaccgcac  120
tgtctccatg tctcaatgat gacttttccg aagctagcca attccagatg gacgaatatg  180
atccattccc tcagtcgtct gaacacataa ctgatcatat gaaggaggac accggcatga  240
tctttgatct caacaactcc gaatatgatt tctcgcagtt tctcgagcaa tttagtaacg  300
aaggcgaaga aaccgagaac attgggggat ataatcaaga tctcctttcg tctgacgtct  360
catcaccaag cgttgatgaa gacaatatga tgggaaacat aaccggttcc ggttggtcca  420
gttatcttgt tgaccattcc gattttgttt atgacaagat ccaagataac gacgacagga  480
acttcatatg a                                                        491

SEQ ID NO: 132        moltype = AA  length = 69
FEATURE               Location/Qualifiers
source                1..69
                      mol_type = protein
                      organism = Thlaspi arvense
SEQUENCE: 132
MSRKPCCVGE GLKKGAWTAE EDKKLISYIH EKEPWLALPH CLHVSMMTFP KLANSRWTNM  60
IHSLSRLNT                                                           69

SEQ ID NO: 133        moltype = DNA  length = 477
FEATURE               Location/Qualifiers
source                1..477
                      mol_type = genomic DNA
                      organism = Thlaspi arvense
SEQUENCE: 133
atgtcaagaa agccatgttg tgtgggagaa gggctgaaga aaggagcatg gaccgccgaa  60
gaagacaaga aactcatcta aggaaccttg gttagctcta ccgcactgtc tccatgtctc  120
aatgatgact tttccgaagc tagccaattc cagatggacg aatatgatcc attccctcag  180
tcgtctgaac acataactga tcatatgaag gaggacaccg gcatgatctt tgatctcaac  240
aactccgaat atgatttctc gcagtttctc gagcaattta gtaacgaagg cgaagaaacc  300
gagaacattg ggggatataa tcaagatctc ctttcgtctg acgtctcatc accaagcgtt  360
gatgaagaca atatgatggg aaacataacc ggttccggtt ggtccagtta tcttgttgac  420
cattccgatt ttgtttatga caagatccaa gataacgacg acaggaactt catatga     477

SEQ ID NO: 134        moltype = AA  length = 26
FEATURE               Location/Qualifiers
source                1..26
                      mol_type = protein
                      organism = Thlaspi arvense
SEQUENCE: 134
MSRKPCCVGE GLKKGAWTAE EDKKLI                                        26
```

```
SEQ ID NO: 135          moltype = DNA  length = 1082
FEATURE                 Location/Qualifiers
source                  1..1082
                        mol_type = genomic DNA
                        organism = Thlaspi arvense
SEQUENCE: 135
atgtcaagaa agccatgttg tgtgggagaa gggctgaaga aaggagcatg gaccgccgaa  60
gaagacaaga aactcatctc ttacatccat gaaacatggc gaaggaggct ggcgtgacat  120
tccccaaaaa gctggactaa aacgatgtgg aaaaagttgt agattgcgat gggctaacta  180
tttgaaaccg gatatcaaga gaggagaatt tagctacgag gaggagcaga ttatcatcat  240
gcttcacgct tcccgtggca acaagtggtc ggtcatagcg agacatttgc ccaaaaggac  300
agacaacgag atcaagaact attggaacac acaccttaaa aaacgcctta tcgatcaagg  360
tattgatccc gtgacccaca agccacttgc ccctagccct agtccggcca cgctcaagcc  420
ttctgatttc caagatgact catcaaacct gggaaactcg gatgagcatt cacattcggg  480
ttctatgtct ccaaaatctc ttcctccgtc ttcaagctcc tgcaatctag cggagataag  540
cagcagtgat gagacaccga aaaatgatgg ttccttgaaa tccaagaaac gttcttttaa  600
gagatcaagt tctacatcaa agctgttaaa caaagttgca tctagggctg cttccattgg  660
aaatatctta tcagcgtcca tggaaaggaa ccttggttag ctctaccgca ctgtctccat  720
gtctcaatga tgacttttcc gaagctagcc aattccagat ggacgaatat gatccattcc  780
ctcagtcgtc tgaacacata actgatcata tgaaggagga caccggcatg atctttgatc  840
tcaacaactc cgaatatgat ttctcgcagt ttctcgagca atttagtaac gaaggcgaag  900
aaaccgagaa cattggggga tataatcaag atctcctttc gtctgacgtc tcatcaccaa  960
gcgttgatga agacaatatg atgggaaaca taaccggttc cggttggtcc agttatcttg  1020
ttgaccattc cgattttgtt tatgacaaga tccaagataa cgacgacagg aacttcatat  1080
ga                                                                1082

SEQ ID NO: 136          moltype = AA  length = 38
FEATURE                 Location/Qualifiers
source                  1..38
                        mol_type = protein
                        organism = Thlaspi arvense
SEQUENCE: 136
MSRKPCCVGE GLKKGAWTAE EDKKLISYIH ETWRRRLA                         38

SEQ ID NO: 137          moltype = DNA  length = 1077
FEATURE                 Location/Qualifiers
source                  1..1077
                        mol_type = genomic DNA
                        organism = Thlaspi arvense
SEQUENCE: 137
atgtcaagaa agccatgttg tgtgggagaa gggctgaaga aaggagcatg gaccgccgaa  60
gaagacaaga aactcatctc ttacatccat gaacatggcg aaggaggctg gcgtgacatt  120
ccccaaaaag ctggactaaa acgatgtgga aaaagttgta gattgcgatg ggctaactat  180
ttgaaaccgg atatcaagag aggagaattt agctacgagg aggagcagat tatcatcatg  240
cttcacgctt cccgtggcaa caagtggtcg gtcatagcga gacatttgcc caaaaggaca  300
gacaacgaga tcaagaacta ttggaacaca caccttaaaa aacgccttat cgatcaaggt  360
attgatcccg tgacccacaa gccacttgcc cctagcccta gtccggccac gctcaagcct  420
tctgatttcc aagatgactc atcaaacctg ggaaactcgg atgagcattc acattcgggt  480
tctatgtctc caaaatctct tcctccgtct tcaagctcct gcaatctagc ggagataagc  540
agcagtgatg agacaccgaa aaatgatggt tccttgaaat ccaagaaacg ttcttttaag  600
agatcaagtt ctacatcaaa gctgttaaac aaagttgcat ctagggctgc ttccattgga  660
aatatcttat cagcgtccaa aggaaccttg gttagctcta ccgcactgtc tccatgtctc  720
aatgatgact tttccgaagc tagccaattc cagatggacg aatatgatcc attccctcag  780
tcgtctgaac acataactga tcatatgaag gaggacaccg gcatgatctt tgatctcaac  840
aactccgaat atgatttctc gcagtttctc gagcaattta gtaacgaagg cgaagaaacc  900
gagaacattg gggatataa tcaagatctc ctttcgtctg acgtctcatc accaagcgtt  960
gatgaagaca atatgatggg aaacataacc ggttccggtt ggtccagtta tcttgttgac  1020
cattccgatt ttgtttatga caagatccaa gataacgacg acaggaactt catatga     1077

SEQ ID NO: 138          moltype = AA  length = 358
FEATURE                 Location/Qualifiers
source                  1..358
                        mol_type = protein
                        organism = Thlaspi arvense
SEQUENCE: 138
MSRKPCCVGE GLKKGAWTAE EDKKLISYIH EHGEGGWRDI PQKAGLKRCG KSCRLRWANY  60
LKPDIKRGEF SYEEEQIIIM LHASRGNKWS VIARHLPKRT DNEIKNYWNT HLKKRLIDQG  120
IDPVTHKPLA PSPSPATLKP SDFQDDSSNL GNSDEHSHSG SMSPKSLPPS SSSCNLAEIS  180
SSDETPKNDG SLKSKKRSFK RSSSTSKLLN KVASRAASIG NILSASKGTL VSSTALSPCL  240
NDDFSEASQF QMDEYDPFPQ SSEHITDHMK EDTGMIFDLN NSEYDFSQFL EQFSNEGEET  300
ENIGGYNQDL LSSDVSSPSV DEDNMMGNIT GSGWSSYLVD HSDFVYDKIQ DNDDRNFI    358

SEQ ID NO: 139          moltype = DNA  length = 1076
FEATURE                 Location/Qualifiers
source                  1..1076
                        mol_type = genomic DNA
                        organism = Thlaspi arvense
SEQUENCE: 139
atgtcaagaa agccatgttg tgtgggagaa gggctgaaga aaggagcatg gaccgccgaa  60
```

```
gaagacaaga aactcatctc ttacatccat gaacatggcg aaggaggctg gcgtgacatt  120
ccccaaaaag ctggactaaa acgatgtgga aaaagttgta gattgcgatg ggctaactat  180
ttgaaaccgg atatcaagag aggagaattt agctacgagg aggagcagat tatcatcatg  240
cttcacgctt cccgtggcaa caagtggtcg gtcatagcga gacatttgcc caaaaggaca  300
gacaacgaga tcaagaacta ttggaacaca caccttaaaa aacgcctat cgatcaaggt  360
attgatcccg tgacccacaa gccacttgcc cctagcccta gtccggccac gctcaagcct  420
tctgatttcc aagatgactc atcaaacctg ggaaactcgg atgagcattc acattcgggt  480
tctatgtctc caaaatctct tcctccgtct tcaagctcct gcaatctagc ggagataagc  540
agcagtgatg agacaccgaa aaatgatggt tccttgaaat ccaagaaacg ttcttttaag  600
agatcaagtt ctacatcaaa gctgttaaac aaagttgcat ctagggctgc ttccattgga  660
aatatcttat cagcgtccaa ggaaccttgg ttagctctac cgcactgtct ccatgtctca  720
atgatgactt ttccgaagct agccaattcc agatggacga atatgatcca ttccctcagt  780
cgtctgaaca cataactgat catatgaagg aggacaccgg catgatcttt gatctcaaca  840
actccgaata tgatttctcg cagtttctcg agcaatttag taacgaaggc gaagaaaccg  900
agaacattgg gggatataat caagatctcc tttcgtctga cgtctcatca ccaagcgttg  960
atgaagacaa tatgatggga aacataaccg gttccggttg gtccagttat cttgttgacc  1020
attccgattt tgtttatgac aagatccaag ataacgacga caggaacttc atatga      1076
```

```
SEQ ID NO: 140         moltype = AA  length = 264
FEATURE                Location/Qualifiers
source                 1..264
                       mol_type = protein
                       organism = Thlaspi arvense
SEQUENCE: 140
MSRKPCCVGE GLKKGAWTAE EDKKLISYIH EHGEGGWRDI PQKAGLKRCG KSCRLRWANY  60
LKPDIKRGEF SYEEEQIIIM LHASRGNKWS VIARHLPKRT DNEIKNYWNT HLKKRLIDQG  120
IDPVTHKPLA PSPSPATLKP SDFQDDSSNL GNSDEHSHSG SMSPKSLPPS SSSCNLAEIS  180
SSDETPKNDG SLKSKKRSFK RSSSTSKLLN KVASRAASIG NILSASKEPW LALPHCLHVS  240
MMTFPKLANS RWTNMIHSLS RLNT                                        264
```

```
SEQ ID NO: 141         moltype = DNA  length = 1079
FEATURE                Location/Qualifiers
source                 1..1079
                       mol_type = genomic DNA
                       organism = Thlaspi arvense
SEQUENCE: 141
atgtcaagaa agccatgttg tgtgggagaa gggctgaaga aaggagcatg gaccgccgaa  60
gaagacaaga aactcatctc ttacatccat gaacatggcg aaggaggctg gcgtgacatt  120
ccccaaaaag ctggactaaa acgatgtgga aaaagttgta gattgcgatg ggctaactat  180
ttgaaaccgg atatcaagag aggagaattt agctacgagg aggagcagat tatcatcatg  240
cttcacgctt cccgtggcaa caagtggtcg gtcatagcga gacatttgcc caaaaggaca  300
gacaacgaga tcaagaacta ttggaacaca caccttaaaa aacgcctat cgatcaaggt  360
attgatcccg tgacccacaa gccacttgcc cctagcccta gtccggccac gctcaagcct  420
tctgatttcc aagatgactc atcaaacctg ggaaactcgg atgagcattc acattcgggt  480
tctatgtctc caaaatctct tcctccgtct tcaagctcct gcaatctagc ggagataagc  540
agcagtgatg agacaccgaa aaatgatggt tccttgaaat ccaagaaacg ttcttttaag  600
agatcaagtt ctacatcaaa gctgttaaac aaagttgcat ctagggctgc ttccattgga  660
aatatcttat cagcgtccat ggaggaacct tggttagctc taccgcactg tctccatgtc  720
tcaatgatga cttttccgaa gctagccaat tccagatgga cgaatatgat ccattccctc  780
agtcgtctga acacataact gatcatatga aggaggacac cggcatgatc tttgatctca  840
acaactccga atatgatttc tcgcagtttc tcgagcaatt tagtaacgaa ggcgaagaaa  900
ccgagaacat tgggggatat aatcaagatc tcctttcgtc tgacgtctca tcaccaagcg  960
ttgatgaaga caatatgatg ggaaacataa ccggttccgg ttggtccagt tatcttgttg  1020
accattccga ttttgtttat gacaagatcc aagataacga cgacaggaac ttcatatga   1079
```

```
SEQ ID NO: 142         moltype = AA  length = 265
FEATURE                Location/Qualifiers
source                 1..265
                       mol_type = protein
                       organism = Thlaspi arvense
SEQUENCE: 142
MSRKPCCVGE GLKKGAWTAE EDKKLISYIH EHGEGGWRDI PQKAGLKRCG KSCRLRWANY  60
LKPDIKRGEF SYEEEQIIIM LHASRGNKWS VIARHLPKRT DNEIKNYWNT HLKKRLIDQG  120
IDPVTHKPLA PSPSPATLKP SDFQDDSSNL GNSDEHSHSG SMSPKSLPPS SSSCNLAEIS  180
SSDETPKNDG SLKSKKRSFK RSSSTSKLLN KVASRAASIG NILSASMEEP WLALPHCLHV  240
SMMTFPKLAN SRWTNMIHSL SRLNT                                       265
```

```
SEQ ID NO: 143         moltype = DNA  length = 1841
FEATURE                Location/Qualifiers
source                 1..1841
                       mol_type = genomic DNA
                       organism = Thlaspi arvense
SEQUENCE: 143
atggagagaa agccctttga ggttgagacg acggagaatc acaaacccta ctccaccgtc  60
gatggcggtg gcgttggttc tgatttgaga tcgccggtcg attcatttga tgacgagcag  120
aaaaagctcg tttacagagg ctggaaagtc atgcctttta tcattggtaa tgagacattt  180
gagaagattg ggatcatagg gacattatca aaccttcttt tgtacctaac tcaagtattc  240
aaccttaaga aagttacagc tgcaacaatc atcaatgcct ttagtggcac aatcaacttc  300
gggactttca tcgctgcttt ccttttggtc gctacaagac tctcagtgta gctgtcatcg  360
```

```
cttgtttcct gggatcgctt gtgatattac tgacggctgc agttcctgca ttgcacccga  420
ctccatgtgg aacacatagc tggtgccaag ggccaagccc gggccagatc gcgttcttgc  480
tgctgggttt agcgtttctt gtggtcggtg cgggtgggat caggccgtgt aacttggctt  540
ttggagctga tcagttcaac cccaaatccg aatccgggaa gaaaggaatc aacagcttct  600
ttaactggta tttcttcacc ttcacgtttg cgcagatcgt ctcgctcacg ctggtcgtgt  660
atatccagtc gaacgtgagc tggacgatcg gtttgctcat ccctgtggct ctgatgttct  720
tggcctgcgt catcttcttt gctggacata aactgtatgt gaaagtgaaa gcctcgggta  780
gtcccttggc tagtatcggt cacgttatca cggcagcgat caagaaacga gggttgaagc  840
aagttaagca gccttggctc gatctttaca accacattcc aactaactat ccaaactcca  900
ccttgaaata caccgaccag tttaggtttc ttgacaaagc agcgattatg accccctgagg  960
acaagctgaa ttccgatgga gctgctttcg atccatggac cctatgtaca ttgcagaaag  1020
tggaagaagt gaaatgcatt gtgagagtga ttccgatctg gtttgcttgc gcgatttact  1080
acctcactgt aactatacag atgacttatc cggtcttcca agcgcagcag agcgaccgga  1140
gattgggttc tggtggcttc aagatccccg cagccaccta tgtggtgttc ttgatgtcgg  1200
gtatgactgt tttcatcgtg ttctacgacc gtgtccttgt cccgttgctc agaagagtga  1260
ccgggttaga aaccggtttg accctcttgc agagagtcgg atcagggatc ttctttgcca  1320
tgttgagttt gttggtctcc gggttcgtag aggaacggag aagaaccttc gccctgacga  1380
aaccgactct cgggatggag ccacgagcgg gagagatctc ctccatgtcg gccatgtggc  1440
tgattccgca gctcttgctt gcaggcgtag gagaggcttt tacagccatt ggacagatgg  1500
agttttatta caagcagttc cctgagaaca tgaagagctt cgctggctct atcttctatg  1560
tcggtgcagg tgtttcgagc tatcttgcta gcttcttgat ctcgactgtt catcgaagaa  1620
ctgaacattc accctccggg aactggttag ctgaggatct gaacaaaggg agactcgatt  1680
acttctactt catgctcacc ggaatcatgg tcgttaacat ggtttacttc ttgataatgt  1740
ctaaatggta tagatacaaa ggcattaacg atgaagcgaa ttctttggtc gagaccaatg  1800
aagaagagac caagcagaaa caagtcaaga attctgtctg a                       1841
```

```
SEQ ID NO: 144         moltype = AA  length = 116
FEATURE                Location/Qualifiers
source                 1..116
                       mol_type = protein
                       organism = Thlaspi arvense
SEQUENCE: 144
MERKPFEVET TENHKPYSTV DGGGVGSDLR SPVDSFDDEQ KKLVYRGWKV MPFIIGNETF  60
EKIGIIGTLS NLLLYLTQVF NLKKVTAATI INAFSGTINF GTFIAAFLLV ATRLSV      116
```

```
SEQ ID NO: 145         moltype = DNA  length = 1843
FEATURE                Location/Qualifiers
source                 1..1843
                       mol_type = genomic DNA
                       organism = Thlaspi arvense
SEQUENCE: 145
atggagagac agcctctcga actcgagtct acggatcacc aaaaaccttc ccccgccgtc  60
tacggtggct ctgttacgac ggttgattct gttgaggaag aagttcagga gaaaaaagtc  120
gtatatagag gctggaaagt catgcccttt atcattggaa atgagacatt cgagaagctt  180
gggatcattg gaacactatc aaaccttctg gtttttttaa cagctgtctt caacatgaag  240
agtatcacag ctgcaacaat cattaacgca ttcagtggca caataaattt cggaactttc  300
gttgctgctt tcctctgcga cacttacttc ggtcgataca agacactaac cgtcgcggtc  360
atcgcctgtt ttcttggatc acttgtgata ctattgacag ctgcagtgcc acaactgcac  420
ccagctccat gtggaacagc gagctcgtgc agcggtccaa gcggtgggca aatcgcgttt  480
cttctgatgg gtctcgggtt tcttgtagtt ggagcgggcg ggatcagacc gtgcaatcta  540
gctttcggag ccgatcagtt caacccgaag agcgagtcag ggagaagagg gactgatagt  600
ttcttcaatt ggtacttctt cagcttcact ttcgcgcaga tcttgtcgct gacgctagtg  660
gtctacatcc agtctaacgt cagctggacg atcggtctaa ccataccggt ggttctaatg  720
ttcttggcct ccgtgatctt ctttgcggga gataagctgt atgtgaaagt caaggcctcg  780
ggtagtccat tggctggtat agctcaagtg atcattgttg caatcaagaa acgcggatta  840
aagcccgtga aacagccttg gcttaacctc tacaattact gccctccaaa acacgcaaac  900
tccattctca aatacaccga ccaattcaga tttcttgata aggcggcgat cttggctccc  960
gaggacaagt tggaggcgga tggtaagcct gcggatccat ggaagctgtg tacgatgcaa  1020
caggtggaag aagtgaagtg catttgtgag agtgcttcct atatggttcg ctgcatcaat  1080
ctactacgta accataaccc agcaaatgac atatccggtc ttccaagccc tgcagagcga  1140
tcgtcgctta ggctcgggag ggttcgtgat ccccgcagcc acctacgtgg tcttcttgat  1200
gacagggatg acggttttca tcatcatcta cgaccgtctc ctcgtgccta ccttgagaag  1260
aataaccggt ctagacaccg ggatcacgct cctgcagaga atcggaaccg ggatcttctt  1320
cgcctttgca agcttagtag tctccggttt cgtcgaggag cggaggagac acattgcgct  1380
gactaaacca actcttggca tggcgccaag aaaaggagaa atctcctcaa tgtcagctat  1440
gtggctcatc ccgcagctca ctctctcggg tgtagccgag gcgtttggag ccatcggaca  1500
gatggagttt tactacaagc agttcccaga aaacatgagg agtttcgcgg gttccatctt  1560
ttatgtagga ataggggttt cgagttacct cggcagcttc ttgattgcaa cggttcaccg  1620
gacgacgcag aactcggcgg gtggtaactg gttggctgag gatttgaaca aaggcagatt  1680
ggattacttc tatttcatga tcgctggaat cttggctgtt aatttcgcct acttcttggt  1740
cgtgtcaaga tggtataggt acaaagaaag tgatgatgat caaaagacag cttctgaaac  1800
caatggagat gtcatcaaac aacaagacaa gaacactgcc tga                   1843
```

```
SEQ ID NO: 146         moltype = AA  length = 461
FEATURE                Location/Qualifiers
source                 1..461
                       mol_type = protein
                       organism = Thlaspi arvense
SEQUENCE: 146
```

```
MERQPLELES TDHQKPSPAV YGGSVTTVDS VEEEVQEKKV VYRGWKVMPF IIGNETFEKL  60
GIIGTLSNLL VFLTAVFNMK SITAATIINA FSGTINFGTF VAAFLCDTYF GRYKTLTVAV  120
IACFLGSLVI LLTAAVPQLH PAPCGTASSC SGPSGGQIAF LLMGLGFLVV GAGGIRPCNL  180
AFGADQFNPK SESGRRGTDS FFNWYFFSFT FAQILSLTLV VYIQSNVSWT IGLTIPVVLM  240
FLASVIFFAG DKLYVKVKAS GSPLAGIAQV IIVAIKKRGL KPVKQPWLNL YNYCPPKHAN  300
SILKYTDQFR FLDKAAILAP EDKLEADGKP ADPWKLCTMQ QVEEVKCICE SASYMVRCIN  360
LLRNHNPAND ISGLPSPAER SSLRLGRVRD PRSHLRGLLD DRDDGFHHHL RPSPRAYLEK  420
NNRSRHRDHA PAENRNRDLL RLCKLSSLRF RRGAEETHCA D                     461

SEQ ID NO: 147         moltype = DNA  length = 1366
FEATURE                Location/Qualifiers
source                 1..1366
                       mol_type = genomic DNA
                       organism = Thlaspi arvense
SEQUENCE: 147
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagtaatgg ggatccagga  300
tcctcatgtt ttggacaaag tttacgagtt tactcaactt ctacgtcctg atcattgtga  360
cggtaacaag agcatcagcg aaacgatcca gacgttttca gagaagttat cagaattgga  420
tataatggtg agaagaatgg taatggaaag cttcgggata gagaagtacc ttgacaaaca  480
cctgaactca acgaattacc gtctgcggct gatgaagtat atagcaccgc ctgatgctga  540
tgctactaat gttgcggctg atgccaaaga tgctgatgat aatgctaaga cgattacaaa  600
tgataaagtt gatgcggctg gtgctaatga tgtagatgct ggtgatatcg ctaatggtat  660
tgctaatctt catattggtg atgatgctaa cgctggtgct aatggtgctg gtgttgatgc  720
taatgatggt ggtgaggatg ctaagactgg tgaggatgct aagactggtg aatgtgctag  780
tgttaagtct aatgccgaag atggtactga tgttaatgcc agtgctgatg ctggtgttac  840
tgttggctct aatgctgatg ctaatgctaa tgctaatgct aatactagta ctgatgctgg  900
tgttggcgat agtgttaaag ctaatggtgg tgctgatgat gttgagaaga aattgggtct  960
accttctcac actgataaga accttataac ggtgctttat caatacgaga ttgaaggctt  1020
ggaggttcta accaaagatg acaagtggat cagactcaaa ccatctcata attctttcgt  1080
tgttatggct ggagattctc tatacgcact tatgaatggt agactaactc gtccctttca  1140
tcgagtaaga gtaacggaga aaaagaagac aagatattca atagcattgt tctcggctcc  1200
aaccgcagat tacatcatag acacaccaaa agaacttgtg gacgagaagc atccacgtat  1260
cttcgaacca tttaactata acgacttgat gagtttctat catagtgaag ctggtcgtaa  1320
agctcgatct actcttgatg ctttctgtgc cgtctctcga gcataa                1366

SEQ ID NO: 148         moltype = AA  length = 116
FEATURE                Location/Qualifiers
source                 1..116
                       mol_type = protein
                       organism = Thlaspi arvense
SEQUENCE: 148
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSERYGDPG SSCFGQSLRV YSTSTS      116

SEQ ID NO: 149         moltype = DNA  length = 1363
FEATURE                Location/Qualifiers
source                 1..1363
                       mol_type = genomic DNA
                       organism = Thlaspi arvense
SEQUENCE: 149
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agaatgggga tccaggatcc  300
tcatgttttg gacaaagttt acgagtttac tcaacttcta cgtcctgatc attgtgacgg  360
taacaagagc atcagcgaaa cgatccagac gttttcagag aagttatcag aattggatat  420
aatggtgaga agaatggtaa tggaaagctt cgggatagag aagtaccttg acaaacacct  480
gaactcaacg aattaccgtc tgcggctgat gaagtatata gcaccgcctg atgctgatgc  540
tactaatgtt gcggctgatg ccaaagatgc tgatgataat gctaagacga ttacaaatga  600
taaagttgat gcggctggtg ctaatgatgt agatgctggt gatatcgcta atggtattgc  660
taatcttcat attggtgatg atgctaacgc tggtgctaat ggtgctggtg ttgatgctaa  720
tgatggtggt gaggatgcta agactggtga ggatgctaag actggtgaat gtgctagtgt  780
taagtctaat gccgaagatg gtactgatgt taatgccagt gctgatgctg gtgttactgt  840
tggctctaat gctgatgcta atgctaatgc taatgctaat actagtactg atgctggtgt  900
tggcgatagt gttaaagcta atggtggtgc tgatgatgtt gagaagaaat tgggtctacc  960
ttctcacact gataagaacc ttataacggt gctttatcaa tacgagattg aaggcttgga  1020
ggttctaacc aaagatgaca agtggatcag actcaaacca tctcataatt ctttcgttgt  1080
tatggctgga gattctctat acgcacttat gaatggtaga ctaactcgtc cctttcatcg  1140
agtaagagta acggagaaaa agaagacaag atattcaata gcattgttct cggctccaac  1200
cgcagattac atcatagaca caccaaaaga acttgtggac gagaagcatc cacgtatctt  1260
cgaaccattt aactataacg acttgatgag tttctatcat agtgaagctg gtcgtaaagc  1320
tcgatctact cttgatgctt tctgtgccgt ctctcgagca taa                   1363

SEQ ID NO: 150         moltype = AA  length = 115
```

```
FEATURE                Location/Qualifiers
source                 1..115
                       mol_type = protein
                       organism = Thlaspi arvense
SEQUENCE: 150
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSENGDPGS SCFGQSLRVY STSTS       115

SEQ ID NO: 151         moltype = DNA  length = 1363
FEATURE                Location/Qualifiers
source                 1..1363
                       mol_type = genomic DNA
                       organism = Thlaspi arvense
SEQUENCE: 151
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagtgggga tccaggatcc  300
tcatgttttg gacaaagttt acgagtttac tcaacttcta cgtcctgatc attgtgacgg  360
taacaagagc atcagcgaaa cgatccagac gttttcagag aagttatcag aattggatat  420
aatggtgaga agaatggtaa tggaaagctt cgggatagag aagtaccttg acaaacacct  480
gaactcaacg aattaccgtc tgcggctgat gaagtatata gcaccgcctg atgctgatgc  540
tactaatgtt gcggctgatg ccaaagatgc tgatgataat gctaagacga ttacaaatga  600
taaagttgat gcggctggtg ctaatgatgt agatgctggt gatatcgcta atggtattgc  660
taatcttcat attggtgatg atgctaacgc tggtgctaat ggtgctggtg ttgatgctaa  720
tgatggtggt gaggatgcta agactggtga ggatgctaag actggtgaat gtgctagtgt  780
taagtctaat gccgaagatg gtactgatgt taatgccagt gctgatgctg gtgttactgt  840
tggctctaat gctgatgcta atgctaatgc taatgctaat actagtactg atgctggtgt  900
tggcgatagt gttaaagcta atggtggtgc tgatgatgtt gagaagaaat tgggtctacc  960
ttctcacact gataagaacc ttataacggt gctttatcaa tacgagattg aaggcttgga  1020
ggttctaacc aaagatgaca agtggatcag actcaaacca tctcataatt ctttcgttgt  1080
tatggctgga gattctctat acgcacttat gaatggtaga ctaactcgtc cctttcatcg  1140
agtaagagta acggagaaaa agaagacaag atattcaata gcattgttct cggctccaac  1200
cgcagattac atcatagaca caccaaaaga acttgtggac gagaagcatc cacgtatctt  1260
cgaaccattt aactataacg acttgatgag tttctatcat agtgaagctg gtcgtaaagc  1320
tcgatctact cttgatgctt tctgtgccgt ctctcgagca taa                    1363

SEQ ID NO: 152         moltype = AA  length = 115
FEATURE                Location/Qualifiers
source                 1..115
                       mol_type = protein
                       organism = Thlaspi arvense
SEQUENCE: 152
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSESGDPGS SCFGQSLRVY STSTS       115

SEQ ID NO: 153         moltype = DNA  length = 1360
FEATURE                Location/Qualifiers
source                 1..1360
                       mol_type = genomic DNA
                       organism = Thlaspi arvense
SEQUENCE: 153
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagggatcc aggatcctca  300
tgttttggac aaagtttacg agtttactca acttctacgt cctgatcatt gtgacggtaa  360
caagagcatc agcgaaacga tccagacgtt ttcagagaag ttatcagaat tggatataat  420
ggtgagaaga atggtaatgg aaagcttcgg gatagagaag taccttgaca aacacctgaa  480
ctcaacgaat taccgtctgc ggctgatgaa gtatatagca ccgcctgatg ctgatgctac  540
taatgttgcg gctgatgcca aagatgctga tgataatgct aagacgatta caaatgataa  600
agttgatgcg gctggtgcta atgatgtaga tgctggtgat atcgctaatg gtattgctaa  660
tcttcatatt ggtgatgatg ctaacgctgg tgctaatggt gctggtgttg atgctaatga  720
tggtggtgag gatgctaaga ctggtgagga tgctaagact ggtgaatgtg ctagtgttaa  780
gtctaatgcc gaagatggta ctgatgttaa tgccagtgct gatgctggtg ttactgttgg  840
ctctaatgct gatgctaatg ctaatgctaa tgctaatact agtactgatg ctggtgttgg  900
cgatagtgtt aaagctaatg gtggtgctga tgatgttgag aagaaattgg gtctaccttc  960
tcacactgat aagaacctta taacggtgct ttatcaatac gagattgaag gcttggaggt  1020
tctaaccaaa gatgacaagt ggatcagact caaaccatct cataattctt tcgttgttat  1080
ggctggagat tctctatacg cacttatgaa tggtagacta actcgtccct ttcatcgagt  1140
aagagtaacg gagaaaaaga agacaagata ttcaatagca ttgttctcgg ctccaaccgc  1200
agattacatc atagacacac caaaagaact tgtggacgag aagcatccac gtatcttcga  1260
accatttaac tataacgact tgatgagttt ctatcatagt gaagctggtc gtaaagctcg  1320
atctactctt gatgctttct gtgccgtctc tcgagcataa                        1360

SEQ ID NO: 154         moltype = AA  length = 114
FEATURE                Location/Qualifiers
```

```
source                1..114
                      mol_type = protein
                      organism = Thlaspi arvense
SEQUENCE: 154
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSERDPGSS CFGQSLRVYS TSTS        114

SEQ ID NO: 155        moltype = DNA  length = 1366
FEATURE               Location/Qualifiers
source                1..1366
                      mol_type = genomic DNA
                      organism = Thlaspi arvense
SEQUENCE: 155
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagttatgg ggatccagga  300
tcctcatgtt ttggacaaag tttacgagtt tactcaactt ctacgtcctg atcattgtga  360
cggtaacaag agcatcagcg aaacgatcca gacgttttca gagaagttat cagaattgga  420
tataatggtg agaagaatgg taatggaaag cttcgggata gagaagtacc ttgacaaaca  480
cctgaactca acgaattacc gtctgcggct gatgaagtat atagcaccgc ctgatgctga  540
tgctactaat gttgcggctg atgccaaaga tgctgatgat aatgctaaga cgattacaaa  600
tgataaagtt gatgcggctg gtgctaatga tgtagatgct ggtgatatcg ctaatggtat  660
tgctaatctt catattggtg atgatgctaa cgctggtgct aatggtgctg gtgttgatgc  720
taatgatggt ggtgaggatg ctaagactgg tgaggatgct aagactggtg aatgtgctag  780
tgttaagtct aatgccgaag atggtactga tgttaatgcc agtgctgatg ctggtgttac  840
tgttggctct aatgctgatg ctaatgctaa tgctaatgct aatactagta ctgatgctgg  900
tgttggcgat agtgttaaag ctaatggtgg tgctgatgat gttgagaaga aattgggtct  960
accttctcac actgataaga accttataac ggtgctttat caatacgaga ttgaaggctt  1020
ggaggttcta accaaagatg acaagtggat cagactcaaa ccatctcata attctttcgt  1080
tgttatggct ggagattctc tatacgcact tatgaatggt agactaactc gtccctttca  1140
tcgagtaaga gtaacggaga aaaagaagac aagatattca atagcattgt tctcggctcc  1200
aaccgcagat tacatcatag acacaccaaa agaacttgtg gacgagaagc atccacgtat  1260
cttcgaacca tttaactata acgacttgat gagtttctat catagtgaag ctggtcgtaa  1320
agctcgatct actcttgatg ctttctgtgc cgtctctcga gcataa                 1366

SEQ ID NO: 156        moltype = AA  length = 116
FEATURE               Location/Qualifiers
source                1..116
                      mol_type = protein
                      organism = Thlaspi arvense
SEQUENCE: 156
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSESYGDPG SSCFGQSLRV YSTSTS      116

SEQ ID NO: 157        moltype = DNA  length = 1357
FEATURE               Location/Qualifiers
source                1..1357
                      mol_type = genomic DNA
                      organism = Thlaspi arvense
SEQUENCE: 157
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttctg gggatccagg atcctcatgt  300
tttggacaaa gtttacgagt ttactcaact tctacgtcct gatcattgtg acggtaacaa  360
gagcatcagc gaaacgatcc agacgttttc agagaagtta tcagaattgg atataatggt  420
gagaagaatg gtaatggaaa gcttcgggat agagaagtac cttgacaaac acctgaactc  480
aacgaattac cgtctgcggc tgatgaagta tatagcaccg cctgatgctg atgctactaa  540
tgttgcggct gatgccaaag atgctgatga taatgctaag acgattacaa atgataaagt  600
tgatgcggct ggtgctaatg atgtagatgc tggtgatatc gctaatggta ttgctaatct  660
tcatattggt gatgatgcta acgctggtgc taatggtgct ggtgttgatg ctaatgatgg  720
tggtgaggat gctaagactg gtgaggatgc taagactggt gaatgtgcta gtgttaagtc  780
taatgccgaa gatggtactg atgttaatgc cagtgctgat gctggtgtta ctgttggctc  840
taatgctgat gctaatgcta atgctaatgc taatactagt actgatgctg gtgttggcga  900
tagtgttaaa gctaatggtg gtgctgatga tgttgagaag aaattgggtc taccttctca  960
cactgataag aaccttataa cggtgcttta tcaatacgag attgaaggct tggaggttct  1020
aaccaaagat gacaagtgga tcagactcaa accatctcat aattctttcg ttgttatggc  1080
tggagattct ctatacgcac ttatgaatgg tagactaact cgtccctttc atcgagtaag  1140
agtaacggag aaaaagaaga caagatattc aatagcattg ttctcggctc caaccgcaga  1200
ttacatcata gacacaccaa aagaacttgt ggacgagaag catccacgta tcttcgaacc  1260
atttaactat aacgacttga tgagtttcta tcatagtgaa gctggtcgta aagctcgatc  1320
tactcttgat gctttctgtg ccgtctctcg agcataa                          1357

SEQ ID NO: 158        moltype = AA  length = 39
FEATURE               Location/Qualifiers
source                1..39
```

```
                        mol_type = protein
                        organism = Thlaspi arvense
SEQUENCE: 158
MFWTKFTSLL NFYVLIIVTV TRASAKRSRR FQRSYQNWI                          39

SEQ ID NO: 159          moltype = DNA  length = 1818
FEATURE                 Location/Qualifiers
source                  1..1818
                        mol_type = genomic DNA
                        organism = Thlaspi arvense
SEQUENCE: 159
atgaacgact acttcctcaa ccagtcaaca gccaccgacg ataacgcgtc ggcggcgatg  60
gaagctttca tcggaacaaa tcactcaact ctctggcccc aaccatctct tcctcctcct  120
cctccactat ctcaattcaa cgaagacact cttcaacaac gtctccaagc tttgatcgaa  180
tcagcaggag aaggctggac ctacgcgatt ttctggcaga tctcacacga tttcgattct  240
tccaccggag acaacacagt gattctcgga tggggagatg ggtactacaa aggggaggaa  300
gataaagaga agaagaagaa tagctcaagt tcgaattcgg cggagcaaga gcatcggaaa  360
agagtaatcc gtgagctgaa ttcgttgatc tccggcggaa ccggagtttc cgatgaatcg  420
aacgacgaag aagtcaccga tactgagtgg ttcttcttgg tctcgatgac acagagcttc  480
atgaacggcg ttgggcttcc cggggagtcg tacttgaact ctcgcgtgat ttggttatcc  540
gggccgggtg ctttaatcgg gtcgggttgc gaacgagcgg gtcaaggtca gatatacggg  600
ttacagacga tggtgtgtat cgcggcggag aacggcgtcg ttgagcttgg ttcatcggag  660
gtgttaagcc atagctcaga tctgatggat aaagtcaaca gtctgttcaa ttccaacaac  720
ggtaatggag aagcttcttc ttgggggttt aatctgaatc cggatcaagg agagaacgat  780
ccggctttgt ggataagcga accgaccacc accggaatcg aatcgggtca ggtaatcccg  840
gcgataaaca acagtaattc caattcaaat tcaaaatccg attctcatca aatctccaag  900
ctcgagaaga acgagagctc gattgaaaac cctagacaac aacaaaatcc gtcgcttgta  960
gagcgagatt tgaatttctc gagttctggg ttgaatcaaa acgggaactt tcaagatggg  1020
tcgtcgcgga tgatgaaatc gaacgaaaca ctgagcttta cggcggagga gagcaacaag  1080
aggaggtctc cggtttcgaa agggagtaac aacgacgaag ggatgctttc tttcagcacc  1140
gtggttcgtt ccgcggcgaa atccgtcgat tcggatcatt ccgatctcga agcgtcggtg  1200
gttaaggaag caattgtcgt tgaaccggag aagaaaccga ggaaacgggg aagaaaaccg  1260
gcgaacggaa gagaggagcc gttgaatcac gtggaagcag agagacagag aagggagaag  1320
ctaaaccaga gattctactc tttgagagct gtggttccca acgtttcgaa aatggacaaa  1380
gcgtctcttc tcggagacgc catttcgtat atcaacgagc ttaaatcgaa gctgcagcaa  1440
gcggaatccg ataaggaaga gattcagaag cagctcgacg ggatgagcaa ggaaggaaac  1500
agggaaggcg gcggcggaac gaaggcgaaa gaacgaaaat gctcgaatca agattcggct  1560
agctcgatag aaatggagat cgacgtgaag atcataggtt gggatgtgat gatacgtgta  1620
caatgcagca agaagaatca tcccggggca agattcatgg aagcgctcaa ggaattggat  1680
ctggaagtga atcacgcaag tttgtcagtg gtgaatgatt tgatgattca acaagccact  1740
gtgaagatgg gaagccagtt tttcaatcat gaccagctca aggttgcttt gatgtcgaaa  1800
gtcggagaag acaattga                                                 1818

SEQ ID NO: 160          moltype = DNA  length = 1818
FEATURE                 Location/Qualifiers
source                  1..1818
                        mol_type = genomic DNA
                        organism = Thlaspi arvense
SEQUENCE: 160
atgaacgact acttcctcaa ccagtcaaca gccaccgacg ataacgcgtc ggcggcgatg  60
gaagctttca tcggaacaaa tcactcaact ctctggcccc aaccatctct tcctcctcct  120
cctccactat ctcaattcaa cgaagacact cttcaacaac gtctccaagc tttgatcgaa  180
tcagcaggag aaggctggac ctacgcgatt ttctggcaga tctcacacga tttcgattct  240
tccaccggag acaacacagt gattctcgga tggggagatg ggtactacaa aggggaggaa  300
gataaagaga agaagaagaa tagctcaagt tcgaattcgg cggagcaaga gcatcggaaa  360
agagtaatcc gtgagctgaa ttcgttgatc tccggcggaa ccggagtttc cgatgaatcg  420
aacgacgaag aagtcaccga tactgagtgg ttcttcttgg tctcgatgac acagagcttc  480
atgaacggcg ttgggcttcc cggggagtcg tacttgaact ctcgcgtgat ttggttatcc  540
gggccgggtg ctttaatcgg gtcgggttgc gaacgagcgg gtcaaggtca gatatacggg  600
ttacagacga tggtgtgtat cgcggcggag aacggcgtcg ttgagcttgg ttcatcggag  660
gtgttaagcc atagctcaga tctgatggat aaagtcaaca gtctgttcaa ttccaacaac  720
ggtaatggag aagcttcttc ttgggggttt aatctgaatc cggatcaagg agagaacgat  780
ccggctttgt ggataagcga accgaccacc accggaatcg aatcgggtca ggtaatcccg  840
gcgataaaca acagtaattc caattcaaat tcaaaatccg attctcatca aatctccaag  900
ctcgagaaga acgagagctc gattgaaaac cctagacaac aacaaaatcc gtcgcttgta  960
gagcgagatt tgaatttctc gagttctggg ttgaatcaaa acgggaactt tcaagatggg  1020
tcgtcgcgga tgatgaaatc gaacgaaaca ctgagcttta cggcggagga gagcaacaag  1080
aggaggtctc cggtttcgaa agggagtaac aacgacgaag ggatgctttc tttcagcacc  1140
gtggttcgtt ccgcggcgaa atccgtcgat tcggatcatt ccgatctcga agcgtcggtg  1200
gttaaggaag caattgtcgt tgaaccggag aagaaaccga ggaaacgggg aagaaaaccg  1260
gcgaacggaa gagaggagcc gttgaatcac gtggaagcag agagacagag aagggagaag  1320
ctaaaccaga gattctactc tttgagagct gtggttccca acgtttcgaa aatggacaaa  1380
gcgtctcttc tcggagacgc catttcgtat atcaacgagc ttaaatcgaa gctgcagcaa  1440
gcggaatccg ataaggaaga gattcagaag cagctcgacg ggatgagcaa ggaaggaaac  1500
agggaaggcg gcggcggaac gaaggcgaaa gaacgaaaat gctcgaatca agattcggct  1560
agctcgatag aaatggagat cgacgtgaag atcataggtt gggatgtgat gatacgtgta  1620
caatgcagca agaagaatca tcccggggca agattcatgg aagcgctcaa ggaattggat  1680
ctggaagtga atcacgcaag tttgtcagtg gtgaatgatt tgatgattca acaagccact  1740
gtgaagatgg gaagccagtt tttcaatcat gaccagctca aggttgcttt gatgtcgaaa  1800
```

```
gtcggagaag acaattga                                                1818

SEQ ID NO: 161         moltype = AA  length = 605
FEATURE                Location/Qualifiers
source                 1..605
                       mol_type = protein
                       organism = Thlaspi arvense
SEQUENCE: 161
MNDYFLNQST ATDDNASAAM EAFIGTNHST LWPQPSLPPP PPLSQFNEDT LQQRLQALIE  60
SAGEGWTYAI FWQISHDFDS STGDNTVILG WGDGYYKGEE DKEKKKNSSS SNSAEQEHRK  120
RVIRELNSLI SGGTGVSDES NDEEVTDTEW FFLVSMTQSF MNGVGLPGES YLNSRVIWLS  180
GPGALIGSGC ERAGQGQIYG LQTMVCIAAE NGVVELGSSE VLSHSSDLMD KVNSLFNSNN  240
GNGEASSWGF NLNPDQGEND PALWISEPTT TGIESGQVIP AINNSNSNSN SKSDSHQISK  300
LEKNESSIEN PRQQQNPSLV ERDLNFSSSG LNQNGNFQDG SSRMMKSNET LSFTAEESNK  360
RRSPVSKGSN NDEGMLSFST VVRSAAKSVD SDHSDLEASV VKEAIVVEPE KKPRKRGRKP  420
ANGREEPLNH VEAERQRREK LNQRFYSLRA VVPNVSKMDK ASLLGDAISY INELKSKLQQ  480
AESDKEEIQK QLDGMSKEGN REGGGGTKAK ERKCSNQDSA SSIEMEIDVK IIGWDVMIRV  540
QCSKKNHPGA RFMEALKELD LEVNHASLSV VNDLMIQQAT VKMGSQFFNH DQLKVALMSK  600
VGEDN                                                              605

SEQ ID NO: 162         moltype = DNA  length = 1332
FEATURE                Location/Qualifiers
source                 1..1332
                       mol_type = genomic DNA
                       organism = Thlaspi arvense
SEQUENCE: 162
atggcggcgt gtttacaatc gaacatccgg ctgaatctga acaatatcgt cggaggaaaa  60
tgcagatccc tcaccgatca gtctcgcacg ccgtgtcgaa taaggtgcgc cgccgcttca  120
cctgggaaaa aacggttcaa catcgctctc cttcctggcg acggtatcgg tcctgaagtc  180
atctccgttg ccaagaatgt gcttcagcaa gctggatctc tcgaaggttc ttctatctct  240
cgctcagttt atttactaat tttgacaaaa ttagtaatca gcgaatgtgt tgcttaccca  300
gaagagtgtg cgtatttgat gtgtatcaca ggactggagt tcaatttcca ggagatgccc  360
atcggaggag cagccttgga tttggtcgga gtggccttgc cggaggaaac cttatcggct  420
gcaaaacagt ctgatgccat acttcttgga gctatcggag ggtacaaatg ggacaacaat  480
gagaaacatc tgagacctga gatggctctg atttaccttc ggagagatct caaagtcttt  540
gctaatctga gacctgcttc agttttgcca cagctagttg atgcatccac cttgaagaga  600
gaagtagcag aaggtgttga tatgatgatt gtaagggagc ttacaggagg aatttacttt  660
ggagagccca gaggcattaa gaccaacgaa aacggagaag aagtcggttt taatacagag  720
ttttacgctg ctcacgagat tgacagaatt gctcgtgttg catttgagac tgctaggaaa  780
cggcgtggca agctgtgttc tgtcgacaaa gccaatgtgt tggatgcatc agtattgtgg  840
aggagaagag taacagcgtt agcctctgag tatccagatg ttgagctctc acatatgtat  900
gtagacaacg ctgcaatgca gcttattcgt gacccgaaac agtttgacac aatcgtcacc  960
aataacattt tcggtgacat attatccgat gaggcctcaa tgatcactgg aagcattggg  1020
atgcttccat ctgctagtct cggtgtatcg ggacctggac tctttgagcc gatacatggt  1080
tctgcgccag atatagctgg tcaggacaag gcaaacccat tggccaccat tctcagcgca  1140
gcgatgcttc tgaaatatgg acttggagaa gagaaggccg caaagaggat cgaggacgcg  1200
gtcttggatg ctctcaacaa agggtttaga accggagaca tctactcccc cggaaataaa  1260
ctggtgggat gcaaggagat gggtgaggag gtgcttaaat cagtggactc cagagttaca  1320
gctactgttt aa                                                      1332

SEQ ID NO: 163         moltype = DNA  length = 1936
FEATURE                Location/Qualifiers
source                 1..1936
                       mol_type = genomic DNA
                       organism = Thlaspi arvense
SEQUENCE: 163
atggcggcgt gtttacaatc gaacatccgg ctgaatctga acaatatcgt cggaggaaaa  60
tgcagatccc tcaccgatca gtctcgcacg ccgtgtcgaa taaggtgcgc cgccgcttca  120
cctgggaaaa aacggttcaa catcgctctc cttcctggcg acggtatcgg tcctgaagtc  180
atctccgttg ccaagaatgt gcttcagcaa gctggatctc tcgaaggttc ttctatctct  240
cgctcagttt atttactaat tttgacaaaa ttagtaatca gcgaatgtgt tgcttaccca  300
gaagagtgtg cgtatttgat gtgtatcaca ggactggagt tcaatttcca ggagatgccc  360
atcggaggag cagccttgga tttggtcgga gtggccttgc cggaggaaac cttatcggct  420
gcaaaacagt ctgatgccat acttcttgga gctatcggag ggtgtgtgtt tgtgtgtctt  480
gtttcttttt ttaattggtc tcttggttca gaaatctgtc tgcttcgagt cttcttctca  540
gcttgagttt tttggatgat tcatggttgg ttggattata ttcaggtaca aatgggacaa  600
caatgagaaa catctgagac ctgagatggc tctgatttac cttcggagag atctcaaagt  660
ctttgctaat ctgagacctg cttcagtttt gccacaggta tatatatata tatatatata  720
tataaacgtt tatctaattc ggtttgatct gcttaccact tgcaattttt acaatcactt  780
gcttgttgtt ctcagctagt tgatgcatcc accttgaaga gagaagtagc agaaggtgtt  840
gatatgatga ttgtaaggga gcttacagga ggaatttact ttggagagcc cagaggcatt  900
aagaccaacg aaaacggaga agaagtcggt tttaatacag agttttacgc tgctcacgag  960
gtcacatact cttcacagtg tggtctatga tatgatgggt ctaaggctat atatgtataa  1020
tataatgcat taattgctca tgttacttcc agattgacag aattgctcgt gttgcatttg  1080
agactgctag gaaacggcgt ggcaagctgt gttctgtcga caaagccaat gtgttggatg  1140
tacgtttgat caacaatttt ttccatttct gtgtgtgtgt gttttttttt ctcgtaatgc  1200
agaattattt ttttcatata ggcatcagta ttgtggagga gaagagtaac agcgttagcc  1260
tctgagtatc cagatgttga gctctcacat atgtatgtag acaacgctgc aatgcagctt  1320
attcgtgacc cgaaacagtt tgacacaatc gtcaccaata acattttcgg tgacatatta  1380
```

```
tccgatgagg cctcaatgat cactggaagc attgggatgc ttccatctgc tagtctcggt  1440
gtatcggtaa ccaacaaatt taaactgaaa atctttcaag gttcctccct gtttattacc  1500
atatatacac atggaatgtt gaaacttgtg tttggatcag ggacctggac tctttgagcc  1560
gatacatggt tctgcgccag atatagctgg tcaggacaag gcaaacccat tggccaccat  1620
tctcagcgca gcgatgcttc tgaaatatgg acttggagaa gagaaggccg caaagaggat  1680
cgaggacgcg gtcttggatg ctctcaacaa agggtttaga accggagaca tctactcccc  1740
cggaaatgta tgttttgatg gtatttttat catttgctta tataataagt taaacaacaa  1800
acagttagta gtatattata tacttttgtg ttattttaat gaaatttgga atgtgaagca  1860
gaaactggtg ggatgcaagg agatgggtga ggaggtgctt aaatcagtgg actccagagt  1920
tacagctact gtttaa                                                  1936
```

```
SEQ ID NO: 164         moltype = AA  length = 443
FEATURE                Location/Qualifiers
source                 1..443
                       mol_type = protein
                       organism = Thlaspi arvense
SEQUENCE: 164
MAACLQSNIR LNLNNIVGGK CRSLTDQSRT PCRIRCAAAS PGKKRFNIAL LPGDGIGPEV  60
ISVAKNVLQQ AGSLEGSSIS RSVYLLILTK LVISECVAYP EECAYLMCIT GLEFNFQEMP  120
IGGAALDLVG VALPEETLSA AKQSDAILLG AIGGYKWDNN EKHLRPEMAL IYLRRDLKVF  180
ANLRPASVLP QLVDASTLKR EVAEGVDMMI VRELTGGIYF GEPRGIKTNE NGEEVGFNTE  240
FYAAHEIDRI ARVAFETARK RRGKLCSVDK ANVLDASVLW RRRVTALASE YPDVELSHMY  300
VDNAAMQLIR DPKQFDTIVT NNIFGDILSD EASMITGSIG MLPSASLGVS GPGLFEPIHG  360
SAPDIAGQDK ANPLATILSA AMLLKYGLGE EKAAKRIEDA VLDALNKGFR TGDIYSPGNK  420
LVGCKEMGEE VLKSVDSRVT ATV                                          443
```

```
SEQ ID NO: 165         moltype = DNA  length = 1635
FEATURE                Location/Qualifiers
source                 1..1635
                       mol_type = genomic DNA
                       organism = Thlaspi arvense
SEQUENCE: 165
atggatactt tagcttcaaa ctcttcgggt ctcaggacca agtcgagtcc cgagacgtcg  60
ccgtttagca acatgtatct cctcacaaca cttcaagccc ttgcggttat ttctctcttg  120
atgatattca agaaaataaa gtattcctct tcacaaaaaa aaaagtttca tcctctcccg  180
ccgggcccca gcgggtttcc agtcgtcgga atgattccgg cgatgcttaa aaaccgtccg  240
gttttccggt ggcttcacag cctcatgaaa gagcttaaca cggagatagc ttgtgttcgt  300
ctaggaaaga ctcacgtgat ccccgtcaca tgtcctaaga tcgcacgtga gattttcaag  360
caacaagacg cactcttcgc gtcgagacca ctcacttatg ctcaaaagat actttccaac  420
ggctacaaaa cctgcgtgat cacaccgttc ggagaacaat tcaagaagat gaggaaagta  480
atcatgacgg agattgtttg tccagcaaga caccgatggt tacacgacaa cagagccgag  540
gaaaccgatc atttaactgc ttggctttac aacatggtta agaaatccga accggtcgat  600
ctccggtttg ttacaaggca ctactgcgga aatgcgatta agaggcttat gttcggaacg  660
aggacgttct cggcgaaaac cgaaaccgac ggtggaccaa ccgtggaaga tatcgagcat  720
atggatgcta tgtttgaagg gttagggttt acgtttgcgt tctgtgtatc ggattatcta  780
ccgatgctta cgggattgga tctaaacgga catgagaaga tcatgagaga agctagtgcg  840
attatggaca aatatcacga tcccattatt gatgagagga ttaagatgtg gagagaagga  900
aagagaactc agattgaaga ttttctagac attttcatct ctatcaagga cgaagctggc  960
cagcctttgc ttaccgctga tgaaatcaaa ccaaccatta aggaacttgt aatggcggcg  1020
ccggacaacc catcaaacgc cgtggaatgg gccatggcgg agatgataaa caaacctgag  1080
attctccaca aagcaatgga agagattgaa agagtcgttg gcaaagaaag actcgtccaa  1140
gaatccgata tcccaaaact taactatctc aaagctatta tccgagaagc tttccgtctg  1200
catcccgtcg ccgccttcaa cctcccacac gtggcacttt ccgacacaac cgtcgctggt  1260
tatcacatcc ctaaggggag tcaagtttta cttagccgtt acggtcttgg tcgtaaccca  1320
aaggtttggt ctgatccact tagctttaaa ccggagagac acctcaatga gtgcttggaa  1380
gtaacgttga ctgagaatga tctccggttt atctcgttta gtaccggaaa aagaggatgt  1440
gctgctccgg cgttaggtac ggcgataacc gtcatgatgc tcgccaggct tttgcaaggg  1500
tttaagtgga agttagctgg aggtgagaca cgtgttgagt tgatggaatc gagtcatgat  1560
atgtttcttg cgacgccttt ggttatggtc ggagaattga gattgtcgga ggatctttac  1620
cccacggtga agtga                                                   1635
```

```
SEQ ID NO: 166         moltype = DNA  length = 2050
FEATURE                Location/Qualifiers
source                 1..2050
                       mol_type = genomic DNA
                       organism = Thlaspi arvense
SEQUENCE: 166
atggatactt tagcttcaaa ctcttcgggt ctcaggacca agtcgagtcc cgagacgtcg  60
ccgtttagca acatgtatct cctcacaaca cttcaagccc ttgcggttat ttctctcttg  120
atgatattca agaaaataaa gtattcctct tcacaaaaaa aaaagtttca tcctctcccg  180
ccgggcccca gcgggtttcc agtcgtcgga atgattccgg cgatgcttaa aaaccgtccg  240
gttttccggt ggcttcacag cctcatgaaa gagcttaaca cggagatagc ttgtgttcgt  300
ctaggaaaga ctcacgtgat ccccgtcaca tgtcctaaga tcgcacgtga gattttcaag  360
caacaagacg cactcttcgc gtcgagacca ctcacttatg ctcaaaagat actttccaac  420
ggctacaaaa cctgcgtgat cacaccgttc ggagaacaat tcaagaagat gaggaaagta  480
atcatgacgg agattgtttg tccagcaaga caccgatggt tacacgacaa cagagccgag  540
gaaaccgatc atttaactgc ttggctttac aacatggtta agaaatccga accggtcgat  600
ctccggtttg ttacaaggca ctactgcgga aatgcgatta agaggcttat gttcggaacg  660
aggacgttct cggcgaaaac cgaaaccgac ggtggaccaa ccgtggaaga tatcgagcat  720
```

```
atggatgcta tgtttgaagg gttagggttt acgtttgcgt tctgtgtatc ggattatcta  780
ccgatgctta cgggattgga tctaaacgga catgagaaga tcatgagaga agctagtgcg  840
attatggaca aatatcacga tcccattatt gatgagagga ttaagatgtg gagagaagga  900
aagagaactc agattgaaga ttttctagac attttcatct ctatcaagga cgaagctggc  960
cagcctttgc ttaccgctga tgaaatcaaa ccaaccatta aggtaactaa ttagatatat  1020
tgaattatat ttattagatt tcttgtcgac taattacgca tattacttat atgtttggat  1080
ttaatatagc agaactaagt ttattattag tattagcaat ttttaagatt aagtggtaaa  1140
aaagtggata caaatgtttt tggggggggg ttctagcgac aacctaagat tttaagttgt  1200
cgttaaaact tttttttttt ctgatttttt aaaaagggta aaacgccaaa acatccatag  1260
tcagaaactt tatgctaatc catagtcaga aactttatgc taatccatag tcagaaactt  1320
tatgtatagc ataaagttta tatttatgtt gacccgtgag tccatgcata gaatagtaaa  1380
acaataatta atcatttata tattttatat tgaataggaa cttgtaatgg cggcgccgga  1440
caacccatca aacgccgtgg aatgggccat ggcggagatg ataaacaaac ctgagattct  1500
ccacaaagca atggaagaga ttgaaagagt cgttggcaaa gaaagactcg tccaagaatc  1560
cgatatccca aaacttaact atctcaaagc tattatccga gaagctttcc gtctgcatcc  1620
cgtcgccgcc ttcaacctcc cacacgtggc actttccgac acaaccgtcg ctggttatca  1680
catccctaag ggagtcaag ttttacttag ccgttacggt cttggtcgta acccaaaggt  1740
ttggtctgat ccacttagct ttaaaccgga gagacacctc aatgagtgct tggaagtaac  1800
gttgactgag aatgatctcc ggtttatctc gtttagtacc ggaaaaagag gatgtgctgc  1860
tccggcgtta ggtacggcga taaccgtcat gatgctcgcc aggcttttgc aagggtttaa  1920
gtggaagtta gctggaggtg agacacgtgt tgagttgatg gaatcgagtc atgatatgtt  1980
tcttgcgacg cctttggtta tggtcggaga attgagattg tcggaggatc tttaccccac  2040
ggtgaagtga                                                         2050

SEQ ID NO: 167          moltype = AA  length = 544
FEATURE                 Location/Qualifiers
source                  1..544
                        mol_type = protein
                        organism = Thlaspi arvense
SEQUENCE: 167
MDTLASNSSG LRTKSSPETS PFSNMYLLTT LQALAVISLL MIFKKIKYSS SQKKKFHPLP  60
PGPSGFPVVG MIPAMLKNRP VFRWLHSLMK ELNTEIACVR LGKTHVIPVT CPKIAREIFK  120
QQDALFASRP LTYAQKILSN GYKTCVITPF GEQFKKMRKV IMTEIVCPAR HRWLHDNRAE  180
ETDHLTAWLY NMVKKSEPVD LRFVTRHYCG NAIKRLMFGT RTFSAKTETD GGPTVEDIEH  240
MDAMFEGLGF TFAFCVSDYL PMLTGLDLNG HEKIMREASA IMDKYHDPII DERIKMWREG  300
KRTQIEDFLD IFISIKDEAG QPLLTADEIK PTIKELVMAA PDNPSNAVEW AMAEMINKPE  360
ILHKAMEEIE RVVGKERLVQ ESDIPKLNYL KAIIREAFRL HPVAAFNLPH VALSDTTVAG  420
YHIPKGSQVL LSRYGLGRNP KVWSDPLSFK PERHLNECLE VTLTENDLRF ISFSTGKRGC  480
AAPALGTAIT VMMLARLLQG FKWKLAGGET RVELMESSHD MFLATPLVMV GELRLSEDLY  540
PTVK                                                               544

SEQ ID NO: 168          moltype = DNA  length = 1188
FEATURE                 Location/Qualifiers
source                  1..1188
                        mol_type = genomic DNA
                        organism = Thlaspi arvense
SEQUENCE: 168
atgatcacca ccacctgttg cactgtggtc gcccagttag gcttgccctt tggatcttcc  60
ttgtcctctc tctgcctgac ccgtccgaac aaaaagccgt ccttgttcac ctcatgttgc  120
tcctctgtgt ccaaaaatgt tggcgctagt gctgctgaca gcaaacacgt cgtggaacgg  180
tggccagagt acattccgaa taagctccct gacaagaact atgtgcgtat ttttgacacg  240
acgctccgtg acggcgaaca agctcctggt gcagccctta ctccaccgca gaagctagag  300
attgcccggc agctcgctaa gctccgagta gacatcatgg aagttggttt ccctgggtcc  360
tctgaggaag agttcgaaac cgtcaagacc atcgccaaga ccgtagggaa cgaggtggat  420
gaggaaacag gctacgtccc agtgatatgc gccctcgcac gatgcaaaca tagagacatt  480
gaggcggttt gggaggcggt gaagtacgca aagaggcctt cgatactcat attcatatct  540
actagtgaca ttcatatgaa acataagttg aaaaagacta aagaagaagt catagagatg  600
gcagcaagta gtattaggtt tgctaagaac ttaggcttca atgacatcca attgggttgc  660
gaagatgccg gcaggtcgga taaggagttt ctatgcaaga ttctaggaga agcgatcaaa  720
gcgggtgcaa ccacgatgaa catggcagac acggtaggga tcaacatgcc ggaagaattt  780
ggagaactcg tgagctacct taaagccaac actcctggaa ttgacgatgt tgtcttaagc  840
gttcattgtc acaacgacct tggtgttgct accgccaacg caatcgccgg tgtgtgtgct  900
ggagcaagac aagttgacgt tacggtcaat ggaataggtg aaagatgtgg gaacgcgcca  960
cttgaagagg tcgtgatggc tttgaaatgc cgaggagcat acctgatgaa tggggtttac  1020
acaagaacag acatacgcca aattatggct actagcaaga tggttcagga atatactggc  1080
ttttatgttc aaccacataa gcccatagtt ggagccaaca gttttttttca tgagagcagc  1140
gatgaatatg atggttgttc aaacattttg caggatatgg attattga              1188

SEQ ID NO: 169          moltype = DNA  length = 1820
FEATURE                 Location/Qualifiers
source                  1..1820
                        mol_type = genomic DNA
                        organism = Thlaspi arvense
SEQUENCE: 169
atgatcacca ccacctgttg cactgtggtc gcccagttag gcttgccctt tggatcttcc  60
ttgtcctctc tctgcctgac ccgtccgaac aaaaagccgt ccttgttcac ctcatgttgc  120
tcctctgtgt ccaaaaatgt tggcgctagt gctgctgaca gcaaacacgt cgtggaacgg  180
tggccagagt acattccgaa taagctccct gacaagaact atgtgcgtat ttttgacacg  240
acgctccgtg acggcgaaca agctcctggt gcagccctta ctccaccgca gaagctagag  300
```

```
attgcccggc agctcgctaa gctccgagta gacatcatgg aagttggttt ccctgggtcc  360
tctgaggaag agttcgaaac cgtcaagacc atcgccaaga ccgtagggaa cgaggttgtt  420
tctctgtttc cttcattttc tagtataaaa atttctacgt tcctactgta tattcagtca  480
accttgtcgc tttggggaca tatgataata tttgaacgaa tattaacata gttttgacgc  540
aaatagtaca aacacaaatt gagtaaatct ccaaatttta ccatagttat atagtaaacg  600
attgatttga ttaggtggat gaggaaacag gctacgtccc agtgatatgc gccctcgcac  660
gatgcaaaca tagagacatt gaggcggttt gggaggcggt gaagtacgca aagaggcctt  720
cgatactcat attcatatct actagtgaca ttcatatgaa acataagttg aaaaagacta  780
aagaagaagt catagagatg gcagcaagta gtattaggtt tgctaagaac ttaggcttca  840
atgacatcca attgggttgc gaagatgccg gcaggtccat atcttaaaac cttaatatac  900
atatatagcc ttttgttaga taatgttaag gatttttgtg aataatgacc atgtcacaaa  960
aattctagcg tgtgattaaa actaagcagg tcggataagg agtttctatg caagattcta  1020
ggagaagcga tcaaagcggg tgcaaccacg atgaacatgg cagacacggt agggatcaac  1080
atgccggaag aatttggaga actcgtgagc taccttaaag ccaacactcc tggaattgac  1140
gatgttgtct taagcgttca ttgtcacaac gaccttggtg ttgctaccgc caacgcaatc  1200
gccgtatttt tctaaccctc tccttcatct catatattta aaatatctat ataaatacat  1260
atagatcatt attgcggtta tattatatac gtagggtgtg tgtgctggag caagacaagt  1320
tgacgttacg gtcaatggaa taggtgaaag atgtgggaac gcgccacttg aagaggtaaa  1380
agatcatgat tatcatcaag accgtcttac actatttgta ggatcggttc catattttta  1440
tatacggccc tgatccatca tcatcaattc atcaacaaca taaatatttt tttggtatgt  1500
ataggtcgtg atggctttga aatgccgagg agcatacctg atgaatgggg tttacacaag  1560
aacagacata cgccaaatta tggctactag caagatggta ttttttacat taatttacac  1620
atggaaaaac gatcgtgcta gttttttttt tatatatgtt ggcattatag taatatatgt  1680
aaattcttga gcaggttcag gaatatactg gcttttatgt tcaaccacat aagcccatag  1740
ttggagccaa cagttttttt catgagagca gcgatgaata tgatggttgt tcaaacattt  1800
tgcaggatat ggattattga                                              1820

SEQ ID NO: 170         moltype = AA  length = 395
FEATURE                Location/Qualifiers
source                 1..395
                       mol_type = protein
                       organism = Thlaspi arvense
SEQUENCE: 170
MITTTCCTVV AQLGLPFGSS LSSLCLTRPN KKPSLFTSCC SSVSKNVGAS AADSKHVVER  60
WPEYIPNKLP DKNYVRIFDT TLRDGEQAPG AALTPPQKLE IARQLAKLRV DIMEVGFPGS  120
SEEEFETVKT IAKTVGNEVD EETGYVPVIC ALARCKHRDI EAVWEAVKYA KRPSILIFIS  180
TSDIHMKHKL KKTKEEVIEM AASSIRFAKN LGFNDIQLGC EDAGRSDKEF LCKILGEAIK  240
AGATTMNMAD TVGINMPEEF GELVSYLKAN TPGIDDVVLS VHCHNDLGVA TANAIAGVCA  300
GARQVDVTVN GIGERCGNAP LEEVVMALKC RGAYLMNGVY TRTDIRQIMA TSKMVQEYTG  360
FYVQPHKPIV GANSFFHESS DEYDGCSNIL QDMDY                             395

SEQ ID NO: 171         moltype = DNA  length = 798
FEATURE                Location/Qualifiers
source                 1..798
                       mol_type = genomic DNA
                       organism = Thlaspi arvense
SEQUENCE: 171
atgttgtatc gaaaagagta cttgtggttc atgatgattt tgtgggccag atctttatca  60
gagggcctaa aatattctcc gtctcttagg aatcttgtaa acacgatgac accttcctta  120
tcaccaatta gatctcacca cgtggcagtt atcggagctg gagccgccgg tttagtagcc  180
gcgcgagagc ttcgacggga aggtcactcg gtggtcgttt tcgagaggca gaatcaggtc  240
ggaggaacat ggatctacac cgatcatgtc gagccggatc cgttaagcgt cgacccgacc  300
cgacccgttg ttcactcgag cgtctatggc tctctccgga ccaaccttcc gcgtgagtgt  360
atgggataca gagacttccc gttcgtgatc cgatccggcg tctcggaatc gagagacccg  420
aggaggtttc cgagtcatag tgaagttctg gcgtatctgc aggatttcgc aaaggagttt  480
cggatcgagg agatgatacg gttcgagacg gcggttgagc gtgttgctcc ggcggaggaa  540
agcgacggcg aagcaggaaa aatgaaatgg aggattgaat ctacagagaa agaggagaaa  600
cttcgtcgcg atgagattta cgatgccgtt gtcgtctgta acggacatta cattgagcct  660
cgtctagctg aaattcctgg tgattcccct ttgattctcc tcttgaagtt tcaacatctt  720
gactttcgat ggattcgtgt gttaataaga ttactctttt gcttcattca agaaaattta  780
gatagaattt ggaaatag                                                798

SEQ ID NO: 172         moltype = DNA  length = 798
FEATURE                Location/Qualifiers
source                 1..798
                       mol_type = genomic DNA
                       organism = Thlaspi arvense
SEQUENCE: 172
atgttgtatc gaaaagagta cttgtggttc atgatgattt tgtgggccag atctttatca  60
gagggcctaa aatattctcc gtctcttagg aatcttgtaa acacgatgac accttcctta  120
tcaccaatta gatctcacca cgtggcagtt atcggagctg gagccgccgg tttagtagcc  180
gcgcgagagc ttcgacggga aggtcactcg gtggtcgttt tcgagaggca gaatcaggtc  240
ggaggaacat ggatctacac cgatcatgtc gagccggatc cgttaagcgt cgacccgacc  300
cgacccgttg ttcactcgag cgtctatggc tctctccgga ccaaccttcc gcgtgagtgt  360
atgggataca gagacttccc gttcgtgatc cgatccggcg tctcggaatc gagagacccg  420
aggaggtttc cgagtcatag tgaagttctg gcgtatctgc aggatttcgc aaaggagttt  480
cggatcgagg agatgatacg gttcgagacg gcggttgagc gtgttgctcc ggcggaggaa  540
agcgacggcg aagcaggaaa aatgaaatgg aggattgaat ctacagagaa agaggagaaa  600
cttcgtcgcg atgagattta cgatgccgtt gtcgtctgta acggacatta cattgagcct  660
```

```
cgtctagctg aaattcctgg tgattcccct ttgattctcc tcttgaagtt tcaacatctt  720
gactttcgat ggattcgtgt gttaataaga ttactctttt gcttcattca agaaaattta  780
gatagaattt ggaaatag                                                798

SEQ ID NO: 173         moltype = AA  length = 265
FEATURE                Location/Qualifiers
source                 1..265
                       mol_type = protein
                       organism = Thlaspi arvense
SEQUENCE: 173
MLYRKEYLWF MMILWARSLS EGLKYSPSLR NLVNTMTPSL SPIRSHHVAV IGAGAAGLVA  60
ARELRREGHS VVVFERQNQV GGTWIYTDHV EPDPLSVDPT RPVVHSSVYG SLRTNLPREC  120
MGYRDFPFVI RSGVSESRDP RRFPSHSEVL AYLQDFAKEF RIEEMIRFET AVERVAPAEE  180
SDGEAGKMKW RIESTEKEEK LRRDEIYDAV VVCNGHYIEP RLAEIPGDSP LILLLKFQHL  240
DFRWIRVLIR LLFCFIQENL DRIWK                                        265

SEQ ID NO: 174         moltype = DNA  length = 1392
FEATURE                Location/Qualifiers
source                 1..1392
                       mol_type = genomic DNA
                       organism = Thlaspi arvense
SEQUENCE: 174
atggtggaaa tagtcaacaa atgcaaaggc cacgtcatca ttttacctta cccagttcaa  60
ggccacctta accccatggt tcagttcgct aaacgtctcg tctccaaagg cgtcaaagtc  120
accatcgcaa ccactaccta caccgccttc tccatctcca ctccatcagt ctccgtcgag  180
ccaatctccg acggatacga cttcatcccc atagctattc ccggtttcag cgtcgacacc  240
tactcggaat ccttcaagct ccacggctcc gaaaccctaa cccgcgtgat cgagaaattc  300
aaatccaccg attccccgat cgattcttta gtctacgact cctttcttcc ctggggactc  360
gacgtcgcca gatccaactc gatttcagct gccgctttct tcaccaacaa cctcacggtt  420
tgttccgtgc tgcgtaattt ctccaccggg gagtttcctc tccccgccga tccagattct  480
gcgccgtacc taatccgtgg cttgccggcg ttgagctacg acgagctgcc ttccttcgtc  540
ggacgccact ggttgagcca cccggagcac gggaaggttc ttctgaatca gttccataac  600
catgaaaacg ccgattggct tttcgtcaat ggattcgaag gcttagaaac acaagattgt  660
gaaactggag aatcagaggc gatgaaggcg acgttgatcg gcccgttgat cccatcggcg  720
tacctcgacg accggataaa agacgataaa gactatggct cgagcctaat gaaaccgctc  780
tcagaggaat gtatggagtg gctcgggact aagccagcaa agtcagtagt tttcgtctcg  840
ttcggttcct ttgggatcct ctttgacaag cagctcgctg aggtagcaaa ggctctgcaa  900
gaatcgaact tgaacttctt gtgggtgatc aaagaagctc atatcgcgaa actgcctgaa  960
gggtttgtgg aatcgaccaa agacagagcc ttgctggttt cttggtgtaa ccagcttgag  1020
gttttagcac acgagtccat cggtttgctt ttgactcact gcggttggaa ctcgacgctt  1080
gaagggttga gtttgggagt gccgatggtg ggtgtgccgc agtggagtga tcagatgaac  1140
gatgctaagt ttgtggagga agtttggaga gttgggtaca gagcgaaaga ggaagctgag  1200
gaaggagtcg tgaagagcga agaagtggtg aggtgtttga aaggagtgat ggaaggagag  1260
agtagtgtga agattagaga gagttcgaag aagtggaaag atttggctgt gaaggcaatg  1320
actgaaggag gaagctctga tcggagcatt gacgagtttg tggagagttt aaggaaggaa  1380
acgttgaggt ag                                                      1392

SEQ ID NO: 175         moltype = DNA  length = 1477
FEATURE                Location/Qualifiers
source                 1..1477
                       mol_type = genomic DNA
                       organism = Thlaspi arvense
SEQUENCE: 175
atggtggaaa tagtcaacaa atgcaaaggc cacgtcatca ttttacctta cccagttcaa  60
ggccacctta accccatggt tcagttcgct aaacgtctcg tctccaaagg cgtcaaagtc  120
accatcgcaa ccactaccta caccgccttc tccatctcca ctccatcagt ctccgtcgag  180
ccaatctccg acggatacga cttcatcccc atagctattc ccggtttcag cgtcgacacc  240
tactcggaat ccttcaagct ccacggctcc gaaaccctaa cccgcgtgat cgagaaattc  300
aaatccaccg attccccgat cgattcttta gtctacgact cctttcttcc ctggggactc  360
gacgtcgcca gatccaactc gatttcagct gccgctttct tcaccaacaa cctcacggtt  420
tgttccgtgc tgcgtaattt ctccaccggg gagtttcctc tccccgccga tccagattct  480
gcgccgtacc taatccgtgg cttgccggcg ttgagctacg acgagctgcc ttccttcgtc  540
ggacgccact ggttgagcca cccggagcac gggaaggttc ttctgaatca gttccataac  600
catgaaaacg ccgattggct tttcgtcaat ggattcgaag gcttagaaac acaagtaaga  660
aagagtccaa gatttacgcg atattgttca attgaaactt ggaattgatg tttttggct  720
tggatttgtg ttcgattagg attgtgaaac tggagaatca gaggcgatga aggcgacgtt  780
gatcggcccg ttgatcccat cggcgtacct cgacgaccgg ataaaagacg ataaagacta  840
tggctcgagc ctaatgaaac cgctctcaga ggaatgtatg gagtggctcg ggactaagcc  900
agcaaagtca gtagttttcg tctcgttcgg ttcctttggg atcctctttg acaagcagct  960
cgctgaggta gcaaaggctc tgcaagaatc gaacttgaac ttcttgtggg tgatcaaaga  1020
agctcatatc gcgaaactgc ctgaagggtt tgtggaatcg accaaagaca gagccttgct  1080
ggtttcttgg tgtaaccagc ttgaggtttt agcacacgag tccatcggtt gctttttgac  1140
tcactgcggt tggaactcga cgcttgaagg gttgagtttg ggagtgccga tggtgggtgt  1200
gccgcagtgg agtgatcaga tgaacgatgc taagtttgtg gaggaagttt ggagagttgg  1260
gtacagagcg aaagaggaag ctgaggaagg agtcgtgaag agcgaagaag tggtgaggtg  1320
tttgaaagga gtgatggaag gagagagtag tgtgaagatt agagagagtt cgaagaagtg  1380
gaaagatttg gctgtgaagg caatgactga aggaggaagc tctgatcgga gcattgacga  1440
gtttgtggag agtttaagga aggaaacgtt gaggtag                           1477
```

```
SEQ ID NO: 176          moltype = AA  length = 463
FEATURE                 Location/Qualifiers
source                  1..463
                        mol_type = protein
                        organism = Thlaspi arvense
SEQUENCE: 176
MVEIVNKCKG HVIILPYPVQ GHLNPMVQFA KRLVSKGVKV TIATTTYTAF SISTPSVSVE  60
PISDGYDFIP IAIPGFSVDT YSESFKLHGS ETLTRVIEKF KSTDSPIDSL VYDSFLPWGL  120
DVARSNSISA AAFFTNNLTV CSVLRNFSTG EFPLPADPDS APYLIRGLPA LSYDELPSFV  180
GRHWLSHPEH GKVLLNQFHN HENADWLFVN GFEGLETQDC ETGESEAMKA TLIGPLIPSA  240
YLDDRIKDDK DYGSSLMKPL SEECMEWLGT KPAKSVVFVS FGSFGILFDK QLAEVAKALQ  300
ESNLNFLWVI KEAHIAKLPE GFVESTKDRA LLVSWCNQLE VLAHESIGCF LTHCGWNSTL  360
EGLSLGVPMV GVPQWSDQMN DAKFVEEVWR VGYRAKEEAE EGVVKSEEVV RCLKGVMEGE  420
SSVKIRESSK KWKDLAVKAM TEGGSSDRSI DEFVESLRKE TLR                  463

SEQ ID NO: 177          moltype = DNA  length = 798
FEATURE                 Location/Qualifiers
source                  1..798
                        mol_type = genomic DNA
                        organism = Thlaspi arvense
SEQUENCE: 177
atgttgtatc gaaaagagta cttgtggttc atgatgattt tgtgggccag atctttatca  60
gagggcctaa aatattctcc gtctcttagg aatcttgtaa acacgatgac accttcctta  120
tcaccaatta gatctcacca cgtggcagtt atcggagctg gagccgccgg tttagtagcc  180
gcgcgagagc ttcgacggga aggtcactcg gtggtcgttt tcgagaggca gaatcaggtc  240
ggaggaacat ggatctacac cgatcatgtc gagccggatc cgttaagcgt cgacccgacc  300
cgacccgttg ttcactcgag cgtctatggc tctctccgga ccaaccttcc gcgtgagtgt  360
atgggataca gagacttccc gttcgtgatc cgatccggcg tctcggaatc gagagacccg  420
aggaggtttc cgagtcatag tgaagttctg gcgtatctgc aggatttcgc aaaggagttt  480
cggatcgagg agatgatacg gttcgagacg gcggttgagc gtgttgctcc ggcggaggaa  540
agcgacggcg aagcaggaaa aatgaaatgg aggattgaat ctacagagaa agaggagaaa  600
cttcgtcgcg atgagattta cgatgccgtt gtcgtctgta acggacatta cattgagcct  660
catctagctg aaattcctgg tgattcccct ttgattctcc tcttgaagtt tcaacatctt  720
gactttcgat ggattcgtgt gttaataaga ttactctttt gcttcattca agaaaattta  780
gatagaattt ggaaatag                                              798

SEQ ID NO: 178          moltype = AA  length = 265
FEATURE                 Location/Qualifiers
source                  1..265
                        mol_type = protein
                        organism = Thlaspi arvense
SEQUENCE: 178
MLYRKEYLWF MMILWARSLS EGLKYSPSLR NLVNTMTPSL SPIRSHHVAV IGAGAAGLVA  60
ARELRREGHS VVVFERQNQV GGTWIYTDHV EPDPLSVDPT RPVVHSSVYG SLRTNLPREC  120
MGYRDFPFVI RSGVSESRDP RRFPSHSEVL AYLQDFAKEF RIEEMIRFET AVERVAPAEE  180
SDGEAGKMKW RIESTEKEEK LRRDEIYDAV VVCNGHYIEP HLAEIPGDSP LILLLKFQHL  240
DFRWIRVLIR LLFCFIQENL DRIWK                                      265

SEQ ID NO: 179          moltype = DNA  length = 1188
FEATURE                 Location/Qualifiers
source                  1..1188
                        mol_type = genomic DNA
                        organism = Thlaspi arvense
SEQUENCE: 179
atgatcacca ccacctgttg cactgtggtc gcccagttag gcttgccctt tggatcttcc  60
ttgtcctctc tctgcctgac ccgtccgaac aaaaagccgt ccttgttcac ctcatgttgc  120
tcctctgtgt ccaaaaatgt tggcgctagt gctgctgaca gcaaacacgt cgtggaacgg  180
tggccagagt acattccgaa taagctccct gacaagaact atgtgcgtat ttttgacacg  240
acgctccgtg acggcgaaca agctcctggt gcagccctta ctccaccgca gaagctagag  300
attgcccggc agctcgctaa gctccgagta gacatcatgg aagttggttt ccctgggtcc  360
tctgaggaag agttcgaaac cgtcaagacc atcgccaaga ccgtagggaa cgaggtggat  420
gaggaaacag gctacgtccc agtgatatgc gccctcgcac gatgcaaaca taaagacatt  480
gaggcggttt gggaggcggt gaagtacgca aagaggcctt cgatactcat attcatatct  540
actagtgaca ttcatatgaa acataagttg aaaaagacta aagaagaagt catagagatg  600
gcagcaagta gtattaggtt tgctaagaac ttaggcttca atgacatcca attgggttgc  660
gaagatgccg gcaggtcgga taaggagttt ctatgcaaga ttctaggaga agcgatcaaa  720
gcgggtgcaa ccacgatgaa catggcagac acggtaggga tcaacatgcc ggaagaattt  780
ggagaactcg tgagctacct taaagccaac actcctggaa ttgacgatgt tgtcttaagc  840
gttcattgtc acaacgacct tggtgttgct accgccaacg caatcgccgg tgtgtgtgct  900
ggagcaagac aagttgacgt tacggtcaat ggaataggtg aaagatgtgg gaacgcgcca  960
cttgaagagg tcgtgatggc tttgaaatgc cgaggagcat acctgatgaa tggggtttac  1020
acaagaacag acatacgcca aattatggct actagcaaga tggttcagga atatactggc  1080
ttttatgttc aaccacataa gcccatagtt ggagccaaca gttttttca tgagagcagc  1140
gatgaatatg atggttgttc aaacattttg caggatatgg attattga            1188

SEQ ID NO: 180          moltype = AA  length = 395
FEATURE                 Location/Qualifiers
source                  1..395
                        mol_type = protein
```

```
                        organism = Thlaspi arvense
SEQUENCE: 180
MITTTCCTVV AQLGLPFGSS LSSLCLTRPN KKPSLFTSCC SSVSKNVGAS AADSKHVVER  60
WPEYIPNKLP DKNYVRIFDT TLRDGEQAPG AALTPPQKLE IARQLAKLRV DIMEVGFPGS  120
SEEEFETVKT IAKTVGNEVD EETGYVPVIC ALARCKHKDI EAVWEAVKYA KRPSILIFIS  180
TSDIHMKHKL KKTKEEVIEM AASSIRFAKN LGFNDIQLGC EDAGRSDKEF LCKILGEAIK  240
AGATTMNMAD TVGINMPEEF GELVSYLKAN TPGIDDVVLS VHCHNDLGVA TANAIAGVCA  300
GARQVDVTVN GIGERCGNAP LEEVVMALKC RGAYLMNGVY TRTDIRQIMA TSKMVQEYTG  360
FYVQPHKPIV GANSFFHESS DEYDGCSNIL QDMDY                             395

SEQ ID NO: 181          moltype = DNA  length = 1188
FEATURE                 Location/Qualifiers
source                  1..1188
                        mol_type = genomic DNA
                        organism = Thlaspi arvense
SEQUENCE: 181
atgatcacca ccacctgttg cactgtggtc gcccagttag gcttgccctt tggatcttcc  60
ttgtcctctc tctgcctgac ccgtccgaac aaaaagccgt ccttgttcac ctcatgttgc  120
tcctctgtgt ccaaaaatgt tggcgctagt gctgctgaca gcaaacacgt cgtggaacgg  180
tggccagagt acattccgaa taagctccct gacaagaact atgtgcgtat tttgacacg   240
acgctccgtg acggcgaaca agctcctggt gcagccctta ctccaccgca gaagctagag  300
attgcccggc agctcgctaa gctccgagta gacatcatgg aagttggttt ccctgggtcc  360
tctgaggaag agttcgaaac cgtcaagacc atcgccaaga ccgtagggaa cgaggtggat  420
gaggaaacag gctacgtccc agtgatatgc gccctcgcac gatgcaaaca tagagacatt  480
gaggcggttt gggaggcggt gaagtacgca aagaggcctt cgatactcat attcatatct  540
actagtgaca ttcatatgaa acataagttg aaaaagacta aagaagaagt catagagatg  600
gcagcaagta gtattaggtt tgctaagaac ttaggcttca atgacatcca attgggttgc  660
gaagatgccg gcaggtcgga taaggagttt ctatgcaaga ttctaggaga agcgatcaaa  720
gcgggtgcaa ccacgatgaa catggcagac acggtaggga tcaacatgcc ggaagaattt  780
ggagaactcg tgagctacct taaagccaac actcctggaa ttgacgatgt tgtcttaagc  840
gttcattgtc acaacgacct tggtgttgct accgccaacg caatcgccgg tgtgtgtgct  900
ggaacaagac aagttgacgt tacggtcaat ggaataggtg aaagatgtgg gaacgcgcca  960
cttgaagagg tcgtgatggc tttgaaatgc cgaggagcat acctgatgaa tggggtttac  1020
acaagaacag acatacgcca aattatggct actagcaaga tggttcagga atatactggc  1080
ttttatgttc aaccacataa gcccatagtt ggagccaaca gttttttca tgagagcagc   1140
gatgaatatg atggttgttc aaacattttg caggatatgg attattga               1188

SEQ ID NO: 182          moltype = AA  length = 395
FEATURE                 Location/Qualifiers
source                  1..395
                        mol_type = protein
                        organism = Thlaspi arvense
SEQUENCE: 182
MITTTCCTVV AQLGLPFGSS LSSLCLTRPN KKPSLFTSCC SSVSKNVGAS AADSKHVVER  60
WPEYIPNKLP DKNYVRIFDT TLRDGEQAPG AALTPPQKLE IARQLAKLRV DIMEVGFPGS  120
SEEEFETVKT IAKTVGNEVD EETGYVPVIC ALARCKHRDI EAVWEAVKYA KRPSILIFIS  180
TSDIHMKHKL KKTKEEVIEM AASSIRFAKN LGFNDIQLGC EDAGRSDKEF LCKILGEAIK  240
AGATTMNMAD TVGINMPEEF GELVSYLKAN TPGIDDVVLS VHCHNDLGVA TANAIAGVCA  300
GTRQVDVTVN GIGERCGNAP LEEVVMALKC RGAYLMNGVY TRTDIRQIMA TSKMVQEYTG  360
FYVQPHKPIV GANSFFHESS DEYDGCSNIL QDMDY                             395

SEQ ID NO: 183          moltype = DNA  length = 1365
FEATURE                 Location/Qualifiers
source                  1..1365
                        mol_type = genomic DNA
                        organism = Thlaspi arvense
SEQUENCE: 183
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagtatgag gatccaggat  300
cctcatgttt tggacaaagt ttacgagttt actcaacttc tacgtcctga tcattgtgac  360
ggtaacaaga gcatcagcga aacgatccag acgttttcag agaagttatc agaattggat  420
ataatggtga gaagaatggt aatggaaagc ttcgggatag agaagtacct tgacaaacac  480
ctgaactcaa cgaattaccg tctgcggctg atgaagtata tagcaccgcc tgatgctgat  540
gctactaatg ttgcggctga tgccaaagat gctgatgata atgctaagac gattacaaat  600
gataaagttg atgcggctgg tgctaatgat gtagatgctg gtgatatcgc taatggtatt  660
gctaatcttc atattggtga tgatgctaac gctggtgcta atggtgctgg tgttgatgct  720
aatgatggtg gtgaggatgc taagactggt gaggatgcta agactggtga atgtgctagt  780
gttaagtcta atgccgaaga tggtactgat gttaatgcca gtgctgatgc tggtgttact  840
gttggctcta atgctgatgc taatgctaat gctaatgcta atactagtac tgatgctggt  900
gttggcgata gtgttaaagc taatggtggt gctgatgatg ttgagaagaa attgggtcta  960
ccttctcaca ctgataagaa ccttataacg gtgctttatc aatacgagat tgaaggcttg  1020
gaggttctaa ccaaagatga caagtggatc agactcaaac catctcataa ttctttcgtt  1080
gttatggctg gagattctct atacgcactt atgaatggta gactaactcg tccctttcat  1140
cgagtaagag taacggagaa aaagaagaca agatattcaa tagcattgtt ctcggctcca  1200
accgcagatt acatcataga cacaccaaaa gaacttgtgg acgagaagca tccacgtatc  1260
ttcgaaccat ttaactataa cgacttgatg agtttctatc atagtgaagc tggtcgtaaa  1320
```

```
gctcgatcta ctcttgatgc tttctgtgcc gtctctcgag cataa                1365

SEQ ID NO: 184          moltype = AA  length = 454
FEATURE                 Location/Qualifiers
source                  1..454
                        mol_type = protein
                        organism = Thlaspi arvense
SEQUENCE: 184
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSESMRIQD PHVLDKVYEF TQLLRPDHCD  120
GNKSISETIQ TFSEKLSELD IMVRRMVMES FGIEKYLDKH LNSTNYRLRL MKYIAPPDAD  180
ATNVAADAKD ADDNAKTITN DKVDAAGAND VDAGDIANGI ANLHIGDDAN AGANGAGVDA  240
NDGGEDAKTG EDAKTGECAS VKSNAEDGTD VNASADAGVT VGSNADANAN ANANTSTDAG  300
VGDSVKANGG ADDVEKKLGL PSHTDKNLIT VLYQYEIEGL EVLTKDDKWI RLKPSHNSFV  360
VMAGDSLYAL MNGRLTRPFH RVRVTEKKKT RYSIALFSAP TADYIIDTPK ELVDEKHPRI  420
FEPFNYNDLM SFYHSEAGRK ARSTLDAFCA VSRA                            454

SEQ ID NO: 185          moltype = DNA  length = 1818
FEATURE                 Location/Qualifiers
source                  1..1818
                        mol_type = genomic DNA
                        organism = Thlaspi arvense
SEQUENCE: 185
atgaacgact acttcctcaa ccagtcaaca gccaccgacg ataacgcgtc ggcggcgatg  60
gaagctttca tcggaacaaa tcactcaact ctctggcccc aaccatctct tcctcctcct  120
cctccactat ctcaattcaa cgaagacact cttcaacaac gtctccaagc tttgatcgaa  180
tcagcaggag aaggctgaac ctacgcgatt ttctggcaga tctcacacga tttcgattct  240
tccaccggag acaacacagt gattctcgga tggggagatg ggtactacaa aggggaggaa  300
gataaagaga agaagaagaa tagctcaagt tcgaattcgg cggagcaaga gcatcggaaa  360
agagtaatcc gtgagctgaa ttcgttgatc tccggcggaa ccggagtttc cgatgaatcg  420
aacgacgaag aagtcaccga tactgagtgg ttcttcttgg tctcgatgac acagagcttc  480
atgaacggcg ttgggcttcc cggggagtcg tacttgaact ctcgcgtgat ttggttatcc  540
gggccgggtg ctttaatcgg gtcgggttgc gaacgagcgg gtcaaggtca gatatacggg  600
ttacagacga tggtgtgtat cgcggcggag aacggcgtcg ttgagcttgg ttcatcggag  660
gtgttaagcc atagctcaga tctgatggat aaagtcaaca gtctgttcaa ttccaacaac  720
ggtaatggag aagcttcttc ttgggggttt aatctgaatc cggatcaagg agagaacgat  780
ccggctttgt ggataagcga accgaccacc accggaatcg aatcgggtca ggtaatcccg  840
gcgataaaca acagtaattc caattcaaat tcaaaatccg attctcatca aatctccaag  900
ctcgagaaga acgagagctc gattgaaaac cctagacaac aacaaaatcc gtcgcttgta  960
gagcgagatt tgaatttctc gagttctggg ttgaatcaaa acgggaactt tcaagatggg  1020
tcgtcgcgga tgatgaaatc gaacgaaaca ctgagcttta cggcggagga gagcaacaag  1080
aggaggtctc cggtttcgaa agggagtaac aacgacgaag ggatgctttc tttcagcacc  1140
gtggttcgtt ccgcggcgaa atccgtcgat tcggatcatt ccgatctcga agcgtcggtg  1200
gttaaggaag caattgtcgt tgaaccggag aagaaaccga ggaaacgggg aagaaaaccg  1260
gcgaacggaa gagaggagcc gttgaatcac gtggaagcag agagacagag aagggagaag  1320
ctaaaccaga gattctactc tttgagagct gtggttccca acgtttcgaa aatggacaaa  1380
gcgtctcttc tcggagacgc catttcgtat atcaacgagc ttaaatcgaa gctgcagcaa  1440
gcggaatccg ataaggaaga gattcagaag cagctcgacg ggatgagcaa ggaaggaaac  1500
agggaaggcg gcggcggaac gaaggcgaaa gaacgaaaat gctcgaatca agattcggct  1560
agctcgatag aaatggagat cgacgtgaag atcataggtt gggatgtgat gatacgtgta  1620
caatgcagca agaagaatca tcccggggca agattcatgg aagcgctcaa ggaattggat  1680
ctggaagtga atcacgcaag tttgtcagtg gtgaatgatt tgatgattca acaagccact  1740
gtgaagatgg gaagccagtt tttcaatcat gaccagctca aggttgcttt gatgtcgaaa  1800
gtcggagaag acaattga                                              1818

SEQ ID NO: 186          moltype = AA  length = 65
FEATURE                 Location/Qualifiers
source                  1..65
                        mol_type = protein
                        organism = Thlaspi arvense
SEQUENCE: 186
MNDYFLNQST ATDDNASAAM EAFIGTNHST LWPQPSLPPP PPLSQFNEDT LQQRLQALIE  60
SAGEG                                                            65

SEQ ID NO: 187          moltype = DNA  length = 1817
FEATURE                 Location/Qualifiers
source                  1..1817
                        mol_type = genomic DNA
                        organism = Thlaspi arvense
SEQUENCE: 187
atgaacgact acttcctcaa ccagtcaaca gccaccgacg ataacgcgtc ggcggcgatg  60
gaagctttca tcggaacaaa tcactcaact ctctggcccc aaccatctct tcctcctcct  120
cctccactat ctcaattcaa cgaagacact cttcaacaac gtctccaagc tttgatcgaa  180
tcagcaggag aaggctggac ctacgcgatt ttctggcaga tctcacacga tttcgattct  240
tccaccggag acaaccagtg attctcggat ggggagatgg gtactacaaa ggggaggaag  300
ataaagagaa gaagaagaat agctcaagtt cgaattcggc ggagcaagag catcggaaaa  360
gagtaatccg tgagctgaat tcgttgatct ccggcggaac cggagtttcc gatgaatcga  420
acgacgaaga agtcaccgat actgagtggt tcttcttggt ctcgatgaca cagagcttca  480
tgaacggcgt tgggcttccc ggggagtcgt acttgaactc tcgcgtgatt tggttatccg  540
```

```
ggccgggtgc tttaatcggg tcgggttgcg aacgagcggg tcaaggtcag atatacgggt  600
tacagacgat ggtgtgtatc gcggcggaga acggcgtcgt tgagcttggt tcatcggagg  660
tgttaagcca tagctcagat ctgatggata aagtcaacag tctgttcaat tccaacaacg  720
gtaatggaga agcttcttct tgggggttta atctgaatcc ggatcaagga gagaacgatc  780
cggctttgtg gataagcgaa ccgaccacca ccggaatcga atcgggtcag gtaatcccgg  840
cgataaacaa cagtaattcc aattcaaatt caaaatccga ttctcatcaa atctccaagc  900
tcgagaagaa cgagagctcg attgaaaacc ctagacaaca acaaaatccg tcgcttgtag  960
agcgagattt gaatttctcg agttctgggt tgaatcaaaa cgggaacttt caagatgggt  1020
cgtcgcggat gatgaaatcg aacgaaacac tgagctttac ggcggaggag agcaacaaga  1080
ggaggtctcc ggtttcgaaa gggagtaaca acgacgaagg gatgctttct ttcagcaccg  1140
tggttcgttc cgcggcgaaa tccgtcgatt cggatcattc cgatctcgaa gcgtcggtgg  1200
ttaaggaagc aattgtcgtt gaaccggaga agaaaccgag gaaacgggga agaaaaccgg  1260
cgaacggaag agaggagccg ttgaatcacg tggaagcaga gagacagaga agggagaagc  1320
taaaccagag attctactct ttgagagctg tggttcccaa cgtttcgaaa atggacaaag  1380
cgtctcttct cggagacgcc atttcgtata tcaacgagct taaatcgaag ctgcagcaag  1440
cggaatccga taaggaagag attcagaagc agctcgacgg gatgagcaag gaaggaaaca  1500
gggaaggcgg cggcggaacg aaggcgaaag aacgaaaatg ctcgaatcaa gattcggcta  1560
gctcgataga aatggagatc gacgtgaaga tcataggttg ggatgtgatg atacgtgtac  1620
aatgcagcaa gaagaatcat cccggggcaa gattcatgga agcgctcaag gaattggatc  1680
tggaagtgaa tcacgcaagt ttgtcagtgg tgaatgattt gatgattcaa caagccactg  1740
tgaagatggg aagccagttt ttcaatcatg accagctcaa ggttgctttg atgtcgaaag  1800
tcggagaaga caattga                                                1817

SEQ ID NO: 188         moltype = AA  length = 86
FEATURE                Location/Qualifiers
source                 1..86
                       mol_type = protein
                       organism = Thlaspi arvense
SEQUENCE: 188
MNDYFLNQST ATDDNASAAM EAFIGTNHST LWPQPSLPPP PPLSQFNEDT LQQRLQALIE  60
SAGEGWTYAI FWQISHDFDS STGDNQ                                      86

SEQ ID NO: 189         moltype = DNA  length = 1818
FEATURE                Location/Qualifiers
source                 1..1818
                       mol_type = genomic DNA
                       organism = Thlaspi arvense
SEQUENCE: 189
atgaacgact acttcctcaa ccagtcaaca gccaccgacg ataacgcgtc ggcggcgatg  60
gaagctttca tcggaacaaa tcactcaact ctctggcccc aaccatctct tcctcctcct  120
cctccactat ctcaattcaa cgaagacact cttcaacaac gtctccaagc tttgatcgaa  180
tcagcaggag aaggctggac ctacgcgatt ttctggcaga tctcacacga tttcgattct  240
tccaccggag acaacacagt gattctcgga tggggagatg ggtactacaa aggggaggaa  300
gataaagaga agaagaagaa tagctcaagt tcgaattcgg cggagcaaga gcatcggaaa  360
agagtaatcc gtgagctgaa ttcgttgatc tccggcggaa ccgaagtttc cgatgaatcg  420
aacgacgaag aagtcaccga tactgagtgg ttcttcttgg tctcgatgac acagagcttc  480
atgaacggcg ttgggcttcc cggggagtcg tacttgaact ctcgcgtgat ttggttatcc  540
gggccgggtg ctttaatcgg gtcgggttgc gaacgagcgg gtcaaggtca gatatacggg  600
ttacagacga tggtgtgtat cgcggcggag aacggcgtcg ttgagcttgg ttcatcggag  660
gtgttaagcc atagctcaga tctgatggat aaagtcaaca gtctgttcaa ttccaacaac  720
ggtaatggag aagcttcttc ttgggggttt aatctgaatc cggatcaagg agagaacgat  780
ccggctttgt ggataagcga accgaccacc accggaatcg aatcgggtca ggtaatcccg  840
gcgataaaca acagtaattc caattcaaat tcaaaatccg attctcatca aatctccaag  900
ctcgagaaga acgagagctc gattgaaaac cctagacaac aacaaaatcc gtcgcttgta  960
gagcgagatt tgaatttctc gagttctggg ttgaatcaaa acgggaactt tcaagatggg  1020
tcgtcgcgga tgatgaaatc gaacgaaaca ctgagcttta cggcggagga gagcaacaag  1080
aggaggtctc cggtttcgaa agggagtaac aacgacgaag ggatgctttc tttcagcacc  1140
gtggttcgtt ccgcggcgaa atccgtcgat tcggatcatt ccgatctcga agcgtcggtg  1200
gttaaggaag caattgtcgt tgaaccggag aagaaaccga ggaaacgggg aagaaaaccg  1260
gcgaacggaa gagaggagcc gttgaatcac gtggaagcag agagacagag aagggagaag  1320
ctaaaccaga gattctactc tttgagagct gtggttccca acgtttcgaa aatggacaaa  1380
gcgtctcttc tcggagacgc catttcgtat atcaacgagc ttaaatcgaa gctgcagcaa  1440
gcggaatccg ataaggaaga gattcagaag cagctcgacg ggatgagcaa ggaaggaaac  1500
agggaaggcg gcggcggaac gaaggcgaaa gaacgaaaat gctcgaatca agattcggct  1560
agctcgatag aaatggagat cgacgtgaag atcataggtt gggatgtgat gatacgtgta  1620
caatgcagca agaagaatca tcccggggca agattcatgg aagcgctcaa ggaattggat  1680
ctggaagtga atcacgcaag tttgtcagtg gtgaatgatt tgatgattca acaagccact  1740
gtgaagatgg gaagccagtt tttcaatcat gaccagctca aggttgcttt gatgtcgaaa  1800
gtcggagaag acaattga                                               1818

SEQ ID NO: 190         moltype = AA  length = 605
FEATURE                Location/Qualifiers
source                 1..605
                       mol_type = protein
                       organism = Thlaspi arvense
SEQUENCE: 190
MNDYFLNQST ATDDNASAAM EAFIGTNHST LWPQPSLPPP PPLSQFNEDT LQQRLQALIE  60
SAGEGWTYAI FWQISHDFDS STGDNTVILG WGDGYYKGEE DKEKKKNSSS SNSAEQEHRK  120
RVIRELNSLI SGGTEVSDES NDEEVTDTEW FFLVSMTQSF MNGVGLPGES YLNSRVIWLS  180
```

```
GPGALIGSGC ERAGQGQIYG LQTMVCIAAE NGVVELGSSE VLSHSSDLMD KVNSLFNSNN  240
GNGEASSWGF NLNPDQGEND PALWISEPTT TGIESGQVIP AINNSNSNSN SKSDSHQISK  300
LEKNESSIEN PRQQQNPSLV ERDLNFSSSG LNQNGNFQDG SSRMMKSNET LSFTAEESNK  360
RRSPVSKGSN NDEGMLSFST VVRSAAKSVD SDHSDLEASV VKEAIVVEPE KKPRKRGRKP  420
ANGREEPLNH VEAERQRREK LNQRFYSLRA VVPNVSKMDK ASLLGDAISY INELKSKLQQ  480
AESDKEEIQK QLDGMSKEGN REGGGGTKAK ERKCSNQDSA SSIEMEIDVK IIGWDVMIRV  540
QCSKKNHPGA RFMEALKELD LEVNHASLSV VNDLMIQQAT VKMGSQFFNH DQLKVALMSK  600
VGEDN                                                             605

SEQ ID NO: 191         moltype = DNA  length = 1109
FEATURE                Location/Qualifiers
source                 1..1109
                       mol_type = genomic DNA
                       organism = Thlaspi arvense
SEQUENCE: 191
atgtcaagaa agccgtgttg tgtcggagaa gggctgaaga aaggggcatg gaccaccgaa  60
gaagacaaga aactcatctc ttacatccac ggcacggtga aggaggctgg cgcgacattc  120
cccaaaaagc tgggttgaaa cggtgtggaa agagttgtag gctgcgatgg actaactacc  180
taaaacctga gatcaaaaga ggcgagttta gttcagagga ggaacagatt atcattatgc  240
ttcatgcttc tcgtggcaac aagtggtcgg tcatagcgag acatttacct agaagaacag  300
acaacgagat caagaactac tggaacacgc atctcaaaaa acgtttgatc gaacagggtg  360
ttgatcccgt gactcacaag cctctagctt ccaactccgg ccctactgcc accacgccgc  420
ctgagaattt gcatttccta gatgaatcta gctcagacaa gcaatactct cggtcgagct  480
caatgccttc cctgtctcgt cttccttcct ccggattcaa cacggtttcc gagatagcca  540
gcaatgttgg gacaccagtt caggtcggtt ccttgagttg caagaaacgt tttaagaaat  600
cgagttcgac atcaaggctt ctgaacaaat ttgcggctaa ggccacttcc atcaaagata  660
tattgtcggc ttccatggaa ggtagctcga gtgctgctac tacaatatca catgcaagct  720
ttttaaatgg cttttctgag cagagtcgca atgaagagga tagttctaac gcatccctga  780
caaatactct agccgaattt gatcccttct ctcagtcatc gttgtacccg gagcatgaga  840
tcaatgttac ttctgatatc ggcatggacc aggtttacga tttctcacaa tttctcgaaa  900
agctcgggag tgaaggccac aacgaactga atgtcgagta tggtcatgat cttcttatgt  960
ccgatgtttc gcaagaagtc tcatcaccta gcgttgatga tcaagacaat atgattggaa  1020
gcttcgaagg ttggtcaaat tatcttcttg accatgctga ttttatatat gacaccgact  1080
cagattccct cgaaaagcat ttcatgtga                                   1109

SEQ ID NO: 192         moltype = AA  length = 45
FEATURE                Location/Qualifiers
source                 1..45
                       mol_type = protein
                       organism = Thlaspi arvense
SEQUENCE: 192
MSRKPCCVGE GLKKGAWTTE EDKKLISYIH GTVKEAGATF PKKLG                  45

SEQ ID NO: 193         moltype = DNA  length = 1018
FEATURE                Location/Qualifiers
source                 1..1018
                       mol_type = genomic DNA
                       organism = Thlaspi arvense
SEQUENCE: 193
atgtcgaaaa gaccatgctg tatcggagaa gggttaaaga aaggagcatg gacgtcaggg  60
gaagacaaaa aactcatctc ttatatccat gaacatggcg aaggaggttg gcgtgacatt  120
cccgaaaaag ctgggctaaa acggttgtgg aaagagttgc agactgcgat gggcgaacta  180
tttgaacccc gatatcaaga gaggaggatt tagctacgag gaagaacaga tcatcatcat  240
gcttcatgct tctcgtggca acaagtggtc agtcatagca agacatttgc cgcaaagaac  300
agacaacgag atcaaaaact attggaacac acatctcaag aaacgcctga tcaataagag  360
cactgattcc gtgacccaca agcctctagc ttcctctaac cctagtccta ccgagcgtaa  420
gaagctcgat tcccaagaag aatccaatcc caaggagcag tcgttacagc cgggttcgaa  480
gtctccagta tctctttccc tttcttcgag tttcaacgac actgtacccg agatcatgac  540
cagtgatgag acgcctctag aaagtggttt cttgagttgc aaaaaaagtg tcgagagatc  600
gagctcaaca tcaaggcttt taaacaaagt tgcagctaga gcttcttcca tcgggagtat  660
cttatcaacc tccatagaag gaactttgag atctcctgca tcgtcctcat gtctcccaaa  720
ctcattgtgt caatcatctg aacacaacaa ggatcaagat ctcggtacga gcattgatct  780
tagcatcccc gattacgatt actcccactt tctcgagcac ttcatcaata gcgaagacga  840
agccgaaaac attggtggct gcaatcaaga tctccttatg tccgatttcc catcaacatt  900
agtggataaa gaaaatatga attttgaaga cataaccggt tggtcaagtt atcttctcga  960
ccatcccagt tttacgtatg aatcggaaca agattccgac gacaacaact tgttatga    1018

SEQ ID NO: 194         moltype = AA  length = 70
FEATURE                Location/Qualifiers
source                 1..70
                       mol_type = protein
                       organism = Thlaspi arvense
SEQUENCE: 194
MSKRPCCIGE GLKKGAWTSG EDKKLISYIH EHGEGGWRDI PEKAGLKRLW KELQTAMGEL  60
FEPRYQERRI                                                         70

SEQ ID NO: 195         moltype = DNA  length = 1067
FEATURE                Location/Qualifiers
source                 1..1067
```

```
                        mol_type = genomic DNA
                        organism = Thlaspi arvense
SEQUENCE: 195
atgtcaagaa agccatgttg tgtgggagaa gggctgaaga aaggagcatg gaccgccgaa  60
gaagacaaga aactcatctc ttacatccat gaacatggcg aaggaggctg gcgtgacatt  120
ccccaaaaag ctggactaaa acgatgtgga aaaagttgta gattgcgatg ggctaactat  180
ttgaaaccgg atatcaagag aggagaattt agctacgagg aggagcagat tatcatcatg  240
cttcacgctt cccgtggcaa caagtggtcg gtcatagcga gacatttgcc caaaaggaca  300
gacaacgaga tcaagaacta ttggaacaca caccttaaaa aacgccttat cgatcaaggt  360
attgatcccg tgacccacaa gccacttgtc cggccacgct caagccttct gatttccaag  420
atgactcatc aaacctggga aactcggatg agcattcaca ttcgggttct atgtctccaa  480
aatctcttcc tccgtcttca agctcctgca atctagcgga gataagcagc agtgatgaga  540
caccgaaaaa tgatggttcc ttgaaatcca agaaacgttc ttttaagaga tcaagttcta  600
catcaaagct gttaaacaaa gttgcatcta gggctgcttc cattggaaat atcttatcag  660
cgtccatgga aggaaccttg gttagctcta ccgcactgtc tccatgtctc aatgatgact  720
tttccgaagc tagccaattc cagatggacg aatatgatcc attccctcag tcgtctgaac  780
acataactga tcatatgaag gaggacaccg gcatgatctt tgatctcaac aactccgaat  840
atgatttctc gcagtttctc gagcaattta gtaacgaagg cgaagaaacc gagaacattg  900
ggggatataa tcaagatctc ctttcgtctg acgtctcatc accaagcgtt gatgaagaca  960
atatgatggg aaacataacc ggttccggtt ggtccagtta tcttgttgac cattccgatt  1020
ttgtttatga caagatccaa gataacgacg acaggaactt catatga               1067

SEQ ID NO: 196          moltype = AA  length = 171
FEATURE                 Location/Qualifiers
source                  1..171
                        mol_type = protein
                        organism = Thlaspi arvense
SEQUENCE: 196
MSRKPCCVGE GLKKGAWTAE EDKKLISYIH EHGEGGWRDI PQKAGLKRCG KSCRLRWANY  60
LKPDIKRGEF SYEEEQIIIM LHASRGNKWS VIARHLPKRT DNEIKNYWNT HLKKRLIDQG  120
IDPVTHKPLV RPRSSLLISK MTHQTWETRM SIHIRVLCLQ NLFLRLQAPA I           171

SEQ ID NO: 197          moltype = DNA  length = 1074
FEATURE                 Location/Qualifiers
source                  1..1074
                        mol_type = genomic DNA
                        organism = Thlaspi arvense
SEQUENCE: 197
atgtcaagaa agccatgttg tgtgggagaa gggctgaaga aaggagcatg gaccgccgaa  60
gaagacaaga aactcatctc ttacatccat gaacatggcg aaggaggctg gcgtgacatt  120
ccccaaaaag ctggactaaa acgatgtgga aaaagttgta gattgcgatg ggctaactat  180
ttgaaaccgg atatcaagag aggagaattt agctacgagg aggagcagat tatcatcatg  240
cttcacgctt cccgtggcaa caagtggtcg gtcatagcga gacatttgcc caaaaggaca  300
gacaacgaga tcaagaacta ttggaacaca caccttaaaa aacgccttat cgatcaaggt  360
attgatcccg tgacccacaa gccacttgcc cctagcccta ccacgctcaa gccttctgat  420
ttccaagatg actcatcaaa cctgggaaac tcggatgagc attcacattc gggttctatg  480
tctccaaaat ctcttcctcc gtcttcaagc tcctgcaatc tagcggagat aagcagcagt  540
gatgagacac cgaaaaatga tggttccttg aaatccaaga aacgttcttt taagagatca  600
agttctacat caaagctgtt aaacaaagtt gcatctaggg ctgcttccat tggaaatatc  660
ttatcagcgt ccatggaagg aaccttggtt agctctaccg cactgtctcc atgtctcaat  720
gatgactttt ccgaagctag ccaattccag atggacgaat atgatccatt ccctcagtcg  780
tctgaacaca taactgatca tatgaaggag gacaccggca tgatctttga tctcaacaac  840
tccgaatatg atttctcgca gtttctcgag caatttagta acgaaggcga agaaaccgag  900
aacattgggg gatataatca agatctcctt tcgtctgacg tctcatcacc aagcgttgat  960
gaagacaata tgatgggaaa cataaccggt tccggttggt ccagttatct tgttgaccat  1020
tccgattttg tttatgacaa gatccaagat aacgacgaca ggaacttcat atga        1074

SEQ ID NO: 198          moltype = AA  length = 356
FEATURE                 Location/Qualifiers
source                  1..356
                        mol_type = protein
                        organism = Thlaspi arvense
SEQUENCE: 198
MSRKPCCVGE GLKKGAWTAE EDKKLISYIH EHGEGGWRDI PQKAGLKRCG KSCRLRWANY  60
LKPDIKRGEF SYEEEQIIIM LHASRGNKWS VIARHLPKRT DNEIKNYWNT HLKKRLIDQG  120
IDPVTHKPLA PSPTLKPSDF QDDSSNLGNS DEHSHSGSMS PKSLPPSSSS CNLAEISSSD  180
ETPKNDGSLK SKKRSFKRSS STSKLLNKVA SRAASIGNIL SASMEGTLVS STALSPCLND  240
DFSEASQFQM DEYDPFPQSS EHITDHMKED TGMIFDLNNS EYDFSQFLEQ FSNEGEETEN  300
IGGYNQDLLS SDVSSPSVDE DNMMGNITGS GWSSYLVDHS DFVYDKIQDN DDRNFI      356

SEQ ID NO: 199          moltype = DNA  length = 1332
FEATURE                 Location/Qualifiers
source                  1..1332
                        mol_type = genomic DNA
                        organism = Thlaspi arvense
SEQUENCE: 199
atggcggcgt gtttacaatc gaacatccgg ctgaatctga acaatatcgt cggaggaaaa  60
tgcagatccc tcaccgatca gtctcgcacg ccgtgtcgaa taaggtgcgc cgccgcttca  120
cctgggaaaa aacggttcaa catcgctctc cttcctggcg acggtatcgg tcctgaagtc  180
```

```
atctccgttg ccaagaatgt gcttcagcaa gctggatctc tcgaaggttc ttctatctct  240
cgctcagttt atttactaat tttgacaaaa ttagtaatca gcgaatgtgt tgcttaccca  300
gaagagtgtg cgtatttgat gtgtatcaca ggactggagt tcaatttcca ggagatgccc  360
atcggaggag cagccttgga tttggtcgga gtggccttgc cggaggaaac cttatcggct  420
gcaaaaacagt ctgatgccat acttcttgga gctatcggag ggtacaaatg ggacaacaat  480
gagaaacatc tgagacctga gatggctctg atttaccttc ggagagatct caaagtcttt  540
gctaatctga gacctgcttc agttttgcca cagctagttg atgcatccac cttgaagaga  600
gaagtagcag aaggtgttga tatgatgatt gtaagggagc ttacaggagg aatttacttt  660
ggagagccca aaggcattaa gaccaacgaa aacggagaag aagtcggttt taatacagag  720
ttttacgctg ctcacgagat tgacagaatt gctcgtgttg catttgagac tgctaggaaa  780
cggcgtggca agctgtgttc tgtcgacaaa gccaatgtgt tggatgcatc agtattgtgg  840
aggagaagag taacagcgtt agcctctgag tatccagatg ttgagctctc acatatgtat  900
gtagacaacg ctgcaatgca gcttattcgt gacccgaaac agtttgacac aatcgtcacc  960
aataacattt tcggtgacat attatccgat gaggcctcaa tgatcactgg aagcattggg  1020
atgcttccat ctgctagtct cggtgtatcg ggacctggac tctttgagcc gatacatggt  1080
tctgcgccag atatagctgg tcaggacaag gcaaacccat tggccaccat tctcagcgca  1140
gcgatgcttc tgaaatatgg acttggagaa gagaaggccg caaagaggat cgaggacgcg  1200
gtcttggatg ctctcaacaa agggtttaga accggagaca tctactcccc cggaaataaa  1260
ctggtgggat gcaaggagat gggtgaggag gtgcttaaat cagtggactc cagagttaca  1320
gctactgttt aa                                                      1332

SEQ ID NO: 200         moltype = AA  length = 443
FEATURE                Location/Qualifiers
source                 1..443
                       mol_type = protein
                       organism = Thlaspi arvense
SEQUENCE: 200
MAACLQSNIR LNLNNIVGGK CRSLTDQSRT PCRIRCAAAS PGKKRFNIAL LPGDGIGPEV  60
ISVAKNVLQQ AGSLEGSSIS RSVYLLILTK LVISECVAYP EECAYLMCIT GLEFNFQEMP  120
IGGAALDLVG VALPEETLSA AKQSDAILLG AIGGYKWDNN EKHLRPEMAL IYLRRDLKVF  180
ANLRPASVLP QLVDASTLKR EVAEGVDMMI VRELTGGIYF GEPKGIKTNE NGEEVGFNTE  240
FYAAHEIDRI ARVAFETARK RRGKLCSVDK ANVLDASVLW RRRVTALASE YPDVELSHMY  300
VDNAAMQLIR DPKQFDTIVT NNIFGDILSD EASMITGSIG MLPSASLGVS GPGLFEPIHG  360
SAPDIAGQDK ANPLATILSA AMLLKYGLGE EKAAKRIEDA VLDALNKGFR TGDIYSPGNK  420
LVGCKEMGEE VLKSVDSRVT ATV                                          443

SEQ ID NO: 201         moltype = DNA  length = 1332
FEATURE                Location/Qualifiers
source                 1..1332
                       mol_type = genomic DNA
                       organism = Thlaspi arvense
SEQUENCE: 201
atggcggcgt gtttacaatc gaacatccgg ctgaatctga acaatatcgt cggaggaaaa  60
tgcagatccc tcaccgatca gtctcgcacg ccgtgtcgaa taaggtgcgc cgccgcttca  120
cctgggaaaa aacggttcaa catcgctctc cttcctggcg acggtatcgg tcctgaagtc  180
atctccgttg ccaagaatgt gcttcagcaa gctggatctc tcgaaggttc ttctatctct  240
cgctcagttt atttactaat tttgacaaaa ttagtaatca gcgaatgtgt tgcttaccca  300
gaagagtgtg cgtatttgat gtgtatcaca ggactggagt tcaatttcca ggagatgccc  360
atcggaggag cagccttgga tttggtcgga gtggccttgc cggaggaaac cttatcggct  420
gcaaaacagt ctgatgccat acttcttgga gctatcggag ggtacaaatg ggacaacaat  480
gagaaacatc tgagacctga gatggctctg atttaccttc ggagagatct caaagtcttt  540
gctaatctga gacctgcttc agttttgcca cagctagttg atgcatccac cttgaagaga  600
gaagtagcag aaggtgttga tatgatgatt gtaagggagc ttacaggagg aatttacttt  660
ggagagccca gaggcattaa gaccaacgaa aacggagaag aagtcggttt taatacagag  720
ttttacgctg ctcacgagat tgacagaatt gctcgtgttg catttgagac tgctaggaaa  780
cggcgtggca agctgtgttc tgtcgacaaa gccaatgtgt tggatgcatc agtattgtgg  840
aggagaagag taacagcgtt agcctctgag tatccagatg ttgagctctc acatatgtat  900
gtagacaacg ctgcaatgca gcttattcgt gacccgaaac agtttgacac aatcgtcacc  960
aataacattt tcggtgacat attatccgat gaggcctcaa tgatcactgg aagcattggg  1020
atgcttccat ctgctagtct cggtgtattg ggacctggac tctttgagcc gatacatggt  1080
tctgcgccag atatagctgg tcaggacaag gcaaacccat tggccaccat tctcagcgca  1140
gcgatgcttc tgaaatatgg acttggagaa gagaaggccg caaagaggat cgaggacgcg  1200
gtcttggatg ctctcaacaa agggtttaga accggagaca tctactcccc cggaaataaa  1260
ctggtgggat gcaaggagat gggtgaggag gtgcttaaat cagtggactc cagagttaca  1320
gctactgttt aa                                                      1332

SEQ ID NO: 202         moltype = AA  length = 443
FEATURE                Location/Qualifiers
source                 1..443
                       mol_type = protein
                       organism = Thlaspi arvense
SEQUENCE: 202
MAACLQSNIR LNLNNIVGGK CRSLTDQSRT PCRIRCAAAS PGKKRFNIAL LPGDGIGPEV  60
ISVAKNVLQQ AGSLEGSSIS RSVYLLILTK LVISECVAYP EECAYLMCIT GLEFNFQEMP  120
IGGAALDLVG VALPEETLSA AKQSDAILLG AIGGYKWDNN EKHLRPEMAL IYLRRDLKVF  180
ANLRPASVLP QLVDASTLKR EVAEGVDMMI VRELTGGIYF GEPRGIKTNE NGEEVGFNTE  240
FYAAHEIDRI ARVAFETARK RRGKLCSVDK ANVLDASVLW RRRVTALASE YPDVELSHMY  300
VDNAAMQLIR DPKQFDTIVT NNIFGDILSD EASMITGSIG MLPSASLGVL GPGLFEPIHG  360
SAPDIAGQDK ANPLATILSA AMLLKYGLGE EKAAKRIEDA VLDALNKGFR TGDIYSPGNK  420
```

```
LVGCKEMGEE VLKSVDSRVT ATV                                        443

SEQ ID NO: 203          moltype = DNA  length = 1635
FEATURE                 Location/Qualifiers
source                  1..1635
                        mol_type = genomic DNA
                        organism = Thlaspi arvense
SEQUENCE: 203
atggatactt tagcttcaaa ctcttcgggt ctcaggacca agtcgagtcc cgagacgtcg  60
ccgtttagca acatgtatct cctcacaaca cttcaagccc ttgcggttat ttctctcttg  120
atgatattca agaaaataaa gtattcctct tcacaaaaaa aaaagtttca tcctctcccg  180
ccgggcccca gcgggtttcc agtcgtcgga atgattccgg cgatgcttaa aaaccgtccg  240
gttttccggt ggcttcacag cctcatgaaa gagcttaaca cggagatagc ttgtgttcgt  300
ctaggaaaga ctcacgtgat ccccgtcaca tgtcctaaga tcgcacgtga gattttcaag  360
caacaagacg cactcttcgc gtcgagacca ctcacttatg ctcaaaagat actttccaac  420
agctacaaaa cctgcgtgat cacaccgttc ggagaacaat tcaagaagat gaggaaagta  480
atcatgacgg agattgtttg tccagcaaga caccgatggt tacacgacaa cagagccgag  540
gaaaccgatc atttaactgc ttggctttac aacatggtta agaaatccga accggtcgat  600
ctccggtttg ttacaaggca ctactgcgga aatgcgatta agaggcttat gttcggaacg  660
aggacgttct cggcgaaaac cgaaaccgac ggtggaccaa ccgtggaaga tatcgagcat  720
atggatgcta tgtttgaagg gttagggttt acgtttgcgt tctgtgtatc ggattatcta  780
ccgatgctta cgggattgga tctaaacgga catgagaaga tcatgagaga agctagtgcg  840
attatggaca aatatcacga tcccattatt gatgagagga ttaagatgtg gagagaagga  900
aagagaactc agattgaaga ttttctagac attttcatct ctatcaagga cgaagctggc  960
cagcctttgc ttaccgctga tgaaatcaaa ccaaccatta aggaacttgt aatggcggcg  1020
ccggacaacc catcaaacgc cgtggaatgg gccatggcgg agatgataaa caaacctgag  1080
attctccaca aagcaatgga agagattgaa agagtcgttg gcaaagaaag actcgtccaa  1140
gaatccgata tcccaaaact taactatctc aaagctatta tccgagaagc tttccgtctg  1200
catcccgtcg ccgccttcaa cctcccacac gtggcacttt ccgacacaac cgtcgctggt  1260
tatcacatcc ctaaggggag tcaagtttta cttagccgtt acggtcttgg tcgtaaccca  1320
aaggtttggt ctgatccact tagctttaaa ccggagagac acctcaatga gtgcttggaa  1380
gtaacgttga ctgagaatga tctccggttt atctcgttta gtaccggaaa aagaggatgt  1440
gctgctccgg cgttaggtac ggcgataacc gtcatgatgc tcgccaggct tttgcaaggg  1500
tttaagtgga agttagctgg aggtgagaca cgtgttgagt tgatggaatc gagtcatgat  1560
atgtttcttg cgacgccttt ggttatggtc ggagaattga gattgtcgga ggatctttac  1620
cccacggtga agtga                                                 1635

SEQ ID NO: 204          moltype = AA  length = 544
FEATURE                 Location/Qualifiers
source                  1..544
                        mol_type = protein
                        organism = Thlaspi arvense
SEQUENCE: 204
MDTLASNSSG LRTKSSPETS PFSNMYLLTT LQALAVISLL MIFKKIKYSS SQKKKFHPLP  60
PGPSGFPVVG MIPAMLKNRP VFRWLHSLMK ELNTEIACVR LGKTHVIPVT CPKIAREIFK  120
QQDALFASRP LTYAQKILSN SYKTCVITPF GEQFKKMRKV IMTEIVCPAR HRWLHDNRAE  180
ETDHLTAWLY NMVKKSEPVD LRFVTRHYCG NAIKRLMFGT RTFSAKTETD GGPTVEDIEH  240
MDAMFEGLGF TFAFCVSDYL PMLTGLDLNG HEKIMREASA IMDKYHDPII DERIKMWREG  300
KRTQIEDFLD IFISIKDEAG QPLLTADEIK PTIKELVMAA PDNPSNAVEW AMAEMINKPE  360
ILHKAMEEIE RVVGKERLVQ ESDIPKLNYL KAIIREAFRL HPVAAFNLPH VALSDTTVAG  420
YHIPKGSQVL LSRYGLGRNP KVWSDPLSFK PERHLNECLE VTLTENDLRF ISFSTGKRGC  480
AAPALGTAIT VMMLARLLQG FKWKLAGGET RVELMESSHD MFLATPLVMV GELRLSEDLY  540
PTVK                                                             544

SEQ ID NO: 205          moltype = DNA  length = 1635
FEATURE                 Location/Qualifiers
source                  1..1635
                        mol_type = genomic DNA
                        organism = Thlaspi arvense
SEQUENCE: 205
atggatactt tagcttcaaa ctcttcgggt ctcaggacca agtcgagtcc cgagacgtcg  60
ccgtttagca acatgtatct cctcacaaca cttcaagccc ttgcggttat ttctctcttg  120
atgatattca agaaaataaa gtattcctct tcacaaaaaa aaaagtttca tcctctcccg  180
ccgggcccca gcgggtttcc agtcgtcgga atgattccgg cgatgcttaa aaaccgtccg  240
gttttccggt ggcttcacag cctcatgaaa gagcttaaca cggagatagc ttgtgttcgt  300
ctaggaaaga ctcacgtgat ccccgtcaca tgtcctaaga tcgcacgtga gattttcaag  360
caacaagacg cactcttcgc gtcgagacca ctcacttatg ctcaaaagat actttccaac  420
ggctacaaaa cctgcgtgat cacaccgttc ggagaacaat tcaagaagat gaggaaagta  480
atcatgacgg agattgtttg tccagcaaga caccgatggt tacacgacaa cagagccgag  540
gaaaccgatc atttaactgc ttggctttac aacatggtta agaaatccga accggtcgat  600
ctccggtttg ttacaaggca ctactgcgga aatgcgatta agaggcttat gttcggaacg  660
aggacgttct cggcgaaaac cgaaaccgac ggtggaccaa ccgtggaaga tatcgagcat  720
atggatgcta tgtttgaagg gttagggttt acgtttgcgt tctgtgtatc ggattatcta  780
ccgatgctta cgggattgga tctaaacgga catgagaaga tcatgagaga agctagtgcg  840
attatggaca aatatcacga tcccattatt gatgagagga ttaagatgtg gagagaagga  900
aagagaactc agattgaaga ttttctagac attttcatct ctatcaagga cgaagctggc  960
cagcctttgc ttaccgctga tgaaatcaaa ccaaccatta aggaacttgt aatggcggcg  1020
ccggacaacc catcaaacgc cgtggaatgg gccatggcgg agatgataaa caaacctgag  1080
attctccaca aagcaatgga agagattgaa agagtcgttg gcaaagaaag actcgtccaa  1140
```

```
gaatccgata tcccaaaact taactatctc aaagctatta tccgagaagc tttccgtctg  1200
catcccgtcg ccgccttcaa cctcccacac gtggcacttt ccgacacaac cgtcgctggt  1260
tatcacatcc ctaaggggag tcaagtttta cttagccgtt acggtcttgg tcgtaaccca  1320
aaggtttggt ctgattcact tagctttaaa ccggagagac acctcaatga gtgcttggaa  1380
gtaacgttga ctgagaatga tctccggttt atctcgttta gtaccggaaa aagaggatgt  1440
gctgctccgg cgttaggtac ggcgataacc gtcatgatgc tcgccaggct tttgcaaggg  1500
tttaagtgga agttagctgg aggtgagaca cgtgttgagt tgatggaatc gagtcatgat  1560
atgtttcttg cgacgccttt ggttatggtc ggagaattga gattgtcgga ggatctttac  1620
cccacggtga agtga                                                   1635

SEQ ID NO: 206          moltype = AA  length = 544
FEATURE                 Location/Qualifiers
source                  1..544
                        mol_type = protein
                        organism = Thlaspi arvense
SEQUENCE: 206
MDTLASNSSG LRTKSSPETS PFSNMYLLTT LQALAVISLL MIFKKIKYSS SQKKKFHPLP  60
PGPSGFPVVG MIPAMLKNRP VFRWLHSLMK ELNTEIACVR LGKTHVIPVT CPKIAREIFK  120
QQDALFASRP LTYAQKILSN GYKTCVITPF GEQFKKMRKV IMTEIVCPAR HRWLHDNRAE  180
ETDHLTAWLY NMVKKSEPVD LRFVTRHYCG NAIKRLMFGT RTFSAKTETD GGPTVEDIEH  240
MDAMFEGLGF TFAFCVSDYL PMLTGLDLNG HEKIMREASA IMDKYHDPII DERIKMWREG  300
KRTQIEDFLD IFISIKDEAG QPLLTADEIK PTIKELVMAA PDNPSNAVEW AMAEMINKPE  360
ILHKAMEEIE RVVGKERLVQ ESDIPKLNYL KAIIREAFRL HPVAAFNLPH VALSDTTVAG  420
YHIPKGSQVL LSRYGLGRNP KVWSDSLSFK PERHLNECLE VTLTENDLRF ISFSTGKRGC  480
AAPALGTAIT VMMLARLLQG FKWKLAGGET RVELMESSHD MFLATPLVMV GELRLSEDLY  540
PTVK                                                               544

SEQ ID NO: 207          moltype = DNA  length = 1509
FEATURE                 Location/Qualifiers
source                  1..1509
                        mol_type = genomic DNA
                        organism = Thlaspi arvense
SEQUENCE: 207
atggaagata tcatcatcgg cgttgtggct ctcgccgccg ttctcctctt cttcctctac  60
caaagcccaa aaaccaaacg gtataagctg cctcccggcc cacggccgct tccggtgatc  120
ggaaacctcc accagcttag ccaggttaac ccacaacggt tcttctatgg atgggccaaa  180
aaatatggac caatcttatc atacaagata ggaaacaaaa caatgatggt aatttcttcg  240
gctgagctaa ccaaagagct tctcaagacg caagatgtca acttcgccaa ccggcctcct  300
caccgtggtc acgagctcat gacctacggc cgaagtgaca tggcgatgaa ccactacaca  360
ccgttgtacc gggagatgag gaagatgggc atgaaccact tgttctcccc cactcgtgta  420
gccacctta agcacgtacg ggaggaggag gctaggagga tgatgtttaa gatcgagaag  480
gctgcggaga gatctgaacc ggtcgatata agcgagctta tgttgacctt cacgaactcg  540
gttgtgtgta ggcaagcttt cgggaagaag tacaatgaag atggggaaga gatgaagaga  600
ttcatcagga ttctttatgg gactcagagc gtattgggga agattttttt ctctgatttt  660
ttcccgttta ctcgctacgt tcttgataat tggaccggcc tcacgaaata tatgatggac  720
tgttttgaaa gacaagacac ttacatacaa gagattatcg atgagacact tgatcccaac  780
aaggtaaagc cagaaacgga gagcatgatc gatctcttga tggaggtcta caaagaacaa  840
ccattcgcct ccaagttcac aattgggaat gtcaaaggcg ttatcttgaa tatagtggtt  900
gcgggaaccg acacggcggc tgcggcggtt gtgtggggga tgacgtatct aatgaagtac  960
cctcaagtta tgaagaaagc tcaagcagaa gtgagagagt atgcaaaaga gaaagatcta  1020
acgtttatta ctgaagacga cgtcaagaac cttccttact tcagagcttt agttaaagaa  1080
accttaagga tcgaaccagt gattcctctc cttatccctc gttgttgcat tcaagacacc  1140
aagatcgccg gttacgatgt ccccgcgggg accacggtca acgtaaacgc gtgggcggtg  1200
tcacgcgacg agaaggagtg gggcccaaac cctgatgaat tcaggcccaa gaggtttctt  1260
gagaaggacg tggacttcaa aggcacggac tatgagttta taccgtttgg gtcaggccgg  1320
agaatgtgcc ctggaatgcg tcttggcgcg gcgatgatcg aggttccgta tgcgaacctt  1380
ttgctcaact ttgacttcaa acttgctgat ggactgaaac cagaagagat caacatggat  1440
gttatgacag gtcttgctat gcacaaggcg gttcatctca ggcttgttcc cgagaaagtg  1500
aggaagtga                                                          1509

SEQ ID NO: 208          moltype = AA  length = 502
FEATURE                 Location/Qualifiers
source                  1..502
                        mol_type = protein
                        organism = Thlaspi arvense
SEQUENCE: 208
MEDIIIGVVA LAAVLLFFLY QSPKTKRYKL PPGPRPLPVI GNLHQLSQVN PQRFFYGWAK  60
KYGPILSYKI GNKTMMVISS AELTKELLKT QDVNFANRPP HRGHELMTYG RSDMAMNHYT  120
PLYREMRKMG MNHLFSPTRV ATFKHVREEE ARRMMFKIEK AAERSEPVDI SELMLTFTNS  180
VVCRQAFGKK YNEDGEEMKR FIRILYGTQS VLGKIFFSDF FPFTRYVLDN WTGLTKYMMD  240
CFERQDTYIQ EIIDETLDPN KVKPETESMI DLLMEVYKEQ PFASKFTIGN VKGVILNIVV  300
AGTDTAAAAV VWGMTYLMKY PQVMKKAQAE VREYAKEKDL TFITEDDVKN LPYFRALVKE  360
TLRIEPVIPL LIPRCCIQDT KIAGYDVPAG TTVNVNAWAV SRDEKEWGPN PDEFRPKRFL  420
EKDVDFKGTD YEFIPFGSGR RMCPGMRLGA AMIEVPYANL LLNFDFKLAD GLKPEEINMD  480
VMTGLAMHKA VHLRLVPEKV RK                                           502

SEQ ID NO: 209          moltype = DNA  length = 1510
FEATURE                 Location/Qualifiers
source                  1..1510
```

```
                        mol_type = genomic DNA
                        organism = Thlaspi arvense
SEQUENCE: 209
atggaagata tcatcatcgg cgttgtggct ctcgccgccg ttctcctctt cttcctctac  60
caaagcccaa aaaccaaacg gtataagctg cctcccggcc cacggccgct tccggtgatc  120
ggaaacctcc accagcttag ccaggttaac ccacaacggt tcttctatgg atgggccaaa  180
aaatatggac caatcttatc atacaaagat aggaaacaaa acaatgatgg taatttcttc  240
ggctgagcta accaaagagc ttctcaagac gcaagatgtc aacttcgcca accggcctcc  300
tcaccgtggt cacgagctca tgacctacgg ccgaagtgac atggcgatga accactacac  360
accgttgtac cgggagatga ggaagatggg catgaaccac ttgttctccc ccactcgtgt  420
agccaccttt aagcacgtac gggaggagga ggctaggagg atgatgttta agatcgagaa  480
ggctgcggag agatctgaac cggtcgatat aagcgagctt atgttgacct tcacgaactc  540
ggttgtgtgt aggcaagctt tcgggaagaa gtacaatgaa gatggggaag agatgaagag  600
attcatcagg attctttatg ggactcagag cgtattgggg aagatttttt tctctgattt  660
tttcccgttt actcgctacg ttcttgataa ttggaccggc ctcacgaaat atatgatgga  720
ctgttttgaa agacaagaca cttacataca agagattatc gatgagacac ttgatcccaa  780
caaggtaaag ccagaaacgg agagcatgat cgatctcttg atggaggtct acaaagaaca  840
accattcgcc tccaagttca caattgggaa tgtcaaaggc gttatcttga atatagtggt  900
tgcgggaacc gacacggcgg ctgcggcggt tgtgtggggg atgacgtatc taatgaagta  960
ccctcaagtt atgaagaaag ctcaagcaga agtgagagag tatgcaaaag agaaagatct  1020
aacgtttatt actgaagacg acgtcaagaa ccttccttac ttcagagctt tagttaaaga  1080
aaccttaagg atcgaaccag tgattcctct ccttatccct cgttgttgca ttcaagacac  1140
caagatcgcc ggttacgatg tccccgcggg gaccacggtc aacgtaaacg cgtgggcggt  1200
gtcacgcgac gagaaggagt ggggcccaaa ccctgatgaa ttcaggcccg agaggtttct  1260
tgagaaggac gtggacttca aaggcacgga ctatgagttt ataccgtttg ggtcaggccg  1320
gagaatgtgc cctggaatgc gtcttggcgc ggcgatgatc gaggttccgt atgcgaacct  1380
tttgctcaac tttgacttca aacttgctga tggactgaaa ccagaagaga tcaacatgga  1440
tgttatgaca ggtcttgcta tgcacaaggc ggttcatctc aggcttgttc ccgagaaagt  1500
gaggaagtga                                                         1510

SEQ ID NO: 210          moltype = AA  length = 81
FEATURE                 Location/Qualifiers
source                  1..81
                        mol_type = protein
                        organism = Thlaspi arvense
SEQUENCE: 210
MEDIIIGVVA LAAVLLFFLY QSPKTKRYKL PPGPRPLPVI GNLHQLSQVN PQRFFYGWAK  60
KYGPILSYKD RKQNNDGNFF G                                            81

SEQ ID NO: 211          moltype = DNA  length = 1510
FEATURE                 Location/Qualifiers
source                  1..1510
                        mol_type = genomic DNA
                        organism = Thlaspi arvense
SEQUENCE: 211
atggaagata tcatcatcgg cgttgtggct ctcgccgccg ttctcctctt cttcctctac  60
caaagcccaa aaaccaaacg gtataagctg cctcccggcc cacggccgct tccggtgatc  120
ggaaacctcc accagcttag ccaggttaac ccacaacggt tcttctatgg atgggccaaa  180
aaatatggac caatcttatc atacaatgat aggaaacaaa acaatgatgg taatttcttc  240
ggctgagcta accaaagagc ttctcaagac gcaagatgtc aacttcgcca accggcctcc  300
tcaccgtggt cacgagctca tgacctacgg ccgaagtgac atggcgatga accactacac  360
accgttgtac cgggagatga ggaagatggg catgaaccac ttgttctccc ccactcgtgt  420
agccaccttt aagcacgtac gggaggagga ggctaggagg atgatgttta agatcgagaa  480
ggctgcggag agatctgaac cggtcgatat aagcgagctt atgttgacct tcacgaactc  540
ggttgtgtgt aggcaagctt tcgggaagaa gtacaatgaa gatggggaag agatgaagag  600
attcatcagg attctttatg ggactcagag cgtattgggg aagatttttt tctctgattt  660
tttcccgttt actcgctacg ttcttgataa ttggaccggc ctcacgaaat atatgatgga  720
ctgttttgaa agacaagaca cttacataca agagattatc gatgagacac ttgatcccaa  780
caaggtaaag ccagaaacgg agagcatgat cgatctcttg atggaggtct acaaagaaca  840
accattcgcc tccaagttca caattgggaa tgtcaaaggc gttatcttga atatagtggt  900
tgcgggaacc gacacggcgg ctgcggcggt tgtgtggggg atgacgtatc taatgaagta  960
ccctcaagtt atgaagaaag ctcaagcaga agtgagagag tatgcaaaag agaaagatct  1020
aacgtttatt actgaagacg acgtcaagaa ccttccttac ttcagagctt tagttaaaga  1080
aaccttaagg atcgaaccag tgattcctct ccttatccct cgttgttgca ttcaagacac  1140
caagatcgcc ggttacgatg tccccgcggg gaccacggtc aacgtaaacg cgtgggcggt  1200
gtcacgcgac gagaaggagt ggggcccaaa ccctgatgaa ttcaggcccg agaggtttct  1260
tgagaaggac gtggacttca aaggcacgga ctatgagttt ataccgtttg ggtcaggccg  1320
gagaatgtgc cctggaatgc gtcttggcgc ggcgatgatc gaggttccgt atgcgaacct  1380
tttgctcaac tttgacttca aacttgctga tggactgaaa ccagaagaga tcaacatgga  1440
tgttatgaca ggtcttgcta tgcacaaggc ggttcatctc aggcttgttc ccgagaaagt  1500
gaggaagtga                                                         1510

SEQ ID NO: 212          moltype = AA  length = 81
FEATURE                 Location/Qualifiers
source                  1..81
                        mol_type = protein
                        organism = Thlaspi arvense
SEQUENCE: 212
MEDIIIGVVA LAAVLLFFLY QSPKTKRYKL PPGPRPLPVI GNLHQLSQVN PQRFFYGWAK  60
```

```
KYGPILSYND RKQNNDGNFF G                                     81

SEQ ID NO: 213          moltype = DNA  length = 1332
FEATURE                 Location/Qualifiers
source                  1..1332
                        mol_type = genomic DNA
                        organism = Thlaspi arvense
SEQUENCE: 213
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtcttttgg acaaagttta cgagtttact  300
caacttctac gtcctgatca ttgtgacggt aacaagagca tcagcgaaac gatccagacg  360
ttttcagaga agttatcaga attggatata atggtgagaa gaatggtaat ggaaagcttc  420
gggatagaga agtaccttga caaacacctg aactcaacga attaccgtct gcggctgatg  480
aagtatatag caccgcctga tgctgatgct actaatgttg cggctgatgc caaagatgct  540
gatgataatg ctaagacgat tacaaatgat aaagttgatg cggctggtgc taatgatgta  600
gatgctggtg atatcgctaa tggtattgct aatcttcata ttggtgatga tgctaacgct  660
ggtgctaatg gtgctggtgt tgatgctaat gatggtggtg aggatgctaa gactggtgag  720
gatgctaaga ctggtgaatg tgctagtgtt aagtctaatg ccgaagatgg tactgatgtt  780
aatgccagtg ctgatgctgg tgttactgtt ggctctaatg ctgatgctaa tgctaatgct  840
aatgctaata ctagtactga tgctggtgtt ggcgatagtg ttaaagctaa tggtggtgct  900
gatgatgttg agaagaaatt gggtctacct tctcacactg ataagaacct tataacggtg  960
ctttatcaat acgagattga aggcttggag gttctaacca aagatgacaa gtggatcaga  1020
ctcaaaccat ctcataattc tttcgttgtt atggctggag attctctata cgcacttatg  1080
aatggtagac taactcgtcc ctttcatcga gtaagagtaa cggagaaaaa gaagacaaga  1140
tattcaatag cattgttctc ggctccaacc gcagattaca tcatagacac accaaaagaa  1200
cttgtggacg agaagcatcc acgtatcttc gaaccattta actataacga cttgatgagt  1260
ttctatcata gtgaagctgg tcgtaaagct cgatctactc ttgatgcttt ctgtgccgtc  1320
tctcgagcat aa                                                1332

SEQ ID NO: 214          moltype = AA  length = 443
FEATURE                 Location/Qualifiers
source                  1..443
                        mol_type = protein
                        organism = Thlaspi arvense
SEQUENCE: 214
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLLDKVYEFT QLLRPDHCDG NKSISETIQT  120
FSEKLSELDI MVRRMVMESF GIEKYLDKHL NSTNYRLRLM KYIAPPDADA TNVAADAKDA  180
DDNAKTITND KVDAAGANDV DAGDIANGIA NLHIGDDANA GANGAGVDAN DGGEDAKTGE  240
DAKTGECASV KSNAEDGTDV NASADAGVTV GSNADANANA NANTSTDAGV GDSVKANGGA  300
DDVEKKLGLP SHTDKNLITV LYQYEIEGLE VLTKDDKWIR LKPSHNSFVV MAGDSLYALM  360
NGRLTRPFHR VRVTEKKKTR YSIALFSAPT ADYIIDTPKE LVDEKHPRIF EPFNYNDLMS  420
FYHSEAGRKA RSTLDAFCAV SRA                                    443

SEQ ID NO: 215          moltype = DNA  length = 1363
FEATURE                 Location/Qualifiers
source                  1..1363
                        mol_type = genomic DNA
                        organism = Thlaspi arvense
SEQUENCE: 215
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagtatggg gatccaggat  300
cctcattttg gacaaagttt acgagtttac tcaacttcta cgtcctgatc attgtgacgg  360
taacaagagc atcagcgaaa cgatccagac gttttcagag aagttatcag aattggatat  420
aatggtgaga agaatggtaa tggaaagctt cgggatagag aagtaccttg acaaacacct  480
gaactcaacg aattaccgtc tgcggctgat gaagtatata gcaccgcctg atgctgatgc  540
tactaatgtt gcggctgatg ccaaagatgc tgatgataat gctaagacga ttacaaatga  600
taaagttgat gcggctggtg ctaatgatgt agatgctggt gatatcgcta atggtattgc  660
taatcttcat attggtgatg atgctaacgc tggtgctaat ggtgctggtg ttgatgctaa  720
tgatggtggt gaggatgcta agactggtga ggatgctaag actggtgaat gtgctagtgt  780
taagtctaat gccgaagatg gtactgatgt taatgccagt gctgatgctg gtgttactgt  840
tggctctaat gctgatgcta atgctaatgc taatgctaat actagtactg atgctggtgt  900
tggcgatagt gttaaagcta atggtggtgc tgatgatgtt gagaagaaat tgggtctacc  960
ttctcacact gataagaacc ttataacggt gctttatcaa tacgagattg aaggcttgga  1020
ggttctaacc aaagatgaca agtggatcag actcaaacca tctcataatt ctttcgttgt  1080
tatggctgga gattctctat acgcacttat gaatggtaga ctaactcgtc cctttcatcg  1140
agtaagagta acggagaaaa agaagacaag atattcaata gcattgttct cggctccaac  1200
cgcagattac atcatagaca caccaaaaga acttgtggac gagaagcatc cacgtatctt  1260
cgaaccattt aactataacg acttgatgag tttctatcat agtgaagctg gtcgtaaagc  1320
tcgatctact cttgatgctt tctgtgccgt ctctcgagca taa              1363

SEQ ID NO: 216          moltype = AA  length = 115
FEATURE                 Location/Qualifiers
```

```
source                  1..115
                        mol_type = protein
                        organism = Thlaspi arvense
SEQUENCE: 216
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSESMGIQD PHFGQSLRVY STSTS       115

SEQ ID NO: 217          moltype = DNA  length = 1364
FEATURE                 Location/Qualifiers
source                  1..1364
                        mol_type = genomic DNA
                        organism = Thlaspi arvense
SEQUENCE: 217
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagtatggg gatccaggat  300
cctcatgttt ggacaaagtt tacgagttta ctcaacttct acgtcctgat cattgtgacg  360
gtaacaagag catcagcgaa acgatccaga cgttttcaga gaagttatca gaattggata  420
taatggtgag aagaatggta atggaaagct tcgggataga gaagtacctt gacaaacacc  480
tgaactcaac gaattaccgt ctgcggctga tgaagtatat agcaccgcct gatgctgatg  540
ctactaatgt tgcggctgat gccaaagatg ctgatgataa tgctaagacg attacaaatg  600
ataaagttga tgcggctggt gctaatgatg tagatgctgg tgatatcgct aatggtattg  660
ctaatcttca tattggtgat gatgctaacg ctggtgctaa tggtgctggt gttgatgcta  720
atgatggtgg tgaggatgct aagactggtg aggatgctaa gactggtgaa tgtgctagtg  780
ttaagtctaa tgccgaagat ggtactgatg ttaatgccag tgctgatgct ggtgttactg  840
ttggctctaa tgctgatgct aatgctaatg ctaatgctaa tactagtact gatgctggtg  900
ttggcgatag tgttaaagct aatggtggtg ctgatgatgt tgagaagaaa ttgggtctac  960
cttctcacac tgataagaac cttataacgg tgctttatca atacgagatt gaaggcttgg  1020
aggttctaac caaagatgac aagtggatca gactcaaacc atctcataat tctttcgttg  1080
ttatggctgg agattctcta tacgcactta tgaatggtag actaactcgt ccctttcatc  1140
gagtaagagt aacggagaaa aagaagacaa gatattcaat agcattgttc tcggctccaa  1200
ccgcagatta catcatagac acaccaaaag aacttgtgga cgagaagcat ccacgtatct  1260
tcgaaccatt taactataac gacttgatga gtttctatca tagtgaagct ggtcgtaaag  1320
ctcgatctac tcttgatgct ttctgtgccg tctctcgagc ataa                  1364

SEQ ID NO: 218          moltype = AA  length = 140
FEATURE                 Location/Qualifiers
source                  1..140
                        mol_type = protein
                        organism = Thlaspi arvense
SEQUENCE: 218
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSESMGIQD PHVWTKFTSL LNFYVLIIVT  120
VTRASAKRSR RFQRSYQNWI                                              140

SEQ ID NO: 219          moltype = DNA  length = 1366
FEATURE                 Location/Qualifiers
source                  1..1366
                        mol_type = genomic DNA
                        organism = Thlaspi arvense
SEQUENCE: 219
atgggttcac tttcaaacac tcctcagctt ccagtcatct acctctcgga ccaaacccta  60
aaaccaggaa gctcaaagtg ggttgaagtc aggagtgatg tccgtaaagc tcttgaagag  120
tacggcggtt tcgaggtgtc gtacgataga gtgtcggagg agcttaagaa gtcggttttg  180
caagccatgg aagagctttt cgcgttacca gttgaggcta aacagagaaa cgtctctcct  240
aaacccttca gcggttattc cactcataac ggtctttccg agagtatggg gatccaggat  300
cctcatgttt ttggacaaag tttacgagtt tactcaactt ctacgtcctg atcattgtga  360
cggtaacaag agcatcagcg aaacgatcca gacgttttca gagaagttat cagaattgga  420
tataatggtg agaagaatgg taatggaaag cttcgggata gagaagtacc ttgacaaaca  480
cctgaactca acgaattacc gtctgcggct gatgaagtat atagcaccgc ctgatgctga  540
tgctactaat gttgcggctg atgccaaaga tgctgatgat aatgctaaga cgattacaaa  600
tgataaagtt gatgcggctg gtgctaatga tgtagatgct ggtgatatcg ctaatggtat  660
tgctaatctt catattggtg atgatgctaa cgctggtgct aatggtgctg gtgttgatgc  720
taatgatggt ggtgaggatg ctaagactgg tgaggatgct aagactggtg aatgtgctag  780
tgttaagtct aatgccgaag atggtactga tgttaatgcc agtgctgatg ctggtgttac  840
tgttggctct aatgctgatg ctaatgctaa tgctaatgct aatactagta ctgatgctgg  900
tgttggcgat agtgttaaag ctaatggtgg tgctgatgat gttgagaaga aattgggtct  960
accttctcac actgataaga accttataac ggtgctttat caatacgaga ttgaaggctt  1020
ggaggttcta accaaagatg acaagtggat cagactcaaa ccatctcata attctttcgt  1080
tgttatggct ggagattctc tatacgcact tatgaatggt agactaactc gtccctttca  1140
tcgagtaaga gtaacggaga aaaagaagac aagatattca atagcattgt tctcggctcc  1200
aaccgcagat tacatcatag acacaccaaa agaacttgtg gacgagaagc atccacgtat  1260
cttcgaacca tttaactata acgacttgat gagtttctat catagtgaag ctggtcgtaa  1320
agctcgatct actcttgatg ctttctgtgc cgtctctcga gcataa                1366

SEQ ID NO: 220          moltype = AA  length = 116
FEATURE                 Location/Qualifiers
```

```
source                  1..116
                        mol_type = protein
                        organism = Thlaspi arvense
SEQUENCE: 220
MGSLSNTPQL PVIYLSDQTL KPGSSKWVEV RSDVRKALEE YGGFEVSYDR VSEELKKSVL  60
QAMEELFALP VEAKQRNVSP KPFSGYSTHN GLSESMGIQD PHVFGQSLRV YSTSTS      116

SEQ ID NO: 221          moltype = DNA  length = 1956
FEATURE                 Location/Qualifiers
source                  1..1956
                        mol_type = genomic DNA
                        organism = Thlaspi arvense
SEQUENCE: 221
atgaagagta gagtcatcct cagccataga gagagaagag ataagaagaa taataacatt  60
aacaacaaag acatctcctg taatttcaca cagattgaaa ccatggagag aaagcccttt  120
gaggttgaga cgacggagaa tcacaaaccc tactccaccg tcgatggcgg tggcgttggt  180
tctgatttga gatcgccggt cgattcattt gatgacgagc agaaaaagct cgtttacaga  240
ggctggaaag tcatgccttt tatcattggt aatgagacat ttgagaagat tgggatcata  300
gggacattat caaaccttct tttgtaccta actcaagtat tcaaccttaa gaaagttaca  360
gctgcaacaa tcatcaatgc ctttagtggc acaatcaact tcgggacttt catcgctgct  420
ttcctctgcg acacttactt tggtcgctac aagactctca gtgtagctgt catcgcttgt  480
ttcctgggat cgcttgtgat attactgacg gctgcagttc ctgcattgca cccgactcca  540
tgtggaacac atagctggtg ccaagggcca agcccgggcc agatcgcgtt cttgctgctg  600
ggtttagcgt ttcttgtggt cggtgcgggt gggatcaggc cgtgtaactt ggcttttgga  660
gctgatcagt tcaaccccaa atccgaatcc gggaagaaag gaatcaacag cttctttaac  720
tggtatttct tcaccttcac gtttgcgcag atcgtctcgc tcacgctggt cgtgtatatc  780
cagtcgaacg tgagctggac gatcggtttg ctcatccctg tggctctgat gttcttggcc  840
tgcgtcatct tctttgctgg acataaactg tatgtgaaag tgaaagcctc gggtagtccc  900
ttggctagta tcggtcacgt tatcacggca gcgatcaaga aacgagggtt gaagcaagtt  960
aagcagcctt ggctcgatct ttacaaccac attccaacta actatccaaa ctccaccttg  1020
aaatacaccg accagtttag gtttcttgac aaagcagcga ttatgacccc tgaggacaag  1080
ctgaattccg atggagctgc tttcgatcca tggaccctat gtacattgca gaaagtggaa  1140
gaagtgaaat gcattgtgag agtgattccg atctggtttg cttgcgcgat ttactacctc  1200
actgtaacta tacagatgac ttatccggtc ttccaagcgc agcagagcga ccggagattg  1260
ggttctggtg gcttcaagat ccccgcagcc acctatgtgg tgttcttgat gtcgggtatg  1320
actgttttca tcgtgttcta cgaccgtgtc cttgtcccgt tgctcagaag agtgaccggg  1380
ttagaaaccg gtttgaccct cttgcagaga gtcggatcag ggatcttctt tgccatgttg  1440
agtttgttgg tctccgggtt cgtagaggaa cggagaagaa ccttcgccct gacgaaaccg  1500
actctcggga tggagccacg agcgggagag atctcctcca tgtcggccat gtggctgatt  1560
ccgcagctct tgtttgcagg cgtaggagag gcttttacag ccattggaca gatggagttt  1620
tattacaagc agttccctga gaacatgaag agcttcgctg gctctatctt ctatgtcggt  1680
gcaggtgttt cgagctatct tgctagcttc ttgatctcga ctgttcatcg aagaactgaa  1740
cattcaccct ccgggaactg gttagctgag gatctgaaca aagggagact cgattacttc  1800
tacttcatgc tcaccggaat catggtcgtt aacatggttt acttcttgat aatgtctaaa  1860
tggtatagat acaaaggcat taacgatgaa gcgaattctt tggtcgagac caatgaagaa  1920
gagaccaagc agaaacaagt caagaattct gtctga                            1956

SEQ ID NO: 222          moltype = AA  length = 651
FEATURE                 Location/Qualifiers
source                  1..651
                        mol_type = protein
                        organism = Thlaspi arvense
SEQUENCE: 222
MKSRVILSHR ERRDKKNNNI NNKDISCNFT QIETMERKPF EVETTENHKP YSTVDGGGVG  60
SDLRSPVDSF DDEQKKLVYR GWKVMPFIIG NETFEKIGII GTLSNLLLYL TQVFNLKKVT  120
AATIINAFSG TINFGTFIAA FLCDTYFGRY KTLSVAVIAC FLGSLVILLT AAVPALHPTP  180
CGTHSWCQGP SPGQIAFLLL GLAFLVVGAG GIRPCNLAFG ADQFNPKSES GKKGINSFFN  240
WYFFTFTFAQ IVSLTLVVYI QSNVSWTIGL LIPVALMFLA CVIFFAGHKL YVKVKASGSP  300
LASIGHVITA AIKKRGLKQV KQPWLDLYNH IPTNYPNSTL KYTDQFRFLD KAAIMTPEDK  360
LNSDGAAFDP WTLCTLQKVE EVKCIVRVIP IWFACAIYYL TVTIQMTYPV FQAQQSDRRL  420
GSGGFKIPAA TYVVFLMSGM TVFIVFYDRV LVPLLRRVTG LETGLTLLQR VGSGIFFAML  480
SLLVSGFVEE RRRTFALTKP TLGMEPRAGE ISSMSAMWLI PQLLFAGVGE AFTAIGQMEF  540
YYKQFPENMK SFAGSIFYVG AGVSSYLASF LISTVHRRTE HSPSGNWLAE DLNKGRLDYF  600
YFMLTGIMVV NMVYFLIMSK WYRYKGINDE ANSLVETNEE ETKQKQVKNS V            651

SEQ ID NO: 223          moltype = DNA  length = 1957
FEATURE                 Location/Qualifiers
source                  1..1957
                        mol_type = genomic DNA
                        organism = Thlaspi arvense
SEQUENCE: 223
atgaagagta gagtcatcct cagccataga gagagaagag ataagaagaa taataacatt  60
aacaacaaag acatctcctg taatttcaca cagattgaaa ccatggagag aaagcccttt  120
gaggttgaga cgacggagaa tcacaaaccc tactccaccg tcgatggcgg tggcgttggt  180
tctgatttga gatcgccggt cgattcattt gatgacgagc agaaaaagct cgtttacaga  240
ggctggaaag tcatgccttt tatcattggt aatgagacat ttgagaagat tgggatcata  300
gggacattat caaaccttct tttgtaccta actcaagtat tcaaccttaa gaaagttaca  360
gctgcaacaa tcatcaatgc ctttagtggc acaatcaact tcgggacttt catcgctgct  420
ttcctctgcg acacttactt tggtcgctac aagactctca gtgtagctgt catcgcttgt  480
```

```
ttcctgggat cgcttgtgat attactgacg gctgcagttc ctgcattgca cccgactcca  540
tgtggaacac atagctggtg ccaagggcca agcccgggcc agatcgcgtt cttgctgctg  600
ggtttagcgt ttcttgtggt cggtgcgggt gggatcaggc cgtgtaactt ggcttttgga  660
gctgatcagt tcaaccccaa atccgaatcc gggaagaaag gaatcaacag cttctttaac  720
tggtatttct tcaccttcac gtttgcgcag atcgtctcgc tcacgctggt cgtgtatatc  780
cagtcgaacg tgagctggac gatcggtttg ctcatccctg tggctctgat gttcttggcc  840
tgcgtcatct tctttgctgg acataaactg tatgtgaaag tgaaagcctc gggtagtccc  900
ttggctagta tcggtcacgt tatcacggca gcgatcaaga aacgagggtt gaagcaagtt  960
aagcagcctt ggctcgatct ttacaaccac attccaacta actatccaaa ctccaccttg  1020
aaatacaccg accagtttag gtttcttgac aaagcagcga ttatgacccc tgaggacaag  1080
ctgaattccg atggagctgc tttcgatcca tggaccctat gtacattgca gaaagtggaa  1140
gaagtgaaat gcatgtgtga gagtgattcc gatctggttt gcttgcgcga tttactacct  1200
cactgtaact atacagatga cttatccggt cttccaagcg cagcagagcg accggagatt  1260
gggttctggt ggcttcaaga tccccgcagc cacctatgtg gtgttcttga tgtcgggtat  1320
gactgttttc atcgtgttct acgaccgtgt ccttgtcccg ttgctcagaa gagtgaccgg  1380
gttagaaacc ggtttgaccc tcttgcagag agtcggatca gggatcttct ttgccatgtt  1440
gagtttgttg gtctccgggt tcgtagagga acggagaaga accttcgccc tgacgaaacc  1500
gactctcggg atggagccac gagcgggaga gatctcctcc atgtcggcca tgtggctgat  1560
tccgcagctc ttgcttgcag gcgtaggaga ggcttttaca gccattggac agatggagtt  1620
ttattacaag cagttccctg agaacatgaa gagcttcgct ggctctatct tctatgtcgg  1680
tgcaggtgtt tcgagctatc ttgctagctt cttgatctcg actgttcatc gaagaactga  1740
acattcaccc tccgggaact ggttagctga ggatctgaac aaagggagac tcgattactt  1800
ctacttcatg ctcaccggaa tcatggtcgt taacatggtt tacttcttga taatgtctaa  1860
atggtataga tacaaaggca ttaacgatga agcgaattct ttggtcgaga ccaatgaaga  1920
agagaccaag cagaaacaag tcaagaattc tgtctga                           1957

SEQ ID NO: 224         moltype = AA  length = 546
FEATURE                Location/Qualifiers
source                 1..546
                       mol_type = protein
                       organism = Thlaspi arvense
SEQUENCE: 224
MKSRVILSHR ERRDKKNNNI NNKDISCNFT QIETMERKPF EVETTENHKP YSTVDGGGVG  60
SDLRSPVDSF DDEQKKLVYR GWKVMPFIIG NETFEKIGII GTLSNLLLYL TQVFNLKKVT  120
AATIINAFSG TINFGTFIAA FLCDTYFGRY KTLSVAVIAC FLGSLVILLT AAVPALHPTP  180
CGTHSWCQGP SPGQIAFLLL GLAFLVVGAG GIRPCNLAFG ADQFNPKSES GKKGINSFFN  240
WYFFTFTFAQ IVSLTLVVYI QSNVSWTIGL LIPVALMFLA CVIFFAGHKL YVKVKASGSP  300
LASIGHVITA AIKKRGLKQV KQPWLDLYNH IPTNYPNSTL KYTDQFRFLD KAAIMTPEDK  360
LNSDGAAFDP WTLCTLQKVE EVKCMCESDS DLVCLRDLLP HCNYTDDLSG LPSAAERPEI  420
GFWWLQDPRS HLCGVLDVGY DCFHRVLRPC PCVAQKSDR VRNRFDPLAE SRIRDLLCHV  480
EFVGLRVRRG TEKNLRPDET DSRDGATSGR DLLHVGHVAD SAALACRRRR GFYSHWTDGV  540
LLQAVP                                                             546

SEQ ID NO: 225         moltype = DNA  length = 1842
FEATURE                Location/Qualifiers
source                 1..1842
                       mol_type = genomic DNA
                       organism = Thlaspi arvense
SEQUENCE: 225
atggagagac agcctctcga actcgagtct acggatcacc aaaaaccttc ccccgccgtc  60
tacggtggct ctgttacgac ggttgattct gttgaggaag aagttcagga gaaaaaagtc  120
gtatatagag gctggaaagt catgcccttt atcattggaa atgagacatt cgagaagctt  180
gggatcattg gaacactatc aaaccttctg gtttttttaa cagctgtctt caacatgaag  240
agtatcacag ctgcaacaat cattaacgca ttcagtggca caataaattt cggaactttc  300
gttgctgctt tcctctgcga cacttacttc ggtcgataca agacactaac cgtcgcggtc  360
atcgcctgtt ttcttggatc acttgtgata ctattgacag ctgcagtgcc acaactgcac  420
ccagctccat gtggaacagc gagctcgtgc agcggtccaa gcggtgggca aatcgcgttt  480
cttctgatgg gtctcgggtt tcttgtagtt ggagcgggcg ggatcagacc gtgcaatcta  540
gctttcggag ccgatcagtt caacccgaag agcgagtcag ggagaagagg gactgatagt  600
ttcttcaatt ggtacttctt cagcttcact ttcgcgcaga tcttgtcgct gacgctagtg  660
gtctacatcc agtctaacgt cagctggacg atcggtctaa ccataccggt ggttctaatg  720
ttcttggcct ccgtgatctt ctttgcggga gataagctgt atgtgaaagt caaggcctcg  780
ggtagtccat tggctggtat agctcaagtg atcattgttg caatcaagaa acgcggatta  840
aagcccgtga aacagccttg gcttaacctc tacaattact gccctccaaa acacgcaaac  900
tccattctca aatacaccga ccaattcaga tttcttgata aggcggcgat cttggctccc  960
gaggacaagt tggaggcgga tggtaagcct gcggatccat ggaagctgtg tacgatgcaa  1020
caggtggaag aagtgaagtg cattgtgaga gtgcttccta tatggttcgc tgcatcaatc  1080
tactacgtaa ccataaccca gcaaatgaca tatccggtct tccaagccct gcagagcgat  1140
cgtcgcttag gctcgggagg gttcgtgatc cccgcagcca cctacgtggt cttcttgatg  1200
acagggatga cggttttcat catcatctac gaccgtctcc tcgtgcctac cttgagaaga  1260
ataaccggtc tagacaccgg gatcacgctc ctgcagagaa tcggaaccgg gatcttcttc  1320
gcctttgcaa gcttagtagt ctccggtttc gtcgaggagc ggaggagaca cattgcgctg  1380
actaaaccaa ctcttggcat ggcgccaaga aaaggagaaa tctcctcaat gtcagctatg  1440
tggctcatcc cgcagctcac tctctcgggt gtagccgagg cgtttggagc catcggacag  1500
atggagtttt actacaagca gttcccagaa aacatgagga gtttcgcggg ttccatcttt  1560
tatgtaggaa taggggtttc gagttacctc ggcagcttct tgattgcaac ggttcaccgg  1620
acgacgcaga actcggcggg tggtaactgg ttggctgagg atttgaacaa aggcagattg  1680
gattacttct atttcatgat cgctggaatc ttggctgtta atttcgccta cttcttggtc  1740
gtgtcaagat ggtataggta caaagaaagt aatgatgatc aaaagacagc ttctgaaacc  1800
```

```
aatggagatg tcatcaaaca acaagacaag aacactgcct ga                      1842

SEQ ID NO: 226          moltype = AA  length = 613
FEATURE                 Location/Qualifiers
source                  1..613
                        mol_type = protein
                        organism = Thlaspi arvense
SEQUENCE: 226
MERQPLELES TDHQKPSPAV YGGSVTTVDS VEEEVQEKKV VYRGWKVMPF IIGNETFEKL  60
GIIGTLSNLL VFLTAVFNMK SITAATIINA FSGTINFGTF VAAFLCDTYF GRYKTLTVAV  120
IACFLGSLVI LLTAAVPQLH PAPCGTASSC SGPSGGQIAF LLMGLGFLVV GAGGIRPCNL  180
AFGADQFNPK SESGRRGTDS FFNWYFFSFT FAQILSLTLV VYIQSNVSWT IGLTIPVVLM  240
FLASVIFFAG DKLYVKVKAS GSPLAGIAQV IIVAIKKRGL KPVKQPWLNL YNYCPPKHAN  300
SILKYTDQFR FLDKAAILAP EDKLEADGKP ADPWKLCTMQ QVEEVKCIVR VLPIWFAASI  360
YYVTITQQMT YPVFQALQSD RRLGSGGFVI PAATYVVFLM TGMTVFIIIY DRLLVPTLRR  420
ITGLDTGITL LQRIGTGIFF AFASLVVSGF VEERRRHIAL TKPTLGMAPR KGEISSMSAM  480
WLIPQLTLSG VAEAFGAIGQ MEFYYKQFPE NMRSFAGSIF YVGIGVSSYL GSFLIATVHR  540
TTQNSAGGNW LAEDLNKGRL NYFYFMIAGI LAVNFAYFLV VSRWYRYKES DDDQKTASET  600
NGDVIKQQDK NTA                                                      613

SEQ ID NO: 227          moltype = DNA  length = 1843
FEATURE                 Location/Qualifiers
source                  1..1843
                        mol_type = genomic DNA
                        organism = Thlaspi arvense
SEQUENCE: 227
atggagagac agcctctcga actcgagtct acggatcacc aaaaaccttc cccgccgtc   60
tacggtggct ctgttacgac ggttgattct gttgaggaag aagttcagga gaaaaaagtc  120
gtatatagag gctggaaagt catgcccttt atcattggaa atgagacatt cgagaagctt  180
gggatcattg gaacactatc aaaccttctg gtttttttaa cagctgtctt caacatgaag  240
agtatcacag ctgcaacaat cattaacgca ttcagtggca caataaattt cggaactttc  300
gttgctgctt tcctctgcga cacttacttc ggtcgataca agacactaac cgtcgcggtc  360
atcgcctgtt ttcttggatc acttgtgata ctattgacag ctgcagtgcc acaactgcac  420
ccagctccat gtggaacagc gagctcgtgc agcggtccaa gcggtgggca aatcgcgttt  480
cttctgatgg gtctcggggt tcttgtagtt ggagcgggcg ggatcagacc gtgcaatcta  540
gctttcggag ccgatcagtt caacccgaag agcgagtcag ggagaagagg gactgatagt  600
ttcttcaatt ggtacttctt cagcttcact ttcgcgcaga tcttgtcgct gacgctagtg  660
gtctacatcc agtctaacgt cagctggacg atcggtctaa ccataccggt ggttctaatg  720
ttcttggcct ccgtgatctt ctttgcggga gataagctgt atgtgaaagt caaggcctcg  780
ggtagtccat tggctggtat agctcaagtg atcattgttg caatcaagaa acgcggatta  840
aagcccgtga aacagccttg gcttaacctc tacaattact gccctccaaa acacgcaaac  900
tccattctca aatacaccga ccaattcaga tttcttgata aggcggcgat cttggctccc  960
gaggacaagt tggaggcgga tggtaagcct gcggatccat ggaagctgtg tacgatgcaa  1020
caggtggaag aagtgaagtg catatgtgag agtgcttcct atatggttcg ctgcatcaat  1080
ctactacgta accataaccc agcaaatgac atatccggtc ttccaagccc tgcagagcga  1140
tcgtcgctta ggctcgggag ggttcgtgat ccccgcagcc acctacgtgg tcttcttgat  1200
gacagggatg acggttttca tcatcatcta cgaccgtctc ctcgtgccta ccttgagaag  1260
aataaccggt ctagacaccg ggatcacgct cctgcagaga atcggaaccg ggatcttctt  1320
cgcctttgca agcttagtag tctccggttt cgtcgaggag cggaggagac acattgcgct  1380
gactaaacca actcttggca tggcgccaag aaaaggagaa atctcctcaa tgtcagctat  1440
gtggctcatc ccgcagctca ctctctcggg tgtagccgag gcgtttggag ccatcggaca  1500
gatggagttt tactacaagc agttcccaga aaacatgagg agtttcgcgg gttccatctt  1560
ttatgtagga ataggggttt cgagttacct cggcagcttc ttgattgcaa cggttcaccg  1620
gacgacgcag aactcggcgg gtggtaactg gttggctgag gatttgaaca aaggcagatt  1680
ggattacttc tatttcatga tcgctggaat cttggctgtt aatttcgcct acttcttggt  1740
cgtgtcaaga tggtataggt acaaagaaag tgatgatgat caaaagacag cttctgaaac  1800
caatggagat gtcatcaaac aacaagacaa gaacactgcc tga                     1843

SEQ ID NO: 228          moltype = AA  length = 461
FEATURE                 Location/Qualifiers
source                  1..461
                        mol_type = protein
                        organism = Thlaspi arvense
SEQUENCE: 228
MERQPLELES TDHQKPSPAV YGGSVTTVDS VEEEVQEKKV VYRGWKVMPF IIGNETFEKL  60
GIIGTLSNLL VFLTAVFNMK SITAATIINA FSGTINFGTF VAAFLCDTYF GRYKTLTVAV  120
IACFLGSLVI LLTAAVPQLH PAPCGTASSC SGPSGGQIAF LLMGLGFLVV GAGGIRPCNL  180
AFGADQFNPK SESGRRGTDS FFNWYFFSFT FAQILSLTLV VYIQSNVSWT IGLTIPVVLM  240
FLASVIFFAG DKLYVKVKAS GSPLAGIAQV IIVAIKKRGL KPVKQPWLNL YNYCPPKHAN  300
SILKYTDQFR FLDKAAILAP EDKLEADGKP ADPWKLCTMQ QVEEVKCICE SASYMVRCIN  360
LLRNHNPAND ISGLPSPAER SSLRLGRVRD PRSHLRGLLD DRDDGFHHHL RPSPRAYLEK  420
NNRSRHRDHA PAENRNRDLL RLCKLSSLRF RRGAEETHCA D                       461

SEQ ID NO: 229          moltype = DNA  length = 1843
FEATURE                 Location/Qualifiers
source                  1..1843
                        mol_type = genomic DNA
                        organism = Thlaspi arvense
SEQUENCE: 229
```

```
atggagagac agcctctcga actcgagtct acggatcacc aaaaaccttc ccccgccgtc  60
tacggtggct ctgttacgac ggttgattct gttgaggaag aagttcagga gaaaaaagtc  120
gtatatagag gctggaaagt catgcccttt atcattggaa atgagacatt cgagaagctt  180
gggatcattg gaacactatc aaaccttctg gtttttttaa cagctgtctt caacatgaag  240
agtatcacag ctgcaacaat cattaacgca ttcagtggca caataaattt cggaactttc  300
gttgctgctt tcctctgcga cacttacttc ggtcgataca agacactaac cgtcgcggtc  360
atcgcctgtt ttcttggatc acttgtgata ctattgacag ctgcagtgcc acaactgcac  420
ccagctccat gtggaacagc gagctcgtgc agcggtccaa gcggtgggca aatcgcgttt  480
cttctgatgg gtctcgggtt tcttgtagtt ggagcgggcg ggatcagacc gtgcaatcta  540
gctttcggag ccgatcagtt caacccgaag agcgagtcag ggagaagagg gactgatagt  600
ttcttcaatt ggtacttctt cagcttcact ttcgcgcaga tcttgtcgct gacgctagtg  660
gtctacatcc agtctaacgt cagctggacg atcggtctaa ccataccggt ggttctaatg  720
ttcttggcct ccgtgatctt ctttgcggga gataagctgt atgtgaaagt caaggcctcg  780
ggtagtccat tggctggtat agctcaagtg atcattgttg caatcaagaa acgcggatta  840
aagcccgtga aacagccttg gcttaacctc tacaattact gccctccaaa acacgcaaac  900
tccattctca aatacaccga ccaattcaga tttcttgata aggcggcgat cttggctccc  960
gaggacaagt tggaggcgga tggtaagcct gcggatccat ggaagctgtg tacgatgcaa  1020
caggtggaag aagtgaagtg catgtgtgag agtgcttcct atatggttcg ctgcatcaat  1080
ctactacgta accataaccc agcaaatgac atatccggtc ttccaagccc tgcagagcga  1140
tcgtcgctta ggctcgggag ggttcgtgat ccccgcagcc acctacgtgg tcttcttgat  1200
gacagggatg acggttttca tcatcatcta cgaccgtctc ctcgtgccta ccttgagaag  1260
aataaccggt ctagacaccg ggatcacgct cctgcagaga atcggaaccg ggatcttctt  1320
cgcctttgca agcttagtag tctccggttt cgtcgaggag cggaggagac acattgcgct  1380
gactaaacca actcttggca tggcgccaag aaaaggagaa atctcctcaa tgtcagctat  1440
gtggctcatc ccgcagctca ctctctcggg tgtagccgag gcgtttggag ccatcggaca  1500
gatggagttt tactacaagc agttcccaga aaacatgagg agtttcgcgg gttccatctt  1560
ttatgtagga ataggggttt cgagttacct cggcagcttc ttgattgcaa cggttcaccg  1620
gacgacgcag aactcggcgg gtggtaactg gttggctgag gatttgaaca aaggcagatt  1680
ggattacttc tatttcatga tcgctggaat cttggctgtt aatttcgcct acttcttggt  1740
cgtgtcaaga tggtataggt acaaagaaag tgatgatgat caaaagacag cttctgaaac  1800
caatggagat gtcatcaaac aacaagacaa gaacactgcc tga                   1843
```

```
SEQ ID NO: 230         moltype = AA  length = 461
FEATURE                Location/Qualifiers
source                 1..461
                       mol_type = protein
                       organism = Thlaspi arvense
SEQUENCE: 230
MERQPLELES TDHQKPSPAV YGGSVTTVDS VEEEVQEKKV VYRGWKVMPF IIGNETFEKL  60
GIIGTLSNLL VFLTAVFNMK SITAATIINA FSGTINFGTF VAAFLCDTYF GRYKTLTVAV  120
IACFLGSLVI LLTAAVPQLH PAPCGTASSC SGPSGGQIAF LLMGLGFLVV GAGGIRPCNL  180
AFGADQFNPK SESGRRGTDS FFNWYFFSFT FAQILSLTLV VYIQSNVSWT IGLTIPVVLM  240
FLASVIFFAG DKLYVKVKAS GSPLAGIAQV IIVAIKKRGL KPVKQPWLNL YNYCPPKHAN  300
SILKYTDQFR FLDKAAILAP EDKLEADGKP ADPWKLCTMQ QVEEVKCMCE SASYMVRCIN  360
LLRNHNPAND ISGLPSPAER SSLRLGRVRD PRSHLRGLLD DRDDGFHHHL RPSPRAYLEK  420
NNRSRHRDHA PAENRNRDLL RLCKLSSLRF RRGAEETHCA D                    461
```

```
SEQ ID NO: 231         moltype = DNA  length = 1108
FEATURE                Location/Qualifiers
source                 1..1108
                       mol_type = genomic DNA
                       organism = Thlaspi arvense
SEQUENCE: 231
atgtcaagaa agccgtgttg tcggagaagg gctgaagaaa ggggcatgga ccaccgaaga  60
agacaagaaa ctcatctctt acatccacga gcacggtgaa ggaggctggc gcgacattcc  120
ccaaaaagct gggttgaaac ggtgtggaaa gagttgtagg ctgcgatgga ctaactacct  180
aaaacctgag atcaaaagag gcgagtttag ttcagaggag gaacagatta tcattatgct  240
tcatgcttct cgtggcaaca agtggtcggt catagcgaga catttaccta gaagaacaga  300
caacgagatc aagaactact ggaacacgca tctcaaaaaa cgtttgatcg aacagggtgt  360
tgatcccgtg actcacaagc ctctagcttc caactccggc cctactgcca ccacgccgcc  420
tgagaatttg catttcctag atgaatctag ctcagacaag caatactctc ggtcgagctc  480
aatgccttcc ctgtctcgtc ttccttcctc cggattcaac acggtttccg agatagccag  540
caatgttggg acaccagttc aggtcggttc cttgagttgc aagaaacgtt ttaagaaatc  600
gagttcgaca tcaaggcttc tgaacaaatt tgcggctaag gccacttcca tcaaagatat  660
attgtcggct tccatggaag gtagctcgag tgctgctact acaatatcac atgcaagctt  720
tttaaatggc ttttctgagc agagtcgcaa tgaagaggat agttctaacg catccctgac  780
aaatactcta gccgaatttg atcccttctc tcagtcatcg ttgtacccgg agcatgagat  840
caatgttact tctgatatcg gcatggacca ggtttacgat ttctcacaat ttctcgaaaa  900
gctcgggagt gaaggccaca acgaactgaa tgtcgagtat ggtcatgatc ttcttatgtc  960
cgatgtttcg caagaagtct catcacctag cgttgatgat caagacaata tgattggaag  1020
cttcgaaggt tggtcaaatt atcttcttga ccatgctgat tttatatatg acaccgactc  1080
agattccctc gaaaagcatt tcatgtga                                   1108
```

```
SEQ ID NO: 232         moltype = AA  length = 32
FEATURE                Location/Qualifiers
source                 1..32
                       mol_type = protein
                       organism = Thlaspi arvense
SEQUENCE: 232
```

```
MSRKPCCRRR AEERGMDHRR RQETHLLHPR AR                          32

SEQ ID NO: 233          moltype = DNA  length = 1108
FEATURE                 Location/Qualifiers
source                  1..1108
                        mol_type = genomic DNA
                        organism = Thlaspi arvense
SEQUENCE: 233
atgtcaagaa agccgtgttg tcggagaagg gctgaagaaa ggggcatgga ccaccgaaga  60
agacaagaaa ctcatctctt acatccacga gcacggtgaa ggaggctggc gcgacattcc  120
ccaaaaagct gggttgaaac ggtgtggaaa gagttgtagg ctgcgatgga ctaactacct  180
aaaacctgag atcaaaagag gcgagtttag ttcagaggag gaacagatta tcattatgct  240
tcatgcttct cgtggcaaca agtggtcggt catagcgaga catttaccta gaagaacaga  300
caacgagatc aagaactact ggaacacgca tctcaaaaaa cgtttgatcg aacagggtgt  360
tgatcccgtg actcacaagc ctctagcttc caactccggc cctactgcca ccacgccgcc  420
tgagaatttg catttcctag atgaatctag ctcagacaag caatactctc ggtcgagctc  480
aatgccttcc ctgtctcgtc ttccttcctc cggattcaac acggtttccg agatagccag  540
caatgttggg acaccagttc aggtcggttc cttgagttgc aagaaacgtt ttaagaaatc  600
gagttcgaca tcaaggcttc tgaacaaatt tgcggctaag gccacttcca tcaaagatat  660
attgtcggct tccatggaag gtagctcgag tgctgctact acaatatcac atgcaagctt  720
tttaaatggc ttttctgagc agagtcgcaa tgaagaggat agttctaacg catccctgac  780
aaatactcta gccgaatttg atcccttctc tcagtcatcg ttgtacccgg agcatgagat  840
caatgttact tctgatatcg gcatggacca ggtttacgat ttctcacaat ttctcgaaaa  900
gctcgggagt gaaggccaca acgaactgaa tgtcgagtat ggtcatgatc ttcttatgtc  960
cgatgtttcg caagaagtct catcacctag cgttgatgat caagacaata tgattggaag  1020
cttcgaaggt tggtcaaatt atcttcttga ccatgctgat tttatatatg acaccgactc  1080
agattccctc gaaaagcatt tcatgtga                                      1108

SEQ ID NO: 234          moltype = AA  length = 32
FEATURE                 Location/Qualifiers
source                  1..32
                        mol_type = protein
                        organism = Thlaspi arvense
SEQUENCE: 234
MSRKPCCRRR AEERGMDHRR RQETHLLHPR AR                          32

SEQ ID NO: 235          moltype = DNA  length = 1955
FEATURE                 Location/Qualifiers
source                  1..1955
                        mol_type = genomic DNA
                        organism = Thlaspi arvense
SEQUENCE: 235
atgaagagta gagtcatcct cagccataga gagagaagag ataagaagaa taataacatt  60
aacaacaaag acatctcctg taatttcaca cagattgaaa ccatggagag aaagcccttt  120
gaggttgaga cgacggagaa tcacaaaccc tactccaccg tcgatggcgg tggcgttggt  180
tctgatttga gatcgccggt cgattcattt gatgacgagc agaaaaagct cgtttacaga  240
ggctggaaag tcatgccttt tatcattggt aatgagacat ttgagaagat tgggatcata  300
gggacattat caaaccttct tttgtaccta actcaagtat tcaaccttaa gaaagttaca  360
gctgcaacaa tcatcaatgc ctttagtggc acaatcaact tcgggacttt catcgctgct  420
ttcctctgcg acacttactt tggtcgctac aagactctca gtgtagctgt catcgcttgt  480
ttcctgggat cgcttgtgat attactgacg gctgcagttc ctgcattgca cccgactcca  540
tgtggaacac atagctggtg ccaagggcca agcccgggcc agatcgcgtt cttgctgctg  600
ggtttagcgt ttcttgtggt cggtgcgggt gggatcaggc cgtgtaactt ggcttttgga  660
gctgatcagt tcaaccccaa atcccgaatcc gggaagaaag gaatcaacag cttctttaac  720
tggtatttct tcaccttcac gtttgcgcag atcgtctcgc tcacgctggt cgtgtatatc  780
cagtcgaacg tgagctggac gatcggtttg ctcatccctg tggctctgat gttcttggcc  840
tgcgtcatct tctttgctgg acataaactg tatgtgaaag tgaaagcctc gggtagtccc  900
ttggctagta tcggtcacgt tatcacggca gcgatcaaga aacgagggtt gaagcaagtt  960
aagcagcctt ggctcgatct ttacaaccac attccaacta actatccaaa ctccaccttg  1020
aaatacaccg accagtttag gtttcttgac aaagcagcga ttatgacccc tgaggacaag  1080
ctgaattccg atggagctgc tttcgatcca tggaccctat gtacattgca gaaagtggaa  1140
gaagtgaaat gcatgtgaga gtgattccga tctggtttgc ttgcgcgatt tactacctca  1200
ctgtaactat acagatgact tatccggtct tccaagcgca gcagagcgac cggagattgg  1260
gttctggtgg cttcaagatc cccgcagcca cctatgtggt gttcttgatg tcgggtatga  1320
ctgttttcat cgtgttctac gaccgtgtcc ttgtcccgtt gctcagaaga gtgaccgggt  1380
tagaaaccgg tttgaccctc ttgcagagag tcggatcagg gatcttcttt gccatgttga  1440
gtttgttggt ctccgggttc gtagaggaac ggagaagaac cttcgccctg acgaaaccga  1500
ctctcgggat ggagccacga gcgggagaga tctcctccat gtcggccatg tggctgattc  1560
cgcagctctt gcttgcaggc gtaggagagg cttttacagc cattggacag atggagtttt  1620
attacaagca gttccctgag aacatgaaga gcttcgctgg ctctatcttc tatgtcggtg  1680
caggtgtttc gagctatctt gctagcttct tgatctcgac tgttcatcga agaactgaac  1740
attcaccctc cgggaactgg ttagctgagg atctgaacaa agggagactc gattacttct  1800
acttcatgct caccggaatc atggtcgtta acatggttta cttcttgata atgtctaaat  1860
ggtatagata caaaggcatt aacgatgaag cgaattcttt ggtcgagacc aatgaagaag  1920
agaccaagca gaaacaagtc aagaattctg tctga                               1955

SEQ ID NO: 236          moltype = AA  length = 385
FEATURE                 Location/Qualifiers
source                  1..385
```

```
                        mol_type = protein
                        organism = Thlaspi arvense
SEQUENCE: 236
MKSRVILSHR ERRDKKNNNI NNKDISCNFT QIETMERKPF EVETTENHKP YSTVDGGGVG  60
SDLRSPVDSF DDEQKKLVYR GWKVMPFIIG NETFEKIGII GTLSNLLLYL TQVFNLKKVT  120
AATIINAFSG TINFGTFIAA FLCDTYFGRY KTLSVAVIAC FLGSLVILLT AAVPALHPTP  180
CGTHSWCQGP SPGQIAFLLL GLAFLVVGAG GIRPCNLAFG ADQFNPKSES GKKGINSFFN  240
WYFFTFTFAQ IVSLTLVVYI QSNVSWTIGL LIPVALMFLA CVIFFAGHKL YVKVKASGSP  300
LASIGHVITA AIKKRGLKQV KQPWLDLYNH IPTNYPNSTL KYTDQFRFLD KAAIMTPEDK  360
LNSDGAAFDP WTLCTLQKVE EVKCM                                       385

SEQ ID NO: 237          moltype = DNA  length = 100
FEATURE                 Location/Qualifiers
source                  1..100
                        mol_type = other DNA
                        organism = synthetic construct
SEQUENCE: 237
attgttgcag ctgtaacttt cttagtttta gagctagaaa tagcaagtta aaataaggct  60
agtccgttat caacttgaaa aagtggcacc gagtcggtgc                      100

SEQ ID NO: 238          moltype = DNA  length = 100
FEATURE                 Location/Qualifiers
source                  1..100
                        mol_type = other DNA
                        organism = synthetic construct
SEQUENCE: 238
attgagccct tctccgacac aacagtttta gagctagaaa tagcaagtta aaataaggct  60
agtccgttat caacttgaaa aagtggcacc gagtcggtgc                      100

SEQ ID NO: 239          moltype = DNA  length = 100
FEATURE                 Location/Qualifiers
source                  1..100
                        mol_type = other DNA
                        organism = synthetic construct
SEQUENCE: 239
attgagcctc cttcaccgtg ctcggtttta gagctagaaa tagcaagtta aaataaggct  60
agtccgttat caacttgaaa aagtggcacc gagtcggtgc                      100

SEQ ID NO: 240          moltype = DNA  length = 70
FEATURE                 Location/Qualifiers
source                  1..70
                        mol_type = other DNA
                        organism = synthetic construct
SEQUENCE: 240
agatagagaa gttatcagaa ttggatataa tttctactgt tgtagattca aggtacttct  60
ctatcccgaa                                                        70

SEQ ID NO: 241          moltype = DNA  length = 70
FEATURE                 Location/Qualifiers
source                  1..70
                        mol_type = other DNA
                        organism = synthetic construct
SEQUENCE: 241
tagattcggg atagagaagt accttgaatc tacaacagta gaaattatat ccaattctga  60
taacttctct                                                        70

SEQ ID NO: 242          moltype = DNA  length = 70
FEATURE                 Location/Qualifiers
source                  1..70
                        mol_type = other DNA
                        organism = synthetic construct
SEQUENCE: 242
agattatgcc gtatccatcg gtcgatctaa tttctactgt tgtagatgtc tggtcggaat  60
atcattatcc                                                        70

SEQ ID NO: 243          moltype = DNA  length = 70
FEATURE                 Location/Qualifiers
source                  1..70
                        mol_type = other DNA
                        organism = synthetic construct
SEQUENCE: 243
tagaggataa tgatattccg accagacatc tacaacagta gaaattagat cgaccgatgg  60
atacggcata                                                        70

SEQ ID NO: 244          moltype = DNA  length = 70
FEATURE                 Location/Qualifiers
source                  1..70
                        mol_type = other DNA
                        organism = synthetic construct
```

```
SEQUENCE: 244
agatagacct tcaaatagtc cctacaataa tttctactgt tgtagatctt ctgaaaaact  60
ctctccttgt                                                         70

SEQ ID NO: 245         moltype = DNA  length = 70
FEATURE                Location/Qualifiers
source                 1..70
                       mol_type = other DNA
                       organism = synthetic construct
SEQUENCE: 245
tagaacaagg agagagtttt tcagaagatc tacaacagta gaaattattg tagggactat  60
ttgaaggtct                                                         70

SEQ ID NO: 246         moltype = DNA  length = 70
FEATURE                Location/Qualifiers
source                 1..70
                       mol_type = other DNA
                       organism = synthetic construct
SEQUENCE: 246
agatacatct ccgcaagtgt ccattcctaa tttctactgt tgtagatcca ctacttcgtc  60
taactccttc                                                         70

SEQ ID NO: 247         moltype = DNA  length = 70
FEATURE                Location/Qualifiers
source                 1..70
                       mol_type = other DNA
                       organism = synthetic construct
SEQUENCE: 247
tagagaagga gttagacgaa gtagtggatc tacaacagta gaaattagga atggacactt  60
gcggagatgt                                                         70

SEQ ID NO: 248         moltype = DNA  length = 70
FEATURE                Location/Qualifiers
source                 1..70
                       mol_type = other DNA
                       organism = synthetic construct
SEQUENCE: 248
agatttaagg ttgaatactt gagttagtaa tttctactgt tgtagatgtg gcacaatcaa  60
cttcgggact                                                         70

SEQ ID NO: 249         moltype = DNA  length = 70
FEATURE                Location/Qualifiers
source                 1..70
                       mol_type = other DNA
                       organism = synthetic construct
SEQUENCE: 249
tagaagtccc gaagttgatt gtgccacatc tacaacagta gaaattacta actcaagtat  60
tcaaccttaa                                                         70

SEQ ID NO: 250         moltype = DNA  length = 70
FEATURE                Location/Qualifiers
source                 1..70
                       mol_type = other DNA
                       organism = synthetic construct
SEQUENCE: 250
agatggagcc gatcagttca acccgaataa tttctactgt tgtagatgcg cagatcttgt  60
cgctgacgct                                                         70

SEQ ID NO: 251         moltype = DNA  length = 70
FEATURE                Location/Qualifiers
source                 1..70
                       mol_type = other DNA
                       organism = synthetic construct
SEQUENCE: 251
tagaagcgtc agcgacaaga tctgcgcatc tacaacagta gaaattattc gggttgaact  60
gatcggctcc                                                         70

SEQ ID NO: 252         moltype = DNA  length = 70
FEATURE                Location/Qualifiers
source                 1..70
                       mol_type = other DNA
                       organism = synthetic construct
SEQUENCE: 252
agatggtagt tagtccatcg cagcctataa tttctactgt tgtagatgtt cagaggagga  60
acagattatc                                                         70

SEQ ID NO: 253         moltype = DNA  length = 70
FEATURE                Location/Qualifiers
source                 1..70
```

```
                          mol_type = other DNA
                          organism = synthetic construct
SEQUENCE: 253
tagagataat ctgttcctcc tctgaacatc tacaacagta gaaattatag gctgcgatgg  60
actaactacc                                                         70

SEQ ID NO: 254            moltype = DNA  length = 70
FEATURE                   Location/Qualifiers
source                    1..70
                          mol_type = other DNA
                          organism = synthetic construct
SEQUENCE: 254
agatatcgaa cagggtgttg atcccgttaa tttctactgt tgtagataac atagaaacgt  60
acttgttgcc                                                         70

SEQ ID NO: 255            moltype = DNA  length = 70
FEATURE                   Location/Qualifiers
source                    1..70
                          mol_type = other DNA
                          organism = synthetic construct
SEQUENCE: 255
tagaggcaac aagtacgttt ctatgttatc tacaacagta gaaattaacg ggatcaacac  60
cctgttcgat                                                         70

SEQ ID NO: 256            moltype = DNA  length = 70
FEATURE                   Location/Qualifiers
source                    1..70
                          mol_type = other DNA
                          organism = synthetic construct
SEQUENCE: 256
agatgctacg aggaggagca gattatctaa tttctactgt tgtagataaa tagttagccc  60
atcgcaatct                                                         70

SEQ ID NO: 257            moltype = DNA  length = 70
FEATURE                   Location/Qualifiers
source                    1..70
                          mol_type = other DNA
                          organism = synthetic construct
SEQUENCE: 257
tagaagattg cgatgggcta actatttatc tacaacagta gaaattagat aatctgctcc  60
tcctcgtagc                                                         70

SEQ ID NO: 258            moltype = DNA  length = 70
FEATURE                   Location/Qualifiers
source                    1..70
                          mol_type = other DNA
                          organism = synthetic construct
SEQUENCE: 258
agataccctt ctccgataca gcatggttaa tttctactgt tgtagattct tcccctgacg  60
tccatgctcc                                                         70

SEQ ID NO: 259            moltype = DNA  length = 70
FEATURE                   Location/Qualifiers
source                    1..70
                          mol_type = other DNA
                          organism = synthetic construct
SEQUENCE: 259
tagaggagca tggacgtcag gggaagaatc tacaacagta gaaattaacc atgctgtatc  60
ggagaagggt                                                         70

SEQ ID NO: 260            moltype = DNA  length = 70
FEATURE                   Location/Qualifiers
source                    1..70
                          mol_type = other DNA
                          organism = synthetic construct
SEQUENCE: 260
agatgtccag cttcgtcagg aacttcctaa tttctactgt tgtagatgag aaaccttctc  60
gtaggagctg                                                         70

SEQ ID NO: 261            moltype = DNA  length = 70
FEATURE                   Location/Qualifiers
source                    1..70
                          mol_type = other DNA
                          organism = synthetic construct
SEQUENCE: 261
tagacagctc ctacgagaag gtttctcatc tacaacagta gaaattagga agttcctgac  60
gaagctggac                                                         70
```